United States Patent
Guzzo et al.

(10) Patent No.: US 9,067,949 B2
(45) Date of Patent: Jun. 30, 2015

(54) BENZOFURO[3,2-C] PYRIDINES AND RELATED ANALOGS AS SEROTONIN SUB-TYPE 6 (5-HT$_6$) MODULATORS FOR THE TREATMENT OF OBESITY, METABOLIC SYNDROME, COGNITION AND SCHIZOPHRENIA

(75) Inventors: Peter R. Guzzo, Niskayuna, NY (US); Alan J. Henderson, Fishers, IN (US); Matthew Isherwood, Delmar, NY (US); Chong Yew Lee, Kuala Lumpur (MY); Animesh Ghosh, Singapore (SG); He Zhao, Madison, CT (US)

(73) Assignee: Albany Molecular Research, Inc., Albany, NY (US)

( * ) Notice: Subject to any disclaimer, the term of this patent is extended or adjusted under 35 U.S.C. 154(b) by 313 days.

(21) Appl. No.: 13/352,864

(22) Filed: Jan. 18, 2012

(65) Prior Publication Data

US 2012/0184531 A1    Jul. 19, 2012

Related U.S. Application Data

(60) Provisional application No. 61/434,286, filed on Jan. 19, 2011.

(51) Int. Cl.
| | |
|---|---|
| *C07D 491/048* | (2006.01) |
| *C07D 307/91* | (2006.01) |
| *C07D 491/18* | (2006.01) |
| *C07D 491/08* | (2006.01) |

(52) U.S. Cl.
CPC .......... *C07D 491/048* (2013.01); *C07D 307/91* (2013.01); *C07D 491/18* (2013.01); *C07D 491/08* (2013.01)

(58) Field of Classification Search
None
See application file for complete search history.

(56) References Cited

U.S. PATENT DOCUMENTS

| | | |
|---|---|---|
| 2,894,942 A | 7/1959 | Hydro et al. |
| 3,518,270 A | 6/1970 | Shavel et al. |
| 3,914,421 A | 10/1975 | Rajagopalan |
| 4,013,652 A | 3/1977 | Rajagopalan |
| 4,115,577 A | 9/1978 | Rajagopalan |
| 4,183,936 A | 1/1980 | Rajagopalan |
| 4,219,550 A | 8/1980 | Rajagopalan |
| 4,238,607 A | 12/1980 | Rajagopalan |
| 5,187,180 A | 2/1993 | Gillard |
| 5,250,537 A | 10/1993 | Mewshaw et al. |
| 5,646,287 A | 7/1997 | Vedejs et al. |
| 5,811,551 A | 9/1998 | Chen et al. |
| 6,156,757 A | 12/2000 | Kennis et al. |
| 6,469,020 B2 | 10/2002 | Batty et al. |
| 6,548,493 B1 | 4/2003 | Robichaud et al. |
| 6,552,017 B1 | 4/2003 | Robichaud et al. |
| 6,951,881 B2 | 10/2005 | Cole et al. |
| 6,995,176 B2 | 2/2006 | Bernotas et al. |
| 2002/0119972 A1 | 8/2002 | Leftheris et al. |
| 2003/0023085 A1 | 1/2003 | Chen et al. |
| 2003/0176694 A1 | 9/2003 | Chen et al. |
| 2003/0232843 A1 | 12/2003 | Cole et al. |
| 2004/0087593 A1 | 5/2004 | Clark et al. |
| 2004/0162332 A1 | 8/2004 | Fu |
| 2004/0214815 A1 | 10/2004 | McWhorter, Jr. et al. |
| 2006/0287299 A1 | 12/2006 | Sheldon |
| 2007/0027178 A1 | 2/2007 | Lee |
| 2007/0066608 A1 | 3/2007 | Bartolome-Nebreda et al. |
| 2007/0123574 A1 | 5/2007 | De Kock et al. |
| 2007/0197629 A1 | 8/2007 | Somei et al. |
| 2007/0244145 A1 | 10/2007 | Kumagai et al. |
| 2008/0194638 A1 | 8/2008 | Dedhiya et al. |
| 2010/0249105 A1 | 9/2010 | Schrimpf et al. |
| 2011/0112122 A1 | 5/2011 | Guzzo et al. |

FOREIGN PATENT DOCUMENTS

| | | | |
|---|---|---|---|
| EP | 0203505 A1 | 12/1986 | |
| EP | 0473550 A1 | 8/1991 | |
| EP | 1230018  * | 8/2002 | .......... C07D 417/12 |
| EP | 1 505 061 A1 | 2/2005 | |

(Continued)

OTHER PUBLICATIONS

Jantzen. Modern Pharmaceutics, 1996, p. 596.*

(Continued)

*Primary Examiner* — Noble Jarrell

(74) *Attorney, Agent, or Firm* — LeClairRyan, a Professional Corporation

(57) ABSTRACT

The present invention relates to benzofuro[3,2-c]pyridine and azepine analogs as serotonin sub-type 6 (5-HT$_6$) modulators, pharmaceutical compositions including these compounds, methods of preparation, and use thereof. These compounds are useful in the treatment of central nervous system disorders including obesity, metabolic syndrome, cognition, schizophrenia, attention deficit hyperactivity disorder, bipolar disorder, rare and orphan diseases, and sleep disorders. The subject compounds have the structure of formula (I)

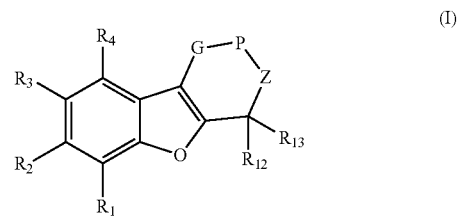

with the substituents being described herein.

52 Claims, No Drawings

(56) References Cited

FOREIGN PATENT DOCUMENTS

| WO | 9933800 | A1 | 7/1999 |
|---|---|---|---|
| WO | 00/35922 | A1 | 6/2000 |
| WO | 00/77001 | A1 | 12/2000 |
| WO | 00/77002 | A1 | 12/2000 |
| WO | 00/77010 | A2 | 12/2000 |
| WO | 01/58869 | A2 | 8/2001 |
| WO | 01/87883 | A1 | 11/2001 |
| WO | 02089729 | A2 | 11/2002 |
| WO | 03/014118 | A1 | 2/2003 |
| WO | 03097598 | A1 | 11/2003 |
| WO | 2004/056324 | A2 | 7/2004 |
| WO | 2006005063 | A2 | 1/2006 |
| WO | 2006064355 | A2 | 6/2006 |
| WO | 2006/101434 | A1 | 9/2006 |
| WO | 2007050795 | A2 | 5/2007 |
| WO | 2008/060190 | A2 | 5/2008 |
| WO | 2008/060190 | A3 | 5/2008 |
| WO | 2008060190 | A2 | 5/2008 |
| WO | 2008081282 | A2 | 7/2008 |
| WO | 2009/055828 | A1 | 4/2009 |
| WO | 2009/120720 | A1 | 10/2009 |
| WO | 2011/044134 | A1 | 4/2011 |
| WO | 2011/087712 | A2 | 7/2011 |

OTHER PUBLICATIONS

Office Action for U.S. Appl. No. 12/898,271 (Oct. 25, 2012).
International Search Report and Written Opinion for PCT/US10/51485 (Dec. 2, 2010).
Gremmen et al., "The Synthesis of New Heterocyclic Bridged Ring Systems. Analogs of Tetrahydro-beta-Carbolines," Tet. Lett. 39:1441-1444 (1998).
Bailey et al., "New Asymmetric Route to Bridged Indole Alkaloids: Formal Enantiospecific Syntheses of (−)-Suaveoline, (−)-Raumacline and (−)-N(b)-Methylraumacline," J. Chem. Soc. Perkin Trans. 1:1209-1214 (1997).
Hoyer et al., "VII. International Union of Pharmacology Classification of Receptors for 5-Hydroxytryptamine (Serotonin)," Pharmacol. Rev. 46(2):157-203 (1994).
Hoffman et al., "Distribution of Serotonin 5-HT(1C) Receptor mRNA in Adult Rat Brain," FEBS Lett. 247(2):453-462 (1989).
Nonogaki et al., "Leptin-Independent Hyperphagia and Type 2 Diabetes in Mice with a Mutated Serotonin 5-HT(2C) Receptor Gene," Nat. Med. 4(10):1152-1156 (1998).
Vickers et al., "Reduced Satiating Effect of d-Fenfluramine in Serotonin 5-HT(2C) Receptor Mutant Mice," Psychopharmacol. 143:309-314 (1999).
Vickers et al., "Comparative Effects of Continuous Infusion of mCPP, Ro 60/0175 and d-Fenfluramine on Food Intake, Water Intake, Body Weight and Locomotor Activity in Rats," Br. J. Pharmacol. 130: 1305-1314 (2000).
Vickers et al., "Evidence that Hypophagia Induced by d-Fenfluramine and d-Norfenfluramine in the Rat is Mediated by 5-HT(2C) Receptors," Neuropharmacol. 41:200-209 (2001).
Mazzola-Pomietto et al., "Evidence that m-Chlorophenylpiperazine-Induced Hyperthermia in Rats is Mediated by Stimulation of 5-HT(2C) Receptors," Psychopharmacol. 123:333-339 (1996).
Sharpley et al., "Slow Wave Sleep in Humans: Role of 5-HT(2A) and 5-HT(2C) Receptors," Neuropharmacol. 33:467-471 (1994).
Rittenhouse et al., "Evidence that ACTH Secretion is Regulated by Serotonin(2A/2C) (5-HT(2A/2C) Receptors," J. Pharmacol. Exp. Ther. 271:1647-1655 (1994).
Di Matteo et al., "Role of 5-HT(2C) Receptors in the Control of Central Dopamine Function," Trends Pharmacol. Sci. 22:229-232 (2001).
Cryan et al., "Antidepressant-Like Behavioral Effects Mediated by 5-Hydroxytryptamine(2C) Receptors," J. Pharmacol. Exp. Ther. 295(3):1120-1126 (2000).
Grottick et al., "Activation of 5-HT(2C) Receptors Reduces the Locomotor and Rewarding Effects of Nicotine," Psychopharmacol. 157:292-298 (2001).
Grottick et al., "Studies to Investigate the Role of 5-HT(2C) Receptors on Cocaine- and Food-Maintained Behavior," J. Pharmacol. Exp. Ther. 295(3):1183-1191 (2000).
Chojnacka-Wojcik et al., "Involvement of 5-HT(2C) Receptors in the m-CPP-Induced Antinociception in Mice," Pol. J. Pharmacol. 46:423-428 (1994).
Millan et al., "5-HT(2C) Receptors Mediate Penile Erections in Rats: Actions of Novel and Selective Agonists and Antagonists," Eur. J. Pharmacol. 325:9-12 (1997).
Mewshaw et al., "Bridged Gamma-Carbolines and Derivatives Possessing Selective and Combined Affinity for 5-HT(2) and D(2) Receptors," J. Med. Chem. 36:1488-1495 (1993).
Mewshaw et al., "Synthesis and in Vitro Evaluation of 5,6,7,8,9,10-Hexahydro-7,10-iminocyclohept[b]indoles: High-Affinity Ligands for the N,N'-Di-o-tolylguanidine-Labeled sigma Binding Site," J. Med. Chem. 36:343-352 (1993).
Kennis et al., "New 2-Substituted 1,2,3,4-Tetrahydrobenzofuro[3,2-c]pyridine Having Highly Active and Potent Central Alpha2-Antagonistic Activity as Potential Antidepressants," Bioorg. Med. Chem. Lett. 10:71-74 (2000).
International Search Report and Written Opinion for PCT/US2012/021708 dated Nov. 28, 2012.
Extended European Search Report for EP 12736835.5 dated Jul. 18, 2014.
First Examination Report for New Zealand patent Application No. 613024 dated Apr. 9, 2014.

* cited by examiner

BENZOFURO[3,2-C] PYRIDINES AND RELATED ANALOGS AS SEROTONIN SUB-TYPE 6 (5-HT$_6$) MODULATORS FOR THE TREATMENT OF OBESITY, METABOLIC SYNDROME, COGNITION AND SCHIZOPHRENIA

This application claims the benefit of U.S. Provisional Patent Application Ser. No. 61/434,286, filed Jan. 19, 2011, which is hereby incorporated by reference in its entirety.

FIELD OF THE INVENTION

The present invention relates to benzofuro[3,2-c]pyridine and azepine analogs as serotonin sub-type 6 (5-HT$_6$) modulators and uses thereof.

BACKGROUND OF THE INVENTION

Various central nervous system (CNS) disorders such as anxiety, depression, motor disorders, etc., are believed to involve a disturbance of the neurotransmitter 5-hydroxytryptamine (5-HT) or serotonin. Serotonin is localized in the central and peripheral nervous systems and is known to affect many types of conditions including psychiatric disorders, motor activity, feeding behavior, sexual activity, and neuroendocrine regulation among others. The effects of serotonin are regulated by the various 5-HT receptor subtypes. Known 5-HT receptors include the 5-HT$_1$ family (e.g. 5-HT$_{1A}$), the 5-HT$_2$ family (e.g. 5-HT$_{2A}$), 5-HT$_3$, 5-HT$_4$, 5-HT$_5$, 5-HT$_6$ and 5-HT$_7$ subtypes.

The biogenic amine serotonin (5-hydroxytryptamine; 5-HT) is a brain neurotransmitter that has been strongly implicated in the pathophysiology and treatment of a wide variety of neuropsychiatric disorders. It exerts its effects through a diverse family of serotonin receptor subtypes. Of the 14 different mammalian serotonin receptors to have been cloned, all but one is a member of the G-protein coupled receptor superfamily. Several of these, including the serotonin 5-HT$_6$ receptor, stimulate adenylyl cyclase via G coupling. Several therapeutically important antidepressant, antianxiety, hallucinogenic, and antipsychotic drugs have high affinity for the 5-HT$_6$ receptor, particularly the atypical antipsychotics such as clozapine. The relevance of the 5-HT$_6$ receptor to psychotherapeutics is indicated both through its unique anatomical distribution and pharmacological properties.

The recently identified human 5-HT$_6$ receptor subtype has been cloned, and the extensive distribution of its mRNA has been reported. Highest levels of 5-HT$_6$ receptor mRNA have been observed in the olfactory tubercle, the striatum, nucleus accumbens, dentate gyrus, and CA1, CA2, and CA3 regions of the hippocampus. Lower levels of 5-HT$_6$ receptor mRNA are seen in the granular layer of the cerebellum, several diencephalic nuclei, amygdalae, and in the cortex. Northern blots have revealed that 5-HT$_6$ receptor mRNA appears to be exclusively present in the brain, with little evidence for its presence in peripheral tissues. The high affinity of a number of antipsychotic agents for the 5-HT$_6$ receptor, in addition to its mRNA localization in striatum, olfactory tubercle and nucleus accumbens suggests that some of the clinical actions of these compounds may be mediated through this receptor. Therefore, 5-HT$_6$ receptor ligands are believed to be of potential use in the treatment of certain CNS disorders such as anxiety, depression, epilepsy, obsessive compulsive disorder, attention deficit disorder, migraine, cognitive memory enhancement (e.g. for the treatment of Alzheimer's disease), sleep disorders, feeding disorders (e.g. anorexia, obesity, or bulimia), neurodegenerative disorders (e.g. stroke or head trauma), panic attacks, withdrawal from drug abuse (e.g. cocaine, ethanol, nicotine or benzodiazepines), schizophrenia, or the like; or in the treatment of certain gastrointestinal disorders such as irritable bowel syndrome.

The high affinity of a number of antipsychotic agents for the 5-HT$_6$ receptor, in addition to its mRNA localization in striatum, olfactory tubercle and nucleus accumbens suggests that some of the clinical actions of these compounds may be mediated through this receptor. Compounds which interact with, stimulate, or inhibit the 5-HT$_6$ receptor are commonly referred to as 5-HT$_6$ ligands. In particular, 5-HT$_6$ selective ligands have been identified as potentially useful in the treatment of certain CNS disorders such as Parkinson's disease, Huntington's disease, anxiety, depression, manic depression, psychoses, epilepsy, obsessive compulsive disorders, migraine, Alzheimer's disease (enhancement of cognitive memory), sleep disorders, feeding disorders such as anorexia, obesity, and bulimia, panic attacks, attention deficit hyperactivity disorder (ADHD), attention deficit disorder (ADD), withdrawal from drug abuse such as cocaine, ethanol, nicotine and benzodiazepines, schizophrenia, bipolar disorder, and also disorders associated with spinal trauma and/or head injury such as hydrocephalus. Such compounds are also expected to be of use in the treatment of certain gastrointestinal (GI) disorders such as functional bowel disorder and irritable bowel syndrome (See for examples Roth et al., *J. Pharmacol. Exp. Ther.* 268:1403-14120 (1994), Sibley et al., *Mol. Pharmacol.* 43:320-327 (1993), Sleight et al., *Neurotransmission* 11:1-5 (1995), and Sleight et al., *Serotonin ID Research Alert* 2(3):115-8 (1997)). Furthermore, the effect of 5-HT$_6$ antagonist and 5-HT$_6$ antisense oligonucleotides to reduce food intake in rats has been reported (Bentley et al., *Br. J. Pharmacol.* Suppl. 126:66 (1999) and Bentley et al., *J. Psychopharmacol.* Suppl. A64:255 (1997)).

Scientific research has revealed a potential therapeutic use for modulators of the 5-HT$_6$ receptor, especially with regard to various CNS disorders. Blocking 5-HT$_6$ receptor function has been shown to enhance cholinergic transmission (Bentley et al., *Br. J. Pharmacol.* 126:1537-1542 (1999) and Riemer et al., *J. Med. Chem.* 46:1273-1276 (2003)). 5-HT$_6$ antagonist have also been shown to reverse cognitive deficits in in vivo cognition models induced by the muscarinic antagonist scopolamine (Woolley et al., *Psychopharmacology* 170:358-367 (2003) and Foley et al., *Neuropsychopharmacology* 29:93-100 (2004)).

Studies have shown that 5-HT$_6$ antagonists increase levels of glutamate and aspartate in the frontal cortex and dorsal hippocampus as well as acetylcholine in the frontal cortex. These neurochemicals are known to be involved in memory and cognition (Dawson et al., *Neuropsychopharmacology* 25(5):662-668 (2001); Gerard et al., *Brain Res.* 746:207-219 (1997); and Riemer et al., *J. Med. Chem.* 46(7):1273-1276 (2003)).

Studies have also shown that 5-HT$_6$ antagonist increases the level of dopamine and noradrenaline in the medial prefrontal cortex (Lacroix et al., *Synapse* 51:158-164 (2004)). In addition, 5-HT$_6$ receptor antagonists have been shown to improve performance in the attentional set shifting task (Hatcher et al., *Psychopharmacology* 181(2):253-9 (2005)). Therefore, 5-HT$_6$ ligands are expected to be useful in the treatment of disorders where cognitive deficits are a feature, such as schizophrenia. Several antidepressants and atypical antipsychotics bind to the 5-HT$_6$ receptor and this may be a factor in their profile of activities (Roth et al., *J. Pharm. Exp. Therapeut.* 268:1402-1420 (1994); Sleight et al., *Exp. Opin.*

Ther. Patents 8:1217-1224 (1998); Kohen et al., J. Neurochem. 66(1):47-56 (1996); Sleight et al., Brit. J. Pharmacol. 124:556-562 (1998); and Bourson et al., Brit. J. Pharmacol. 125:1562-1566 (1998)).

Stean et al., Brit. J. Pharmacol. 127 Proc. Supplement 131P (1999), have described the potential use of 5-HT$_6$ modulators in the treatment of epilepsy. 5-HT$_6$ receptors have also been linked to generalized stress and anxiety states (Yoshioka et al., Life Sciences 62(17/18):1473-1477 (1998)). 5-HT$_6$ agonists have been shown to elevate levels of GABA in brain regions associated with anxiety and shown positive effects in models predictive of obsessive-compulsive disorder (Schechter et al., NeuroRx. 2(4):590-611 (2005)). The use of modulators for this receptor is therefore expected for a wide range of CNS disorders.

Moreover, a reduction in food intake in rats has been reported using 5-HT$_6$ receptor modulators (Bentley et al., Br. J. Pharmacol. Suppl. 126:66 (1999); Bentley et al. J. Psychopharmacol. Suppl. A64:255 (1997); Pendharkar et al., Society for Neuroscience (2005); Heal et al. Pharmacol. Ther. 117, 207-231 (2008)). 5-HT$_6$ receptor modulators may therefore also be useful in the treatment of feeding disorders like anorexia, obesity, bulimia and similar disorders and also type 2 diabetes.

The importance of psychoactive drugs in present treatment of mental illness, and the presence of serious and undesirable side-effects with their use, makes the development of improved drugs of great interest. Furthermore, the need for a safe, efficacious treatment for obesity is highly desirable. Animal models useful in screening assays provide a benefit by determining candidate agents that have improved specificity of action.

The present invention is directed to novel compounds which provide alternatives in overcoming these and other deficiencies in the art.

SUMMARY OF THE INVENTION

A first aspect of the present invention relates to a compound of formula (I):

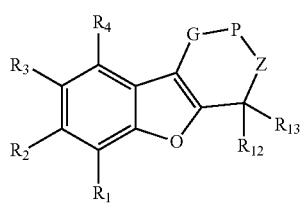

(I)

wherein:

G is —(CR$_5$R$_6$)$_n$—, where n=1, 2
Z is —(CR$_{10}$R$_{11}$)$_m$—, where m=1, 2
P is N—R$_7$ or CR$_{21}$—OR$_{22}$
R$_1$ and R$_4$ are independently H, halogen, CF$_3$, CHF$_2$, CH$_2$F, OH, OR$_{15}$, —C(O)R$_{15}$, —C(O)OR$_{15}$, —C(O)NR$_{15}$R$_{16}$, —NHR$_{15}$, —NR$_{15}$R$_{16}$, —SR$_{15}$, —S(O)R$_{15}$, —S(O)$_2$R$_{15}$, NH$_2$, CN, NO$_2$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, mono or polycyclic aryl, or mono or polycyclic heteroaryl containing from 1 to 5 heteroatoms selected from the group consisting of nitrogen, sulfur, and oxygen, each R$_1$ or R$_4$ optionally substituted from 1 to 3 times with substituents selected from the group consisting of halogen, OH, OR$_{17}$, —C(O)R$_{17}$, —C(O)OR$_{17}$, —C(O)NR$_{17}$R$_{18}$, —NHR$_{17}$, —NR$_{17}$R$_{18}$, —SR$_{17}$, —S(O)R$_{17}$, —S(O)$_2$R$_{17}$, NH$_2$, CN, NO$_2$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, mono or polycyclic aryl, and mono or polycyclic heteroaryl containing from 1 to 5 heteroatoms selected from the group consisting of nitrogen, sulfur, and oxygen;

R$_2$ and R$_3$ are independently H, R$_{14}$S(O)$_2$—, R$_{14}$S(O)—, R$_{14}$S—, R$_{14}$—(CR$_{19}$R$_{20}$)—;

R$_5$, R$_6$, R$_{10}$, and R$_{11}$ are independently H, C$_1$-C$_6$ alkyl, C$_2$-C$_6$ alkenyl, C$_2$-C$_6$ alkynyl, C$_1$-C$_6$ alkoxy, C$_3$-C$_6$ cycloalkyl, C$_4$-C$_7$ cycloalkylalkyl, aryl C$_1$-C$_6$ alkyl, mono or polycyclic aryl, or mono or polycyclic heteroaryl containing from 1 to 5 heteroatoms selected from the group consisting of nitrogen, sulfur, and oxygen, each R$_5$, R$_6$, R$_8$, R$_9$, R$_{10}$, or R$_{11}$ optionally substituted from 1 to 3 times with substituents selected from the group consisting of halogen, OH, OR$_{17}$, —C(O)R$_{17}$, —C(O)OR$_{17}$, —C(O)NR$_{17}$R$_{18}$, —NHR$_{17}$, —NR$_{17}$R$_{18}$, —SR$_{17}$, —S(O)R$_{17}$, —S(O)$_2$R$_{17}$, NH$_2$, CN, NO$_2$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, mono or polycyclic aryl, and mono or polycyclic heteroaryl containing from 1 to 5 heteroatoms selected from the group consisting of nitrogen, sulfur, and oxygen; or R$_6$ and R$_{10}$ can combine to form a —(CH$_2$)$_n$—, wherein n represents an integer from 2 to 3;

R$_7$ is independently H, OH, OR$_{15}$, —C(O)R$_{15}$, —C(O)OR$_{15}$, —C(O)NR$_{15}$R$_{16}$, —S(O)R$_{15}$, —S(O)$_2$R$_{15}$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, aryl C$_1$-C$_6$ alkyl, mono or polycyclic aryl, or mono or polycyclic heteroaryl containing from 1 to 5 heteroatoms selected from the group consisting of nitrogen, sulfur, and oxygen, each R$_7$ optionally substituted from 1 to 3 times with substituents selected from the group consisting of halogen, OH, NH$_2$, CN, NO$_2$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, mono or polycyclic aryl, and mono or polycyclic heteroaryl containing from 1 to 5 heteroatoms selected from the group consisting of nitrogen, sulfur, and oxygen;

R$_{12}$ and R$_{13}$ are independently H, halogen, CF$_3$, CHF$_2$, CH$_2$F, OH, OR$_{15}$, —C(O)R$_{15}$, —C(O)OR$_{15}$, —C(O)NR$_{15}$R$_{16}$, —NHR$_{15}$, —NR$_{15}$R$_{16}$, —SR$_{15}$, —S(O)R$_{15}$, —S(O)$_2$R$_{15}$, NH$_2$, CN, NO$_2$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, mono or polycyclic aryl, or mono or polycyclic heteroaryl containing from 1 to 5 heteroatoms selected from the group consisting of nitrogen, sulfur, and oxygen, each R$_{12}$ or R$_{13}$ optionally substituted from 1 to 3 times with substituents selected from the group consisting of halogen, OH, NH$_2$, CN, NO$_2$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, mono or polycyclic aryl, and mono or polycyclic heteroaryl containing from 1 to 5 heteroatoms selected from the group consisting of nitrogen, sulfur, and oxygen; or R$_{14}$ is independently a substituted or unsubstituted mono or polycyclic aryl or substituted or unsubstituted mono or polycyclic heteroaryl containing from 1 to 5 heteroatoms selected from the group consisting of oxygen, nitrogen, and sulfur, each R$_{14}$ optionally substituted from 1 to 4 times for each cyclic ring with substituents selected from the group consisting of H, OH, OR$_{15}$, —C(O)R$_{15}$, —C(O)OR$_{15}$, —C(O)NR$_{15}$R$_{16}$, —NHR$_{15}$, —NR$_{15}$R$_{16}$, —SR$_{15}$, —S(O)R$_{15}$, —S(O)$_2$R$_{15}$, NH$_2$, CN, NO$_2$, halogen, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, mono or polycyclic aryl, and mono or polycyclic heteroaryl containing from 1 to 5 heteroatoms selected from the group consisting of nitrogen, sulfur, and oxygen, each one of the R$_{14}$ substituents further optionally substituted from 1 to 3 times with substituents selected from the group consisting of halogen, H, OH, $OR_{17}$, —$C(O)R_{17}$, —$C(O)OR_{17}$, —$C(O)NR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_{15}$, $R_{16}$, $R_{17}$, and $R_{18}$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl or a monocyclic heteroaryl containing from 1-5 heteroatoms selected from the group consisting of nitrogen, oxygen, and sulfur, each $R_{15}$, $R_{16}$, $R_{17}$, or $R_{18}$ optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and a monocyclic aryl; or $R_{15}$ and $R_{16}$ or $R_{17}$ and $R_{18}$ can combine to form a 3- to 7-membered heterocyclyl or a mono heteroaryl each containing from 1 to 5 heteroatoms selected from the group consisting of nitrogen, sulfur, and oxygen, wherein the heterocyclyl or heteroaryl are optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl, and monocyclic heteroaryl;

$R_{19}$ and $R_{20}$ are independently H or $C_1$-$C_6$ alkyl. $R_{19}$ and $R_{20}$ can combine to form a —$(CH_2)_n$— where n represents an integer from 4-7.

$R_{21}$ and $R_{22}$ are independently H or $C_1$-$C_6$ alkyl;

with the provisos that (a) when $R_6$ and $R_{10}$ combine, $R_6$ and $R_{10}$ are not on adjacent carbons; (b) when n=2, m=1 (c) at least one of $R_2$ and $R_3$, but not both, is H;

or an oxide thereof, a pharmaceutically acceptable salt thereof, a solvate thereof, or prodrug thereof.

A second aspect of the present invention relates to a method for modulating serotonin sub-type 6. This method involves providing a compound of formula I and contacting a serotonin receptor with said compound under conditions effective to modulate serotonin sub-type 6.

A third aspect of the present invention relates to a process for preparation of a product compound of formula (I):

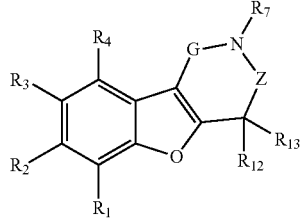

(I)

wherein:
G is —$(CR_5R_6)_n$—, where n=1, 2
Z is —$(CR_{10}R_{11})_m$—, where m=1, 2
$R_1$ and $R_4$ are independently H, halogen, $CF_3$, $CHF_2$, $CH_2F$, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_1$ or $R_4$ optionally substituted from 1 to 3 times with substituents selected from the group consisting of halogen, OH, $OR_{17}$, —$C(O)R_{17}$, —$C(O)OR_{17}$, —$C(O)NR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_2$ and $R_3$ are independently H, $R_{14}S(O)_2$—, $R_{14}S(O)$—, $R_{14}S$—, $R_{14}$—$(CR_{19}R_{20})$—$R_5$, $R_6$, $R_{10}$, and $R_{11}$ are independently H, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen, each $R_5$, $R_6$, $R_8$, $R_9$, $R_{10}$, or $R_{11}$ optionally substituted from 1 to 3 times with substituents selected from the group consisting of halogen, OH, $OR_{17}$, —$C(O)R_{17}$, —$C(O)OR_{17}$, —$C(O)NR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen; or $R_6$ and $R_{10}$ can combine to form a —$(CH_2)_n$—, wherein n represents an integer from 2 to 3;

$R_7$ is independently H, OH, $OR_{15}$, —$C(O)R_{15}$, —$C(O)OR_{15}$, —$C(O)NR_{15}R_{16}$, —$S(O)R_{15}$, —$S(O)_2R_{15}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen, each $R_7$ optionally substituted from 1 to 3 times with substituents selected from the group consisting of halogen, OH, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_{12}$ and $R_{13}$ are independently H, halogen, $CF_3$, $CHF_2$, $CH_2F$, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_{12}$ or $R_{13}$ optionally substituted from 1 to 3 times with substituents selected from the group consisting of halogen, OH, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen; or $R_{14}$ is independently a substituted or unsubstituted mono or polycyclic aryl or substituted or unsubstituted mono or polycyclic heteroaryl containing from 1 to 5 heteroatoms selected from the group consisting of oxygen, nitrogen, and sulfur, each $R_{14}$ optionally substituted from 1 to 4 times for each cyclic ring with substituents selected from the group consisting of H, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, halogen, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen, each one of the $R_{14}$ substituents further optionally substituted from 1 to 3 times with substituents selected from the group consisting of halogen, H, OH, $OR_{17}$, —$C(O)R_{17}$, —$C(O)OR_{17}$, —$C(O)NR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_{15}$, $R_{16}$, $R_{17}$, and $R_{18}$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl or a monocyclic heteroaryl containing from 1-5 heteroatoms selected from the group consisting of nitrogen, oxygen, and sulfur, each $R_{15}$, $R_{16}$, $R_{17}$, or $R_{18}$ optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and a monocyclic aryl; or $R_{15}$ and $R_{16}$ or $R_{17}$ and $R_{18}$ can combine to form a 3- to 7-membered heterocyclyl or a mono heteroaryl each containing from 1 to 5 heteroatoms selected from the group consisting of nitrogen, sulfur, and oxygen, wherein the heterocyclyl or heteroaryl are optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl, and monocyclic heteroaryl;

$R_{19}$ and $R_{20}$ are independently H or $C_1$-$C_6$ alkyl. $R_{19}$ and $R_{20}$ can combine to form a —$(CH_2)_n$— where n represents an integer from 4-7;

with the provisos that (a) when $R_6$ and $R_8$ combine, $R_6$ and $R_8$ are not on adjacent carbons; (b) when $R_8$ and $R_{12}$ combine, $R_8$ and $R_{12}$ are not on adjacent carbons; and (c) at least one of $R_2$ and $R_3$, but not both, is H;

or an oxide thereof, a pharmaceutically acceptable salt thereof, a solvate thereof, or prodrug thereof, said process comprising:

providing a first intermediate compound having the structure:

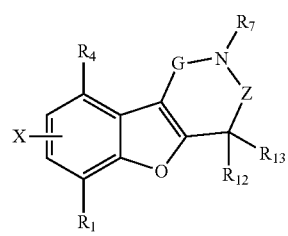

(II)

wherein X is Br, Cl, or I
and converting the first intermediate compound to the compound of formula (I).

Another aspect of the present invention relates to a process for the preparation of a compound of formula (VI) having the structure:

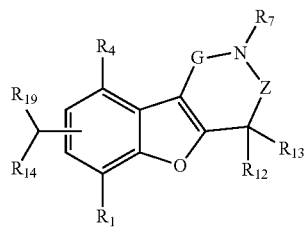

(VI)

wherein:
G is —$(CR_5R_6)_n$—, where n=1, 2
Z is —$(CR_{10}R_{11})_m$—, where m=1, 2
$R_1$ and $R_4$ are independently H, halogen, $CF_3$, $CHF_2$, $CH_2F$, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_1$ or $R_4$ optionally substituted from 1 to 3 times with substituents selected from the group consisting of halogen, OH, $OR_{17}$, —$C(O)R_{17}$, —$C(O)OR_{17}$, —$C(O)NR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_5$, $R_6$, $R_{10}$, and $R_{11}$ are independently H, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen, each $R_5$, $R_6$, $R_8$, $R_9$, $R_{10}$, or $R_{11}$ optionally substituted from 1 to 3 times with substituents selected from the group consisting of halogen, OH, $OR_{17}$, —$C(O)R_{17}$, —$C(O)OR_{17}$, —$C(O)NR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen; or $R_6$ and $R_{10}$ can combine to form a —$(CH_2)_n$—, wherein n represents an integer from 2 to 3;

$R_7$ is independently H, OH, $OR_{15}$, —$C(O)R_{15}$, —$C(O)OR_{15}$, —$C(O)NR_{15}R_{16}$, —$S(O)R_{15}$, —$S(O)_2R_{15}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen, each $R_7$ optionally substituted from 1 to 3 times with substituents selected from the group consisting of halogen, OH, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_{12}$ and $R_{13}$ are independently H, halogen, $CF_3$, $CHF_2$, $CH_2F$, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_{12}$ or $R_{13}$ optionally substituted from 1 to 3 times with substituents selected from the group consisting of halogen, OH, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen; or $R_{14}$ is independently a substituted or unsubstituted mono or polycyclic aryl or substituted or unsubstituted mono or polycyclic heteroaryl containing from 1 to 5 heteroatoms selected from the group consisting of oxygen, nitrogen, and sulfur, each $R_{14}$ optionally substituted from 1 to 4 times for each cyclic ring with substituents selected from the group consisting of H, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, halogen, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen, each one of the $R_{14}$ substituents further optionally substituted from 1 to 3 times with substituents selected from the group consisting of halogen, H, OH, $OR_{17}$, —$C(O)R_{17}$, —$C(O)OR_{17}$, —$C(O)NR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_{15}$, $R_{16}$, $R_{17}$, and $R_{18}$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl or a monocyclic heteroaryl containing from 1-5 heteroatoms selected from the group consisting of nitrogen, oxygen, and sulfur, each $R_{15}$, $R_{16}$, $R_{17}$, or $R_{18}$ optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and a monocyclic aryl; or $R_{15}$ and $R_{16}$ or $R_{17}$ and $R_{18}$ can combine to form a 3- to 7-membered heterocyclyl or a mono heteroaryl each containing from 1 to 5 heteroatoms selected from the group consisting of nitrogen, sulfur, and oxygen, wherein the heterocyclyl or heteroaryl are optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl, and monocyclic heteroaryl;

$R_{19}$ is independently H or $C_1$-$C_6$ alkyl with the provisos that (a) when $R_6$ and $R_8$ combine, $R_6$ and $R_8$ are not on adjacent carbons; (b) when $R_8$ and $R_{12}$ combine, $R_8$ and $R_{12}$ are not on adjacent carbons; and (c) at least one of $R_2$ and $R_3$, but not both, is H;

or an oxide thereof, a pharmaceutically acceptable salt thereof, a solvate thereof, or prodrug thereof. The process comprises:

providing a first intermediate compound having the structure:

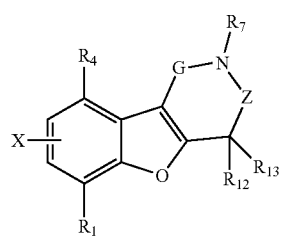

(II)

wherein X is Br, Cl, or I reacting the first intermediate compound (II) with a lithiating agent; and quenching the lithiated first intermediate compound with an aldehyde or ketone under conditions effective to produce the second intermediate compound (VII) of the following formula:

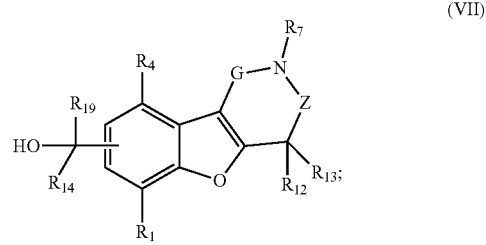

(VII)

and reacting the second intermediate compound (VII) under conditions effective to de-oxygenate a hydroxyl group attached to the carbon adjacent to $R_{14}$ to produce the compound of formula (VI).

Another aspect of the present invention relates to a process for preparation of a compound of formula (VIII):

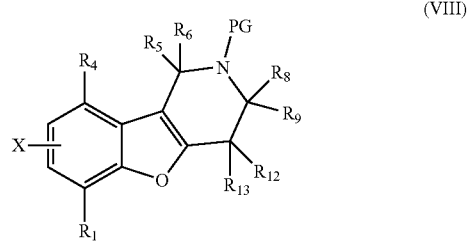

(VIII)

wherein

X is Br, Cl, or I;

$R_1$ and $R_4$ are independently H, halogen, $CF_3$, $CHF_2$, $CH_2F$, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_1$ or $R_4$ optionally substituted from 1 to 3 times with substituents selected from the group consisting of halogen, OH, $OR_{17}$, —C(O)R$_{17}$, —C(O)OR$_{17}$, —C(O)NR$_{17}$R$_{18}$, —NHR$_{17}$, —NR$_{17}$R$_{18}$, —SR$_{17}$, —S(O)R$_{17}$, —S(O)$_2$R$_{17}$, NH$_2$, CN, NO$_2$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, mono or polycyclic aryl, and mono or polycyclic heteroaryl containing from 1 to 5 heteroatoms selected from the group consisting of nitrogen, sulfur, and oxygen;

R$_5$, R$_6$, R$_8$, and R$_9$ are independently H, C$_1$-C$_6$ alkyl, C$_2$-C$_6$ alkenyl, C$_2$-C$_6$ alkynyl, C$_1$-C$_6$ alkoxy, C$_3$-C$_6$ cycloalkyl, C$_4$-C$_7$ cycloalkylalkyl, aryl C$_1$-C$_6$ alkyl, mono or polycyclic aryl, or mono or polycyclic heteroaryl containing from 1 to 5 heteroatoms selected from the group consisting of nitrogen, sulfur, and oxygen, each R$_5$, R$_6$, R$_8$, or R$_9$ optionally substituted from 1 to 3 times with substituents selected from the group consisting of halogen, OH, OR$_{17}$, —C(O)R$_{17}$, —C(O)OR$_{17}$, —C(O)NR$_{17}$R$_{18}$, —NHR$_{17}$, —NR$_{17}$R$_{18}$, —SR$_{17}$, —S(O)R$_{17}$, —S(O)$_2$R$_{17}$, NH$_2$, CN, NO$_2$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, mono or polycyclic aryl, and mono or polycyclic heteroaryl containing from 1 to 5 heteroatoms selected from the group consisting of nitrogen, sulfur, and oxygen; or R$_6$ and R$_8$ can combine to form a —(CH$_2$)$_n$—, wherein n represents an integer from 2 to 3;

R$_{12}$ and R$_{13}$ are independently H, halogen, CF$_3$, CHF$_2$, CH$_2$F, OH, OR$_{15}$, —C(O)R$_{15}$, —C(O)OR$_{15}$, —C(O)NR$_{15}$R$_{16}$, —NHR$_{15}$, —NR$_{15}$R$_{16}$, —SR$_{15}$, —S(O)R$_{15}$, —S(O)$_2$R$_{15}$, NH$_2$, CN, NO$_2$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, mono or polycyclic aryl, or mono or polycyclic heteroaryl containing from 1 to 5 heteroatoms selected from the group consisting of nitrogen, sulfur, and oxygen, each R$_{12}$ or R$_{13}$ optionally substituted from 1 to 3 times with substituents selected from the group consisting of halogen, OH, NH$_2$, CN, NO$_2$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, mono or polycyclic aryl, and mono or polycyclic heteroaryl containing from 1 to 5 heteroatoms selected from the group consisting of nitrogen, sulfur, and oxygen;

R$_{15}$, R$_{16}$, R$_{17}$, and R$_{18}$ are independently H, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, a monocyclic aryl or a monocyclic heteroaryl containing from 1-5 heteroatoms selected from the group consisting of nitrogen, oxygen, and sulfur, each R$_{15}$, R$_{16}$, R$_{17}$, or R$_{18}$ optionally substituted from 1 to 3 times with substituents selected from the group consisting of halogen, OH, CN, NO$_2$, NH$_2$, H, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, and a monocyclic aryl; or R$_{15}$ and R$_{16}$ or R$_{17}$ and R$_{18}$ can combine to form a 3- to 7-membered heterocyclyl or a mono heteroaryl each containing from 1 to 5 heteroatoms selected from the group consisting of nitrogen, sulfur, and oxygen, wherein the heterocyclyl or heteroaryl are optionally substituted from 1 to 3 times with substituents selected from the group consisting of halogen, OH, CN, NO$_2$, NH$_2$, H, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, a monocyclic aryl, and monocyclic heteroaryl, or an oxide thereof, a pharmaceutically acceptable salt thereof, a solvate thereof, or prodrug thereof, said process comprises:

providing a phenoxylanine derivative compound having the formula:

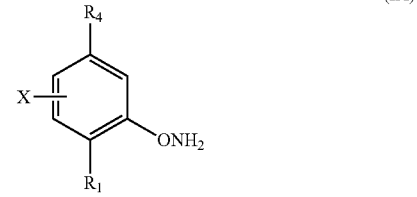

(IX)

and reacting the phenoxylamine derivative compound with a piperidone derivative compound having the structure:

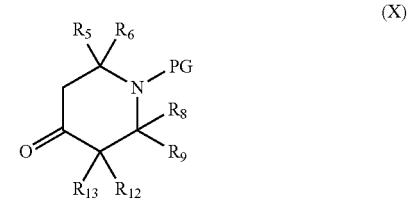

(X)

wherein PG is H or a protective group under conditions effective to form the compound of formula (VIII).

Another aspect of the present invention relates to a process for preparation of a compound of formula (XI):

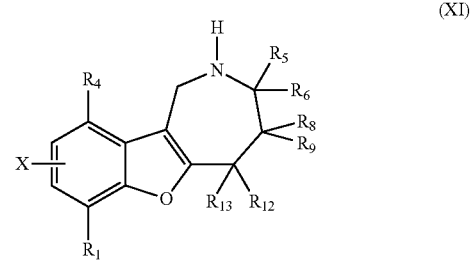

(XI)

wherein
X is Br, Cl, or I;
R$_1$ and R$_4$ are independently H, halogen, CF$_3$, CHF$_2$, CH$_2$F, OH, OR$_{15}$, —C(O)R$_{15}$, —C(O)OR$_{15}$, —C(O)NR$_{15}$R$_{16}$, —NHR$_{15}$, —NR$_{15}$R$_{16}$, —SR$_{15}$, —S(O)R$_{15}$, —S(O)$_2$R$_{15}$, NH$_2$, CN, NO$_2$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, mono or polycyclic aryl, or mono or polycyclic heteroaryl containing from 1 to 5 heteroatoms selected from the group consisting of nitrogen, sulfur, and oxygen, each R$_1$ or R$_4$ optionally substituted from 1 to 3 times with substituents selected from the group consisting of halogen, OH, OR$_{17}$, —C(O)R$_{17}$, —C(O)OR$_{17}$, —C(O)NR$_{17}$R$_{18}$, —NHR$_{17}$, —NR$_{17}$R$_{18}$, —SR$_{17}$, —S(O)R$_{17}$, —S(O)$_2$R$_{17}$, NH$_2$, CN, NO$_2$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, mono or polycyclic aryl, and mono or polycyclic heteroaryl containing from 1 to 5 heteroatoms selected from the group consisting of nitrogen, sulfur, and oxygen;

R$_5$, R$_6$, R$_8$, and R$_9$ are independently H, C$_1$-C$_6$ alkyl, C$_2$-C$_6$ alkenyl, C$_2$-C$_6$ alkynyl, C$_1$-C$_6$ alkoxy, C$_3$-C$_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen, each $R_5$, $R_6$, $R_8$, or $R_9$ optionally substituted from 1 to 3 times with substituents selected from the group consisting of halogen, OH, $OR_{17}$, —$C(O)R_{17}$, —$C(O)OR_{17}$, —$C(O)NR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_{12}$ and $R_{13}$ are independently H, halogen, $CF_3$, $CHF_2$, $CH_2F$, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_{12}$ or $R_{13}$ optionally substituted from 1 to 3 times with substituents selected from the group consisting of halogen, OH, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_{15}$, $R_{16}$, $R_{17}$, and $R_{18}$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl or a monocyclic heteroaryl containing from 1-5 heteroatoms selected from the group consisting of nitrogen, oxygen, and sulfur, each $R_{15}$, $R_{16}$, $R_{17}$, or $R_{18}$ optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and a monocyclic aryl; or $R_{15}$ and $R_{16}$ or $R_{17}$ and $R_{18}$ can combine to form a 3- to 7-membered heterocyclyl or a mono heteroaryl each containing from 1 to 5 heteroatoms selected from the group consisting of nitrogen, sulfur, and oxygen, wherein the heterocyclyl or heteroaryl are optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl, and monocyclic heteroaryl, or an oxide thereof, a pharmaceutically acceptable salt thereof, a solvate thereof, or prodrug thereof, said process comprises:

providing a starting compound having the structure:

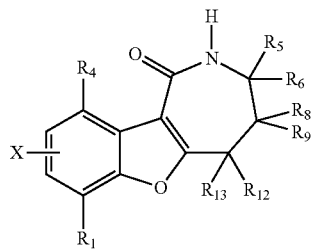

(XII)

and converting said starting compound under conditions effective to form the compound of formula (XI).

Another aspect of the present invention relates to a process for preparation of a compound formula (XVII):

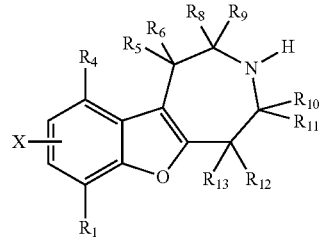

(XVII)

wherein

X is Br, Cl, or I;

$R_1$ and $R_4$ are independently H, halogen, $CF_3$, $CHF_2$, $CH_2F$, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_1$ or $R_4$ optionally substituted from 1 to 3 times with substituents selected from the group consisting of halogen, OH, $OR_{17}$, —$C(O)R_{17}$, —$C(O)OR_{17}$, —$C(O)NR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_5$, $R_6$, $R_8$, and $R_9$ are independently H, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen, each $R_5$, $R_6$, $R_8$, and $R_9$ are optionally substituted from 1 to 3 times with substituents selected from the group consisting of halogen, OH, $OR_{17}$, —$C(O)R_{17}$, —$C(O)OR_{17}$, —$C(O)NR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_{12}$ and $R_{13}$ are independently H, halogen, $CF_3$, $CHF_2$, $CH_2F$, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_{12}$ or $R_{13}$ optionally substituted from 1 to 3 times with substituents selected from the group consisting of halogen, OH, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_{15}$, $R_{16}$, $R_{17}$, and $R_{18}$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl or a monocyclic heteroaryl containing from 1-5 heteroatoms selected from the group consisting of nitrogen, oxygen, and sulfur, each $R_{15}$, $R_{16}$, $R_{17}$, or $R_{18}$ optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and a monocyclic aryl; or $R_{15}$ and $R_{16}$ or $R_{17}$ and $R_{18}$ can combine to form a 3- to 7-membered heterocyclyl or a mono heteroaryl each containing from 1 to 5 heteroatoms selected from the group consisting of nitrogen, sulfur, and oxygen, wherein the heterocyclyl or heteroaryl are optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl, and monocyclic heteroaryl, or an oxide thereof, a pharmaceutically acceptable salt thereof, a solvate thereof, or prodrug thereof, said process comprises:

providing a starting compound having the structure:

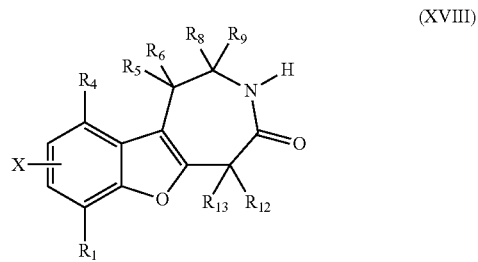

(XVIII)

and converting said starting compound under conditions effective to form the compound of formula (XVII).

Another aspect of the present invention relates to a process for preparation of a compound formula (XXI):

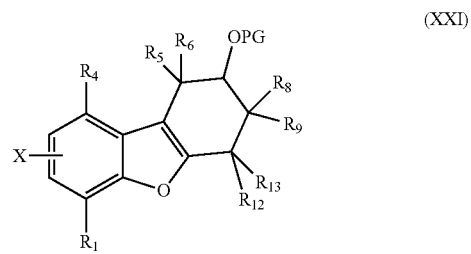

(XXI)

wherein

PG is a protecting group that can be removed under acidic or basic conditions

X is Br, Cl, or I;

$R_1$ and $R_4$ are independently H, halogen, $CF_3$, $CHF_2$, $CH_2F$, OH, $OR_{15}$, —C(O)$R_{15}$, —C(O)O$R_{15}$, —C(O)N$R_{15}R_{16}$, —NH$R_{15}$, —N$R_{15}R_{16}$, —S$R_{15}$, —S(O)$R_{15}$, —S(O)$_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_1$ or $R_4$ optionally substituted from 1 to 3 times with substituents selected from the group consisting of halogen, OH, $OR_{17}$, —C(O)$R_{17}$, —C(O)O$R_{17}$, —C(O)N$R_{17}R_{18}$, —NH$R_{17}$, —N$R_{17}R_{18}$, —S$R_{17}$, —S(O)$R_{17}$, —S(O)$_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_5$, $R_6$, $R_8$, and $R_9$ are independently H, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen, each $R_5$, $R_6$, $R_8$, and $R_9$ are optionally substituted from 1 to 3 times with substituents selected from the group consisting of halogen, OH, $OR_{17}$, —C(O)$R_{17}$, —C(O)O$R_{17}$, —C(O)N$R_{17}R_{18}$, —NH$R_{17}$, —N$R_{17}R_{18}$, —S$R_{17}$, —S(O)$R_{17}$, —S(O)$_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_{12}$ and $R_{13}$ are independently H, halogen, $CF_3$, $CHF_2$, $CH_2F$, OH, $OR_{15}$, —C(O)$R_{15}$, —C(O)O$R_{15}$, —C(O)N$R_{15}R_{16}$, —NH$R_{15}$, —N$R_{15}R_{16}$, —S$R_{15}$, —S(O)$R_{15}$, —S(O)$_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_{12}$ or $R_{13}$ optionally substituted from 1 to 3 times with substituents selected from the group consisting of halogen, OH, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_{15}$, $R_{16}$, $R_{17}$, and $R_{18}$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl or a monocyclic heteroaryl containing from 1-5 heteroatoms selected from the group consisting of nitrogen, oxygen, and sulfur, each $R_{15}$, $R_{16}$, $R_{17}$, or $R_{18}$ optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and a monocyclic aryl; or $R_{15}$ and $R_{16}$ or $R_{17}$ and $R_{18}$ can combine to form a 3- to 7-membered heterocyclyl or a mono heteroaryl each containing from 1 to 5 heteroatoms selected from the group consisting of nitrogen, sulfur, and oxygen, wherein the heterocyclyl or heteroaryl are optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl, and monocyclic heteroaryl, or an oxide thereof, a pharmaceutically acceptable salt thereof, a solvate thereof, or prodrug thereof, said process comprises:

providing a starting compound having the structure:

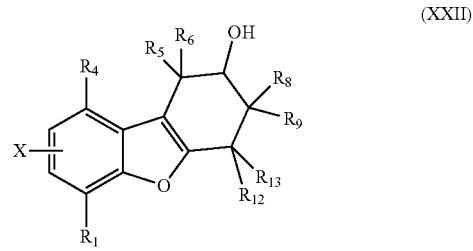

(XXII)

and converting said starting compound under conditions effective to form the compound of formula (XXI).

Additional aspects of the present invention include pharmaceutical compositions comprising a compound of this invention and a pharmaceutically acceptable carrier and, optionally, one or more additional active agent(s) as discussed below. Further aspects include methods of treating a disease state related to or modulated by the 5-$HT_6$ receptor, in a patient, such as humans or animals (e.g. rat, mice, pigs, horses, monkeys, cows, sheep, guinea pigs, dogs, and cats).

The compounds of the present invention are effective in modulating the activity of the 5-$HT_6$ receptor in humans or animals, (e.g. rat, mice, pigs, horses, monkeys, cows, sheep, guinea pigs, dogs, and cats). These compounds exhibit excellent activity for 5-$HT_6$ receptors, especially where such activity affects states associated with CNS disorders including motor, mood, personality, behavioral, psychiatric, cognitive, and neurodegenerative disorders, such as, but not limited to, Alzheimer's disease (enhancement of cognitive memory), Parkinson's disease, Huntington's disease, anxiety, depression, manic depression, epilepsy, obsessive compulsive disorders, migraine, sleep disorders, feeding disorders such as obesity, anorexia, and bulimia, panic attacks, attention deficit hyperactivity disorder (ADHD), attention deficit disorder (ADD), withdrawal from drug abuse such as cocaine, ethanol, nicotine and benzodiazepines, psychoses, such as schizophrenia, bipolar disorder, and also disorders associated with spinal trauma and/or head injury such as hydrocephalus. Such compounds are also useful for the treatment of memory/cognitive impairment associated with Alzheimer's disease, schizophrenia, Parkinson's disease, Huntington's disease Pick's disease, Creutzfeld-Jakob disease, HIV, cardiovascular disease, head trauma or age-related cognitive decline. In addition, such compounds are also expected to be of use in the treatment of certain gastrointestinal (GI) disorders such as, but not limited to, functional bowel disorder, constipation, including chronic constipation, gastroesophageal reflux disease (GERD), nocturnal-GERD, and irritable bowel syndrome (IBS), including diarrhea-predominant IBS (IBS-c), constipation-predominant IBS (IBS-c) and alternating constipation/diarrhea IBS.

In addition to their use in therapeutic medicine, the compounds of formula I, salts, oxides thereof, solvates or solvated salts thereof, may also be useful as pharmacological tools in the development and standardization of in vitro and in vivo test systems for the evaluation of the effects of modulators of 5$HT_6$ related activity in laboratory animals such as cats, dogs, rabbits, monkeys, rats and mice, as part of the search for new therapeutics agents.

DETAILED DESCRIPTION OF THE INVENTION

A first aspect of the present invention relates to a compound of formula (I):

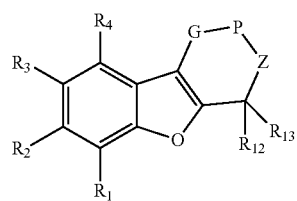

(I)

wherein:
G is —$(CR_5R_6)_n$—, where n=1, 2
Z is —$(CR_{10}R_{11})_m$—, where m=1, 2
P is N—$R_7$ or $CR_{21}$—$OR_{22}$ $R_1$ and $R_4$ are independently H, halogen, $CF_3$, $CHF_2$, $CH_2F$, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_1$ or $R_4$ optionally substituted from 1 to 3 times with substituents selected from the group consisting of halogen, OH, $OR_{17}$, —$C(O)R_{17}$, —$C(O)OR_{17}$, —$C(O)NR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_2$ and $R_3$ are independently H, $R_{14}S(O)_2$—, $R_{14}S(O)$—, $R_{14}S$—, $R_{14}$—$(CR_{19}R_{20})$—

$R_5$, $R_6$, $R_{10}$, and $R_{11}$ are independently H, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen, each $R_5$, $R_6$, $R_8$, $R_9$, $R_{10}$, or $R_{11}$ optionally substituted from 1 to 3 times with substituents selected from the group consisting of halogen, OH, $OR_{17}$, —$C(O)R_{17}$, —$C(O)OR_{17}$, —$C(O)NR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen; or $R_6$ and $R_{10}$ can combine to form a —$(CH_2)_n$—, wherein n represents an integer from 2 to 3;

$R_7$ is independently H, OH, $OR_{15}$, —$C(O)R_{15}$, —$C(O)OR_{15}$, —$C(O)NR_{15}R_{16}$, —$S(O)R_{15}$, —$S(O)_2R_{15}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen, each $R_7$ optionally substituted from 1 to 3 times with substituents selected from the group consisting of halogen, OH, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_{12}$ and $R_{13}$ are independently H, halogen, $CF_3$, $CHF_2$, $CH_2F$, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_{12}$ or $R_{13}$ optionally substituted from 1 to 3 times with substituents selected from the group consisting of halogen, OH, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen; or $R_{14}$ is independently a substituted or unsubstituted mono or polycyclic aryl or substituted or unsubstituted mono or polycyclic heteroaryl containing from 1 to 5 heteroatoms selected from the group consisting of oxygen, nitrogen, and sulfur, each $R_{14}$ optionally substituted from 1 to 4 times for each cyclic ring with substituents selected from the group consisting of H, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, halogen, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen, each one of the $R_{14}$ substituents further optionally substituted from 1 to 3 times with substituents selected from the group consisting of halogen, H, OH, $OR_{17}$, —$C(O)R_{17}$, —$C(O)OR_{17}$, —$C(O)NR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_{15}$, $R_{16}$, $R_{17}$, and $R_{18}$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl or a monocyclic heteroaryl containing from 1-5 heteroatoms selected from the group consisting of nitrogen, oxygen, and sulfur, each $R_{15}$, $R_{16}$, $R_{17}$, or $R_{18}$ optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and a monocyclic aryl; or $R_{15}$ and $R_{16}$ or $R_{17}$ and $R_{18}$ can combine to form a 3- to 7-membered heterocyclyl or a mono heteroaryl each containing from 1 to 5 heteroatoms selected from the group consisting of nitrogen, sulfur, and oxygen, wherein the heterocyclyl or heteroaryl are optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl, and monocyclic heteroaryl;

$R_{19}$ and $R_{20}$ are independently H or $C_1$-$C_6$ alkyl, wherein $R_{19}$ and $R_{20}$ can combine to form a —$(CH_2)_n$— where n represents an integer from 4-7.

$R_{21}$ and $R_{22}$ are independently H or $C_1$-$C_6$ alkyl;
with the provisos that (a) when $R_6$ and $R_{10}$ combine, $R_6$ and $R_{10}$ are not on adjacent carbons; (b) when n=2, m=1 (c) at least one of $R_2$ and $R_3$, but not both, is H;
or an oxide thereof, a pharmaceutically acceptable salt thereof, a solvate thereof, or prodrug thereof.

As used above, and throughout the description of the present invention, the following terms, unless otherwise indicated, shall be understood to have the following meanings.

As used herein, the term "halo" or "halogen" means fluoro, chloro, bromo, or iodo.

As used herein, the term "optionally substituted" indicates that a group may have a substituent at each substitutable atom of the group (including more than one substituent on a single atom), and the identity of each substituent is independent of the others.

The term "substituted" or "substitution" of an atom means that one or more hydrogen on the designated atom is replaced with a selection from the indicated group, provided that the designated atom's normal valency is not exceeded. "Unsubstituted" atoms bear all of the hydrogen atoms dictated by their valency. When a substituent is oxo (i.e., =O), then 2 hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent. Exemplary substituents include, without limitation, oxo, thio (i.e. =S), nitro, cyano, halo, OH, $NH_2$, $C_1$-$C_6$ alkyl, $C_1$-$C_6$ alkoxy, $C_2$-$C_6$ alkenyl, $C_2$-$C_6$ alkynyl, $C_3$-$C_6$ cycloalkyl, $C_4$-$C_7$ cycloalkylalkyl, monocyclic aryl, monocyclic heteroaryl, polycyclic aryl, and polycyclic heteroaryl.

As used herein, the term "monocyclic" indicates a molecular structure having one ring.

As used herein, the term "polycyclic" indicates a molecular structure having two or more rings, including, but not limited to, fused, bridged, or spiro rings.

The term "alkyl" means an aliphatic hydrocarbon group which may be straight or branched having about 1 to about 6 carbon atoms in the chain. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, and 3-pentyl.

The term "alkenyl" means an aliphatic hydrocarbon group containing a carbon-carbon double bond and which may be straight or branched having about 2 to about 6 carbon atoms in the chain. Preferred alkenyl groups have 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl.

The term "alkynyl" means an aliphatic hydrocarbon group containing a carbon-carbon triple bond and which may be straight or branched having about 2 to about 6 carbon atoms in the chain. Preferred alkynyl groups have 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl.

As used herein, "aryl" refers to aromatic monocyclic or polycyclic ring system containing from 6 to 19 carbon atoms, where the ring system may be optionally substituted. Aryl groups of the present invention include, but are not limited to, groups such as phenyl, naphthyl, azulenyl, phenanthrenyl, anthracenyl, fluorenyl, pyrenyl, triphenylenyl, chrysenyl, and naphthacenyl.

As used herein, "heterocyclyl" refers to a stable 3- to 18-membered ring radical which consists of carbon atoms and from one to five heteroatoms selected from the group consisting of nitrogen, oxygen and sulfur. For purposes of this invention, the heterocyclyl radical may be a monocyclic, or a polycyclic ring system, which may include fused, bridged, or spiro ring systems; and the nitrogen, carbon, or sulfur atoms in the heterocyclyl radical may be optionally oxidized; the nitrogen atom may be optionally quaternized; and the ring radical may be partially or fully saturated. Examples of such heterocyclyl radicals include, without limitation, azepinyl, azocanyl, pyranyl dioxanyl, dithianyl, 1,3-dioxolanyl, tetrahydrofuryl, dihydropyrrolidinyl, decahydroisoquinolyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, 2-oxoazepinyl, oxazolidinyl, oxiranyl, piperidinyl, piperazinyl, 4-piperidonyl, pyrrolidinyl, pyrazolidinyl, thiazolidinyl, tetrahydropyranyl, thiamorpholinyl, thiamorpholinyl sulfoxide, and thiamorpholinyl sulfone.

The term "heteroaryl" means an aromatic monocyclic or multi-cyclic ring system of about 5 to about 14 ring atoms, preferably about 5 to about 10 ring atoms, in which one or more of the atoms in the ring system is/are element(s) other than carbon, for example, nitrogen, oxygen, or sulfur. In the case of multi-cyclic ring system, only one of the rings needs to be aromatic for the ring system to be defined as "heteroaryl". Preferred heteroaryls contain about 5 to 6 ring atoms. The prefix aza, oxa, thia, or thio before heteroaryl means that at least a nitrogen, oxygen, or sulfur atom, respectively, is present as a ring atom. A nitrogen atom of a heteroaryl is optionally oxidized to the corresponding N-oxide. Representative heteroaryls include pyridyl, 2-oxo-pyridinyl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, 2-oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, and the like.

Suitable aryl groups for the substituents of the present invention, include, but are not limited to phenyl, naphthyl, azulenyl, fluorenyl, phenanthrenyl, anthracenyl, pyrenyl, triphenylenyl, chrysenyl, and naphthacenyl. Suitable heteroaryl groups of the present invention include, but are not limited to pyrrolyl, pyrazolyl, imidazolyl, triazolyl, furyl, thiophenyl, oxazolyl, isoxazolyl, thiazolyl, isothiazolyl, oxadiazolyl, thiadiazolyl, pyridyl, pyrazinyl, pyrimidinyl, pyridazinyl, triazinyl, thienopyrrolyl, furopyrrolyl, indolyl, azaindolyl, isoindolyl, indolinyl indolizinyl, indazolyl, benzimidazolyl, imidazopyridinyl, benzotriazolyl, benzoxazolyl, benzoxadiazolyl, benzothiazolyl, pyrazolopyridinyl, triazolopyridinyl, thienopyridinyl, benzothiadiazolyl, benzofuyl, benzothiophenyl, quinolinyl, isoquinolinyl, tetrahydroquinolinyl, tetrahydroisoquinolinyl, cinnolinyl, quinazolinyl, quinolizilinyl, phthalazinyl, benzotriazinyl, chromenyl, and naphthyridinyl. Exemplary substituted hetroaryl include without limitation pyridyl, 2-oxo-pyridin-1-yl, pyrimidinyl, pyridazinyl, pyrazinyl, 1,2,4-triazinyl, 1,3,5-triazinyl, furanyl, pyrrolyl, thiophenyl, pyrazolyl, imidazolyl, oxazolyl, isoxazolyl, thiazolyl, isothiazolyl, 1,2,3-triazolyl, 1,2,4-triazolyl, 1,2,3-oxadiazolyl, 1,3,4-oxadiazolyl, 1,2,3-thiadiazolyl, 1,3,4-thiadiazolyl, tetrazolyl, indolyl, isoindolyl, benzofuranyl, benzothiophenyl, indolinyl, oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, furo[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 2-oxo-2,3-dihydro-1H-benzo[d]imidazole, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, and 3-oxo-[1,2,4]triazolo[4,3-a]pyridinyl.

The term "alkoxy" means groups of from 1 to 6 carbon atoms of a straight, branched, or cyclic configuration and combinations thereof attached to the parent structure through an oxygen. Examples include methoxy, ethoxy, propoxy, isopropoxy, cyclopropyloxy, cyclohexyloxy, and the like. Lower-alkoxy refers to groups containing one to four carbons. For the purposes of the present patent application, alkoxy also includes methylenedioxy and ethylenedioxy in which each oxygen atom is bonded to the atom, chain, or ring from which the methylenedioxy or ethylenedioxy group is pendant so as to form a ring.

As used herein, "cycloalkyl" refers to a non-aromatic saturated or unsaturated mono- or polycyclic ring system which may contain 3 to 6 carbon atoms; and which may include at least one double bond. Exemplary cycloalkyl groups include, without limitation, cyclopropyl, cyclobutyl, cyclopentyl, cyclohexyl, cyclopropenyl, cyclobutenyl, cyclopentenyl, cyclohexenyl, anti-bicyclopropane, or syn-bicyclopropane.

As used herein, "cycloalkylalkyl" refers to a radical of the formula —$R^a R^b$ where $R^a$ is an alkyl radical as defined above and $R^b$ is a cycloalkyl radical as defined above. The alkyl radical and the cycloalkyl radical may be optionally substituted as defined above.

The term "arylalkyl" refers to a radical of the formula —$R^a R^b$ where $R^a$ is an alkyl radical as defined above and $R^b$ is an aryl radical as defined above. The alkyl radical and the aryl radical may be optionally substituted as defined above.

The term "aryarylalkyl" refers to a radical of the formula —$R^a R^b R^c$ where $R^a$ is an alkyl as defined above, $R^b$ is an aryl radical as defined above, and $R^c$ is an aryl radical as defined above. The alkyl radical and both aryl radicals may be optionally substituted as defined above.

The term "haloalkyl" means both branched and straight-chain alkyl substituted with one or more halogen, wherein the alkyl group is as herein described.

Further heterocycles and hetaryls are described in Katritzky et al., eds., "Comprehensive Heterocyclic Chemistry: The Structure, Reactions, Synthesis and Use of Heterocyclic Compounds," Vol. 1-8, Pergamon Press, N.Y. (1984), which is hereby incorporated by reference in its entirety.

This invention also envisions the "quaternization" of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

The term "compounds of the invention", and equivalent expressions, are meant to embrace compounds of general formula I as hereinbefore described, which expression includes the prodrugs, the pharmaceutically acceptable salts, the oxides, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

The term "method of treating" means amelioration or relief from the symptoms and/or effects associated with the disorders described herein.

Compounds described herein may contain one or more asymmetric centers and may thus give rise to enantiomers, diastereomers, and other stereoisomeric forms. Each chiral center may be defined, in terms of absolute stereochemistry, as (R)- or (S)-. The present invention is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

As used herein, and as would be understood by the person of skill in the art, the recitation of "a compound" is intended to include salts, solvates, oxides, and inclusion complexes of that compound as well as any stereoisomeric form, or a mixture of any such forms of that compound in any ratio. Thus, in accordance with some embodiments of the invention, a compound as described herein, including in the contexts of pharmaceutical compositions, methods of treatment, and compounds per se, is provided as the salt form.

The term "solvate" refers to a compound of formula I in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

Inclusion complexes are described in Remington, *The Science and Practice of Pharmacy*, 19th Ed. 1:176-177 (1995), which is hereby incorporated by reference in its entirety. The most commonly employed inclusion complexes are those with cyclodextrins, and all cyclodextrin complexes, natural and synthetic, are specifically encompassed within the claims.

The term "pharmaceutically acceptable salt" refers to salts prepared from pharmaceutically acceptable non-toxic acids or bases including inorganic acids and bases and organic acids and bases. Since the compounds of formula I contain a basic nitrogen, salts may be prepared from pharmaceutically acceptable non-toxic acids including inorganic and organic acids. Suitable pharmaceutically acceptable acid addition salts for the compounds of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine), and procaine.

The configuration of any carbon-carbon double bond appearing herein is selected for convenience only and is not intended to designate a particular configuration; thus a carbon-carbon double bond depicted arbitrarily herein as E may be Z, E, or a mixture of the two in any proportion.

The abbreviations Me, Et, Ph, and Bn represent methyl, ethyl, phenyl, and benzyl respectively. A comprehensive list of abbreviations utilized by organic chemists (i.e. persons of ordinary skill in the art) appears in the first issue of each volume of the Journal of Organic Chemistry. The list, which is typically presented in a table entitled "Standard List of Abbreviations," is incorporated herein by reference in its entirety.

The term "therapeutically effective amount" is meant to describe an amount of compound of the present invention effective in modulating 5-$HT_6$ activity and thus producing the desired therapeutic effect. Such amounts generally vary according to a number of factors well within the purview of ordinarily skilled artisans given the description provided herein to determine and account for. These include, without limitation: the particular subject, as well as its age, weight, height, general physical condition, and medical history, the particular compound used, as well as the carrier in which it is formulated and the route of administration selected for it; and, the nature and severity of the condition being treated.

The term "pharmaceutical composition" means a composition comprising a compound of formula I and at least one component comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. As used herein, the term "pharmaceutically acceptable carrier" is used to mean any carrier, diluent, adjuvant, excipient, or vehicle, as described herein. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monosterate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgment, suitable for use in contact with the cells of humans and lower animals without undue toxicity, irritation, allergic response and the like, and are commensurate with a reasonable benefit/risk ratio.

The term "pharmaceutically acceptable dosage forms" means dosage forms of the compound of the invention, and includes, for example, tablets, dragees, powders, elixirs, syrups, liquid preparations, including suspensions, sprays, inhalants tablets, lozenges, emulsions, solutions, granules, capsules, and suppositories, as well as liquid preparations for injections, including liposome preparations. Techniques and formulations generally may be found in Remington's Pharmaceutical Sciences, Mack Publishing Co., Easton, Pa., latest edition, which is hereby incorporated by reference in its entirety.

The term "pharmaceutically acceptable prodrugs" as used herein means those prodrugs of the compounds useful according to the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" means compounds that are rapidly transformed in vivo to yield the parent compound of the above formula, for example by hydrolysis in blood. Functional groups which may be rapidly transformed, by metabolic cleavage, in vivo form a class of groups reactive with the carboxyl group of the compounds of this invention. They include, but are not limited to, such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: "Design of Prodrugs," H. Bundgaard, ed., Elsevier (1985); "Methods in Enzymology," K. Widder et al, Ed., Academic Press, 42, p. 309-396 (1985); "A Textbook of Drug Design and Development," Krogsgaard-Larsen and H. Bundgaard, ed., Chapter 5; "Design and Applications of Prodrugs," p. 113-191 (1991); "Advanced Drug Delivery Reviews," H. Bundgard, 8, p. 1-38 (1992); *Journal of Pharmaceutical Sciences,* 77:285 (1988); Nakeya et al, *Chem. Pharm. Bull.,* 32:692 (1984); Higuchi et al., "Pro-drugs as Novel Delivery Systems," Vol. 14 of the A.C.S. Symposium Series, and Bioreversible Carriers in Drug Design, Edward B. Roche, ed., American Pharmaceutical Association and Pergamon Press (1987), which are incorporated herein by reference in their entirety. Examples of prodrugs include, but are not limited to, acetate, formate, and benzoate derivatives of alcohol and amine functional groups in the compounds of the invention.

One embodiment of the compound of formula (I) relates to the compound of formula (Ia):

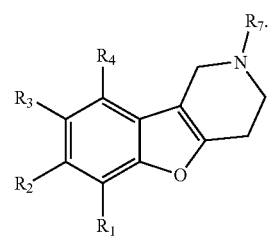

(Ia)

Another embodiment of the present invention relates to compounds of formula (Ia) where
$R_1$ and $R_4$ are H or $C_1$-$C_6$ alkyl;
$R_2$ is $R_{14}S(O)_2$—;
$R_3$ is H;
$R_7$ is H or $C_1$-$C_6$ alkyl; and
$R_{14}$ is substituted or unsubstituted phenyl, substituted or unsubstituted heteroaryl, substituted or unsubstituted polycyclic aryl, or substituted or unsubstituted polycyclic heteroaryl. Particular examples of $R_7$ substituents of this embodiment include H, methyl, and ethyl.

Another embodiment of the present invention relates to compounds of formula (Ia) where
$R_1$ and $R_4$ are H or $C_1$-$C_6$ alkyl;
$R_2$ is H;
$R_3$ is $R_{14}S(O)_2$—;
$R_7$ is H or $C_1$-$C_6$ alkyl; and
$R_{14}$ is substituted or unsubstituted phenyl, substituted or unsubstituted heteroaryl, substituted or unsubstituted polycyclic aryl, or substituted or unsubstituted polycyclic heteroaryl. Particular examples of $R_7$ substituents of this embodiment include H, methyl, and ethyl.

Another embodiment of the present invention relates to compounds of formula (Ia) where
$R_1$ is Br, Cl, F, or I;
$R_4$ is H;
$R_7$ is H or $C_1$-$C_6$ alkyl; and
$R_{14}$ is substituted or unsubstituted phenyl, substituted or unsubstituted heteroaryl, substituted or unsubstituted polycyclic aryl, or substituted or unsubstituted polycyclic heteroaryl. In this embodiment of the present invention, at least one of $R_2$ and $R_3$, but not both, is $R_{14}S(O)_2$—.

Another embodiment of the present invention relates to compounds of formula (Ia) where
$R_1$ is OMe, OEt, OCF$_3$, or OBn;
$R_4$ is H or $C_1$-$C_6$ alkyl;
$R_7$ is H or $C_1$-$C_6$ alkyl; and
$R_{14}$ is substituted or unsubstituted phenyl, substituted or unsubstituted heteroaryl, substituted or unsubstituted polycyclic aryl, or substituted or unsubstituted polycyclic heteroaryl. Particular examples of $R_7$ substituents of this embodiment include H, methyl, and ethyl.

Another embodiment of the present invention relates to compounds of formula (Ia) where
$R_1$ is H, $C_1$-$C_6$ alkyl, Cl, O—$C_1$-$C_6$ alkyl;
$R_2$ is $R_{14}S(O)$—;
$R_3$ is H
$R_4$ is H;
$R_7$ is H or $C_1$-$C_6$ alkyl; and
$R_{14}$ is substituted or unsubstituted phenyl, substituted or unsubstituted heteroaryl, substituted or unsubstituted polycyclic aryl, or substituted or unsubstituted polycyclic heteroaryl. Particular examples of $R_7$ substituents of this embodiment include H, methyl, and ethyl.

Another embodiment of the present invention relates to compounds of formula (Ia) where
  $R_1$ is H, $C_1$-$C_6$ alkyl, Cl, O—$C_1$-$C_6$ alkyl;
  $R_2$ is H;
  $R_3$ is $R_{14}$S(O)—;
  $R_4$ is H;
  $R_7$ is H or $C_1$-$C_6$ alkyl; and
  $R_{14}$ is substituted or unsubstituted phenyl, substituted or unsubstituted heteroaryl, substituted or unsubstituted polycyclic aryl, or substituted or unsubstituted polycyclic heteroaryl. Particular examples of $R_7$ substituents of this embodiment include H, methyl, and ethyl.

Another embodiment of the present invention relates to compounds of formula (Ia) where
  $R_1$ is H, $C_1$-$C_6$ alkyl, Cl, O—$C_1$-$C_6$ alkyl;
  $R_2$ is $R_{14}$S—;
  $R_3$ is H
  $R_4$ is H;
  $R_7$ is H or $C_1$-$C_6$ alkyl; and
  $R_{14}$ is substituted or unsubstituted phenyl, substituted or unsubstituted heteroaryl, substituted or unsubstituted polycyclic aryl, or substituted or unsubstituted polycyclic heteroaryl. Particular examples of $R_7$ substituents of this embodiment include H, methyl, and ethyl.

Another embodiment of the present invention relates to compounds of formula (Ia) where
  $R_1$ is H, $C_1$-$C_6$ alkyl, Cl, O—$C_1$-$C_6$ alkyl;
  $R_2$ is H;
  $R_3$ is $R_{14}$S—;
  $R_4$ is H;
  $R_7$ is H or $C_1$-$C_6$ alkyl; and
  $R_{14}$ is substituted or unsubstituted phenyl, substituted or unsubstituted heteroaryl, substituted or unsubstituted polycyclic aryl, or substituted or unsubstituted polycyclic heteroaryl. Particular examples of $R_7$ substituents of this embodiment include H, methyl, and ethyl.

Another embodiment of the present invention relates to compounds of formula (Ia) where
  $R_1$ is H, $C_1$-$C_6$ alkyl, Cl, O—$C_1$-$C_6$ alkyl;
  $R_2$ is $R_{14}$—(CR$_{19}$R$_{20}$)—;
  $R_3$ is H
  $R_4$ is H;
  $R_7$ is H or $C_1$-$C_6$ alkyl;
  $R_{14}$ is substituted or unsubstituted phenyl, substituted or unsubstituted heteroaryl, substituted or unsubstituted polycyclic aryl, or substituted or unsubstituted polycyclic heteroaryl; and
  $R_{19}$ and $R_{20}$ are independently H or $C_1$-$C_6$ alkyl. Particular examples of $R_7$ substituents of this embodiment include H, methyl, and ethyl.

Another embodiment of the present invention relates to compounds of formula (Ia) where
  $R_1$ is H, $C_1$-$C_6$ alkyl, Cl, O—$C_1$-$C_6$ alkyl;
  $R_2$ is H;
  $R_3$ is $R_{14}$—(CR$_{19}$R$_{20}$)—
  $R_4$ is H;
  $R_7$ is H or $C_1$-$C_6$ alkyl;
  $R_{14}$ is substituted or unsubstituted phenyl, substituted or unsubstituted heteroaryl, substituted or unsubstituted polycyclic aryl, or substituted or unsubstituted polycyclic heteroaryl; and.
  $R_{19}$ and $R_{20}$ are independently H or $C_1$-$C_6$ alkyl. Particular examples of $R_7$ substituents of this embodiment include H, methyl, and ethyl.

Yet another embodiment of the compound of formula (I) relates to the compounds formula (Ib):

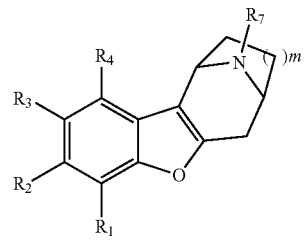

(Ib)

where
  m is 1 or 2;
  $R_1$ is H or $C_1$-$C_6$ alkyl;
  $R_4$ is H or $C_1$-$C_6$ alkyl;
  $R_7$ is H or $C_1$-$C_6$ alkyl; and
  $R_{14}$ is substituted or unsubstituted phenyl, substituted or unsubstituted heteroaryl, substituted or unsubstituted polycyclic aryl, or substituted or unsubstituted polycyclic heteroaryl. Particular sub-compounds of formula (Ib) include compounds when m is 1 and, more particularly, when $R_2$ is H, and $R_3$ is $R_{14}$S(O)$_2$— or, when m is 1, $R_2$ is $R_{14}$S(O)$_2$— and $R_3$ is H. Other particular sub-compounds of formula (Ib) include compounds when m is 2, $R_2$ is H and $R_3$ is $R_{14}$S(O)$_2$—. Other sub-compounds of this group include compounds when m is 2, $R_2$ is $R_{14}$S(O)$_2$— and $R_3$ is H.

Another aspect of the compound of formula (I) relates to a process for the preparation of a compound of formula (Ic):

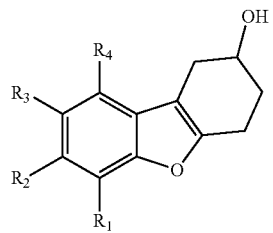

(Ic)

wherein:
  $R_1$ is H, $C_1$-$C_6$ alkyl, Cl, O—$C_1$-$C_6$ alkyl;
  $R_2$ is $R_{14}$S(O)$_2$—;
  $R_3$ is H
  $R_4$ is H;
  $R_{14}$ is substituted or unsubstituted phenyl, substituted or unsubstituted heteroaryl, substituted or unsubstituted polycyclic aryl, or substituted or unsubstituted polycyclic heteroaryl. Particular examples of $R_7$ substituents of this embodiment include H, methyl, and ethyl.

One embodiment of the present invention which relates to compounds of formula (Ic) where:
  $R_1$ is H, $C_1$-$C_6$ alkyl, Cl, O—$C_1$-$C_6$ alkyl;
  $R_2$ is H;
  $R_3$ is $R_{14}$S(O)$_2$—;
  $R_4$ is H;
  $R_{14}$ is substituted or unsubstituted phenyl, substituted or unsubstituted heteroaryl, substituted or unsubstituted polycyclic aryl, or substituted or unsubstituted polycyclic heteroaryl. Examples of $R_7$ substituents of this embodiment include H, methyl, and ethyl.

As to the compounds according to formula (I), particular examples of $R_{14}$ are a substituted or unsubstituted monocyclic aryl (e.g., a substituted or unsubstituted phenyl), a substituted or unsubstituted polycyclic aryl (e.g., naphthyl, azulenyl, fluorenyl, phenanthrenyl, anthracenyl, pyrenyl, triphenylenyl, chrysenyl, or naphthacenyl), a substituted or unsubstituted monocyclic heteroaryl (e.g., pyrrolyl, pyrazolyl, imidazolyl, triazolyl, furyl, thiophenyl, oxazolyl, isoxazolyl, thiazolyl, isothiazolyl, oxadiazolyl, thiadiazolyl, pyridyl, pyrazinyl, pyrimidinyl, pyridazinyl, or triazinyl), or a substituted or unsubstituted polycyclic heteroaryl (e.g., thienopyrrolyl, furopyrrolyl, indolyl, azaindolyl, isoindolyl, indolinyl indolizinyl, indazolyl, benzimidazolyl, imidazopyridinyl, benzotriazolyl, benzoxazolyl, benzoxadiazolyl, benzothiazolyl, pyrazolopyridinyl, triazolopyridinyl, thienopyridinyl, benzothiadiazolyl, benzofuyl, benzothiophenyl, quinolinyl, isoquinolinyl, tetrahydroquinolinyl, tetrahydroisoquinolinyl, cinnolinyl, quinazolinyl, quinolizilinyl, phthalazinyl, benzotriazinyl, chromenyl, or naphthyridinyl).

One embodiment of the present invention relates to pharmaceutically acceptable salts, or non-salt forms, of any of the compounds of formula (I) described herein.

Single enantiomers, any mixture of enantiomers, including racemic mixtures, or diastereomers (both separated and as any mixtures) of the compounds of the present invention are also included within the scope of the invention.

Another embodiment of the present invention, described herein, involves the (+)-stereoisomer of the compound of formula (I).

Another embodiment of the present invention, described herein, involves the (−)-stereoisomer of the compound of formula (I).

The present invention also relates to a pharmaceutical composition comprising:

a compound of formula (I) and a pharmaceutically acceptable carrier.

The scope of the present invention also encompasses active metabolites of the present compounds.

Another aspect of the present invention relates to a method for modulating serotonin sub-type 6. This method involves providing a compound of formula (I) and contacting a serotonin receptor with said compound under conditions effective to modulate serotonin sub-type 6. The serotonin receptor maybe a subclass $5HT_6$ receptor and can be mutated or modified. Contacting is carried out by administering the compound of formula (I) to a subject. This method also includes selecting a subject with a central nervous system disorder.

Administration of the compound of the present invention can be, without limitation, carried out systematically or at the site where the central nervous system is manifested. Exemplary methods of administering the compounds of the present invention include, without limitation, parental, oral, subcutaneous, intravenous, intramuscular, extraperitoneal, intranasal instillation, by inhalation, or by application to mucuous membrane administration.

The central nervous system disorder according to the present invention is a condition associated or related to a brain and spinal cord ailment. Preferred central nervous system disorder treated according to the method of the present invention include obesity, metabolic syndrome, cognition, and schizophrenia. The method of the present invention may also be extended, without limitation, to other central nervous system disorders such as Alzheimer's disease, anxiety, depression, convulsive disorders such as epilepsy, personality disorders, obsessive compulsive disorders, migraine, cognitive disorders such as memory dysfunction, sleep disorders, feeding disorders such as anorexia, bulimia, panic attacks, withdrawal from drug abuse, attention deficit hyperactive disorder (ADHD), attention deficit disorder (ADD), dementia, memory loss, disorders associated with spinal trauma and/or head injury, stroke, diabetes type 2, binge disorders, bipolar disorders, psychoses, Parkinson's disease, Huntington's disease, neurodegenerative disorders characterized by impaired neuronal growth, and pain.

As described above, the compounds of the present invention are useful as $5\text{-}HT_6$ modulators. A $5\text{-}HT_6$ receptor modulator is an agent which can either inhibit (e.g., an antagonist), partially activate (e.g., a partial agonist) or fully activate (e.g., an agonist) the $5\text{-}HT_6$ receptor. A $5\text{-}HT_6$ receptor modulator which is a partial agonist can bind the $5\text{-}HT_6$ receptor but only results in partial efficacy relative to a full receptor agonist. Modulators which are partial agonists may be considered ligands which display both agonistic and antagonistic effects depending upon the level of serotonin (endogenous $5\text{-}HT_6$ agonist). For example, when both full agonist (e.g. serotonin) and partial agonist are present, the partial agonist acts as a competitive antagonist, competing with the full agonist for receptor occupancy and producing a net decrease in the receptor activation observed with the full agonist alone (Williams et al., *Principles and Practice of Pharmacology for Anaesthetists*, $4^{th}$ Ed., Calvey et al., eds., Blackwell Science Asia Pty Ltd., Carlton South, Vic (2001), which is hereby incorporated by reference in its entirety). Clinically, partial agonists can activate receptors to give a desired submaximal response when inadequate amounts of the endogenous ligand are present or they can reduce the overstimulation of receptors when excess amounts of endogenous ligand are present (Zhu, *Biomed. Pharmacother.* 59(3):76-89 (2005), which is hereby incorporated by reference in its entirety). Such $5\text{-}HT_6$ agonists and antagonists are preferably $5\text{-}HT_6$ receptor selective (i.e. agents that selectively agonize the $5\text{-}HT_6$ receptor in some cases and antagonize that receptor in other cases).

Thus, in one embodiment of the present invention, the compound of formula (I) or pharmaceutically acceptable salt thereof is a $5\text{-}HT_6$ receptor antagonist.

In another embodiment of the present invention, the compound of formula (I) or pharmaceutically acceptable salt thereof is a $5\text{-}HT_6$ receptor partial agonist, which may result in a net increase or a net decrease in activation of the $5\text{-}HT_6$ receptor in the patient. In addition to being partial agonists, the compounds of the present invention also demonstrate full agonist potency toward $5\text{-}HT_6$ receptors.

Additional aspects of the present invention include pharmaceutical compositions comprising a compound of this invention and a pharmaceutically acceptable carrier and, optionally, one or more additional active agent(s) as discussed below. Further aspects include methods of treating a disease state related to or modulated by the $5\text{-}HT_6$ receptor, in a patient, such as humans or animals (e.g. rat, mice, pigs, horses, monkeys, cows, sheep, guinea pigs, dogs, and cats).

While it may be possible for compounds of formula (I) to be administered as the raw chemical, it will often be preferable to present them as part of a pharmaceutical composition. Accordingly, another aspect of the present invention is a pharmaceutical composition containing a therapeutically effective amount of a compound of formula I, or a pharmaceutically acceptable salt or solvate thereof, and a pharmaceutically acceptable carrier or diluent. The carrier must be "acceptable" in the sense of being compatible with the other ingredients of the formulation and not deleterious to the recipient thereof. Furthermore, when reference is made in an independent claim to a compound or a pharmaceutically acceptable salt thereof, it will be understood that claims which depend from that independent claim which refer to such a compound also include pharmaceutically acceptable salts of the compound, even if explicit reference is not made to the salts.

In one embodiment of the present invention, the pharmaceutical composition further comprises one or more other therapeutic ingredients, e.g., other compounds effective in the treatment of CNS that are known to persons of skill in the art. Such other therapeutic agents are described below.

The amount of active ingredient that may be combined with the carrier materials to produce a single dosage form will vary depending upon the host treated and the particular mode of administration. For example, a formulation intended for the oral administration of humans may vary from about 5 to about 95% of the total composition. Dosage unit forms will generally contain between from about 1 mg to about 500 mg of active ingredient.

Any pharmaceutically acceptable liquid carrier suitable for preparing solutions, suspensions, emulsions, syrups and elixirs may be employed in the composition of the invention. Compounds of formula (I) may be dissolved or suspended in a pharmaceutically acceptable liquid carrier such as water, an organic solvent, or a pharmaceutically acceptable oil or fat, or a mixture thereof. The liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration, the carrier may also be an oily ester such as ethyl oleate or isopropyl myristate.

Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine, and tris(hydroxymethyl)aminomethane; alkali metal salts, such as but not limited to lithium, potassium, and sodium; alkali earth metal salts, such as but not limited to barium, calcium, and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, cycloalkyl and heterocyclyl esters of acidic groups, including, but not limited to, carboxylic acids, phosphoric acids, phosphinic acids, sulfonic acids, sulfinic acids, and boronic acids. Pharmaceutical acceptable enol ethers include, but are not limited to, derivatives of formula C=C(OR) where R is hydrogen, alkyl, alkenyl, alkynyl, aryl, heteroaryl, cycloalkyl, or heterocyclyl. Pharmaceutically acceptable enol esters include, but are not limited to, derivatives of formula C=C(OC(O)R) where R is hydrogen, alkyl, alkenyl, alkynyl, aryl, heteroaryl, cycloalkyl, or heterocyclyl. Pharmaceutical acceptable solvates and hydrates are complexes of a compound with one or more solvent or water molecules, or 1 to about 100, or 1 to about 10, or one to about 2, 3 or 4, solvent or water molecules.

It will be understood, however, that the specific dose level for any particular patient will depend upon a variety of factors, including the activity of the specific compound employed, the age, body weight, general health, sex, diet time of administration, route of administration, rate of excretion, drug combination and the severity of the particular disease undergoing therapy.

All methods comprise administering to the patient in need of such treatment an effective amount of one or more compounds of the invention.

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

The compounds of the invention can be administered alone or as an active ingredient of a formulation. Thus, the present invention also includes pharmaceutical compositions of one or more compounds of formula I containing, for example, one or more pharmaceutically acceptable carriers. The compounds of the invention can be administered in a form where the active ingredient is substantially pure.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition), which are hereby incorporated by reference in their entirety.

The compounds can be administered as the sole active agent or in combination with other pharmaceutical agents such as other agents used in the treatment of CNS disorders, such as psychoses, especially schizophrenia and bipolar disorder, obsessive-compulsive disorder, Parkinson's disease, cognitive impairment and/or memory loss, (e.g., nicotinic α-7 agonists, PDF4 inhibitors, PDE10 inhibitors, other $5\text{-HT}_6$ receptor ligands), calcium channel blockers, muscarinic M1 and M2 modulators, adenosine receptor modulators, ampakines, NMDA-R modulators, mGluR modulators, dopamine modulators, serotonin modulators, canabinoid modulators, and cholinesterase inhibitors (e.g., donepezil, rivastigimine, and galanthanamine). In such combinations, each active ingredient can be administered either in accordance with their usual dosage range or in accordance with a dose below their usual dosage range.

The compounds can be administered in combination with other pharmaceutical agents used in the treatment of schizophrenia, e.g., Clozaril, Zyprexa, Risperidone, and Seroquel. Thus, the invention also includes methods for treating schizophrenia, including memory impairment associated with schizophrenia, comprising administering to a patient, simultaneously or sequentially, the compound of the invention and one or more additional agents used in the treatment of schizophrenia such as, but not limited to, Clozaril, Zyprexa, Risperidone, and Seroquel. In methods using simultaneous administration, the agents can be present in a combined composition or can be administered separately. As a result, the invention also includes compositions comprising a compound according to formula (I) and one or more additional pharmaceutical agents used in the treatment of schizophrenia, e.g., Clozaril, Zyprexa, Risperidone, and Seroquel. Similarly, the invention also includes kits containing a composition comprising a compound according to formula (I) and another composition comprising one or more additional pharmaceutical agents used in the treatment of schizophrenia, e.g., Clozaril, Zyprexa, Risperidone, and Seroquel. The compounds of formula (I) may further be used with other pharmaceutical agents known in the treatment of metabolic diseases such as diabetes or obesity. Suitable examples of known agents of treating diabetes include Metformin, Sitagliptin, and Exenatide amongst others. Exemplary agents for treating obesity include, without limitation, Orlistat, Phentermine, and Lorcaserin.

Solid carriers suitable for use in the composition of the invention include one or more substances which may also act as flavoring agents, lubricants, solubilizers, suspending agents, fillers, glidants, compression aides, binders, tablet-disintegrating agents, or encapsulating materials. In powders, the carrier may be a finely divided solid which is in admixture with a finely divided compound of formula (I). In tablets, the formula (I) compound may be mixed with a carrier having the necessary compression properties in suitable proportions and compacted in the shape and size desired. Said powders and tablets may contain up to 99% by weight of the formula (I) compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes, and ion exchange resins.

Formulations suitable for oral administration may be presented as discrete units such as capsules, cachets, or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary, or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active, or dispersing agent. Molded tablets may be made by molding in a suitable machine a mixture of the powdered compound moistened with an inert liquid diluent. The tablets may optionally be coated or scored and may be formulated so as to provide sustained, delayed, or controlled release of the active ingredient therein. The pharmaceutical compositions may include a "pharmaceutically acceptable inert carrier", and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or non-aqueous techniques, "Pharmaceutically acceptable carrier" also encompasses controlled release means.

Pharmaceutical compositions may also optionally include other therapeutic ingredients, anti-caking agents, preservatives, sweetening agents, colorants, flavors, desiccants, plasticizers, dyes, and the like. Any such optional ingredient must be compatible with the compound of formula (I) to insure the stability of the formulation. The composition may contain other additives as needed, including for example lactose, glucose, fructose, galactose, trehalose, sucrose, maltose, raffinose, maltitol, melezitose, stachyose, lactitol, palatinite, starch, xylitol, mannitol, myoinositol, and the like, and hydrates thereof, and amino acids, for example alanine, glycine and betaine, and peptides and proteins, for example albumen.

Examples of excipients for use as the pharmaceutically acceptable carriers and the pharmaceutically acceptable inert carriers and the aforementioned additional ingredients include, but are not limited to binders, fillers, disintegrants, lubricants, anti-microbial agents, and coating agents.

A third aspect of the present invention relates to a process for preparation of a product compound of formula (I):

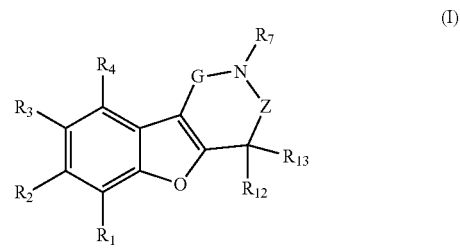

wherein:

G is —$(CR_5R_6)_n$—, where n=1, 2

Z is —$(CR_{10}R_{11})_m$—, where m=1, 2

$R_1$ and $R_4$ are independently H, halogen, $CF_3$, $CHF_2$, $CH_2F$, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_1$ or $R_4$ optionally substituted from 1 to 3 times with substituents selected from the group consisting of halogen, OH, $OR_{17}$, —$C(O)R_{17}$, —$C(O)OR_{17}$, —$C(O)NR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_2$ and $R_3$ are independently H, $R_{14}S(O)_2$—, $R_{14}S(O)$—, $R_{14}S$—, $R_{14}$—$(CR_{19}R_{20})$—$R_5$, $R_6$, $R_{10}$, and $R_{11}$ are independently H, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen, each $R_5$, $R_6$, $R_8$, $R_9$, $R_{10}$, or $R_{11}$ optionally substituted from 1 to 3 times with substituents selected from the group consisting of halogen, OH, $OR_{17}$, —$C(O)R_{17}$, —$C(O)OR_{17}$, —$C(O)NR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen; or $R_6$ and $R_{10}$ can combine to form a —$(CH_2)_n$—, wherein n represents an integer from 2 to 3;

$R_7$ is independently H, OH, $OR_{15}$, —$C(O)R_{15}$, —$C(O)OR_{15}$, —$C(O)NR_{15}R_{16}$, —$S(O)R_{15}$, —$S(O)_2R_{15}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen, each $R_7$ optionally substituted from 1 to 3 times with substituents selected from the group consisting of halogen, OH, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_{12}$ and $R_{13}$ are independently H, halogen, $CF_3$, $CHF_2$, $CH_2F$, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_{12}$ or $R_{13}$ optionally substituted from 1 to 3 times with substituents selected from the group consisting of halogen, OH, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen; or $R_{14}$ is independently a substituted or unsubstituted mono or polycyclic aryl or substituted or unsubstituted mono or polycyclic heteroaryl containing from 1 to 5 heteroatoms selected from the group consisting of oxygen, nitrogen, and sulfur, each $R_{14}$ optionally substituted from 1 to 4 times for each cyclic ring with substituents selected from the group consisting of H, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, halogen, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen, each one of the $R_{14}$ substituents further optionally substituted from 1 to 3 times with substituents selected from the group consisting of halogen, H, OH, $OR_{17}$, —$C(O)R_{17}$, —$C(O)OR_{17}$, —$C(O)NR_{17}R_{18}$, —$NHR_{17}$, —$NR_{17}R_{15}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_{15}$, $R_{16}$, $R_{17}$, and $R_{18}$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl or a monocyclic heteroaryl containing from 1-5 heteroatoms selected from the group consisting of nitrogen, oxygen, and sulfur, each $R_{15}$, $R_{16}$, $R_{17}$, or $R_{18}$ optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and a monocyclic aryl; or $R_{15}$ and $R_{16}$ or $R_{17}$ and $R_{18}$ can combine to form a 3- to 7-membered heterocyclyl or a mono heteroaryl each containing from 1 to 5 heteroatoms selected from the group consisting of nitrogen, sulfur, and oxygen, wherein the heterocyclyl or heteroaryl are optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl, and monocyclic heteroaryl;

$R_{19}$ and $R_{20}$ are independently H or $C_1$-$C_6$ alkyl. $R_{19}$ and $R_{20}$ can combine to form a —$(CH_2)_n$— where n represents an integer from 4-7;

with the provisos that (a) when $R_6$ and $R_8$ combine, $R_6$ and $R_8$ are not on adjacent carbons; (b) when $R_8$ and $R_{12}$ combine, $R_8$ and $R_{12}$ are not on adjacent carbons; and (c) at least one of $R_2$ and $R_3$, but not both, is H;

or an oxide thereof, a pharmaceutically acceptable salt thereof, a solvate thereof, or prodrug thereof, said process comprising:

providing a first intermediate compound having the structure:

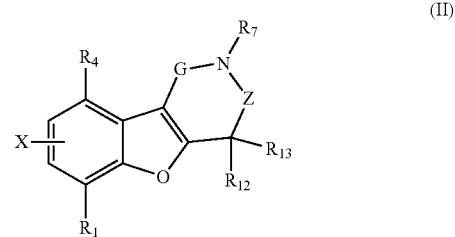

(II)

wherein X is Br, Cl, or I
and converting the first intermediate compound to the compound of formula (I).

In the reactions described hereinafter, it may be necessary to protect reactive functional groups, for example hydroxyl, amino, imino, thio, or carboxy groups, where these are desired in the final product, to avoid their unwanted participation in the reactions. Conventional protecting groups may be used in accordance with standard practice and as described below.

The methods of synthesis of the present invention involve standard amide bond formation conditions that are familiar to one skilled in the art of organic synthesis. This typically involves activation of the carboxyl component followed by reaction of the amine. Suitable activating groups include, but are not limited to, acyl halides, acyl azides, acylimidazoles, anhydrides, and esters as described by Montalbetti et al., *Tetrahedron*, 61:10827 (2005), which is hereby incorporated by reference in its entirety. Preferred activating reagents include thionyl chloride ($SOCl_2$), oxalyl chloride ($COCl)_2$, phosphorus oxychloride ($POCl_3$), carbonyl diimidazole (CDI), dicyclohexyl carbodiimide (DCC), 1-ethyl-3-(3-dimethylaminopropyl)carbodiimide) (EDCI), 1-hydroxybenzotriazole (HOBt), O-(1H-benzotriazol-1-yl)-N,N,N',N'-tetramethyluronium hexafluorophosphate (HATU), and 1-propanephosphonic acid cyclic anhydride (T3P).

Compounds useful according to the invention may be prepared by the application or adaptation of known methods, by which is meant methods used heretofore or described in the literature, for example, those described by Larock, *Comprehensive Organic Transformations*, Wiley-VCH Publishers, New York (1989), which is hereby incorporated by reference in its entirety.

A compound of the present invention including a group containing one or more nitrogen ring atoms, may be converted to the corresponding compound wherein one or more nitrogen ring atom of the group is oxidized to an N-oxide, preferably by reacting with a peracid, for example peracetic acid in acetic acid or m-chloroperoxybenzoic acid in an inert solvent such as dichloromethane, at a temperature from about room temperature to reflux, preferably at elevated temperature.

In the synthetic process described herein suitable counterions include, but are not limited to, $Li^+$ and $Na^+$.

Palladium catalysts used in the synthesis of the compounds of the present invention may be of various oxidative state. Thus, the process for preparation of the compounds of the present invention would employ, without limitation, Pd (0), Pd (II), or Pd (IV). Examples of such Palladium catalysts include, without limitation, bis(benzonitrile) palladium (II) chloride, palladium diacetate, palladium dibenzylidene acetone, tetrakis(triphenylphosphine) palladium, bis(triphenylphosphine) palladium (II) dichloride, bis(diphenylphosphineferrocene) palladium (II) dichloride, and bis(diphenylphosphineferrocene) palladium.

Furthermore, the process of the present invention employs various bases and acids depending on the reaction performed. For example, Brönsted or Lewis bases or acids may also be used for the present process of preparation. Exemplary bases include, without limitation, triethylamine, pyridine, piperidine, 2,6-lutidine, pyrrolidine, toludine, diisopropylamine, diisopropyl ethylamine, sodium hydride, sodium hydroxide, and sodium carbonate. Exemplary Lewis acid according to the present invention include without limitation titanium tetrachloride, aluminum chloride, boron trifluoride, boron tribromide, dimethylboron bromide, phosphorous pentachloride, tin dichloride, and tin tetrachloride.

For purposes of nucleophilic or electrophilic additions and substitutions identified in the process of preparation of the compounds of the present invention (including synthetic intermediate), various leaving or electrophilic groups have been used. Such groups include, without limitation, halogen, mesyl, triflate, acetyl, or tosyl.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl (t-Boc or Boc), benzyloxycarbonyl, and the like. Suitable protecting groups for mercapto include —C(O)—R (where R is alkyl, aryl or aralkyl), p-methoxybenzyl, trityl and the like. Suitable protecting groups for carboxylic acid include alkyl, aryl or aralkyl esters.

Protecting groups may be added or removed in accordance with standard techniques, which are well-known to those skilled in the art and as described herein. The use of protecting groups is described in detail in Green et al., *Protective Groups in Organic Synthesis*, 2nd Ed., Wiley-Interscience (1991), which is hereby incorporated by reference in its entirety.

In one embodiment of this aspect of the present invention the process for preparation of the compound of formula (I) involves reacting the first intermediate compound with a heteroarylsulfonyl salt or arylsulfonyl salt under conditions effective to form the compound of formula (I).

In another embodiment of this aspect of the invention, the process for preparation involves sulfonating the first intermediate compound in the presence of an organolithium and sulfur dioxide under conditions effective to produce a lithium sulfinate intermediate compound having the structure:

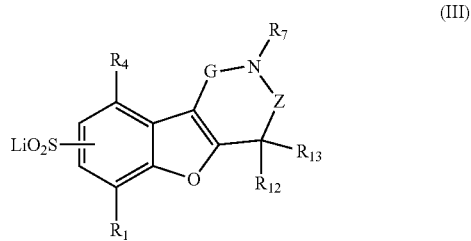

The lithium sulfinate intermediate compound is then subjected to arylation or heteroarylation under conditions effective to produce the compound of formula I.

Suitable organolithium compounds for the lithiation include without limitation n-butyllithium, t-butyllithium, sec-butyllithium, phenyl lithium, and lithium diisopropyl amide.

Yet in another embodiment of this aspect of the invention, the process for preparation involves halogenating the lithium sulfinate intermediate compound under conditions effective to produce a halosulfonyl intermediate compound having the structure:

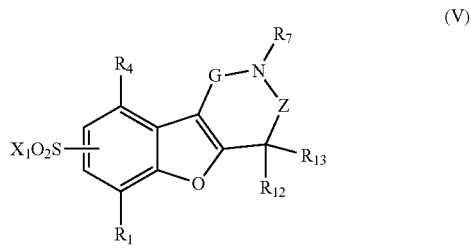

where $X_1$ is Cl, Br, or I. The halosulfonyl intermediate compound is then arylated under conditions effective to produce the first intermediate. Examples of halogenting agents include without limitation N-bromosuccinimide, N-chlorosuccinimide, and N-iodosuccinimide.

Another aspect of the present invention relates to a process for the preparation of a compound of formula (VI) having the structure:

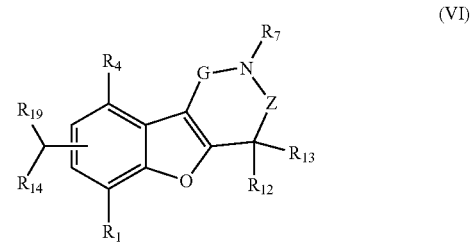

wherein:
G is —$(CR_5R_6)_n$—, where n=1, 2
Z is —$(CR_{10}R_{11})_m$—, where m=1, 2
$R_1$ and $R_4$ are independently H, halogen, $CF_3$, $CHF_2$, $CH_2F$, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —S(O)$_2$R$_{15}$, NH$_2$, CN, NO$_2$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, mono or polycyclic aryl, or mono or polycyclic heteroaryl containing from 1 to 5 heteroatoms selected from the group consisting of nitrogen, sulfur, and oxygen, each R$_1$ or R$_4$ optionally substituted from 1 to 3 times with substituents selected from the group consisting of halogen, OH, OR$_{17}$, —C(O)R$_{17}$, —C(O)OR$_{17}$, —C(O)NR$_{17}$R$_{18}$, —NHR$_{17}$, —NR$_{17}$R$_{18}$, —SR$_{17}$, —S(O)R$_{17}$, —S(O)$_2$R$_{17}$, NH$_2$, CN, NO$_2$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, mono or polycyclic aryl, and mono or polycyclic heteroaryl containing from 1 to 5 heteroatoms selected from the group consisting of nitrogen, sulfur, and oxygen;

R$_5$, R$_6$, R$_{10}$, and R$_{11}$ are independently H, C$_1$-C$_6$ alkyl, C$_2$-C$_6$ alkenyl, C$_2$-C$_6$ alkynyl, C$_1$-C$_6$ alkoxy, C$_3$-C$_6$ cycloalkyl, C$_4$-C$_7$ cycloalkylalkyl, aryl C$_1$-C$_6$ alkyl, mono or polycyclic aryl, or mono or polycyclic heteroaryl containing from 1 to 5 heteroatoms selected from the group consisting of nitrogen, sulfur, and oxygen, each R$_5$, R$_6$, R$_8$, R$_9$, R$_{10}$, or R$_{11}$ optionally substituted from 1 to 3 times with substituents selected from the group consisting of halogen, OH, OR$_{17}$, —C(O)R$_{17}$, —C(O)OR$_{17}$, —C(O)NR$_{17}$R$_{18}$, —NHR$_{17}$, —NR$_{17}$R$_{18}$, —SR$_{17}$, —S(O)R$_{17}$, —S(O)$_2$R$_{17}$, NH$_2$, CN, NO$_2$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, mono or polycyclic aryl, and mono or polycyclic heteroaryl containing from 1 to 5 heteroatoms selected from the group consisting of nitrogen, sulfur, and oxygen; or R$_6$ and R$_{10}$ can combine to form a —(CH$_2$)$_n$—, wherein n represents an integer from 2 to 3;

R$_7$ is independently H, OH, OR$_{15}$, —C(O)R$_{15}$, —C(O)OR$_{15}$, —C(O)NR$_{15}$R$_{16}$, —S(O)R$_{15}$, —S(O)$_2$R$_{15}$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, aryl C$_1$-C$_6$ alkyl, mono or polycyclic aryl, or mono or polycyclic heteroaryl containing from 1 to 5 heteroatoms selected from the group consisting of nitrogen, sulfur, and oxygen, each R$_7$ optionally substituted from 1 to 3 times with substituents selected from the group consisting of halogen, OH, NH$_2$, CN, NO$_2$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, mono or polycyclic aryl, and mono or polycyclic heteroaryl containing from 1 to 5 heteroatoms selected from the group consisting of nitrogen, sulfur, and oxygen;

R$_{12}$ and R$_{13}$ are independently H, halogen, CF$_3$, CHF$_2$, CH$_2$F, OH, OR$_{15}$, —C(O)R$_{15}$, —C(O)OR$_{15}$, —C(O)NR$_{15}$R$_{16}$, —NHR$_{15}$, —NR$_{15}$R$_{16}$, —SR$_{15}$, —S(O)R$_{15}$, —S(O)$_2$R$_{15}$, NH$_2$, CN, NO$_2$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, mono or polycyclic aryl, or mono or polycyclic heteroaryl containing from 1 to 5 heteroatoms selected from the group consisting of nitrogen, sulfur, and oxygen, each R$_{12}$ or R$_{13}$ optionally substituted from 1 to 3 times with substituents selected from the group consisting of halogen, OH, NH$_2$, CN, NO$_2$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, mono or polycyclic aryl, and mono or polycyclic heteroaryl containing from 1 to 5 heteroatoms selected from the group consisting of nitrogen, sulfur, and oxygen; or R$_{14}$ is independently a substituted or unsubstituted mono or polycyclic aryl or substituted or unsubstituted mono or polycyclic heteroaryl containing from 1 to 5 heteroatoms selected from the group consisting of oxygen, nitrogen, and sulfur, each R$_{14}$ optionally substituted from 1 to 4 times for each cyclic ring with substituents selected from the group consisting of H, OH, OR$_{15}$, —C(O)R$_{15}$, —C(O)OR$_{15}$, —C(O)NR$_{15}$R$_{16}$, —NHR$_{15}$, —NR$_{15}$R$_{16}$, —SR$_{15}$, —S(O)R$_{15}$, —S(O)$_2$R$_{15}$, NH$_2$, CN, NO$_2$, halogen, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, mono or polycyclic aryl, and mono or polycyclic heteroaryl containing from 1 to 5 heteroatoms selected from the group consisting of nitrogen, sulfur, and oxygen, each one of the R$_{14}$ substituents further optionally substituted from 1 to 3 times with substituents selected from the group consisting of halogen, H, OH, OR$_{17}$, —C(O)R$_{17}$, —C(O)OR$_{17}$, —C(O)NR$_{17}$R$_{18}$, —NHR$_{17}$, —NR$_{17}$R$_{18}$, —SR$_{17}$, —S(O)R$_{17}$, —S(O)$_2$R$_{17}$, NH$_2$, CN, NO$_2$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, mono or polycyclic aryl, and mono or polycyclic heteroaryl containing from 1 to 5 heteroatoms selected from the group consisting of nitrogen, sulfur, and oxygen;

R$_{15}$, R$_{16}$, R$_{17}$, and R$_{18}$ are independently H, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, a monocyclic aryl or a monocyclic heteroaryl containing from 1-5 heteroatoms selected from the group consisting of nitrogen, oxygen, and sulfur, each R$_{15}$, R$_{16}$, R$_{17}$, or R$_{18}$ optionally substituted from 1 to 3 times with substituents selected from the group consisting of halogen, OH, CN, NO$_2$, NH$_2$, H, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, and a monocyclic aryl; or R$_{15}$ and R$_{16}$ or R$_{17}$ and R$_{18}$ can combine to form a 3- to 7-membered heterocyclyl or a mono heteroaryl each containing from 1 to 5 heteroatoms selected from the group consisting of nitrogen, sulfur, and oxygen, wherein the heterocyclyl or heteroaryl are optionally substituted from 1 to 3 times with substituents selected from the group consisting of halogen, OH, CN, NO$_2$, NH$_2$, H, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, a monocyclic aryl, and monocyclic heteroaryl;

R$_{19}$ is independently H or C$_1$-C$_6$ alkyl with the provisos that (a) when R$_6$ and R$_8$ combine, R$_6$ and R$_8$ are not on adjacent carbons; (b) when R$_8$ and R$_{12}$ combine, R$_8$ and R$_{12}$ are not on adjacent carbons; and (c) at least one of R$_2$ and R$_3$, but not both, is H;

or an oxide thereof, a pharmaceutically acceptable salt thereof, a solvate thereof, or prodrug thereof. The process comprises:

providing a first intermediate compound having the structure:

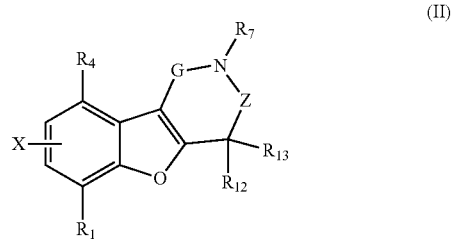

(II)

wherein X is Br, Cl, or I reacting the first intermediate compound (II) with a lithiating agent; and quenching the lithiated first intermediate compound with an aldehyde or ketone under conditions effective to produce the second intermediate compound (VII) of the following formula:

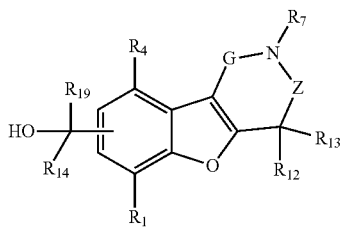

(VII)

reacting the second intermediate compound (VII) under conditions effective to de-oxygenates a hydroxyl group attached to the carbon adjacent to $R_{14}$ and to produce the compound of formula (VI). Suitable lithiating agents include n-butyllithium, sec-butyllithium, and tert-butyllithium.

Another aspect of the present invention relates to a process for the preparation of a compound of formula (VIII):

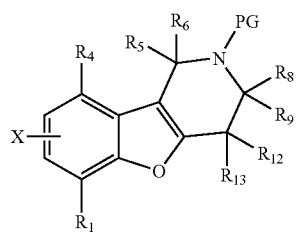

(VIII)

wherein

X is Br, Cl, or I;

$R_1$ and $R_4$ are independently H, halogen, $CF_3$, $CHF_2$, $CH_2F$, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_1$ or $R_4$ optionally substituted from 1 to 3 times with substituents selected from the group consisting of halogen, OH, $OR_{17}$, —$C(O)R_{17}$, —$C(O)OR_{17}$, —$C(O)NR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_5$, $R_6$, $R_8$, and $R_9$ are independently H, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen, each $R_5$, $R_6$, $R_8$, or $R_9$ optionally substituted from 1 to 3 times with substituents selected from the group consisting of halogen, OH, $OR_{17}$, —$C(O)R_{17}$, —$C(O)OR_{17}$, —$C(O)NR_{17}R_{18}$, —$NHR_{17}$, —$NR_{17}R_{15}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen; or $R_6$ and $R_8$ can combine to form a —$(CH_2)_n$—, wherein n represents an integer from 2 to 3;

$R_{12}$ and $R_{13}$ are independently H, halogen, $CF_3$, $CHF_2$, $CH_2F$, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_{12}$ or $R_{13}$ optionally substituted from 1 to 3 times with substituents selected from the group consisting of halogen, OH, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_{15}$, $R_{16}$, $R_{17}$, and $R_{18}$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl or a monocyclic heteroaryl containing from 1-5 heteroatoms selected from the group consisting of nitrogen, oxygen, and sulfur, each $R_{15}$, $R_{16}$, $R_{17}$, or $R_{18}$ optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and a monocyclic aryl; or $R_{15}$ and $R_{16}$ or $R_{17}$ and $R_{18}$ can combine to form a 3- to 7-membered heterocyclyl or a mono heteroaryl each containing from 1 to 5 heteroatoms selected from the group consisting of nitrogen, sulfur, and oxygen, wherein the heterocyclyl or heteroaryl are optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl, and monocyclic heteroaryl, or an oxide thereof, a pharmaceutically acceptable salt thereof, a solvate thereof, or prodrug thereof, said process comprises:

providing a phenoxylanine derivative compound having the formula:

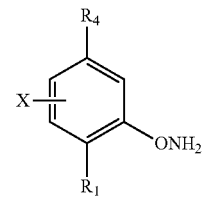

(IX)

and reacting the phenoxylamine derivative compound with a piperidone derivative compound having the structure:

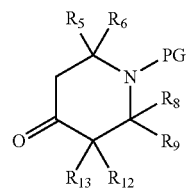

(X)

wherein PG is H or a protective group under conditions effective to form the compound of formula (VIII).

Another aspect of the present invention relates to a process for the preparation of a compound of formula (XI):

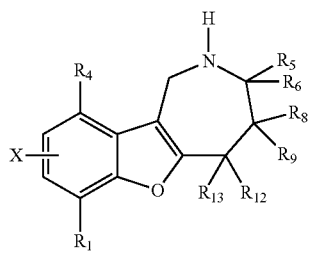

(XI)

wherein

X is Br, Cl, or I;

$R_1$ and $R_4$ are independently H, halogen, $CF_3$, $CHF_2$, $CH_2F$, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_1$ or $R_4$ optionally substituted from 1 to 3 times with substituents selected from the group consisting of halogen, OH, $OR_{17}$, —$C(O)R_{17}$, —$C(O)OR_{17}$, —$C(O)NR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_5$, $R_6$, $R_8$, and $R_9$ are independently H, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen, each $R_5$, $R_6$, $R_8$, or $R_9$ optionally substituted from 1 to 3 times with substituents selected from the group consisting of halogen, OH, $OR_{17}$, —$C(O)R_{17}$, —$C(O)OR_{17}$, —$C(O)NR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_{12}$ and $R_{13}$ are independently H, halogen, $CF_3$, $CHF_2$, $CH_2F$, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_{12}$ or $R_{13}$ optionally substituted from 1 to 3 times with substituents selected from the group consisting of halogen, OH, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_{15}$, $R_{16}$, $R_{17}$, and $R_{18}$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl or a monocyclic heteroaryl containing from 1-5 heteroatoms selected from the group consisting of nitrogen, oxygen, and sulfur, each $R_{15}$, $R_{16}$, $R_{17}$, or $R_{18}$ optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and a monocyclic aryl; or $R_{15}$ and $R_{16}$ or $R_{17}$ and $R_{18}$ can combine to form a 3- to 7-membered heterocyclyl or a mono heteroaryl each containing from 1 to 5 heteroatoms selected from the group consisting of nitrogen, sulfur, and oxygen, wherein the heterocyclyl or heteroaryl are optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl, and monocyclic heteroaryl, or an oxide thereof, a pharmaceutically acceptable salt thereof, a solvate thereof, or prodrug thereof, said process comprises:

providing a starting compound having the structure:

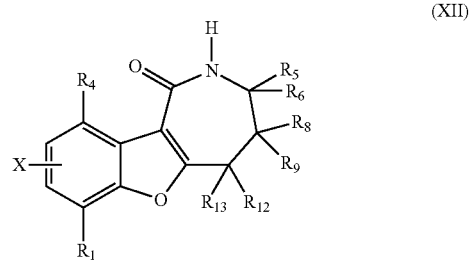

(XII)

and converting said starting compound under conditions effective to form the compound of formula (XI).

The step of providing a starting compound comprises:
providing a precursor compound having the structure:

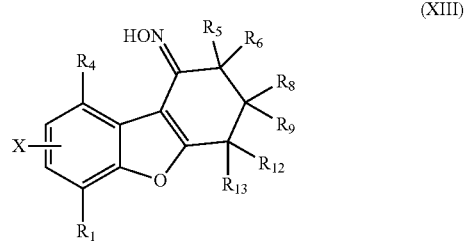

(XIII)

and converting the precursor compound under conditions effective to form the starting compound. The step of providing a precursor compound comprises:

providing a reactant compound having the structure:

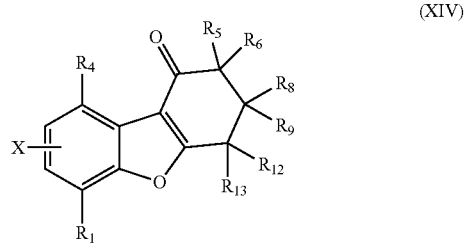

(XIV)

and converting the reactant compound under conditions effective to form the precursor compound. The step of providing a reactant compound comprises:

reacting a phenoxylamine derivative having the formula (IX) with a diketone compound having the structure:

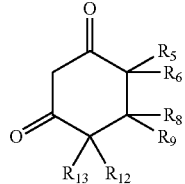
(XV)

under conditions effective to form said reactant compound. The phenoxylamine is prepared by reacting a phenol derivative having the formula:

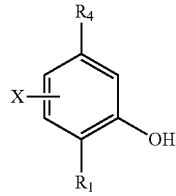
(XVI)

with an aminating reagent under conditions effective to form said phenoxylamine. The aminating reagent can be hydroxylamine-O-sulfonic acid or O-mesitylsulfonyl-hydroxylamine.

Another aspect of the present invention relates to a process for preparation of a compound of formula (XVII):

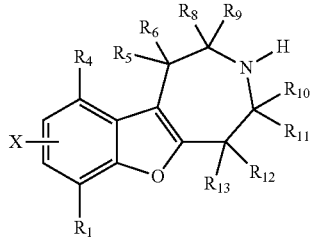
(XVII)

wherein
X is Br, Cl, or I;
$R_1$ and $R_4$ are independently H, halogen, $CF_3$, $CHF_2$, $CH_2F$, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_1$ or $R_4$ optionally substituted from 1 to 3 times with substituents selected from the group consisting of halogen, OH, $OR_{17}$, —$C(O)R_{17}$, —$C(O)OR_{17}$, —$C(O)NR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_5$, $R_6$, $R_8$, and $R_9$ are independently H, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen, each $R_5$, $R_6$, $R_8$, and $R_9$ are optionally substituted from 1 to 3 times with substituents selected from the group consisting of halogen, OH, $OR_{17}$, —$C(O)R_{17}$, —$C(O)OR_{17}$, —$C(O)NR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_{12}$ and $R_{13}$ are independently H, halogen, $CF_3$, $CHF_2$, $CH_2F$, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_{12}$ or $R_{13}$ optionally substituted from 1 to 3 times with substituents selected from the group consisting of halogen, OH, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_{15}$, $R_{16}$, $R_{17}$, and $R_{18}$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl or a monocyclic heteroaryl containing from 1-5 heteroatoms selected from the group consisting of nitrogen, oxygen, and sulfur, each $R_{15}$, $R_{16}$, $R_{17}$, or $R_{18}$ optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and a monocyclic aryl; or $R_{15}$ and $R_{16}$ or $R_{17}$ and $R_{18}$ can combine to form a 3- to 7-membered heterocyclyl or a mono heteroaryl each containing from 1 to 5 heteroatoms selected from the group consisting of nitrogen, sulfur, and oxygen, wherein the heterocyclyl or heteroaryl are optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl, and monocyclic heteroaryl, or an oxide thereof, a pharmaceutically acceptable salt thereof, a solvate thereof, or prodrug thereof, said process comprises:

providing a starting compound having the structure:

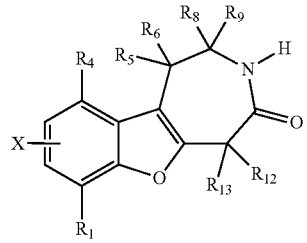
(XVIII)

and
converting said starting compound under conditions effective to form the compound of formula (XVII).

According to one embodiment of this aspect of the invention, providing a starting compound involves providing a precursor compound having the structure:

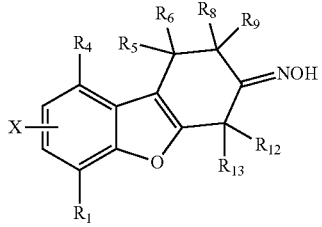

(XIX)

and
converting the precursor compound under conditions effective to form the starting compound.

The precursor compound can be provided by providing a reactant compound having the structure:

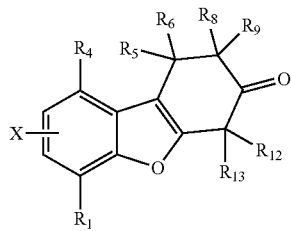

(XX)

and
converting the reactant compound under conditions effective to form the precursor compound.

Another aspect of the present invention relates to a process for preparation of a compound formula (XXI):

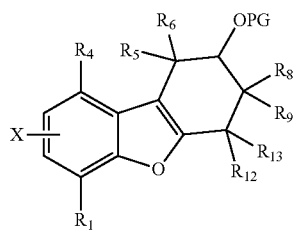

(XXI)

wherein
PG is a protecting group that can be removed under acidic or basic conditions
X is Br, Cl, or I;
$R_1$ and $R_4$ are independently H, halogen, $CF_3$, $CHF_2$, $CH_2F$, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_1$ or $R_4$ optionally substituted from 1 to 3 times with substituents selected from the group consisting of halogen, OH, $OR_{17}$, —$C(O)R_{17}$, —$C(O)OR_{17}$, —$C(O)NR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_5$, $R_6$, $R_8$, and $R_9$ are independently H, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen, each $R_5$, $R_6$, $R_8$, and $R_9$ are optionally substituted from 1 to 3 times with substituents selected from the group consisting of halogen, OH, $OR_{17}$, —$C(O)R_{17}$, —$C(O)OR_{17}$, —$C(O)NR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_{12}$ and $R_{13}$ are independently H, halogen, $CF_3$, $CHF_2$, $CH_2F$, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_{12}$ or $R_{13}$ optionally substituted from 1 to 3 times with substituents selected from the group consisting of halogen, OH, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_{15}$, $R_{16}$, $R_{17}$, and $R_{18}$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl or a monocyclic heteroaryl containing from 1-5 heteroatoms selected from the group consisting of nitrogen, oxygen, and sulfur, each $R_{15}$, $R_{16}$, $R_{17}$, or $R_{18}$ optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and a monocyclic aryl; or $R_{15}$ and $R_{16}$ or $R_{17}$ and $R_{18}$ can combine to form a 3- to 7-membered heterocyclyl or a mono heteroaryl each containing from 1 to 5 heteroatoms selected from the group consisting of nitrogen, sulfur, and oxygen, wherein the heterocyclyl or heteroaryl are optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl, and monocyclic heteroaryl, or an oxide thereof, a pharmaceutically acceptable salt thereof, a solvate thereof, or prodrug thereof, said process comprises:
providing a starting compound having the structure:

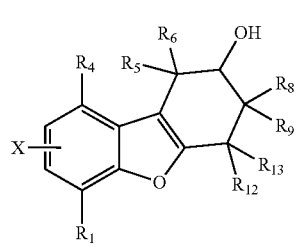

(XXII)

and
converting said starting compound under conditions effective to form the compound of formula (XXI).

The step of providing a starting compound comprises:

providing a precursor compound having the structure:

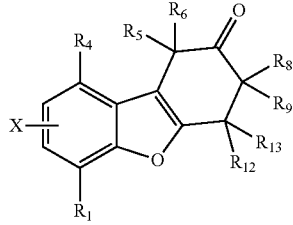

(XXIII)

and converting the reactant compound under conditions effective to form the precursor compound. The providing a reactant compound step comprises:

reacting a phenoxylamine derivative having the formula (IX) with a diketone derivative compound having the structure:

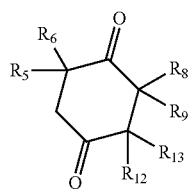

(XXIV)

under conditions effective to form said reactant compound.

It is also contemplated, for synthetic purposes, that compound 1 of scheme 1 is a representative radical of the mono or polycyclic aryl or mono or polycyclic heterorayl $R_{14}S(O)_2$— substituent of the compound of formula (I), substituent which may be optionally substituted with substituents defined herein.

Scheme 1

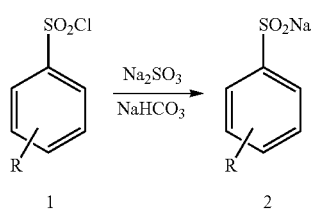

Compounds of formula 2 can be prepared from the corresponding sulfonyl chloride by treatment with aqueous sodium sulfite and sodium bicarbonate at 0° C. followed by heating to 65° C.

Scheme 2

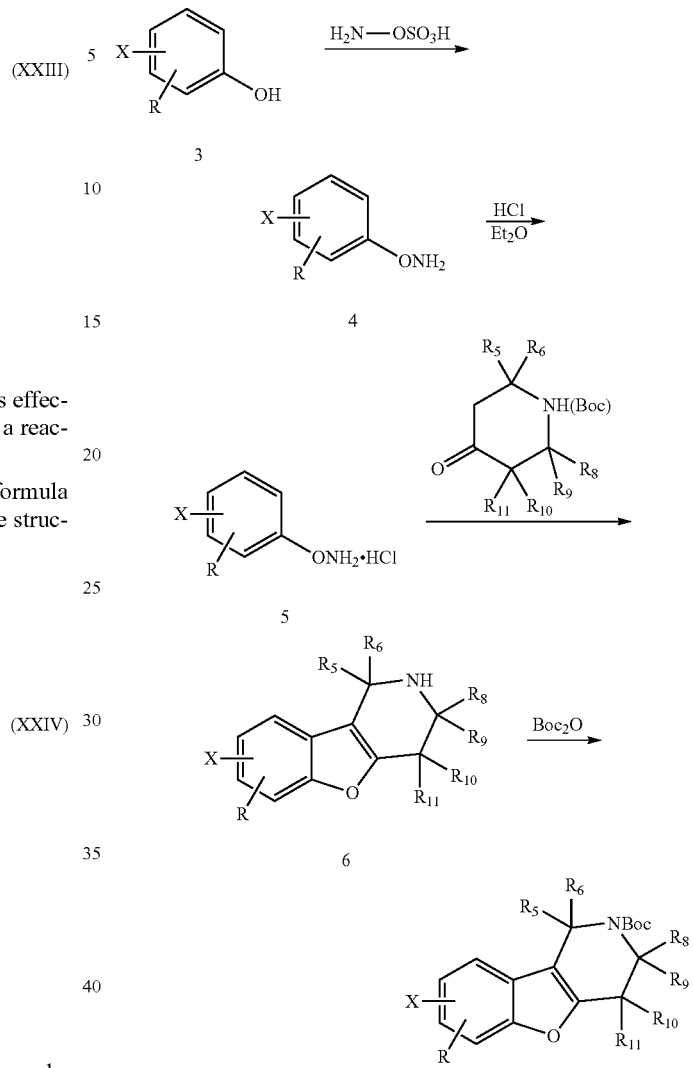

Compounds of formula 7 (where X=Br or I) can be prepared via a four step procedure starting from the corresponding phenol 3. Treatment with hydroxylamine-O-sulfonic acid under basic conditions (KOH, IPA, H$_2$O, toluene) at 80° C. can be used to prepare compounds of formula 4. Alternatively, the aminating agent 10 (prepared in two steps from hydroxylamine hydrochloride as in scheme 3) can be used in place of hydroxylamine-O-sulfonic acid for this step. Furthermore, an alternative method for synthesizing compounds of formula 4 may be undertaken using a two step procedure as outlined in scheme 4. 2-hydroxyisoindoline-1,3-dione is coupled with a boronic acid of compound 11 using copper acetate in pyridine and 1,2-dichloroethane to provide compounds of formula 12. Compounds of formula 12 are transformed into compounds of formula 4 via removal of the protecting group using hydrazine hydrate in chloroform/methanol. Subsequent formation of the HCl salt is followed by a thermal cycloaddition reaction with a suitable ketone to provide the compounds of formula 6. Compounds of formula 6 can generally be transformed into compounds of formula 7 via treatment with Boc anhydride, triethylamine and catalytic N,N-dimethylaminopyridine in methylene chloride at room temperature.

Scheme 3

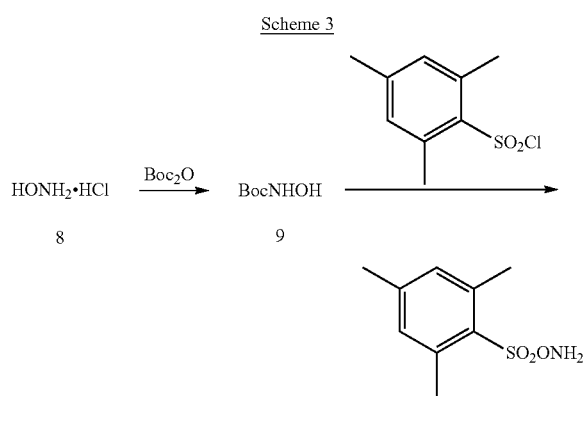

Scheme 4

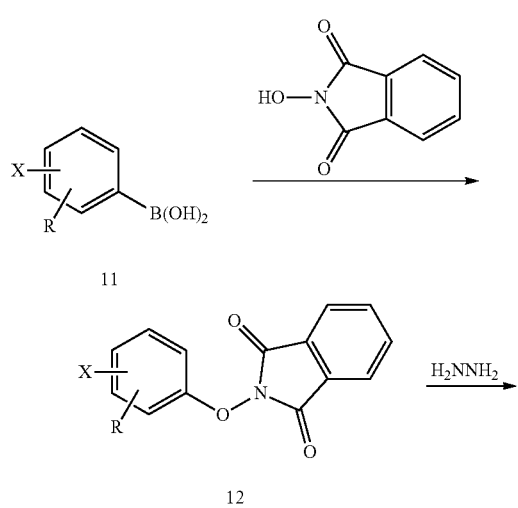

Scheme 5

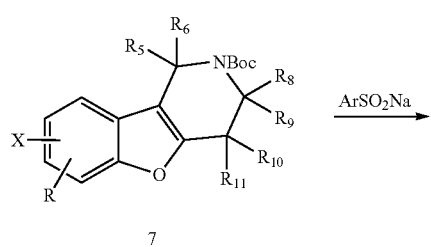

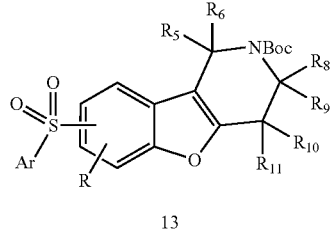

Compounds of formula 13 (where Ar=an aromatic substituent as defined in the claims) can be prepared from compounds of formula 7 via a palladium catalyzed procedure using $Pd_2(dba)_3$ and xantphos with cesium carbonate and tetrabutylammonium chloride in toluene at reflux. Alternatively, in certain instances, the reaction is carried out in the absence of tetrabutylammonium chloride.

Scheme 6

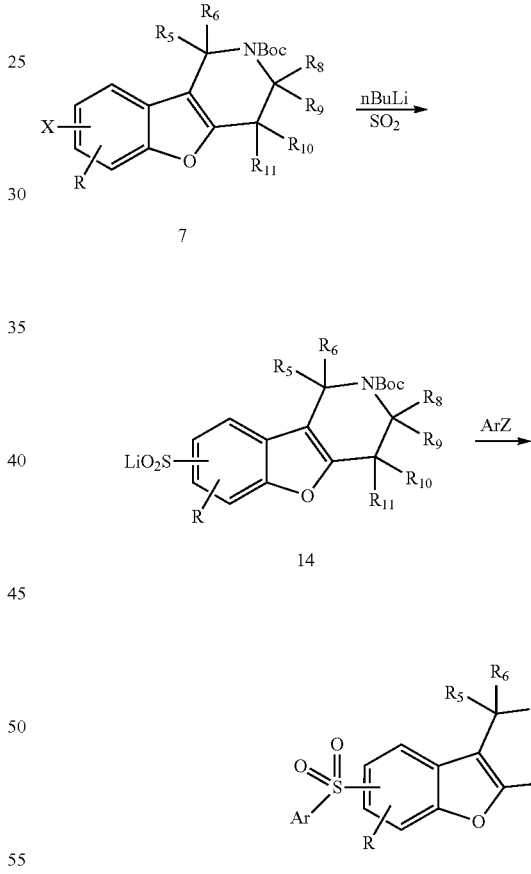

An alternative method for accessing compounds of formula 13 can also be used where compound 7 is converted to a lithium sulfinate salt of formula 14 via lithium halogen exchange using n-butyl lithium at −78° C. followed by quenching of the aryllithium intermediate with sulfur dioxide at −78° C. Conversion of compounds of formula 14 to compounds of formula 13 can be achieved via reaction with an aryl halide ArZ (Z=Cl, Br, I) using the same palladium-catalyzed coupling conditions highlighted in scheme 5.

Scheme 7

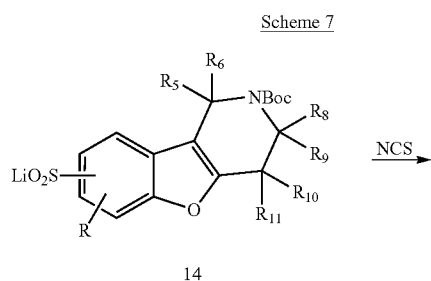

14

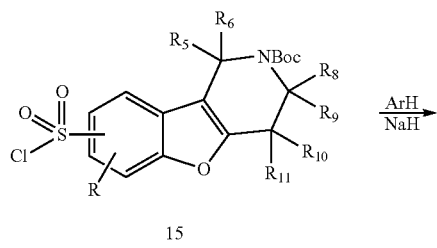

15

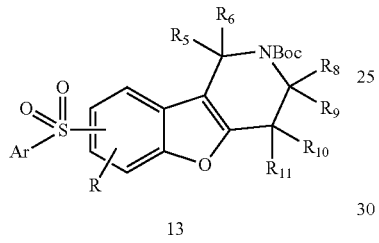

13

Alternatively, compounds of formula 13 (where Ar=heteroatom-linked aromatic substituents such as indoles) can be prepared via a 2 step procedure starting from compounds of formula 14. Treatment with N-chlorosuccinimide in methylene chloride at 0° C. provides compounds of formula 15. Subsequent treatment with the sodium or lithium salt of an aromatic substituent bearing a heteroatom (such as indoles, prepared from sodium hydride in THF at room temperature) provides compounds of formula 13.

Scheme 8

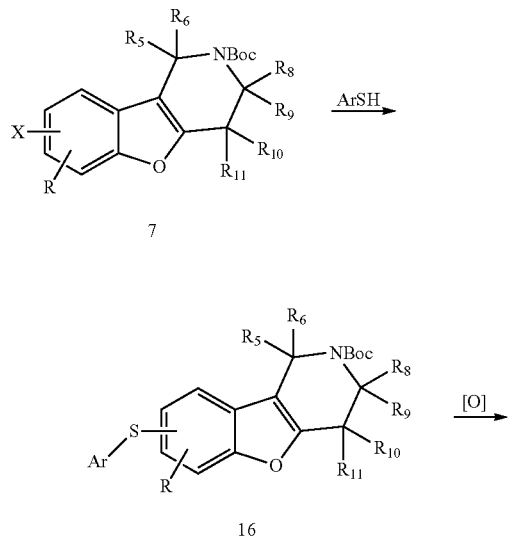

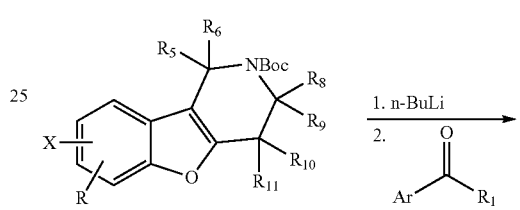

17

Compounds of formula 16 can be prepared from compounds of formula 7 via palladium catalysed chemistry using $Pd_2(dba)_3$ and xantphos with N,N-diisopropylamine in dioxane at 110° C. Compounds of formula 16 can be oxidized to compounds of formula 17 using m-chloroperoxybenzoic acid in methylene chloride at room temperature.

Scheme 9

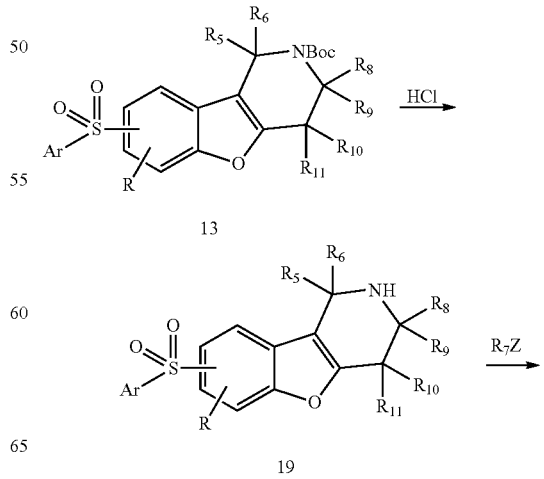

Compounds of formula 18 can be prepared from compounds of formula 7 via lithiation with n-butyllithium in THF at −78° C. followed by quenching with an aldehyde or ketone.

Scheme 10

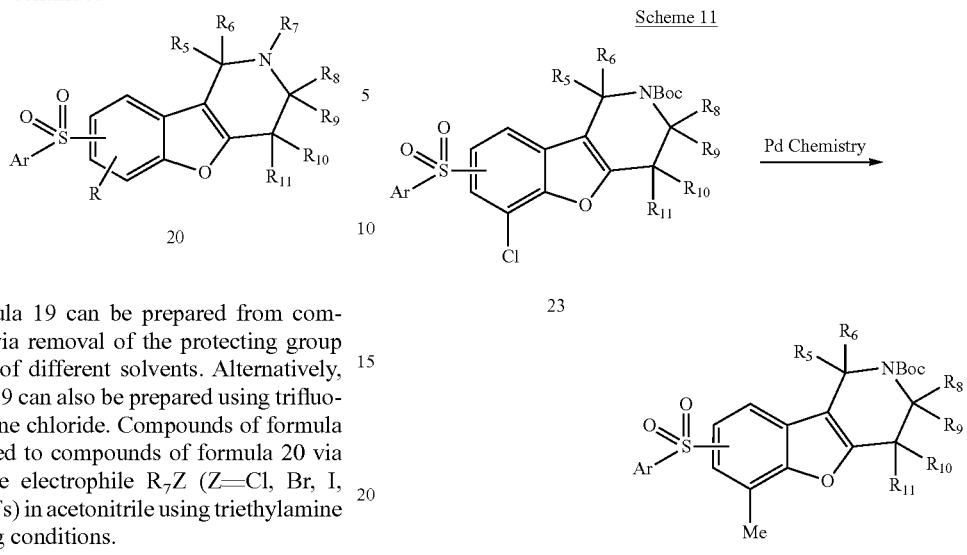

Compounds of formula 19 can be prepared from compounds of formula 13 via removal of the protecting group using HCl in a variety of different solvents. Alternatively, compounds of formula 19 can also be prepared using trifluoroacetic acid in methylene chloride. Compounds of formula 19 can also be elaborated to compounds of formula 20 via reaction with a suitable electrophile $R_7Z$ (Z=Cl, Br, I, $OSO_2Me$, $OSO_2CF_3$, OTs) in acetonitrile using triethylamine as a base under refluxing conditions.

Compounds of formula 24 can be prepared from compounds of formula 23 via a palladium catalyzed methylation using $Pd(PPh_3)_4$ and trimethylboroxine with potassium carbonate as base in DMF at 130° C.

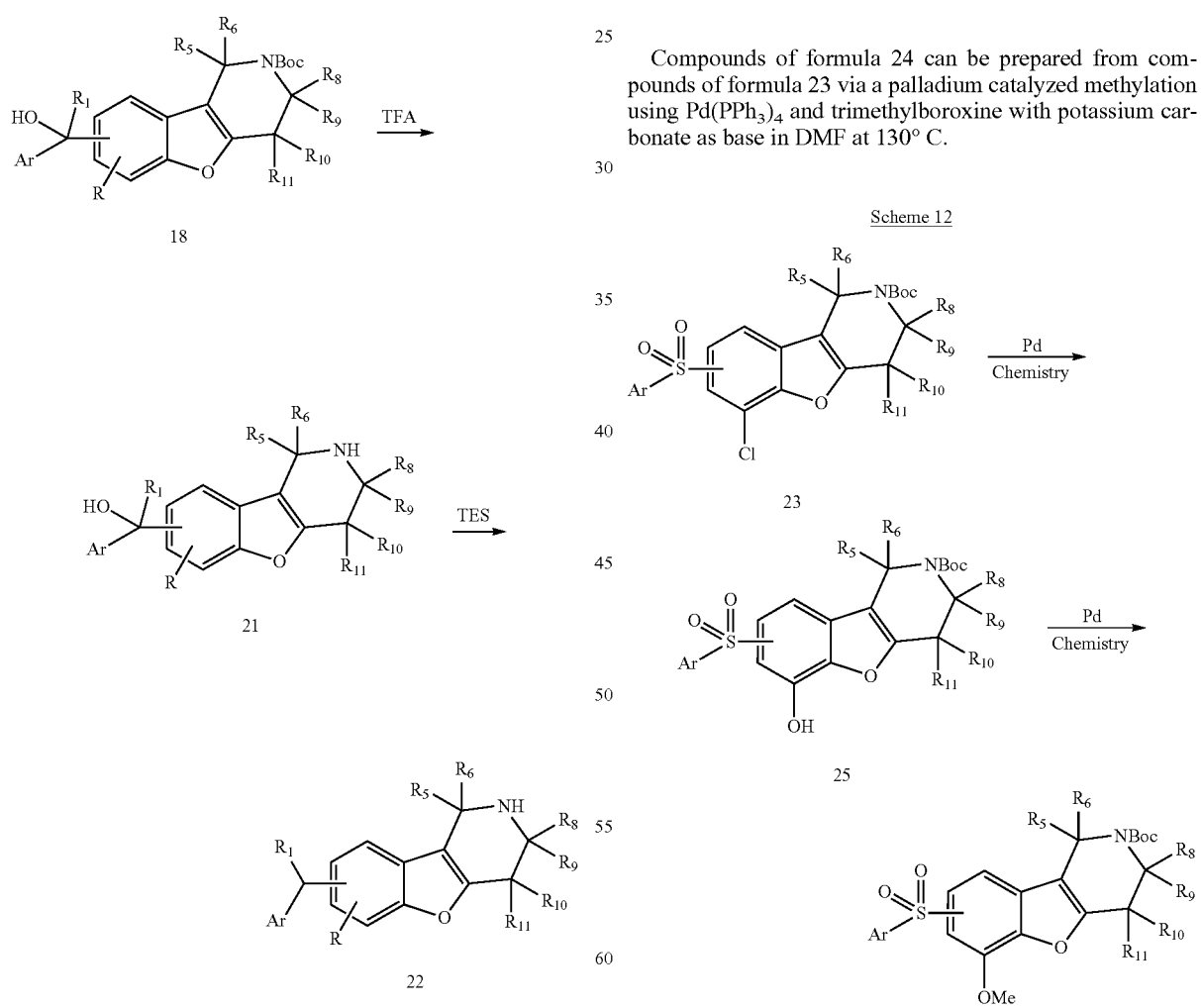

Compounds of formula 22 can be prepared from the deprotected version of compounds of formula 18 (compounds of formula 21) by treatment with triethylsilane and trifluoroacetic acid in boron trifluoride-diethylether complex at 0° C.

Compounds of formula 26 can be prepared via a 2-step conversion from compounds of formula 23. Compounds of formula 25 are prepared via a palladium catalyzed hydrolysis using Pd$_2$(dba)$_3$ and 2-di-tert-butylphosphino-3,4,5,6-tetramethyl-2',4',6'-triisopropyl-1,1'-biphenyl with potassium hydroxide in water and dioxane at reflux Compounds of formula 25 can be elaborated to compounds of formula 26 via reaction with dimethylsulfoxide using potassium carbonate as a base in acetone under refluxing conditions.

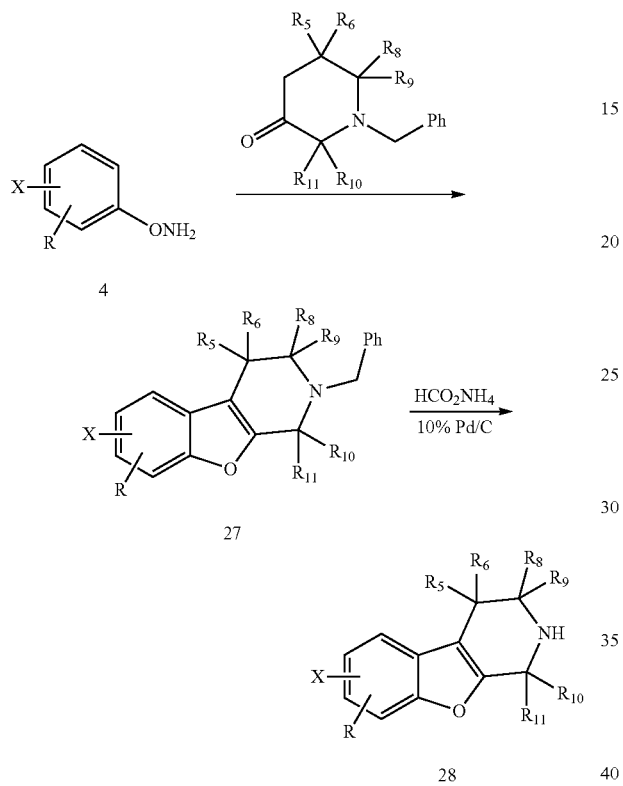

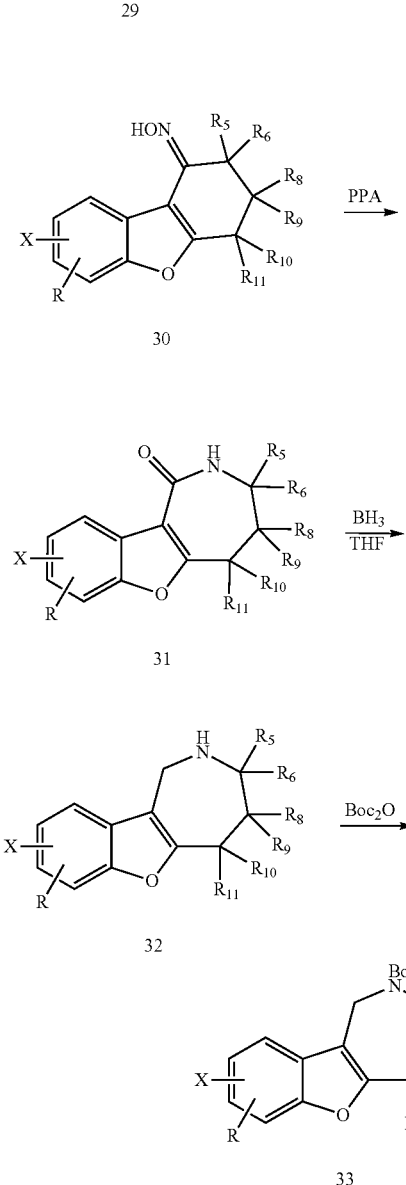

Compounds of formula 27 (where X is Br or I) can be prepared from the corresponding phenoxylamine 4 via a thermal cycloaddition reaction under acidic conditions. Intermediate 27 can be deprotected using palladium-catalysed hydrogenation to prepare compounds of formula 28, which can be reprotected with a Boc group and elaborated to exemplified compounds using methods outlined in schemes 5-10. Alternatively, compounds of formula 27 can be directly elaborated to exemplified compounds with the benzyl group intact using methods outlined in schemes 5-10. This protecting group can be removed in the final step using palladium-catalysed hydrogenation.

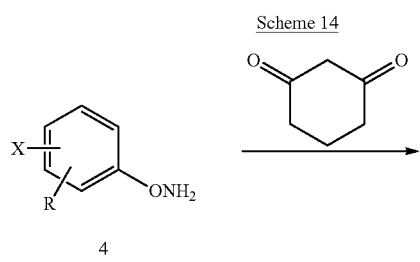

Compounds of formula 33 (where X is Br or I) can be prepared via a five step procedure starting from the corresponding phenoxylamine 4. Thermal cycloaddition using 1,3-cyclohexadione under acidic conditions can be used to prepare compounds of formula 29. Conversion to the oxime 30 followed by a Beckmann Rearrangement using polyphosphoric acid can be used to prepare compounds of formula 31. Reduction to the amine 32 followed by Boc protection can be used to generate intermediates of formula 33. These can be elaborated to exemplified compounds using methods outlined in schemes 5-10.

Scheme 15

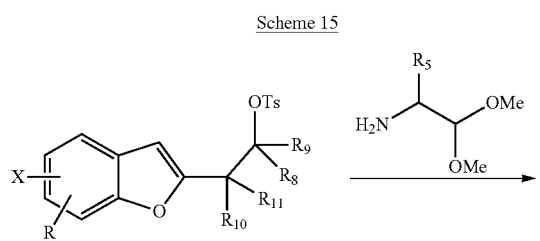

34

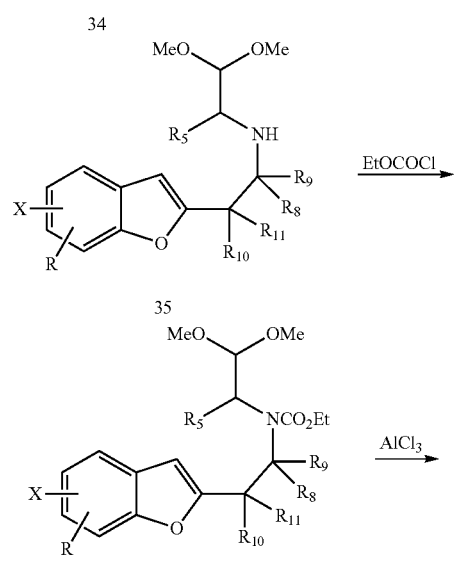

35

36

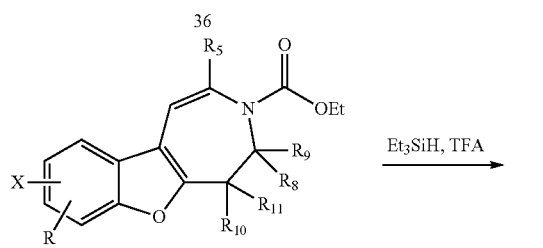

37

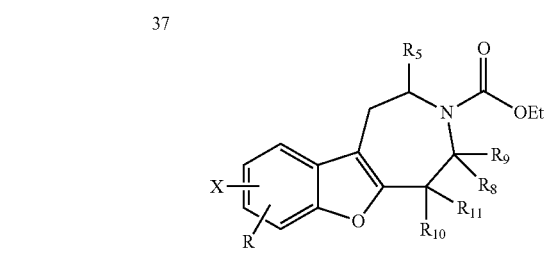

38

Compounds of formula 38 (where X is Br or I) can be prepared via a four step procedure starting from the corresponding tosylate 34. Amination using an aminoacetal under refluxing conditions can be used to prepare compounds of formula 35. Ethylcarbamate protection of the amine followed by a Lewis acid catalyzed cyclization using aluminum trichloride can be used to prepare compounds of formula 37. Triethylsilane-mediated reduction of the enamine can be used to generate intermediates of formula 38. These can be elaborated to exemplified compounds using methods outlined in schemes 5-10 coupled with base-catalyzed carbamate protecting group removal.

EXAMPLES

The Examples set forth below are for illustrative purposes only and are not intended to limit, in any way, the scope of the present invention.

Example 1

Analytical Methods and Materials

Unless otherwise noted, reagents and solvents were used as received from commercial suppliers. Proton nuclear magnetic resonance (NMR) spectra were obtained on Bruker spectrometers at 300, 400 or 500 MHz. Spectra are given in ppm (δ) and coupling constants, J, are reported in Hertz. Tetramethylsilane (TMS) was used as an internal standard. Mass spectra were collected using either a Finnigan LCQ Duo LCMS ion trap electrospray ionization (ESI) or a mass Varian 1200 L single quadrapole mass spectrometer (ESI). High performance liquid chromatograph (HPLC) analyses were obtained using a Luna C18(2) column (250×4.6 mm, Phenomenex) with UV detection at 254 nm or 223 nm using a standard solvent gradient program (Method A or Method B).

Method A

| Time (min) | Flow (mL/min) | % A | % B |
|---|---|---|---|
| 0.0 | 1.0 | 90.0 | 10.0 |
| 20 | 1.0 | 10.0 | 90.0 |
| 30 | 1.0 | 10.0 | 90.0 |

A = Water with 0.05% Trifluoroacetic Acid
B = Acetonitrile with 0.05% Trifluoroacetic Acid Method B

| Time (min) | Flow (mL/min) | % A | % B |
|---|---|---|---|
| 0.0 | 1.0 | 98.0 | 2.0 |
| 25 | 1.0 | 10.0 | 90.0 |
| 30 | 1.0 | 10.0 | 90.0 |

A = Water with 0.025% Trifluoroacetic Acid
B = Acetonitrile with 0.025% Trifluoroacetic Acid Unless otherwise stated, chiral purifications were performed using either a chiral pack OD or AD preparative HPLC column eluting at 100 mL/min. Chiral purity was confirmed by analytical chiral HPLC (OD or AD column) and optical rotation measured using a polarimeter.

Example 2

Preparation of Sodium 3-chloro-benzenesulfinate

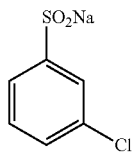

A solution of sodium sulphite (627 mg, 4.98 mmol) and sodium bicarbonate (418 mg, 4.98 mmol) in water (13 mL) was stirred vigorously with 3-chlorobenzenesulfonyl chloride (500 mg, 2.36 mmol) at 0° C. for 30 min then heated at 65° C. for 3 h. After cooling to ambient temperature, the reaction mixture was washed with dichloromethane (2×20 mL) and lyophilized. The resulting white solid was stirred with methanol (10 mL) for 5 min and the insoluble inorganic salts removed by filtration. The filtrate was concentrated in vacuo to approximately 3 mL and an equal volume of diethyl ether added. The precipitated solid containing residual inorganic salts was filtered and set aside. The remaining filtrate was diluted with excess diethyl ether, filtered and the filtered solid dried in vacuo to give sodium 3-chloro-benzenesulfinate (306 mg, 65%) as a white solid: $^1$H NMR (DMSO-$d_6$, 300 MHz) δ 7.43 (br s, 1H), 7.35-7.39 (m, 1H), 7.32 (d, J=7.2 Hz, 1H), 7.26 (dt, J=7.5, 1.8 Hz, 1H).

Example 3

Preparation of Sodium 3-fluoro-benzenesulfinate

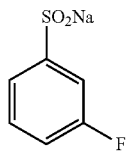

Sodium 3-fluoro-benzenesulfinate was prepared from 3-fluoro-benzenesulfonyl chloride following the procedure of Example 2 to give the product (9.3 g, 99%) as a white solid: $^1$H NMR (D$_2$O, 300 MHz) δ 7.51 (td, J=7.8, 5.1 Hz, 1H), 7.39-7.43 (m, 1H), 7.35 (ddd, J=8.6, 2.7 Hz, 1.5 Hz, 1H), 7.16-7.23 (m, 1H).

Example 4

Preparation of Sodium 3-trifluoromethoxybenzenesulfinate

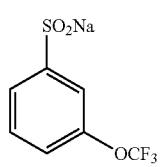

Sodium 3-trifluoromethoxy-benzenesulfinate was prepared from 3-trifluoromethoxy-benzenesulfonyl chloride following the procedure of Example 2 to give the product (219 mg, 46%) as a white solid: $^1$H NMR (CD$_3$OD, 300 MHz) δ 7.60-7.64 (m, 1H), 7.49-7.56 (m, 2H), 7.24-7.28 (m, 1H).

Example 5

Preparation of Sodium 3-methoxy-benzenesulfinate

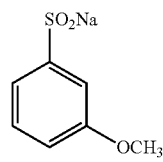

Sodium 3-methoxy-benzenesulfinate was prepared from 3-methoxy-benzenesulfonyl chloride following the procedure of Example 2 to give the product (205 mg, 43%) as a white solid: $^1$H NMR (CD$_3$OD, 300 MHz) δ 7.38-7.42 (m, 1H), 7.28-7.35 (m, 1H), 7.19-7.26 (m, 1H), 6.89-7.01 (m, 1H), 3.82 (s, 3H).

Example 6

Preparation of Sodium 3-cyano-benzenesulfinate

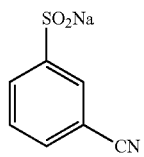

Sodium 3-cyano-benzenesulfinate was prepared from 3-cyano-benzenesulfonyl chloride following the procedure of Example 2 to give the product (750 mg, 80%) as a white solid: $^1$H NMR (CD$_3$OD, 300 MHz) δ 7.90-7.96 (m, 2H), 7.71-7.75 (m, 1H), 7.61 (t, J=7.2 Hz, 1H).

Example 7

Preparation of Sodium 3-difluoromethoxy-benzenesulfinate

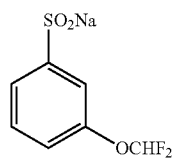

Sodium 3-difluoromethoxy-benzenesulfinate was prepared from 3-difluoromethoxy-benzenesulfonyl chloride following the procedure of Example 2 to give the product (780 mg, 80%) as a white solid: $^1$H NMR (CD$_3$OD, 300 MHz) δ 7.42-7.50 (m, 3H), 7.11-7.14 (m, 1H), 6.84 (t, J=74.1 Hz, 1H).

Example 8

Preparation of Sodium 3-methoxy-benzenesulfinate

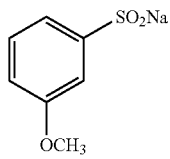

Sodium 3-methoxy-benzenesulfinate was prepared from 3-methoxy-benzenesulfonyl chloride following the procedure of Example 2 to give the product (0.58 g, 73%) as a white solid: $^1$H NMR (CD$_3$OD, 300 MHz) δ 7.31 (t, J=7.8 Hz, 1H), 7.25-7.26 (m, 1H), 7.21 (dt, J=7.5, 1.2 Hz, 1H), 6.91 (ddd, J=7.9, 2.7, 1.2 Hz, 1H), 3.83 (s, 3H).

Example 9

Preparation of Sodium 3-nitro-benzenesulfinate

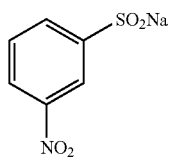

Sodium 3-nitro-benzenesulfinate was prepared from 3-nitro-benzenesulfonyl chloride following the procedure of Example 2 to give the product (1.7 g, 60%) as a yellow solid: $^1$H NMR (CD$_3$OD, 300 MHz) δ 8.42 (t, J=2.1 Hz, 1H), 8.29 (ddd, J=8.2, 1.8, 0.6 Hz, 1H), 7.98 (d, J=7.5 Hz, 1H), 7.72 (t, J=7.8 Hz, 1H).

Example 10

Preparation of Sodium 3-trifluoro-methylbenzenesulfinate

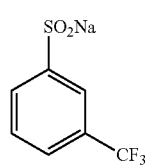

Sodium 3-trifluoromethyl-benzenesulfinate was prepared from 3-trifluoromethyl-benzenesulfonyl chloride following the procedure of Example 2 to give the product (1.0 g, 50%) as a white solid: $^1$H NMR (CD$_3$OD, 300 MHz) δ 7.96 (s, 1H), 7.88 (d, J=7.2 Hz, 1H), 7.58-7.68 (m, 2H).

Example 11

Preparation of Sodium 3-methyl-benzenesulfinate

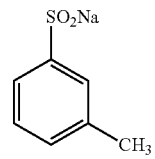

Sodium 3-methyl-benzenesulfinate was prepared from sodium 3-methyl-benzenesulfonyl chloride following the procedure of Example 2 to give the product (1.0 g, 50%) as a white solid: $^1$H NMR (CD$_3$OD, 300 MHz) δ 7.42-7.47 (m, 2H), 7.29 (t, J=7.5 Hz, 1H), 7.18 (d, J=7.8 Hz, 1H), 2.37 (s, 3H).

Example 12

Preparation of Sodium 4-cyano-benzenesulfinate

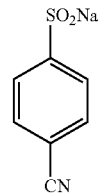

Sodium 4-cyano-benzenesulfinate was prepared from 4-cyano-benzenesulfonyl chloride following the procedure of Example 2 to give the product (1.87 g, 64%) as a white solid: $^1$H NMR (CD$_3$OD, 300 MHz) δ 7.78-7.80 (m, 4H).

Example 13

Preparation of Sodium 4-nitro-benzenesulfinate

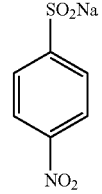

Sodium 4-nitro-benzenesulfinate was prepared from 4-nitro-benzenesulfonyl chloride following the procedure of Example 2 to give the product (0.98 g, 37%) as a yellow solid: $^1$H NMR (CD$_3$OD, 300 MHz) δ 8.28 (d, J=6.9 Hz, 2H), 7.86 (d, J=7.0 Hz, 2H).

Example 14

Preparation of Sodium 4-methyl-benzenesulfinate

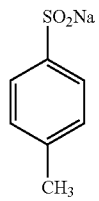

Sodium 4-methyl-benzenesulfinate was prepared from sodium 4-methyl-benzenesulfonyl chloride following the procedure of Example 2 to give the product (3.5 g, 75%) as a white solid: $^1$H NMR (D$_2$O, 300 MHz) δ 7.49 (d, J=8.1 Hz, 2H), 7.32 (d, J=8.1 Hz, 2H), 2.34 (s, 3H).

Example 15

Preparation of Sodium 4-methoxy-benzenesulfinate

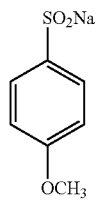

Sodium 4-methoxy-benzenesulfinate was prepared from 4-methoxybenzenesulfonyl chloride following the procedure of Example 2 to give the product (1.8 g, 99%) as a white solid. $^1$H NMR (CD$_3$OD, 300 MHz) δ 7.57 (d, J=9.0 Hz, 2H), 6.95 (d, J=8.7 Hz, 2H), 3.80 (s, 3H).

Example 16

Preparation of Sodium 4-trifluoromethoxy-benzenesulfinate

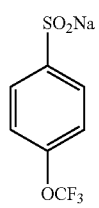

Sodium 4-trifluoromethoxy-benzenesulfinate was prepared from 4-trifluorobenzenesulfonyl chloride following the procedure of Example 2 to give the product (1.49 g, 96%) as a white solid: $^1$H NMR (CD$_3$OD, 300 MHz) δ 7.71-7.75 (m, 2H), 7.30-7.33 (m, 2H).

Example 17

Preparation of Sodium 4-fluoro-benzenesulfinate

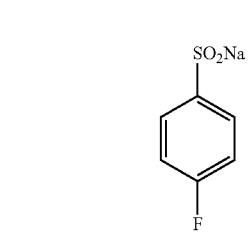

Sodium 4-fluoro-benzenesulfinate was prepared from 4-fluoro-benzenesulfonyl chloride following the procedure of Example 2 to give the product (1.6 g, 86%) as a white solid: $^1$H NMR (CD$_3$OD, 300 MHz) δ 7.63-7.68 (m, 2H), 7.08-7.16 (m, 2H)

Example 18

Preparation of Sodium 4-trifluoromethylbenzenesulfinate

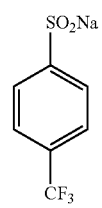

Sodium 4-trifluoromethyl-benzenesulfinate was prepared from 4-trifluoromethylbenzenesulfonyl chloride following the procedure of Example 2 to give the product (1.8 g, 94%) as a white solid: $^1$H NMR (CD$_3$OD, 300 MHz) δ 7.82 (d, J=8.4 Hz, 2H), 7.72 (d, J=8.1 Hz, 2H).

Example 19

Preparation of Sodium 4-chloro-benzenesulfinate

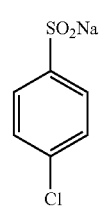

Sodium 4-chloro-benzenesulfinate was prepared from 4-chloro-benzenesulfonyl chloride following the procedure of Example 2 to give the product (5.0 g, 38%) as a white solid: $^1$H NMR (CD$_3$OD, 300 MHz) δ 7.54-7.57 (m, 2H), 7.47-7.51 (m, 2H).

Example 20

Preparation of Sodium 2-methyl-benzenesulfinate

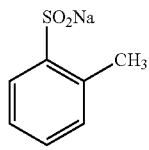

Sodium 2-methylbenzenesulfinate was prepared from sodium 2-methyl-benzenesulfonyl chloride following the procedure of Example 2 to give the product (1.0 g, 50%) as a white solid: $^1$H NMR (D$_2$O, 300 MHz) δ 7.54-7.63 (m, 2H), 7.02-7.07 (m, 2H), 3.84 (s, 3H).

Example 21

Preparation of Sodium 2,3-dichloro-benzenesulfinate

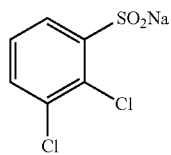

Sodium 2,3-dichloro-benzenesulfinate was prepared from 2,3-dichloro-benzenesulfonyl chloride following the procedure of Example 2 to give the product (0.85 g, 43%) as a white solid: $^1$H NMR (CD$_3$OD, 300 MHz) δ 7.79 (dd, J=7.5, 1.5 Hz, 1H), 7.49 (dd, J=7.8, 1.8 Hz, 1H), 7.36 (t, J=7.8 Hz, 1H).

Example 22

Preparation of Sodium 3,5-difluoro-benzenesulfinate

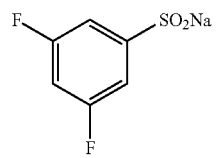

Sodium 3,5-difluoro-benzenesulfinate was prepared from 3,5-difluoro-benzenesulfonyl chloride following the procedure of Example 2 to give the product (0.46 g, 49%) as a white solid: $^1$H NMR (CD$_3$OD, 300 MHz) δ 7.18-7.23 (m, 2H), 6.91 (tt, J=9.0, 2.4 Hz, 1H).

Example 23

Preparation of Sodium 3,5-dichloro-benzenesulfinate

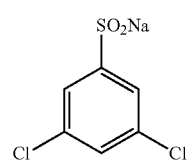

Sodium 3,5-dichloro-benzenesulfinate was prepared from 3,5-difluorobenzenesulfonyl chloride following the procedure of Example 2 to give the product (1.4 g, 77%) as a white solid: $^1$H NMR (CD$_3$OD, 300 MHz) δ 7.54-7.55 (m, 2H), 7.40-7.42 (m, 1H).

Example 24

Preparation of Sodium naphthalene-1-sulfinate

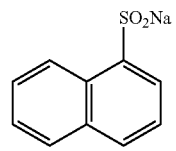

Sodium naphthalene-1-sulfinate was prepared from sodium naphthalene-1-sulfonyl chloride following the procedure of Example 2 to give the product (0.73 g, 51%) as a white solid: $^1$H NMR (D$_2$O, 300 MHz) δ 8.57-8.61 (m, 1H), 7.98-8.01 (m, 2H), 7.90 (dd, J=6.0, 1.2 Hz, 1H), 7.56-7.65 (m, 3H).

Example 25

Preparation of Sodium naphthalene-2-sulfinate

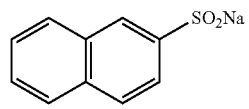

Sodium napthalene-2-sulfinate was prepared from napthalene-2-sulfonyl chloride following the procedure of Example 2 to give the product (3.83 g, 100%) as a white solid: ¹H NMR (CD₃OD, 300 MHz) δ 8.09 (s, 1H), 7.78-7.95 (m, 4H), 7.46-7.55 (m 2H).

Example 26

Preparation of Sodium thiophene-3-sulfinate

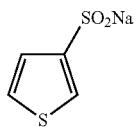

Sodium thiophene-3-sulfinate was prepared from thiophene-3-sulfonyl chloride following the procedure of Example 2 to give the product (400 mg, 86%) as a white solid: ¹H NMR (CD₃OD, 300 MHz) δ 7.57 (dd, J=3.0, 1.2 Hz, 1H), 7.39 (dd, J=5.1, 3.0 Hz, 1H), 7.27 (dd, J=5.1, 1.2 Hz, 1H).

Example 27

Preparation of 2-Methyl-8-(phenylsulfonyl)-1,2,3,4-tetrahydrobenzofuro[3,2c]pyridine hydrochloride

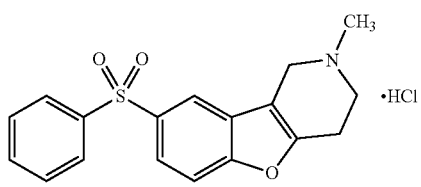 [SMILES: CN1CCc2oc3ccc(S(=O)(=O)c4ccccc4)cc3c2C1 ; Cl]

Step A: To a mixture of 1-fluoro-4-iodobenzene (448 mg, 2.00 mmol) and sodium benzenesulfinate (755 mg, 1.50 mmol) in DMF (5 mL) under a nitrogen atmosphere was added copper (I) trifluoromethanesulfonate benzene complex (443 mg, 2.70 mmol). The reaction was stirred at 65° C. overnight, diluted with ethyl acetate then washed with water and brine. The organic layer was dried over sodium sulfate and concentrated in vacuo to give the crude material which was purified by flash column chromatography (85:15 to 80:20 hexanes/ethyl acetate) to give 1-fluoro-4-(phenylsulfonyl)-benzene (103 mg, 22%) as a white solid: ¹H NMR (CDCl₃, 300 MHz) δ 7.99-7.92 (m, 4H), 7.58-7.49 (m, 3H), 7.18 (t, J=8.4 Hz, 1H), 7.21-7.15 (m, 1H).

Step B: To a solution of 1-fluoro-4-(phenylsulfonyl)-benzene (103 mg, 0.42 mmol) and 1-methylpiperidine-4-one oxime (59 mg, 0.51 mmol) in DMF (2.5 mL) under a nitrogen atmosphere was added sodium hydride (60% dispersion in mineral oil) (34 mg, 0.85 mmol). The reaction mixture was stirred at ambient temperature for 2 h before diluting with ethyl acetate. The resulting solution was washed with water and brine. The organic layer was dried over sodium sulfate and concentrated in vacuo to give the crude product which was purified by flash column chromatography (50:50 ethyl acetate/hexane: 10% ammonium hydroxide in methanol 96:4) to provide 1-methylpiperidin-4-one-O-4-(phenylsulfonyl)phenyl oxime (70 mg, 48%) as an off-white solid: ¹H NMR (CDCl₃, 300 MHz) δ 7.93-7.86 (m, 3H), 7.54-7.45 (m, 2H), 7.34-7.26 (m, 4H), 2.62-2.58 (m, 4H), 2.55-2.49 (m, 4H), 2.34 (s, 3H); ESI MS m/z 345 [M+H]⁺.

Step C: To a solution of 1-methylpiperidin-4-one-O-4-(phenylsulfonyl)phenyl oxime (262 mg, 0.76 mmol) in glacial acetic acid (3.8 mL) under a nitrogen atmosphere was added concentrated sulfuric acid (0.38 mL). The mixture was refluxed at 110° C. for 3 h. The resultant solution was basified with 10% aqueous potassium carbonate (pH 10), extracted with chloroform, washed with water then brine, dried over sodium sulfate and concentrated in vacuo to give the crude product which was purified by flash column chromatography (90:9:1 dichloromethane/methanol/ammonium hydroxide) to provide 2-methyl-8-(phenylsulfonyl)-1,2,3,4-tetrahydrobenzofuro[3,2-c]pyridine (135 mg, 54%) as an off-white solid: ¹H NMR (CDCl₃, 300 MHz) δ 8.04 (d, J=1.8 Hz, 1H), 7.94 (dd, J=8.0 Hz, 1.8 Hz, 2H), 7.80 (dd, J=8.6 Hz, 1.8 Hz, 1H), 7.54-7.26 (m, 4H), 3.59 (s, 2H), 2.90-2.84 (m, 4H), 2.55 (s, 3H).

Step D: 2-Methyl-8-(phenylsulfonyl)-1,2,3,4-tetrahydrobenzofuro[3,2-c]pyridine (13 mg, 0.04 mmol) was treated with 1.25M HCl in methanol (3 mL). After 10 min the solution was concentrated in vacuo to give 2-methyl-8-(phenylsulfonyl)-1,2,3,4-tetrahydrobenzofuro[3,2-c]pyridine hydrochloride (18 mg, 90%, AUC HPLC 96.8%) as an off-white solid: mp 272° C. ¹H NMR (DMSO-d₆, 300 MHz) δ 11.16 (s, 1H), 8.35 (d, J=1.8 Hz, 1H), 7.99-7.95 (m, 2H), 7.92 (dd, J=8.7, 1.8 Hz, 1H), 7.84 (d, J=8.7 Hz, 1H), 7.71-7.59 (m, 3H), 4.65 (br s, 1H), 4.36 (br s, 1H), 3.78 (br s, 1H), 3.57 (br s, 1H), 3.21 (br s, 2H), 2.95 (s, 3H); ESI MS m/z 328 [M+H]⁺.

Example 28

Preparation of 8-(Phenylsulfonyl)-1,2,3,4-tetrahydrobenzofuro[3,2-c]pyridine hydrochloride

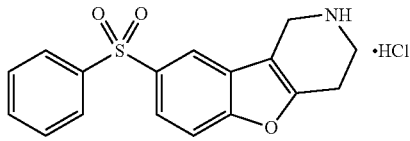 [SMILES: O=S(=O)(c1ccccc1)c1ccc2oc3c(c2c1)CNCC3 ; Cl]

Step A: To a stirred solution of 2-methyl-8-(phenylsulfonyl)-1,2,3,4-tetrahydrobenzofuro[3,2-c]pyridine (135 mg, 0.41 mmol) in 1,2 dichloroethane (2.5 mL) was added 1,8-bis(dimethylamino)naphthalene (176 mg, 0.82 mmol). After 15 min 1-chloroethyl chloroformate (0.07 mL, 0.62 mmol) was added and stirring continued at ambient temperature for 3 h before heating to 50° C. for 30 min. After cooling, the reaction mixture was concentrated in vacuo to give the crude carbamate which was treated directly with 1N NaOH (0.5 mL) in methanol (1.0 mL) and refluxed for 1 h. The reaction mixture was concentrated in vacuo and purified by flash column chromatography (SiO₂, 90:9:1 dichloromethane/methanol/ammonium hydroxide) in methanol to give 8-(phenylsulfonyl)-1,2,3,4-tetrahydrobenzofuro[3,2-c]pyridine (14 mg, 11%): ¹H NMR (CDCl₃, 300 MHz) δ 8.05 (d, J=1.8 Hz, 1H), 7.97-7.93 (m, 2H), 7.80 (dd, J=8.7, 1.8 Hz, 1H), 7.54-7.46 (m, 4H), 4.01-3.98 (m, 2H), 3.25 (t, J=6.0 Hz, 2H), 2.83-2.77 (m, 2H).

Step B: 8-(Phenylsulfonyl)-1,2,3,4-tetrahydrobenzofuro[3,2-c]pyridine (14 mg, 0.04 mmol) was treated with 1.25M HCl in methanol (3 mL). After stirring for 10 min the reaction mixture was concentrated in vacuo to give 8-(phenylsulfonyl)-1,2,3,4-tetrahydrobenzofuro[3,2-c]pyridine hydrochloride (12 mg, 88%, AUC HPLC>99%) as a white solid: mp 243° C.: ¹H NMR (CD₃OD, 300 MHz) δ 8.27 (d, J=1.8 Hz, 1H), 8.01-7.93 (m, 3H), 7.70 (d, J=9.0 Hz, 1H), 7.64-7.53 (m, 3H), 4.48 (t, J=1.8 Hz, 2H), 3.68 (t, J=6.0 Hz, 2H), 3.22-3.17 (m, 2H); ESI MS m/z 314 [M+H]$^+$.

Example 29

Preparation of 8-(3-Fluorophenylsulfonyl)-1,2,3,4-tetrahydrobenzofuro[3,2-c]pyridine hydrochloride

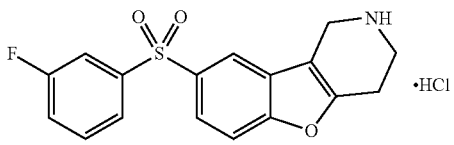 [SMILES: O=S(=O)(c1cccc(F)c1)c1ccc2oc3c(c2c1)CNCC3 ; Cl]

Step A: A solution of 4-bromophenol (61.20 g, 353.7 mmol) and potassium hydroxide (24.8 g, 353.7 mmol) in 2-propanol (53 mL), toluene (85 mL) and water (9 mL) was heated to 80° C. for 40 min. A solution of hydroxylamine-O-sulfonic acid (10.0 g, 88.4 mmol) in water (53 mL) was added dropwise into the stirred reaction mixture over 30 min at 80° C. After a further 10 min the reaction mixture was cooled to ambient temperature, treated with 10% aqueous sodium hydroxide solution and extracted with diethyl ether. The organic extract was dried over sodium sulfate, filtered and treated with 2M hydrochloric acid in diethyl ether (177 mL). The solution was concentrated in vacuo to give O-(4-bromophenyl)hydroxylamine hydrochloride (11.47 g, 58%) as a white solid: $^1$H NMR (DMSO-d$_6$, 300 MHz) δ 9.67 (br s, 3H), 7.53-7.46 (m, 2H), 7.16-7.09 (m, 2H).

Step B: The product of step A (13.7 g, 61.02 mmol) and tert-butyl 4-oxopiperidine-1-carboxylate (13.37 g, 67.12 mmol) in acetic acid (36 mL) and concentrated sulfuric acid (4 mL) were heated to 110° C. for 2 h. After concentrating in vacuo the reaction mixture was diluted with dichloromethane (100 mL) and water (200 mL), basified with saturated aqueous potassium carbonate solution at 0° C. and extracted with dichloromethane. The organic extracts were dried over sodium sulfate, filtered and concentrated in vacuo. The residue was dissolved in 2-propanol (102 mL) and water (120 mL) before addition of potassium carbonate (9.5 g, 68.95 mmol) and di-tert-butyl dicarbonate (15 g, 68.9 mmol). The reaction mixture was stirred at 0° C. for 2 h then diluted with water (200 mL) and extracted three times with dichloromethane. The organic extracts were dried over sodium sulfate, filtered and concentrated in vacuo. The residue was purified by flash column chromatography (SiO$_2$, 90:10 hexane/ethyl acetate) to give tert-butyl 8-bromo-3,4-dihydrobenzofuro[3,2-c]pyridine-2(1H)-carboxylate (8.7 g, 40%) as a light-pink solid: $^1$H NMR (CDCl$_3$, 300 MHz) δ 7.53 (d, J=1.2 Hz, 1H), 7.36-7.25 (m, 2H), 4.51 (s, 2H), 3.82 (t, J=5.4 Hz, 2H), 2.84 (t, J=5.4 Hz, 2H), 1.50 (s, 9H).

Step C: A mixture of product of step B (300 mg, 0.85 mmol), sodium 3-fluorobenzenesulfinate (186 mg, 1.02 mmol), di-palladium-tris(dibenzylideneacetone) (78 mg, 0.08 mmol), cesium carbonate (416 mg, 1.28 mmol) and xantphos (99 mg, 0.17 mmol) was suspended in anhydrous toluene (4.5 mL). The reaction flask was purged with argon, sealed and heated to 120° C. for 14 h. The reaction mixture was cooled to ambient temperature, diluted with dichloromethane and filtered through a celite bed. The filtrate was concentrated in vacuo to give the crude product which was purified by flash column chromatography (SiO$_2$, 3:2 hexanes/ethyl acetate) providing tert-butyl 8-(3-fluorophenylsulfonyl)-3,4-dihydrobenzofuro[3,2-c]pyridine-2(1H)-carboxylate (135 mg, 37%) as a pale yellow solid: $^1$H NMR (CDCl$_3$, 300 MHz) δ 8.08 (s, 1H), 7.83 (dd, J=8.7, 1.8 Hz, 1H), 7.77-7.72 (m, 1H), 7.65 (dt, J=7.8, 2.1 Hz, 1H), 7.53 (d, J=8.4 Hz, 1H), 7.51-7.44 (m, 1H), 7.25-7.20 (m, 1H), 4.58 (s, 2H), 3.84 (t, J=5.4 Hz, 2H), 2.91-2.84 (m, 2H), 1.55 (s, 9H).

Step D: To a solution of the product from step C (135 mg, 0.30 mmol) in dichloromethane (1 mL) and methanol (0.5 mL) was added 2M HCl in diethyl ether (4 mL). After stirring for 14 h at ambient temperature the reaction mixture was diluted with diethyl ether to induce precipitation. The reaction mixture was concentrated in vacuo to give 8-(3-fluorophenylsulfonyl)-1,2,3,4-tetrahydrobenzofuro[3,2-c]pyridine hydrochloride (96 mg, 96%, AUC HPLC>99%) as an off-white solid: mp 262-272° C. dec; $^1$H NMR (CD$_3$OD, 300 MHz) δ 8.31-8.27 (m, 1H), 7.97 (dd, J=8.7, 2.1 Hz, 1H), 7.84-7.78 (m, 1H), 7.76-7.69 (m, 2H), 7.64-7.56 (m, 1H), 7.42-7.35 (m, 1H), 4.49 (s, 2H), 3.69 (t, J=6.0 Hz, 2H), 3.23-3.17 (m, 2H); APCI MS m/z 332 [M+H]$^+$.

Example 30

Preparation of 8-(3-Chlorophenylsulfonyl)-1,2,3,4-tetrahydrobenzofuro[3,2-c]pyridine hydrochloride

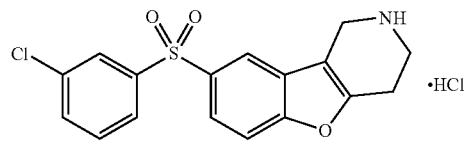 [SMILES: O=S(=O)(c1cccc(Cl)c1)c1ccc2oc3c(c2c1)CNCC3 ; Cl]

Step A: The product of Example 29, step B (230 mg, 0.65 mmol) and sodium 3-chlorobenzenesulfinate (155 mg, 0.78 mmol) were coupled using the procedure of Example 29, step C. Purification by flash column chromatography (SiO$_2$, 3:2 hexanes/ethyl acetate) provided tert-butyl 8-(3-chlorophenylsulfonyl)-3,4-dihydrobenzofuro[3,2-c]pyridine-2(1H)-carboxylate (78 mg, 26%) as a pale yellow solid: $^1$H NMR (CDCl$_3$, 300 MHz) δ 8.08 (s, 1H), 7.93 (t, J=1.8 Hz, 1H), 7.86-7.83 (m, 1H), 7.83-7.81 (m, 1H), 7.56-7.48 (m, 2H), 7.43 (t, J=7.8 Hz, 1H), 4.58 (s, 2H), 3.84 (t, J=5.4 Hz, 2H), 2.91-2.84 (m, 2H), 1.51 (s, 9H).

Step B: The product from step A (76 mg, 0.17 mmol) was deprotected following the procedure of Example 29, step D providing 8-(3-chlorophenylsulfonyl)-1,2,3,4-tetrahydrobenzofuro[3,2-c]pyridine hydrochloride (48 mg, 74%, AUC HPLC 96.8%) as an off-white solid: mp 245-252° C. dec; $^1$H NMR (CD$_3$OD, 300 MHz) δ 8.30 (br s, 1H), 7.99-7.95 (m, 2H), 7.94-7.89 (m, 1H), 7.73 (d, J=8.7 Hz, 1H), 7.66-7.62 (m, 1H), 7.56 (d, J=7.8 Hz, 1H), 4.49 (s, 2H), 3.69 (t, J=6.0 Hz, 2H), 3.20 (t, J=6.0 Hz, 2H); APCI MS m/z 348 [M+H]⁺.

Example 31

Preparation of 8-(4-Fluorophenylsulfonyl)-1,2,3,4-tetrahydrobenzofuro[3,2-c]pyridine hydrochloride

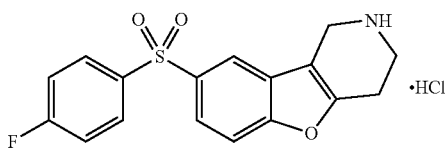 [SMILES: O=S(=O)(c1ccc(F)cc1)c1ccc2oc3c(c2c1)CNCC3 ; Cl]

Step A: The product of Example 29, step B and sodium 4-fluorobenzenesulfinate were coupled using the procedure of Example 29, step C. Purification by flash column chromatography (SiO₂, 75:25 hexane/ethyl acetate) provided tert-butyl 8-(4-fluorophenylsulfonyl)-3,4-dihydrobenzofuro[3,2-c]pyridine-2(1H)-carboxylate (217 mg, 36%) as a pale yellow solid: ¹H NMR (CDCl₃, 300 MHz) δ 8.07 (s, 1H), 8.01-7.91 (m, 2H), 7.81 (dd, J=8.7, 1.8 Hz, 1H), 7.52 (d, J=8.4 Hz, 1H), 7.22-7.11 (m, 2H), 4.57 (s, 2H), 3.89-3.76 (m, 2H), 2.92-2.80 (m, 2H), 1.51 (s, 9H).

Step B: To the product obtained in step A (150 mg, 0.31 mmol) in dichloromethane (3 mL) was added trifluoroacetic acid (0.6 mL). After stirring for 2 h at ambient temperature the reaction mixture was quenched with 10% sodium bicarbonate solution (20 mL) and extracted with dichloromethane. The organic extract was dried over sodium sulfate, filtered, and concentrated in vacuo. The residue was purified by flash column chromatography (SiO₂, 90:10 dichloromethane/methanol) to give 8-(4-fluorophenylsulfonyl)-1,2,3,4-tetrahydrobenzofuro[3,2-c]pyridine (60 mg, 52%) as a white solid: ¹H NMR (CDCl₃, 300 MHz) δ 8.03 (d, J=1.8 Hz, 1H), 8.00-7.92 (m, 2H), 7.78 (dd, J=8.7, 2.1 Hz, 1H), 7.51 (d, J=9.0 Hz, 1H), 7.21-7.10 (m, 2H), 4.00 (t, J=2.1 Hz, 2H), 3.25 (t, J=5.7 Hz, 2H), 2.84-2.76 (m, 2H).

Step C: The product of step B (60 mg, 0.10 mmol) was converted to hydrochloride salt by dissolving in methanol and treating with 1.25 M HCl in methanol. The reaction mixture was concentrated in vacuo to give 8-(4-fluorophenylsulfonyl)-1,2,3,4-tetrahydrobenzofuro[3,2-c]pyridine hydrochloride (60 mg, 90%, AUC HPLC>99%) as a white solid: mp 270-280° C. <<MP data>>; ¹H NMR (CD₃OD, 300 MHz) δ 8.27 (d, J=1.8 Hz, 1H), 8.10-8.00 (m, 2H), 7.95 (dd, J=8.7, 2.1 Hz, 1H), 7.71 (d, J=8.7 Hz, 1H), 7.36-7.25 (m, 2H), 4.81 (t, J=1.5 Hz, 2H), 3.69 (t, J=6.0 Hz, 2H), 3.24-3.16 (m, 2H); APCI MS m/z 332 [M+H]⁺.

Example 32

Preparation of 8-(4-Chlorophenylsulfonyl)-1,2,3,4-tetrahydrobenzofuro[3,2-c]pyridine hydrochloride

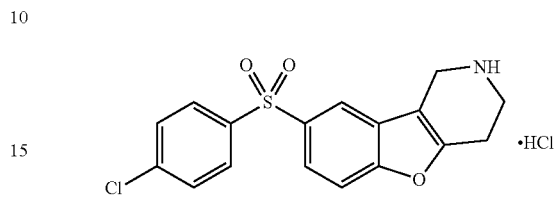

Step A: The product of Example 29, step B and sodium 4-chlorobenzenesulfinate were coupled using the procedure of Example 29, step C. Purification by flash column chromatography (SiO₂, 85:15 hexane/ethyl acetate) provided tert-butyl 8-(4-chlorophenylsulfonyl)-3,4-dihydrobenzofuro[3,2-c]pyridine-2(1H)-carboxylate (118 mg, 37%) as a yellow solid: ¹H NMR (CDCl₃, 300 MHz) δ 8.06 (s, 1H), 7.92-7.85 (m, 2H), 7.80 (dd, J=8.7, 1.8 Hz, 1H), 7.51 (d, J=8.7 Hz, 1H), 7.49-7.43 (m, 2H), 4.57 (s, 2H), 3.83 (t, J=5.4 Hz, 2H), 2.92-2.81 (m, 2H), 1.51 (s, 9H).

Step B: The product of step A (118 mg, 0.26 mmol) was Boc-deprotected by treating with 4N HCl in dioxane (2 mL). After stirring for 2 h at ambient temperature the reaction mixture was quenched with 10% sodium bicarbonate solution (20 mL) and extracted with dichloromethane. The organic extract was dried over sodium sulfate, filtered and concentrated in vacuo. The residue was purified by flash column chromatography (SiO₂, 95:5 chloroform/methanol) to give 8-(4-chlorophenylsulfonyl)-1,2,3,4-tetrahydrobenzofuro[3,2-c]pyridine hydrochloride (80 mg, 87%) as a white solid: ¹H NMR (CDCl₃, 300 MHz) δ 8.02 (d, J=1.8 Hz, 1H), 7.91-7.84 (m, 2H), 7.78 (dd, J=8.7, 2.1 Hz, 1H), 7.50 (d, J=8.4 Hz, 1H), 7.48-7.41 (m, 2H), 3.99 (t, J=2.1 Hz, 2H), 3.24 (t, J=5.7 Hz, 2H), 2.85-2.76 (m, 2H).

Step C: The product of step B (35 mg, 0.10 mmol) was converted to hydrochloride salt by dissolving in methanol and treating with 1.25 M HCl in methanol. The reaction mixture was concentrated in vacuo to give 8-(4-chlorophenylsulfonyl)-1,2,3,4-tetrahydrobenzofuro[3,2-c]pyridine hydrochloride (36 mg, 94%, AUC HPLC>99%) as a white solid: mp 302-305° C.; ¹H NMR (DMSO-d₆, 300 MHz) δ 9.50 (br s, 2H), 8.41 (d, J=1.8 Hz, 1H), 8.02-7.81 (m, 4H), 7.69 (d, J=8.4 Hz, 2H), 4.39 (s, 2H), 3.53 (t, J=6.0 Hz, 2H), 3.17-3.07 (m, 2H); APCI MS m/z 348 [M+H]⁺.

Example 33

Preparation of 8-(4-Methoxyphenylsulfonyl)-1,2,3,4-tetrahydrobenzofuro[3,2-c]pyridine hydrochloride

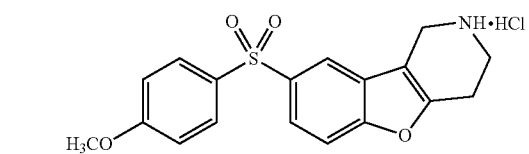 [SMILES: COc1ccc(S(=O)(=O)c2ccc3oc4c(c3c2)CNCC4)cc1 ; Cl]

Step A: The product of Example 29, step B and sodium 4-methoxybenzenesulfinate were coupled using the procedure of Example 29, step C. Purification by flash column chromatography (SiO$_2$, 4:1 hexane/ethyl acetate) provided tert-butyl 8-(4-methoxyphenylsulfonyl)-3,4-dihydrobenzofuro[3,2-c]pyridine-2(1H)-carboxylate (221 mg, 41%) as a light-yellow solid: $^1$H NMR (CDCl$_3$, 300 MHz) δ 8.05 (s, 1H), 7.90-7.86 (m, 2H), 7.79 (d, J=9.0 Hz, 1H), 7.48 (d, J=8.7 Hz, 1H), 6.98-6.91 (m, 2H), 4.56 (s, 2H), 3.83 (m, 5H), 2.86 (m, 2H), 1.50 (s, 9H).

Step B: To the product of step A (221 mg, 0.50 mmol) in dichloromethane and methanol was added 2 M HCl in diethyl ether (5 mL). After stirring for 18 h, the product was filtered, washed with diethyl ether and lyophilized to give 8-(4-methoxyphenylsulfonyl)-1,2,3,4-tetrahydrobenzofuro[3,2-c]pyridine hydrochloride (50 mg, 30%) as a white solid: mp 270-272° C.; $^1$H NMR (DMSO-d$_6$, 300 MHz) δ 9.64 (s, 2H), 8.35 (d, J=1.5 Hz, 1H), 7.92-7.78 (m, 4H), 7.14-7.09 (m, 2H), 4.38 (s, 2H), 3.82 (s, 3H), 3.52 (t, J=6.0 Hz, 2H), 3.13 (t, J=5.4 Hz, 2H); APCI MS m/z 344 [M+H]$^+$.

Example 34

Preparation of 8-(4-Cyanophenylsulfonyl)-1,2,3,4-tetrahydrobenzofuro[3,2-c]pyridine hydrochloride

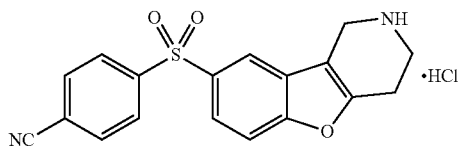 [SMILES: N#Cc1ccc(S(=O)(=O)c2ccc3oc4c(c3c2)CNCC4)cc1 ; Cl]

Step A: The product of Example 29, step B and sodium 4-cyanobenzenesulfinate were coupled using the procedure of Example 29, step C. Purification by flash column chromatography (SiO$_2$, 3:2 hexane/ethyl acetate) provided tert-butyl 8-(4-cyanophenylsulfonyl)-3,4-dihydrobenzofuro[3,2-c]pyridine-2(1H)-carboxylate (107 mg, 34%) as a pale yellow solid: $^1$H NMR (CDCl$_3$, 300 MHz) δ 8.09-8.03 (m, 3H), 7.84 (dd, J=5.7, 3.9 Hz, 1H), 7.80-7.76 (m, 2H), 7.55 (d, J=8.4 Hz, 1H), 4.58 (s, 2H), 3.84 (t, J=5.7 Hz, 2H), 2.91-2.82 (m, 2H), 1.51 (s, 9H).

Step B: The product of step A was deprotected following the procedure of Example 33, step B to give 8-(4-cyanophenylsulfonyl)-1,2,3,4-tetrahydrobenzofuro[3,2-c]pyridine hydrochloride (65 mg, 84%, AUC HPLC>99%) as a white solid: mp 295-301° C. dec; $^1$H NMR (CD$_3$OD, 300 MHz) δ 8.31 (d, J=1.8 Hz, 1H), 8.18-8.13 (m, 2H), 7.98 (dd, J=8.7, 1.8 Hz, 1H), 7.94-7.91 (m, 2H), 7.74 (d, J=8.7 Hz, 1H), 4.50-4.44 (m, 2H), 3.69 (t, J=6.0 Hz, 2H), 3.22-3.17 (m, 2H); ESI MS m/z 339 [M+H]$^+$.

Example 35

Preparation of 8-(4-Methylphenylsulfonyl)-1,2,3,4-tetrahydrobenzofuro[3,2-c]pyridine hydrochloride

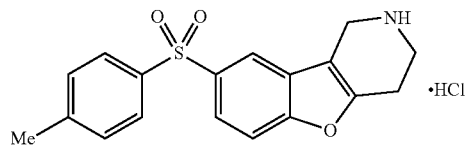 [SMILES: Cc1ccc(S(=O)(=O)c2ccc3oc4c(c3c2)CNCC4)cc1 ; Cl]

Step A: The product of Example 29, step B and sodium 4-methylbenzenesulfinate were coupled using the procedure of Example 29, step C. Purification by flash column chromatography (SiO$_2$, 90:10 to 50:50 hexane/ethyl acetate) provided tert-butyl 8-(4-methylphenylsulfonyl)-3,4-dihydrobenzofuro[3,2-c]pyridine-2(1H)-carboxylate (65 mg, 33%) as a colorless oil: $^1$H NMR (CDCl$_3$, 300 MHz) δ 8.07 (br s, 1H), 7.86-7.78 (m, 3H), 7.49 (d, J=8.7 Hz, 1H), 7.28 (d, J=8.1 Hz, 2H), 4.57 (br s, 2H), 3.88-3.78 (m, 2H), 2.90-2.82 (m, 2H), 2.38 (s, 3H), 1.51 (s, 9H).

Step B: The product of step A was deprotected following the procedure of Example 33, step B to give 8-(4-methylphenylsulfonyl)-1,2,3,4-tetrahydrobenzofuro[3,2-c]pyridine hydrochloride (30 mg, 58%) as an off-white solid: mp 265-270° C.; $^1$H NMR (DMSO-d$_6$, 300 MHz) δ 8.37 (d, J=8.5 Hz, 1H), 7.89-7.78 (m, 4H), 7.41 (d, J=8.1 Hz, 2H), 4.38 (br s, 2H), 3.56-3.47 (m, 2H), 3.25-3.08 (m, 2H), 2.36 (s, 3H); ESI MS m/z 328 [M+H]$^+$

Example 36

Preparation of 8-(4-Aminophenylsulfonyl)-1,2,3,4-tetrahydrobenzofuro[3,2-c]pyridine hydrochloride

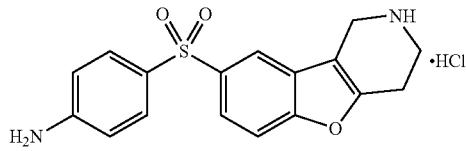 [SMILES: Nc1ccc(S(=O)(=O)c2ccc3oc4c(c3c2)CNCC4)cc1 ; Cl]

Step A: The product of Example 29, step B and sodium 4-nitrobenzenesulfinate were coupled using the procedure of Example 29, step C. Purification by flash column chromatography (SiO$_2$, 3:2 hexane/ethyl acetate) provided tert-butyl 8-(4-nitrophenylsulfonyl)-3,4-dihydrobenzofuro[3,2-c]pyridine-2(1H)-carboxylate (96 mg, 25%) as a pale yellow solid: $^1$H NMR (CDCl$_3$, 300 MHz) δ 8.08 (s, 1H), 7.83 (dd, J=8.7, 1.8 Hz, 1H), 7.77-7.72 (m, 1H), 7.65 (dt, J=7.8, 2.1 Hz, 1H), 7.53 (d, J=8.4 Hz, 1H), 7.50-7.44 (m, 1H), 7.25-7.20 (m, 1H), 4.58 (s, 2H), 3.84 (t, J=5.7 Hz, 2H), 2.91-2.82 (m, 2H), 1.55 (s, 9H).

Step B: To a solution of product from step A (96 mg, 0.20 mmol) in ethanol (4.0 mL) and water (2.0 mL) was added iron powder (57 mg, 1.02 mmol) and ammonium chloride (12 mg, 0.22 mmol). After refluxing for 3 h, the reaction mixture was filtered through a bed of celite and the celite bed washed repeatedly with ethyl acetate. The filtrate was dried over anhydrous sodium sulfate, filtered, and concentrated in vacuo to give a crude product which was purified by flash column chromatography (SiO$_2$, 3:2 hexanes/ethyl acetate) to give the product tert-butyl 8-(4-aminophenylsulfonyl)-3,4-dihydrobenzofuro[3,2-c]pyridine-2(1H)-carboxylate (76 mg, 87%) as an off-white solid: $^1$H NMR (CDCl$_3$, 300 MHz) δ 8.22-8.19 (m, 1H), 7.88 (dd, J=8.7, 1.8 Hz, 1H), 7.81-7.75 (m, 2H), 7.67 (d, J=8.4 Hz, 1H), 6.97-6.91 (m, 2H), 4.48 (s, 2H), 3.54-3.52 (m, 2H), 3.23-3.16 (m, 2H), 1.55 (s, 9H).

Step C: The product of step B was deprotected following the procedure of Example 33, step B to give 8-(4-aminophenylsulfonyl)-1,2,3,4-tetrahydrobenzofuro[3,2-c]pyridine hydrochloride (56 mg, 87%, AUC HPLC 97.1%) as a white solid: mp 305-314° C. dec; $^1$H NMR (CD$_3$OD, 300 MHz) δ 8.18 (d, J=1.8 Hz, 1H), 7.86 (dd, J=8.7, 1.8 Hz, 1H), 7.71-7.64 (m, 3H), 6.80-6.74 (m, 2H), 4.47 (s, 2H), 3.68 (t, J=6.0 Hz, 2H), 3.22-3.19 (m, 2H); ESI MS m/z 329 [M+H]$^+$.

Example 37

Preparation of 8-(3,5-Difluorophenylsulfonyl)-1,2,3,4-tetrahydrobenzofuro[3,2-c]pyridine hydrochloride

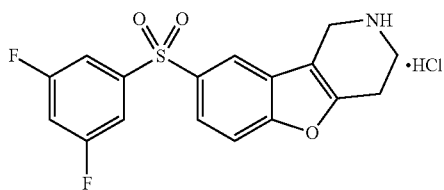 [SMILES: O=S(=O)(c1cc(F)cc(F)c1)c1ccc2oc3c(c2c1)CNCC3 ; Cl]

Step A: The product of Example 29, step B and sodium 3,5-difluorobenzenesulfinate were coupled using the procedure of Example 29, step C. Purification by flash column chromatography (SiO$_2$, 3:2 hexane/ethyl acetate) provided tert-butyl 8-(3,5-difluorophenylsulfonyl)-3,4-dihydrobenzofuro[3,2-c]pyridine-2(1H)-carboxylate (191 mg, 50%) as a pale yellow solid: $^1$H NMR (CDCl$_3$, 300 MHz) δ 8.08 (s, 1H), 7.82 (dd, J=8.4, 1.8 Hz, 1H), 7.55 (d, J=8.7 Hz, 1H), 7.49-7.45 (m, 2H), 7.02-6.94 (m, 1H), 4.59 (s, 2H), 3.84 (t, J=5.4 Hz, 2H), 2.91-2.84 (m, 2H), 1.51 (s, 9H).

Step B: The product of step A was deprotected following the procedure of Example 33, step B to give 8-(3,5-difluorophenylsulfonyl)-1,2,3,4-tetrahydrobenzofuro[3,2-c]pyridine hydrochloride (136 mg, 92%, AUC HPLC 96%) as an off-white solid: mp 275-281° C. dec; $^1$H NMR (CD$_3$OD, 300 MHz) δ 8.33 (br s, 1H), 7.99 (dd, J=9.0, 1.8 Hz, 1H), 7.74 (d, J=9.0 Hz, 1H), 7.66-7.61 (m, 2H), 7.34-7.25 (m, 1H), 4.49 (s, 2H), 3.69 (t, J=6.3 Hz, 2H), 3.21 (t, J=6.0 Hz, 2H); APCI MS m/z 350 [M+H]$^+$.

Example 38

Preparation of 8-(3,5-Dichlorophenylsulfonyl)-1,2,3,4-tetrahydrobenzofuro[3,2-c]pyridine hydrochloride

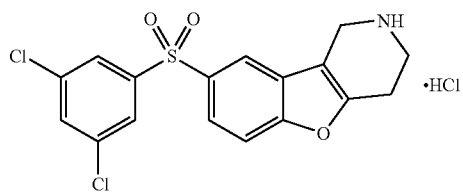 [SMILES: O=S(=O)(c1cc(Cl)cc(Cl)c1)c1ccc2oc3c(c2c1)CNCC3 ; Cl]

Step A: The product of Example 29, step B and sodium 3,5-dichlorobenzenesulfinate were coupled using the procedure of Example 29, step C. Purification by flash column chromatography (SiO$_2$, 85:15 hexane/ethyl acetate) provided tert-butyl 8-(3,5-dichlorophenylsulfonyl)-3,4-dihydrobenzofuro[3,2-c]pyridine-2(1H)-carboxylate (147 mg, 43%) as a yellow oil: $^1$H NMR (CDCl$_3$, 300 MHz) δ 8.07 (s, 1H), 7.85-7.78 (m, 3H), 7.56 (d, J=8.7 Hz, 1H), 7.50 (t, J=1.8 Hz, 1H), 4.59 (s, 2H), 3.84 (t, J=5.4 Hz, 2H), 2.93-2.82 (m, 2H), 1.51 (s, 9H).

Step B: The product of step A was deprotected using the procedure of Example 32, step B. Purification by flash column chromatography (SiO$_2$, 95:5 chloroform/methanol) provided 8-(3,5-dichlorophenylsulfonyl)-1,2,3,4-tetrahydrobenzofuro[3,2-c]pyridine (110 mg, 94%) as a white solid: $^1$H NMR (CDCl$_3$, 300 MHz) δ 8.03 (d, J=1.8 Hz, 1H), 7.83-7.76 (m, 3H), 7.54 (d, J=8.4 Hz, 1H), 7.49 (t, J=1.8 Hz, 1H), 4.02 (t, J=2.1 Hz, 2H), 3.26 (t, J=5.7 Hz, 2H), 2.86-2.77 (m, 2H).

Step C: The product of step B (30 mg, 0.08 mmol) was converted to hydrochloride salt by dissolving in methanol and treating with 1.25 M HCl in methanol. The reaction mixture was concentrated in vacuo to give 8-(3,5-dichlorophenylsulfonyl)-1,2,3,4-tetrahydrobenzofuro[3,2-c]pyridine hydrochloride (32 mg, 98%, AUC HPLC 98.3%) as a white solid: mp 312-315° C.; $^1$H NMR (DMSO-d$_6$, 300 MHz) δ 9.43 (br s, 2H), 8.50 (d, J=1.8 Hz, 1H), 8.06-7.96 (m, 4H), 7.86 (d, J=8.7 Hz, 1H), 4.40 (s, 2H), 3.54 (t, J=6.0 Hz, 2H), 3.17-3.07 (m, 2H); APCI MS m/z 382 [M+H]$^+$.

Example 39

Preparation of 8-(1-Naphthylsulfonyl)-1,2,3,4-tetrahydrobenzofuro[3,2-c]pyridine hydrochloride

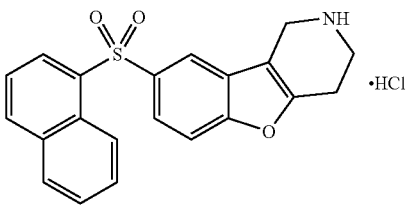 [SMILES: O=S(=O)(c1ccc2oc3c(c2c1)CNCC3)c1cccc2ccccc12 ; Cl]

Step A: The product of Example 29, step B and sodium 1-naphthylsulfinate were coupled using the procedure of Example 29, step C. Purification by flash column chromatography (SiO$_2$, 75:25 hexane/ethyl acetate) provided tert-butyl 8-(1-naphthylsulfonyl)-3,4-dihydrobenzofuro[3,2-c]pyridine-2(1H)-carboxylate (76 mg, 26%) as a colorless oil: $^1$H NMR (CDCl$_3$, 300 MHz) δ 8.67 (d, J=8.1 Hz, 1H), 8.51 (dd, J=7.5, 1.2 Hz, 1H), 8.18-8.01 (m, 2H), 7.92-7.76 (m, 2H), 7.67-7.41 (m, 4H), 4.58-4.47 (m, 2H), 3.81 (br s, 2H), 2.83 (br s, 2H), 1.50 (s, 9H).

Step B: The product of step A was deprotected using the procedure of Example 32, step B. Purification by flash column chromatography (SiO$_2$, 95:5 chloroform/methanol) provided 8-(1-naphthylsulfonyl)-1,2,3,4-tetrahydrobenzofuro[3,2-c]pyridine (48 mg, 80%) as a white solid: $^1$H NMR (CDCl$_3$, 300 MHz) δ 8.66 (d, J=8.4 Hz, 1H), 8.53-8.45 (m, 1H), 8.12-8.02 (m, 2H), 7.91-7.84 (m, 1H), 7.79 (dd, J=8.7, 2.1 Hz, 1H), 7.65-7.40 (m, 4H), 4.02-3.90 (m, 2H), 3.22 (t, J=5.7 Hz, 2H), 2.82-2.70 (m, 2H).

Step C: The product of step B was converted to the hydrochloride salt by dissolving in methanol and treating with 1.25 M HCl in methanol. The reaction mixture was concentrated in vacuo to give 8-(1-naphthylsulfonyl)-1,2,3,4-tetrahydrobenzofuro[3,2-c]pyridine hydrochloride (52 mg, 100%, AUC HPLC 94.5%) as a white solid: mp 200-202° C.; $^1$H NMR (DMSO-d$_6$, 300 MHz) δ 9.51 (br s, 2H), 8.61-8.45 (m, 3H), 8.33 (d, J=8.1 Hz, 1H), 8.14-8.05 (m, 1H), 7.87 (dd, J=8.7, 2.1 Hz, 1H), 7.82-7.74 (m, 2H), 7.69-7.57 (m, 2H), 4.39 (s, 2H), 3.58-3.45 (m, 2H), 3.10 (t, J=5.7 Hz, 2H); ESI MS m/z 364 [M+H]$^+$.

Example 40

Preparation of 8-(2-Naphthylsulfonyl)-1,2,3,4-tetrahydrobenzofuro[3,2-c]pyridine hydrochloride

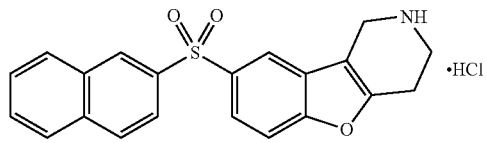 [SMILES: O=S(=O)(c1ccc2ccccc2c1)c1ccc2oc3c(c2c1)CNCC3 ; Cl]

Step A: The product of Example 29, step B and sodium 2-naphthylsulfinate were coupled using the procedure of Example 29, step C. Purification by flash column chromatography (SiO$_2$, 80:20 hexane/ethyl acetate) provided tert-butyl 8-(2-naphthylsulfonyl)-3,4-dihydrobenzofuro[3,2-c]pyridine-2(1H)-carboxylate (450 mg, 85%) as an orange solid: $^1$H NMR (CDCl$_3$, 300 MHz) δ 8.58 (s, 1H), 8.14 (s, 1H), 8.02-7.82 (m, 5H), 7.66-7.56 (m, 2H), 7.50 (d, J=8.7 Hz, 1H), 4.57 (s, 2H), 3.82 (t, J=5.4 Hz, 2H), 2.90-2.80 (m, 2H), 1.50 (s, 9H).

Step B: The product of step A was deprotected using the procedure of Example 32, step B. Purification by flash column chromatography (SiO$_2$, 95:5 chloroform/methanol) provided 8-(2-naphthylsulfonyl)-1,2,3,4-tetrahydrobenzofuro[3,2-c]pyridine (210 mg, 60%) as a white solid: $^1$H NMR (CDCl$_3$, 300 MHz) δ 8.57 (d, J=0.6 Hz, 1H), 8.09 (d, J=1.8 Hz, 1H), 8.00-7.81 (m, 5H), 7.65-7.54 (m, 2H), 7.48 (d, J=8.7 Hz, 1H), 3.98 (t, J=2.1 Hz, 2H), 3.22 (t, J=5.7 Hz, 2H), 2.82-2.73 (m, 2H).

Step C: The product of step B (50 mg, 0.10 mmol) was converted to hydrochloride salt by dissolving in chloroform and treating with 1.25 M HCl in methanol. The reaction mixture was concentrated in vacuo to give 8-(2-naphthylsulfonyl)-1,2,3,4-tetrahydrobenzofuro[3,2-c]pyridine hydrochloride (52 mg, 95%, AUC HPLC>99%) as a white solid: mp 267-270° C.; $^1$H NMR (DMSO-d$_6$, 300 MHz) δ 9.58 (br s, 2H), 8.71 (s, 1H), 8.45 (d, J=1.8 Hz, 1H), 8.24-8.17 (m, 1H), 8.12 (d, J=8.7 Hz, 1H), 8.06-7.88 (m, 3H), 7.82 (d, J=8.7 Hz, 1H), 7.77-7.65 (m, 2H), 4.39 (s, 2H), 3.57-3.47 (m, 2H), 3.16-3.06 (m, 2H); ESI MS m/z 364 [M+H]$^+$.

Example 41

Preparation of 8-(1H-Indol-1-ylsulfonyl)-1,2,3,4-tetrahydrobenzofuro[3,2-c]pyridine hydrochloride

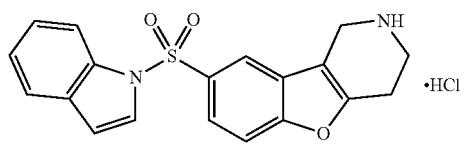 [SMILES: O=S(=O)(c1ccc2oc3c(c2c1)CNCC3)n1ccc2ccccc21 ; Cl]

Step A: n-Butyllithium (1.6M solution in hexanes, 0.85 mL, 1.36 mmol) was added to a solution of the product of Example 29, step B (0.40 g, 1.14 mmol) in THF (4 mL) at −78° C. over 10 min. The mixture was held at this temperature for a further 10 min and sulfur dioxide was bubbled in for 2 min. After holding for a further 20 min, the reaction was allowed to warm to room temperature. The mixture was held for 20 min, quenched with MeOH and concentrated. The residue was triturated with ether (30 mL) providing lithium 2-(tert-butoxycarbonyl)-1,2,3,4-tetrahydrobenzofuro[3,2-c]pyridine-8-sulfinate (472 mg) as a yellow solid which contained residual lithium n-butylsulfinate. $^1$H NMR (CDCl$_3$, 500 MHz) δ 8.16 (s, 1H), 7.96 (dd, J=8.8, 2.0 Hz, 1H), 7.62 (d, J=8.9 Hz, 1H), 4.61 (br s, 2H), 3.87 (br s, 2H), 2.92 (br s, 2H), 1.52 (s, 9H).

Step B: N-Chlorosuccinimide (220 mg, 1.65 mmol) was added to a suspension of the product of step A (472 mg) in CH$_2$Cl$_2$ (5 mL) at 0° C. over 2 min. The reaction was then allowed to warm to room temperature and held for 3 h. The mixture was diluted with CH$_2$Cl$_2$ (20 mL) and filtered. The filtrates were concentrated and purified by flash column chromatography (silica gel, hexane/ethyl acetate, 100:0 to 40:60) providing tert-butyl 8-(chlorosulfonyl)-3,4-dihydrobenzofuro[3,2-c]pyridine-2(1H)-carboxylate (300 mg, 71%) as a white foamy solid. $^1$H NMR (CDCl$_3$, 500 MHz) δ 8.16 (s, 1H), 7.96 (dd, J=8.8, 2.0 Hz, 1H), 7.62 (d, J=8.9 Hz, 1H), 4.61 (br s, 2H), 3.87 (br s, 2H), 2.92 (br s, 2H), 1.52 (s, 9H).

Step C: Sodium hydride (60% suspension in mineral oil, 19 mg, 0.484 mmol) was added to a solution of indole (42 mg, 0.363 mmol) in THF (1.5 mL) under N$_2$ at room temperature, and the reaction stirred for 30 min. The product of step B (90 mg, 0.242 mmol) was then added and the reaction held for 2 h. It was quenched with H$_2$O (10 mL), diluted with ether (10 mL) and the organic phase removed. The aqueous phase was extracted with ether (2×10 mL) and the combined organic phases dried over Na$_2$SO$_2$ and concentrated. Purification by combiflash (silica gel, hexane/ethyl acetate, 100:0 to 40:60) provided tert-butyl 8-(1H-indol-1-yl-sulfonyl)-3,4-dihydrobenzofuro[3,2-c]pyridine-2(1H)-carboxylate (28 mg, 25%) as a clear oil. $^1$H NMR (CDCl$_3$, 300 MHz) δ 8.02 (d, J=9.0 Hz, 2H), 7.76 (dd, J=9.1, 2.2 Hz, 1H), 7.60 (d, J=4.0 Hz, 1H), 7.51 (d, J=8.4 Hz, 1H), 7.42 (d, J=8.7 Hz, 1H), 7.33 (t, J=1.4 Hz, 1H), 7.28 (t, J=1.4 Hz, 1H), 6.66 (d, J=3.6 Hz, 1H), 4.53 (br s, 2H), 3.80 (t, J=6.2 Hz, 2H), 2.82 (t, J=6.2 Hz, 2H), 1.52 (s, 9H).

Step D: The product of step C (28 mg, 0.06 mmol) was Boc deprotected and converted to the hydrochloride salt following the procedure of Example 29, step D to provide 8-(1H-indol-1-ylsulfonyl)-1,2,3,4-tetrahydrobenzofuro[3,2-c]pyridine hydrochloride (24 mg, 100%) as a white solid: mp 283-286° C.; $^1$H NMR (DMSO-$d_6$, 300 MHz) δ 9.44 (s, 2H), 9.15 (br s, 1H), 8.51 (d, J=1.8 Hz, 1H), 7.99 (d, J=9.1 Hz, 1H), 7.89 (dd, J=8.8, 2.0 Hz, 1H), 7.80 (m, 1H), 7.59 (d, J=8.5 Hz, 1H), 7.31 (dt, J=3.9, 1.7 Hz, 1H), 7.22 (dt, J=3.7, 1.0 Hz, 1H), 6.84 (dd, J=3.7, 0.7 Hz, 1H), 4.36 (br s, 2H), 3.51 (t, J=6.1 Hz, 2H), 3.08 (t, J=6.0 Hz, 2H), ESI MS m/z 353 [M+H]$^+$; HPLC (Method A)>99% (AUC), $t_R$=13.64 min.

Example 42

Preparation of 8-(6-fluoro-1H-indol-1-ylsulfonyl)-1,2,3,4-tetrahydrobenzofuro[3,2-c]pyridine hydrochloride

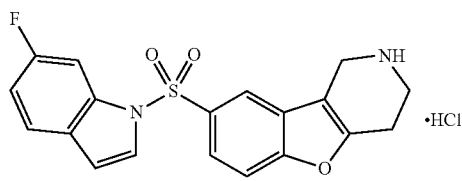 [SMILES: O=S(=O)(c1ccc2oc3c(c2c1)CNCC3)n1ccc2ccc(F)cc21 ; Cl]

Step A: The product of Example 41, step B was reacted with 6-fluoroindole following the procedure of Example 41, step C providing tert-butyl 8-(6-fluoro-1H-indol-1-ylsulfonyl)-3,4-dihydrobenzofuro[3,2-c]pyridine-2(1H)-carboxylate (63 mg, 55%) as a white foamy solid: $^1$H NMR (CDCl$_3$, 300 MHz) δ 8.02 (s, 1H), 7.75 (dd, J=9.6, 2.1 Hz, 2H), 7.58 (d, J=4.0 Hz, 1H), 7.44 (m, 2H), 6.96 (dt, J=4.5, 2.5 Hz, 1H), 6.63 (d, J=4.1 Hz, 1H), 4.55 (br s, 2H), 3.81 (br s, 2H), 2.84 (br s, 2H), 1.51 (s, 9H).

Step B: The product of step A was deprotected and converted to the hydrochloride salt following the procedure of Example 29, step D to provide 8-(6-fluoro-1H-indol-1-ylsulfonyl)-1,2,3,4-tetrahydrobenzofuro[3,2-c]pyridine hydrochloride (49 mg, 90%) as a white solid: mp 199-203° C.; $^1$H NMR (DMSO-$d_6$, 300 MHz) δ 9.38 (s, 2H), 8.59 (d, J=2.2 Hz, 1H), 7.95 (dd, J=8.8, 2.1 Hz, 1H), 7.78 (m, 3H), 7.62 (dd, J=8.8, 5.6 Hz, 1H), 7.12 (dt, J=4.8, 2.4 Hz, 1H), 6.85 (dd, J=3.7, 0.7 Hz, 1H), 4.37 (br s, 2H), 3.52 (t, J=6.0 Hz, 2H), 3.09 (t, J=6.1 Hz, 2H), ESI MS m/z 371 [M+H]$^+$; HPLC (Method A)>99% (AUC), $t_R$=13.94 min.

Example 43

Preparation of 8-(3-Methyl-1H-indol-1-ylsulfonyl)-1,2,3,4-tetrahydrobenzofuro[3,2-c]pyridine hydrochloride

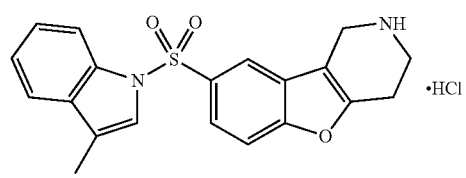 [SMILES: Cc1cn(S(=O)(=O)c2ccc3oc4c(c3c2)CNCC4)c2ccccc12 ; Cl]

Step A: The product of Example 41, step B was reacted with 3-methylindole following the procedure of Example 41, step C providing tert-butyl 8-(3-methyl-1H-indol-1-ylsulfonyl)-3,4-dihydrobenzofuro[3,2-c]pyridine-2(1H)-carboxylate (36 mg, 32%) as a clear oil: $^1$H NMR (CDCl$_3$, 300 MHz) δ 8.02 (m, 2H), 7.74 (d, J=8.7 Hz, 1H), 7.42 (t, J=8.4 Hz, 2H), 7.34 (s, 1H), 7.30 (dd, J=8.4, 1.3 Hz, 1H), 7.21 (dt, J=3.7, 1.0 Hz, 1H), 4.53 (br s, 2H), 3.80 (br s, 2H), 2.84 (br s, 2H), 2.22 (s, 3H), 1.51 (s, 9H).

Step B: The product of step A was deprotected and converted to the hydrochloride salt following the procedure of Example 29, step D to provide 8-(3-methyl-1H-indol-1-ylsulfonyl)-1,2,3,4-tetrahydrobenzofuro[3,2-c]pyridine hydrochloride (30 mg, 97%) as a white solid: mp 293-296° C.; $^1$H NMR (DMSO-$d_6$, 300 MHz) δ 9.40 (s, 2H), 8.46 (s, 1H), 7.97 (d, J=7.7 Hz, 1H), 7.83 (d, J=9.9 Hz, 1H), 7.79 (d, J=7.7 Hz, 1H), 7.59 (s, 1H), 7.52 (d, J=7.7 Hz, 1H), 7.34 (t, J=8.3 Hz, 1H), 7.25 (t, J=7.5 Hz, 1H), 4.36 (br s, 2H), 3.51 (t, J=5.5 Hz, 2H), 3.07 (t, J=5.8 Hz, 2H), ESI MS m/z 367 [M+H]$^+$; HPLC (Method A)>99% (AUC), $t_R$=14.19 min.

Example 44

Preparation of 6-Chloro-8-(phenylsulfonyl)-1,2,3,4-tetrahydrobenzofuro[3,2-c]pyridine hydrochloride

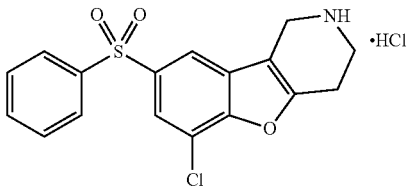 [SMILES: O=S(=O)(c1ccccc1)c1cc(Cl)c2oc3c(c2c1)CNCC3 ; Cl]

Step A: 4-bromo-2-chlorophenol (110 g, 0.53 mol) was reacted with hydroxylamine-O-sulfonic acid (15 g, 0.13 mol) using the procedure of Example 29, step A to give O-(2-chloro-4-bromophenyl)hydroxylamine hydrochloride (13.4 g, 28%) as a light brown solid: $^1$H NMR (DMSO, 400 MHz) δ 7.61 (d, J=2.0 Hz, 1H), 7.48 (d, J=2.4 Hz, 1H), 7.47 (s, 1H), 5.81 (br s, 3H).

Step B: The product of step A was reacted with tert-butyl 4-oxopiperidine-1-carboxylate then Boc protected following the procedure of Example 29, step B. Purification by flash column chromatography (SiO$_2$, 95:5 hexanes/ethyl acetate) provided tert-butyl 6-chloro-8-bromo-3,4-dihydrobenzofuro

[3,2-c]pyridine-2(1H)-carboxylate (3.9 g, 20%) as a pink solid: ¹H NMR (CDCl₃, 300 MHz) δ 7.44 (d, J=1.5 Hz, 1H), 7.38 (d, J=1.5 Hz, 1H), 4.50 (s, 2H), 3.88 (t, J=5.4 Hz, 2H), 2.89 (t, J=5.4 Hz, 2H), 1.49 (s, 9H).

Step C: The product of step B was coupled with sodium benzenesulfinate using the procedure of Example 29, step C. Purification by flash column chromatography (SiO₂, 3:2 hexane/ethyl acetate) provided tert-butyl 6-chloro-8-phenylsulfonyl-3,4-dihydrobenzofuro[3,2-c]pyridine-2(1H)-carboxylate (750 mg, 43%) as an off-white solid: ¹H NMR (CDCl₃, 300 MHz) δ 7.98-7.94 (m, 3H), 7.84 (d, J=1.2 Hz, 1H), 7.58-7.49 (m, 3H), 4.56 (s, 2H), 3.83 (t, J=5.7 Hz, 2H), 2.90 (br s, 2H), 1.49 (s, 9H).

Step D: The product of step C was deprotected and converted to the hydrochloride salt following the procedure of Example 29, step D to provide 6-chloro-8-(phenylsulfonyl)-1,2,3,4-tetrahydrobenzofuro[3,2-c]pyridine hydrochloride (357 mg, 62%) as a white solid: mp 290-294° C.; ¹H NMR (DMSO-d₆, 300 MHz) δ 9.41 (s, 2H), 8.41 (s, 1H), 8.04-8.01 (m, 3H), 7.73-7.61 (m, 3H), 4.39 (s, 2H), 3.52 (t, J=5.7 Hz, 2H), 3.15 (m, 2H); ESI MS m/z 348 [M+H]⁺.

Example 45

Preparation of 6-Chloro-8-(3-trifluoromethylphenylsulfonyl)-1,2,3,4-tetrahydrobenzofuro[3,2-c]pyridine hydrochloride

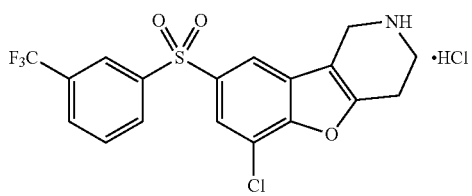 [SMILES: O=S(=O)(c1cccc(C(F)(F)F)c1)c1cc(Cl)c2oc3c(c2c1)CNCC3 ; Cl]

Step A: The product of Example 44, step B was coupled with sodium 3-trifluoromethylbenzenesulfinate using the procedure of Example 29, step C. Purification by flash column chromatography (SiO₂, 3:2 hexane/ethyl acetate) provided tert-butyl 6-chloro-8-(3-trifluoromethylphenylsulfonyl)-3,4-dihydrobenzofuro[3,2-c]pyridine-2(1H)-carboxylate (130 mg, 33%) as an off-white solid: ¹H NMR (CDCl₃, 400 MHz) δ 8.26 (s, 1H), 8.15 (d, J=8.0 Hz, 1H), 7.94-8.06 (m, 1H), 7.86-7.81 (m, 2H), 7.73-7.63 (m, 1H), 4.58 (m, 2H), 3.84 (m, 2H), 2.92 (m, 2H), 1.48 (s, 9H).

Step B: To the product of step A (130 mg, 0.25 mmol) in dichloromethane, was added trifluoroacetic acid (0.48 mL) at 0° C. After stirring for 3 h, the reaction mixture was concentrated in vacuo, treated with saturated sodium bicarbonate solution and extracted with dichloromethane. The organic extract was dried over sodium sulfate, and concentrated in vacuo. The residue was purified by column chromatography in (SiO₂, 90:10 dichloromethane/methanol) and the free base treated directly with 1.25M HCl in methanol to give 6-chloro-8-(3-trifluoromethylphenylsulfonyl)-1,2,3,4-tetrahydrobenzofuro[3,2-c]pyridine hydrochloride (28 mg, 27%) as a white solid: ¹H NMR (DMSO-d₆, 300 MHz) δ 9.51 (s, 2H), 8.51 (d, J=1.5 Hz, 1H), 8.37-8.34 (m, 2H), 8.18 (d, J=1.5 Hz, 1H), 8.10 (d, J=7.8 Hz, 1H), 7.89 (t, J=7.8 Hz, 1H), 4.38 (s, 2H), 3.52 (t, J=5.2 Hz, 2H), 3.17 (t, J=5.4 Hz, 2H); APCI MS m/z 416 [M+H]⁺.

Example 46

Preparation of 6-Chloro-8-(3-chlorophenylsulfonyl)-1,2,3,4-tetrahydrobenzofuro[3,2-c]pyridine hydrochloride

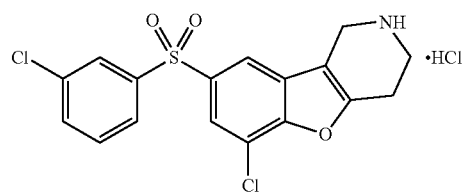 [SMILES: O=S(=O)(c1cccc(Cl)c1)c1cc(Cl)c2oc3c(c2c1)CNCC3 ; Cl]

Step A: The product of Example 44, step B was coupled with sodium 3-chlorobenzenesulfinate using the procedure of Example 29, step C. Purification by flash column chromatography (SiO₂, 3:2 hexane/ethyl acetate) provided tert-butyl 6-chloro-8-(3-chlororophenylsulfonyl)-3,4-dihydrobenzofuro[3,2-c]pyridine-2(1H)-carboxylate (130 mg, 35%) as an off-white solid: ¹H NMR (CDCl₃, 300 MHz) δ 8.01-7.95 (m, 1H), 7.94-7.91 (m, 1H), 7.86-7.81 (m, 2H), 7.56-7.52 (m, 1H), 7.49-7.44 (m, 1H), 4.58 (s, 2H), 3.84 (m, 2H), 2.91 (m, 2H), 1.48 (s, 9H).

Step B: The product of step A was deprotected following the procedure of Example 45, step B to give 6-chloro-8-(3-chlorophenylsulfonyl)-1,2,3,4-tetrahydrobenzofuro[3,2-c]pyridine hydrochloride (50 mg, 50%) as a white solid: ¹H NMR (DMSO-d₆, 400 MHz) δ 9.52 (s, 2H), 8.46 (d, J=1.6 Hz, 1H), 8.18-8.13 (m, 2H), 8.01-7.99 (m, 1H), 7.79-7.77 (m, 1H), 7.66 (t, J=8.0 Hz, 1H), 4.39 (s, 2H), 3.53 (t, J=5.6 Hz, 2H), 3.16 (t, J=5.6 Hz, 2H); APCI MS m/z 382 [M+H]⁺.

Example 47

Preparation of 6-Chloro-8-(3-fluorophenylsulfonyl)-1,2,3,4-tetrahydrobenzofuro[3,2-c]pyridine hydrochloride

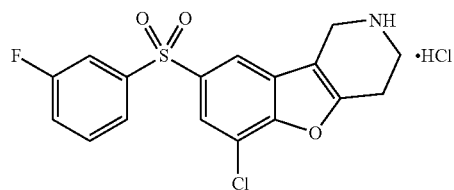 [SMILES: O=S(=O)(c1cccc(F)c1)c1cc(Cl)c2oc3c(c2c1)CNCC3 ; Cl]

Step A: Sodium 3-fluorobenzenesulfinate was coupled with the product of Example 44, step B following the procedure of Example 29, step C. The crude product was purified by flash column chromatography (SiO₂, 3:2 hexanes/ethyl acetate) to give tert-butyl 6-chloro-8-(3-fluorophenylsulfonyl)-3,4-dihydrobenzofuro[3,2-c]pyridine-2(1H)-carboxylate (100 mg, 41%) as an off-white solid: ¹H NMR (CDCl₃, 300 MHz) δ 7.97 (s, 1H), 7.84-7.83 (d, J=1.5 Hz, 1H), 7.78-7.33 (m, 1H), 7.67-7.63 (m, 1H), 7.56-7.47 (m, 1H), 7.30-7.24 (m, 1H), 4.57 (s, 2H), 3.84 (t, J=5.4 Hz, 2H), 2.91 (t, J=5.4 Hz, 2H), 1.50 (s, 9H).

Step B: The product of step A was deprotected following the procedure of Example 45, step B to give 6-chloro-8-(3-fluorophenylsulfonyl)-1,2,3,4-tetrahydrobenzofuro[3,2-c]pyridine hydrochloride (40 mg, 48%) as a white solid: mp 276-278° C.; ¹H NMR (DMSO-d₆, 400 MHz) δ 9.26 (s, 2H), 8.44 (d, J=2.0 Hz, 1H), 8.14 (d, J=1.6 Hz, 1H), 7.94-7.86 (m, 2H), 7.72-7.67 (m, 1H), 7.60-7.58 (m, 1H), 4.42 (s, 2H), 3.56 (t, J=6.0 Hz, 2H), 3.16 (t, J=6.0 Hz, 2H); APCI MS m/z 366 [M+H]⁺.

Example 48

Preparation of 6-Chloro-8-(3-cyanophenylsulfonyl)-1,2,3,4-tetrahydrobenzofuro[3,2-c]pyridine hydrochloride

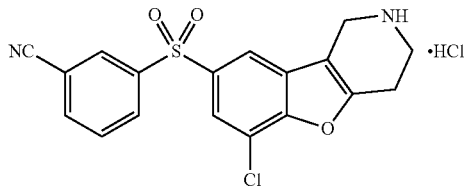 [SMILES: N#Cc1cccc(S(=O)(=O)c2cc(Cl)c3oc4c(c3c2)CNCC4)c1 ; Cl]

Step A: Sodium 3-cyanobenzenesulfinate was coupled with the product of Example 44, step B following the procedure of Example 29, step C. The crude product was purified by flash column chromatography (SiO₂, 3:2 hexanes/ethyl acetate) to give tert-butyl 6-chloro-8-(3-cyanophenylsulfonyl)-3,4-dihydrobenzofuro[3,2-c]pyridine-2(1H)-carboxylate (30 mg, 12%) as an off-white solid: ¹H NMR (CDCl₃, 300 MHz) δ 8.22-8.17 (m, 2H), 7.98 (s, 1H), 7.86-7.83 (m, 2H), 7.70-7.64 (m, 1H), 4.59 (s, 2H), 3.85 (t, J=5.7 Hz, 2H), 2.92 (t, J=5.7 Hz, 2H), 1.48 (s, 9H).

Step B: The product of step A was deprotected following the procedure of Example 45, step B to give 6-chloro-8-(3-cyanophenylsulfonyl)-1,2,3,4-tetrahydrobenzofuro[3,2-c]pyridine hydrochloride (15 mg, 50%) as a white solid: mp 272-274° C.; ¹H NMR (DMSO-d₆, 400 MHz) δ 9.42 (s, 2H), 8.57 (t, J=1.6 Hz, 1H), 8.46 (d, J=1.6 Hz, 1H), 8.33 (ddd, J=8.0, 2.0, 1.2 Hz, 1H), 8.17 (dt, J=8.0, 1.2 Hz, 1H), 8.15 (d, J=2.0 Hz, 1H), 7.84 (t, J=8.0 Hz, 1H), 4.38 (s, 2H), 3.53 (t, J=5.6 Hz, 2H), 3.16 (t, J=5.6 Hz, 2H); APCI MS m/z 373 [M+H]⁺.

Example 49

Preparation of 6-Chloro-8-(4-chlorophenylsulfonyl)-1,2,3,4-tetrahydrobenzofuro[3,2-c]pyridine hydrochloride

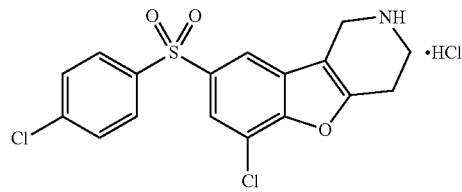 [SMILES: O=S(=O)(c1ccc(Cl)cc1)c1cc(Cl)c2oc3c(c2c1)CNCC3 ; Cl]

Step A: Sodium 4-chlorobenzenesulfinate was coupled with the product of Example 44, step B following the procedure of Example 29, step C. The crude product was purified by flash column chromatography (SiO₂, 3:2 hexanes/ethyl acetate) to give tert-butyl 6-chloro-8-(4-chlorophenylsulfonyl)-3,4-dihydrobenzofuro[3,2-c]pyridine-2(1H)-carboxylate (120 mg, 48%) as an off-white solid: ¹H NMR (CDCl₃, 300 MHz) δ 7.95 (s, 1H), 7.90-7.89 (m, 1H), 7.88-7.87 (m, 1H), 7.82-7.81 (m, 1H), 7.51-7.50 (m, 1H), 7.48-7.47 (m, 1H), 4.56 (s, 2H), 3.84 (t, J=5.4 Hz, 2H), 2.91 (t, J=5.4 Hz, 2H), 1.48 (s, 9H).

Step B: The product of step A was deprotected and converted to the hydrochloride salt following the procedure of Example 29, step D to provide 6-chloro-8-(4-chlorophenylsulfonyl)-1,2,3,4-tetrahydrobenzofuro[3,2-c]pyridine hydrochloride (80 mg, 76%) as an off-white solid: mp 282-284° C.; ¹H NMR (DMSO-d₆, 300 MHz) δ 9.54 (s, 2H), 8.41 (d, J=1.8 Hz, 1H), 8.05-8.01 (m, 3H), 7.73-7.69 (m, 2H), 4.37 (s, 2H), 3.52 (t, J=5.7 Hz, 2H), 3.17 (t, J=5.1 Hz, 2H); APCI MS m/z 382 [M+H]⁺.

Example 50

Preparation of 6-Chloro-8-(1-methyl-1H-indol-3-ylsulfonyl)-1,2,3,4-tetrahydrobenzofuro[3,2-c]pyridine

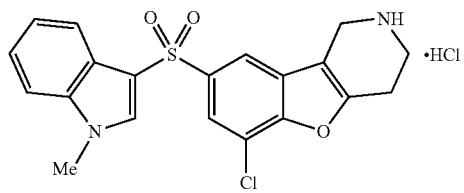 [SMILES: Cn1cc(S(=O)(=O)c2cc(Cl)c3oc4c(c3c2)CNCC4)c2ccccc21 ; Cl]

Step A: To a solution of the product of Example 44, step B (200 mg, 0.53 mmol) and 3-iodo-1-methyl-1H-indole (1.63 mg, 0.63 mmol) in anhydrous DMF (4 mL), was added Cu (I) triflate benzene complex (200 mg, 0.39 mmol). The reaction mixture was stirred at 65-70° C. for 4 h. After cooling to ambient temperature, the reaction mixture was quenched with water and extracted with ethyl acetate. The organic layer was washed with brine, dried over sodium sulfate, filtered and concentrated in vacuo to give the crude product which was purified by flash column chromatography (SiO₂, 5:1 hexanes/ethyl acetate) to give tert-butyl 6-chloro-8-(1-methyl-1H-indol-3-ylsulfonyl)-3,4-dihydrobenzofuro[3,2-c]pyridine-2 (1H)-carboxylate (20 mg, 7%) as an off-white solid: ¹H NMR (CDCl₃, 300 MHz) δ 8.07-8.03 (m, 1H), 7.93-7.91 (m, 2H), 7.83 (s, 1H), 7.38-7.27 (m, 3H), 4.55 (s, 2H), 3.85 (s, 3H), 3.64-3.61 (m, 2H), 2.85-2.81 (m, 2H), 1.50 (s, 9H).

Step B: The product of step A was deprotected and converted to the hydrochloride salt following the procedure of Example 29, step D to provide 6-chloro-8-(1-methyl-1H-indol-3-ylsulfonyl)-1,2,3,4-tetrahydrobenzofuro[3,2-c]pyridine (17 mg, 100%) as an off-white solid: mp 262-264° C.; ¹H NMR (DMSO-d₆, 300 MHz) δ 9.52 (s, 2H), 8.42 (d, J=1.5 Hz, 1H), 8.29 (s, 1H), 7.94 (d, J=1.8 Hz, 1H), 7.85-7.83 (m, 1H), 7.58 (d, J=8.1 Hz, 1H), 7.34-7.22 (m, 2H), 4.41 (s, 2H), 3.53 (t, J=5.7 Hz, 2H), 3.16 (t, J=5.7 Hz, 2H); APCI MS m/z 401 [M+H]⁺.

Example 51

Preparation of 8-(1H-Indol-1-ylsulfonyl)-6-chloro-1,2,3,4-tetrahydrobenzofuro[3,2-c]pyridine hydrochloride

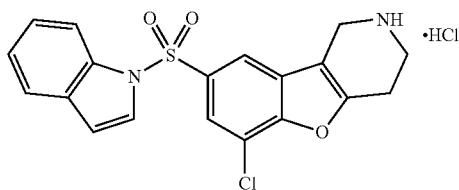 [SMILES: O=S(=O)(c1cc(Cl)c2oc3c(c2c1)CNCC3)n1ccc2ccccc21 ; Cl]

Step A: The product of Example 44, step B (1.0 g, 2.59 mmol) was sulfonylated using the procedure of Example 41, step A to provide the crude product lithium 2-(tert-butoxycarbonyl)-6-chloro-1,2,3,4-tetrahydrobenzofuro[3,2-c]pyridine-8-sulfinate (1.07 g) as a yellow solid which contained residual lithium n-butylsulfinate.

Step B: The product of step A (200 mg, 0.53 mmol) was converted to the sulfonyl chloride using the procedure of Example 41, step B to provide tert-butyl 6-chloro-8-(chlorosulfonyl)-3,4-dihydrobenzofuro[3,2-c]pyridine-2(1H)-carboxylate (65 mg, 30%) as a pale yellow solid: ¹H NMR (CDCl₃, 400 MHz) δ 8.06-8.05 (m, 1H), 7.98 (d, J=2.0 Hz, 1H), 4.60 (s, 2H), 3.88 (m, 2H), 2.96 (m, 2H), 1.50 (s, 9H).

Step C: The product of step B and indole were reacted using the procedure of Example 41, step C to provide tert-butyl 8-(1H-indol-1-ylsulfonyl)-6-chloro-3,4-dihydrobenzofuro[3,2-c]pyridine-2(1H)-carboxylate (35 mg, 45%) as an off-white solid: ¹H NMR (CDCl₃, 300 MHz) δ 8.00 (d, J=8.1 Hz, 1H), 7.89 (s, 1H), 7.73 (d, J=1.5 Hz, 1H), 7.58 (d, J=3.6 Hz, 1H), 7.52 (d, J=7.8 Hz, 1H), 7.36-7.30 (m, 1H), 7.25-7.20 (m, 1H), 6.69-6.68 (m, 1H), 4.52 (s, 2H), 3.80 (t, J=5.4 Hz, 2H), 2.88 (t, J=5.1 Hz, 2H), 1.50 (s, 9H).

Step D: The product of step C was deprotected and converted to the hydrochloride salt following the procedure of Example 29, step D to provide 8-(1H-indol-1-ylsulfonyl)-6-chloro-1,2,3,4-tetrahydrobenzofuro[3,2-c]pyridine hydrochloride (28 mg, 98%) as an off-white solid: ¹H NMR (DMSO-d6, 400 MHz) δ 9.60 (s, 2H), 8.53 (d, J=1.6 Hz, 1H), 8.05 (d, J=2.0 Hz, 1H), 8.02 (dd, J=8.2, 0.4 Hz, 1H), 7.88 (d, J=3.6 Hz, 1H), 7.61-7.59 (m, 1H), 7.37-7.33 (m, 1H), 7.27- 7.23 (m, 1H), 6.87 (dd, J=3.8, 0.8 Hz, 1H), 4.36 (s, 2H), 3.51 (t, J=6.0 Hz, 2H), 3.13 (t, J=5.6 Hz, 2H); APCI MS m/z 387 [M+H]+.

Example 52

Preparation of 6-Fluoro-8-(phenylsulfonyl)-1,2,3,4-tetrahydrobenzofuro[3,2-c]pyridine hydrochloride

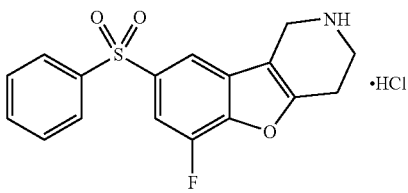 [SMILES: O=S(=O)(c1ccccc1)c1cc(F)c2oc3c(c2c1)CNCC3 ; Cl]

Step A: 4-Bromo-2-fluorophenol (20.0 g, 104.7 mmol) was reacted with hydroxylamine-O-sulfonic acid (2.9 g, 26.1 mmol) following the procedure of Example 29, step A to give O-(2-fluoro-4-bromophenyl)hydroxylamine hydrochloride (2.5 g, 39%) as an off-white solid: ¹H NMR (DMSO, 300 MHz) δ 7.59-7.41 (m, 2H), 7.38-7.34 (m, 1H), 5.97 (br s, 3H).

Step B: The product of step A was reacted with tert-butyl 4-oxopiperidine-1-carboxylate then Boc protected following the procedure of Example 29, step B. Purification by flash column chromatography (SiO₂, 9:1 hexanes/ethyl acetate) provided tert-butyl 6-fluoro-8-bromo-3,4-dihydrobenzofuro[3,2-c]pyridine-2(1H)-carboxylate (320 mg, 14%) as an off-white solid: ¹H NMR (CDCl₃, 400 MHz) δ 7.33 (s, 1H), 7.16 (dd, J=10.0, 1.6 Hz, 1H), 4.51 (br s, 2H), 3.83 (br s, 2H), 2.88 (br s, 2H), 1.51 (s, 9H).

Step C: The product of step B was coupled with sodium benzenesulfinate using the procedure of Example 29, step C. Purification by flash column chromatography (SiO₂, 7:3 hexane/ethyl acetate) provided tert-butyl 6-fluoro-8-phenylsulfonyl-3,4-dihydrobenzofuro[3,2-c]pyridine-2(1H)-carboxylate (141 mg, 57%) as a light-yellow solid: ¹H NMR (CDCl₃, 300 MHz) δ 7.97-7.94 (m, 2H), 7.88 (br s, 1H), 7.61-7.47 (m, 4H), 4.57 (s, 2H), 3.84 (t, J=5.4 Hz, 2H), 2.89 (br s, 2H), 1.51 (s, 9H).

Step D: The product of step C was deprotected and converted to the hydrochloride salt following the procedure of Example 29, step D to provide 6-fluoro-8-(phenylsulfonyl)-1,2,3,4-tetrahydrobenzofuro[3,2-c]pyridine hydrochloride (100 mg, AUC HPLC>99%) as an off-white solid: mp 232-250° C.; ¹H NMR (DMSO-d₆, 300 MHz) δ 9.63 (s, 2H), 8.29 (d, J=1.5 Hz, 1H), 8.03-7.99 (m, 2H), 7.90 (dd, J=10.2, 1.5

Hz, 1H), 7.70-7.60 (m, 3H), 4.39 (s, 2H), 3.53 (t, J=6.0 Hz, 2H), 3.15 (t, J=5.7 Hz, 2H); ESI MS m/z 332 [M+H]+.

Example 53

Preparation of 6-Methyl-8-(phenylsulfonyl)-1,2,3,4-tetrahydrobenzofuro[3,2-c]pyridine hydrochloride

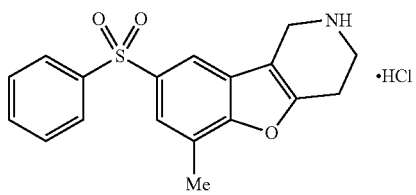 [SMILES: Cc1cc(S(=O)(=O)c2ccccc2)cc2c3c(oc12)CCNC3 ; Cl]

Step A: A solution of the product of Example 44, step C (85 mg, 0.189 mmol), trimethylboraxine (0.026 mL, 0.189 mmol), potassium carbonate (78 mg, 0.567 mmol) and tetrakis-(triphenylphosphine)palladium (21.8 mg, 0.0189 mmol) in water/1,4-dioxane (1:10, 0.55 mL) was heated to 110° C. for 5 h and then stirred at ambient temperature for 15 h. The reaction mixture was then filtered through a celite bed and concentrated in vacuo to afford the crude product which was then purified by column chromatography (SiO$_2$, 8:2 hexanes/ethyl acetate) to provide tert-butyl 6-methyl-8-phenylsulfonyl-3,4-dihydrobenzofuro[3,2-c]pyridine-2(1H)-carboxylate (43 mg, 53%): $^1$H NMR (CDCl$_3$, 300 MHz) δ 7.98-7.94 (m, 3H), 7.63 (s, 1H), 7.54-7.46 (m, 3H), 4.56 (s, 2H), 3.83 (br s, 2H), 2.86 (br s, 2H), 2.51 (s, 3H), 1.51 (s, 9H).

Step B: The product of step A was deprotected and converted to the hydrochloride salt following the procedure of Example 29, step D to provide 6-methyl-8-(phenylsulfonyl)-1,2,3,4-tetrahydrobenzofuro[3,2-c]pyridine hydrochloride (14 mg, 39%, AUC HPLC>99%) as an off-white solid: $^1$H NMR (CD$_3$OD, 400 MHz) δ 8.08 (d, J=1.5 Hz, 1H), 7.99-7.96 (m, 2H), 7.75 (d, J=0.9 Hz, 1H), 7.64-7.54 (m, 3H), 4.45 (t, J=1.6 Hz, 2H), 3.67 (t, J=6.4 Hz, 2H), 3.19 (t, J=2.0 Hz, 2H), 2.55 (s, 3H); APCI MS m/z 328 [M+H]+.

Example 54

Preparation of 6-Methoxy-8-(phenylsulfonyl)-1,2,3,4-tetrahydrobenzofuro[3,2-c]pyridine hydrochloride

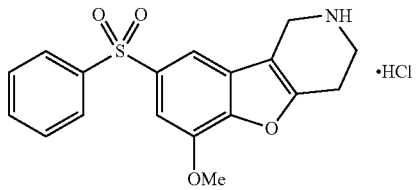 [SMILES: COc1cc(S(=O)(=O)c2ccccc2)cc2c3c(oc12)CCNC3 ; Cl]

Step A: A mixture of the product of Example 44, step C (1.41 g, 3.14 mmol), di-palladium-tris(dibenzylideneacetone) (575 mg, 0.62 mmol), potassium hydroxide (387 mg, 6.91 mmol) and 2-(di-tert-butylphosphino)-2',4',6'-triisopropyl-3,4,5,6-tetramethyl-1,1'-biphenyl (121 mg, 0.25 mmol) in water (14 mL) and 1,4-dioxane (14 mL) was heated to 110° C. for 24 h. After cooling to ambient temperature, the reaction mixture was neutralized with 1N aqueous HCl, filtered through celite bed and extracted with ethyl acetate (4×30 mL). The combined organic extracts were washed with brine, dried over Na$_2$SO$_4$ and concentrated in vacuo to give the crude product which was purified by column chromatography (SiO$_2$, 7:3 hexanes/ethyl acetate) providing tert-butyl 6-hydroxy-8-phenylsulfonyl-3,4-dihydrobenzofuro[3,2-c]pyridine-2(1H)-carboxylate (470 mg, 34%): $^1$H NMR (CDCl$_3$, 300 MHz) δ 7.93-7.90 (m, 2H), 7.62 (br s, 1H), 7.55-7.43 (m, 3H), 7.39 (d, J=1.8 Hz, 1H), 4.54 (s, 2H), 3.81 (t, J=5.4 Hz, 2H), 2.83 (t, J=5.7 Hz, 2H), 1.51 (s, 9H).

Step B: To a solution of the product of step A (470 mg, 1.06 mmol) in acetone (45 mL) under a nitrogen atmosphere was added potassium carbonate (1.34 g, 9.7 mmol) and dimethylsulfate (0.22 mL, 2.11 mmol). The reaction mixture was refluxed for 2 h, cooled to ambient temperature and filtered. The filtrate was concentrated in vacuo and the residue purified by column chromatography (SiO$_2$, 8:2, hexanes/ethyl acetate) to provide tert-butyl 6-methoxy-8-phenylsulfonyl-3,4-dihydrobenzofuro[3,2-c]pyridine-2(1H)-carboxylate (400 mg, 82%) as an off-white solid: $^1$H NMR (CDCl$_3$, 400 MHz) δ 7.96-7.94 (m, 2H), 7.71 (br s, 1H), 7.58-7.48 (m, 3H), 7.33 (s, 1H), 4.55 (s, 2H), 4.04 (s, 3H), 3.82 (br s, 2H), 2.87 (br s, 2H), 1.50 (s, 9H).

Step C: The product of step B was deprotected and converted to the hydrochloride salt following the procedure of Example 29, step D to provide 6-methoxy-8-(phenylsulfonyl)-1,2,3,4-tetrahydrobenzofuro[3,2-c]pyridine hydrochloride (303 mg, AUC HPLC>99%) as an off-white solid: mp 197-202° C.; $^1$H NMR (DMSO-d$_6$, 300 MHz) δ 9.55 (s, 2H), 8.02-7.98 (m, 3H), 7.68-7.58 (m, 3H), 7.45 (d, J=1.5 Hz, 1H), 4.36 (s, 2H), 4.02 (s, 3H), 3.51 (t, J=6.0 Hz, 2H), 3.10 (t, J=5.4 Hz, 2H); ESI MS m/z 344 [M+H]+.

Example 55

Preparation of 2-(3-Trifluoromethylphenyl)sulfonyl-6,7,8,9,10-pentahydro-7,10-epiminocyclohepta[b]benzofuran hydrochloride

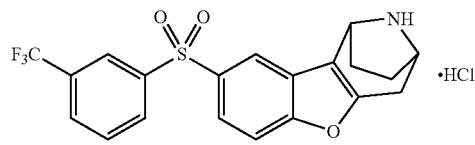 [SMILES: O=S(=O)(c1cccc(C(F)(F)F)c1)c1ccc2oc3c(c2c1)C1CCC(C3)N1 ; Cl]

Step A: O-(4-Bromophenyl)hydroxylamine (2.0 g, 8.9 mmol) and nortropinone hydrochloride (2.7 g, 16.7 mmol) were dissolved in a mixture of HOAc (7.2 mL) and conc. H$_2$SO$_4$ (0.8 mL) and the reaction heated to 120° C. for 18 h. The mixture was concentrated providing the crude intermediate 2-bromo-6,7,8,9,10-pentahydro-7,10-epiminocyclohepta[b]benzofuran. This was suspended in H$_2$O (35 mL) and K$_2$CO$_3$ added until pH neutral. IPA (20 mL) was added followed by Boc anhydride (3.69 g, 16.9 mmol) and the reaction stirred at room temperature for 1 h. The resultant suspension was filtered and the solids washed with H$_2$O. These were then dissolved in CH$_2$Cl$_2$, dried over Na$_2$SO$_3$ and concentrated providing tert-butyl 2-bromo-6,7,8,9,10-pentahydro-7,10-epiminocyclohepta[b]benzofuran-carboxylate (1.5 g, 45%) as beige foam: $^1$H NMR (CDCl$_3$, 300 MHz) δ 7.58 (d, J=1.6 Hz, 1H), 7.29 (m, 2H), 5.10 (d, J=26 Hz, 1H), 4.65 (d, J=29 Hz, 1H), 3.44 (br s, 1H), 2.53 (d, J=17 Hz, 1H), 2.34 (m, 1H), 2.18 (m, 1H), 1.96 (m, 1H), 1.65 (m, 1H), 1.41 (s, 9H).

Step B: The product of step A was coupled with sodium 3-trifluoromethylbenzenesulfinate using the procedure of Example 29, step C. Purification by flash column chromatography (SiO$_2$, 100:0 to 30:70 hexane/ethyl acetate) provided tert-butyl 2-(3-trifluoromethylphenyl)sulfonyl-6,7,8,9,10-pentahydro-7,10-epiminocyclohepta[b]benzofuran-carboxylate (118 mg, 59%) as a white solid: $^1$H NMR (CDCl$_3$, 300 MHz) δ 8.24 (s, 1H), 8.15 (d, J=7.4 Hz, 2H), 7.81 (d, J=8.4 Hz, 2H), 7.66 (t, J=8.0 Hz, 1H), 7.53 (d, J=8.9 Hz, 1H), 5.20 (br s, 1H), 4.68 (d, J=32 Hz, 1H), 3.40 (br s, 1H), 2.56 (d, J=16 Hz, 1H), 2.39 (m, 1H), 2.21 (m, 1H), 1.99 (m, 1H), 1.68 (m, 1H), 1.40 (s, 9H).

Step C: The product of step B was deprotected and converted to the hydrochloride salt following the procedure of Example 29, step D to provide 2-(3-trifluoromethylphenyl)sulfonyl-6,7,8,9,10-pentahydro-7,10-epiminocyclohepta[b]benzofuran hydrochloride (100 mg, 100%) as a white solid: mp 296-298° C.; $^1$H NMR (DMSO-d$_6$, 500 MHz) δ 9.62 (s, 1H), 9.29 (s, 1H), 8.60 (d, J=2.3 Hz, 1H), 8.30 (d, J=8.1 Hz, 1H), 8.26 (s, 1H), 8.10 (d, J=8.5 Hz, 1H), 8.00 (dd, J=8.8, 2.0 Hz, 1H), 7.89 (t, J=7.9 Hz, 1H), 7.85 (d, J=8.8 Hz, 1H), 5.34 (d, J=3.8 Hz, 1H), 4.50 (s, 1H), 3.43 (dd, J=18, 4.7 Hz, 1H), 3.01 (d, J=17 Hz, 1H), 2.26 (m, 3H), 1.87 (m, 1H); ESI MS m/z 408 [M+H]$^+$; HPLC (Method A)>99% (AUC), $t_R$=13.72 min.

Example 56

Preparation of 2-(3-Chlorophenyl)sulfonyl-6,7,8,9,10-pentahydro-7,10-epiminocyclohepta[b]benzofuran hydrochloride

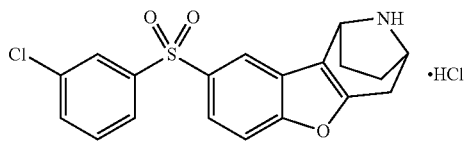 [SMILES: O=S(=O)(c1cccc(Cl)c1)c1ccc2oc3c(c2c1)C1CCC(C3)N1 ; Cl]

Step A: The product of Example 55, step A (150 mg, 0.397 mmol) was coupled with sodium 3-chlorobenzenesulfinate following the procedure of Example 29, step C. Purification by flash column chromatography (silica gel, hexanes/EtOAc, 100:0 to 30:70) provided tert-butyl 2-(3-chlorophenyl)sulfonyl-6,7,8,9,10-pentahydro-7,10-epiminocyclohepta[b]benzofuran-carboxylate (122 mg, 65%) as a waxy white solid: $^1$H NMR (CDCl$_3$, 300 MHz) δ 8.12 (s, 1H), 7.94 (s, 1H), 7.85 (d, J=8.8 Hz, 1H), 7.80 (d, J=7.2 Hz, 1H), 7.51 (d, J=9.1 Hz, 2H), 7.44 (t, J=8.6 Hz, 1H), 5.18 (d, J=31 Hz, 1H), 4.68 (d, J=61 Hz, 1H), 3.42 (d, J=55 Hz, 1H), 2.56 (d, J=18 Hz, 1H), 2.37 (m, 1H), 2.22 (m, 1H), 2.01 (m, 1H), 1.69 (m, 1H), 1.42 (s, 9H).

Step B: The product of step A was deprotected and converted to the hydrochloride salt following the procedure of Example 29, step D to provide 2-(3-chlorophenyl)sulfonyl-6,7,8,9,10-pentahydro-7,10-epiminocyclohepta[b]benzofuran hydrochloride (87 mg, 88%) as a white solid: mp 285-288° C.; $^1$H NMR (DMSO-d$_6$, 500 MHz) δ 9.67 (s, 1H), 9.27 (s, 1H), 8.56 (d, J=1.9 Hz, 1H), 8.02 (t, J=1.9 Hz, 1H), 7.95 (m, 2H), 7.84 (d, J=8.8 Hz, 1H), 7.77 (m, 1H), 7.66 (t, J=7.9 Hz, 1H), 5.35 (d, J=3.2 Hz, 1H), 4.50 (t, J=5.5 Hz, 1H), 3.43 (dd, J=18, 4.7 Hz, 1H), 3.02 (d, J=17 Hz, 1H), 2.26 (m, 3H), 1.87 (m, 1H); ESI MS m/z 374 [M+H]$^+$; HPLC (Method A)=97.9% (AUC), $t_R$=13.20 min.

Example 57

Preparation of 2-(3-Fluorophenyl)sulfonyl-6,7,8,9,10-pentahydro-7,10-epiminocyclohepta[b]benzofuran hydrochloride

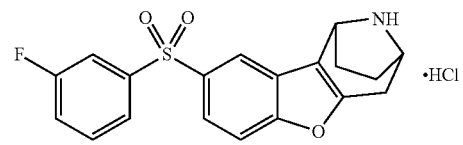 [SMILES: O=S(=O)(c1cccc(F)c1)c1ccc2oc3c(c2c1)C1CCC(C3)N1 ; Cl]

Step A: The product of Example 55, step A (150 mg, 0.397 mmol) was coupled with sodium 3-fluorobenzenesulfinate following the procedure of Example 29, step C. Purification by flash column chromatography (silica gel, hexanes/EtOAc, 100:0 to 30:70) provided tert-butyl 2-(3-fluorophenyl)sulfonyl-6,7,8,9,10-pentahydro-7,10-epiminocyclohepta[b]benzofuran-carboxylate (112 mg, 62%) as a waxy white solid. $^1$H NMR (CDCl$_3$, 300 MHz) δ 8.13 (s, 1H), 7.78 (m, 2H), 7.66 (td, J=8.0, 2.1 Hz, 1H), 7.49 (m, 2H), 7.25 (m, 1H), 5.19 (br s, 1H), 4.63 (br s, 1H), 3.40 (br s, 1H), 2.55 (d, J=18 Hz, 1H), 2.36 (m, 1H), 2.22 (m, 1H), 1.99 (dt, J=5.8, 2.2 Hz, 1H), 1.65 (m, 1H), 1.40 (s, 9H).

Step B: The product of step A was deprotected and converted to the hydrochloride salt following the procedure of Example 29, step D to provide 2-(3-fluorophenyl)sulfonyl-6,7,8,9,10-pentahydro-7,10-epiminocyclohepta[b]benzofuran hydrochloride (85 mg, 91%) as a white solid: mp 200-210° C.; $^1$H NMR (DMSO-d$_6$, 500 MHz) δ 9.77 (s, 1H), 9.34 (s, 1H), 8.54 (d, J=1.9 Hz, 1H), 7.94 (dd, J=8.8, 1.9 Hz, 1H), 7.83 (m, 1H), 7.69 (m, 1H), 7.55 (m, 1H), 5.34 (d, J=4.0 Hz, 1H), 4.49 (t, J=5.4 Hz, 1H), 3.44 (dd, J=18, 4.6 Hz, 1H), 3.01 (d, J=17 Hz, 1H), 2.28 (m, 3H), 1.86 (m, 1H); ESI MS m/z 358 [M+H]; HPLC (Method A)>99% (AUC), $t_R$=12.64 min.

Example 58

Preparation of 2-(3-Methyl-1H-indol-1-yl)sulfonyl-6,7,8,9,10-pentahydro-7,10-epiminocyclohepta[b]benzofuran hydrochloride

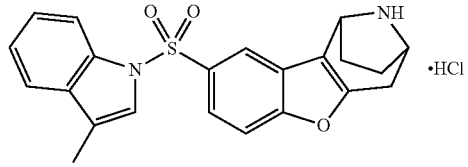 [SMILES: Cc1cn(S(=O)(=O)c2ccc3oc4c(c3c2)C2CCC(C4)N2)c2ccccc12 ; Cl]

Step A: The product of Example 55, step A (750 mg, 1.98 mmol) was sulfonylated following the procedure of Example 41, step A. The crude product was converted to the sulfonyl chloride following the procedure of Example 41, step B providing tert-butyl 2-chlorosulfonyl-6,7,8,9,10-pentahydro-7,10-epiminocyclohepta[b]benzofuran-carboxylate (327 mg, 41%) as a white foamy solid. $^1$H NMR (CDCl$_3$, 300 MHz) δ 8.20 (d, J=2.0 Hz, 1H), 7.95 (m, 1H), 7.60 (d, J=9.3 Hz, 1H), 5.21 (d, J=13 Hz, 1H), 4.71 (d, J=37 Hz, 1H), 3.47 (br s, 1H), 2.60 (d, J=16 Hz, 1H), 2.39 (m, 1H), 2.25 (m, 1H), 2.03 (m, 1H), 1.69 (m, 1H), 1.43 (s, 9H).

Step B: The product of step A and 3-methylindole were coupled following the procedure of Example 41, step C. Purification by combiflash (silica gel, hexane/ethyl acetate, 100:0 to 40:60) provided tert-butyl 2-(3-methyl-1H-indol-1-yl)sulfonyl-6,7,8,9,10-pentahydro-7,10-epiminocyclohepta[b]benzofuran-carboxylate (51 mg, 46%) as an oil: $^1$H NMR (CDCl$_3$, 500 MHz) δ 8.06 (s, 1H), 8.03 (d, J=8.3 Hz, 1H), 7.71 (d, J=9.4 Hz, 1H), 7.44 (d, J=7.8 Hz, 1H), 7.38 (d, J=10 Hz, 1H), 7.34 (s, 1H), 7.31 (t, J=7.7 Hz, 1H), 7.22 (d, J=7.6 Hz, 1H), 5.14 (d, J=54 Hz, 1H), 4.65 (d, J=49 Hz, 1H), 3.38 (d, J=41 Hz, 1H), 2.50 (d, J=17 Hz, 1H), 2.34 (m, 1H), 2.20 (m, 1H), 1.93 (dt, J=5.8, 2.2 Hz, 1H), 1.61 (m, 1H), 1.38 (s, 9H).

Step C: The product of step B was deprotected and converted to the hydrochloride salt following the procedure of Example 29, step D to provide 2-(3-methyl-1H-indol-1-yl)sulfonyl-6,7,8,9,10-pentahydro-7,10-epiminocyclohepta[b]benzofuran hydrochloride (25 mg, 57%) as a white solid: mp 195-199° C.; $^1$H NMR (DMSO-d$_6$, 500 MHz) δ 9.70 (s, 1H), 9.21 (s, 1H), 8.57 (d, J=2.5 Hz, 1H), 7.98 (d, J=9.8 Hz, 1H), 7.83 (dd, J=9.6, 2.7 Hz, 1H), 7.77 (d, J=8.8 Hz, 1H), 7.59 (s, 1H), 7.52 (d, J=7.8 Hz, 1H), 7.34 (t, J=7.7 Hz, 1H), 7.26 (t, J=7.5 Hz, 1H), 5.33 (d, J=5.7 Hz, 1H), 4.47 (br s, 1H), 3.38 (dd, J=18, 4.4 Hz, 1H), 2.97 (d, J=18 Hz, 1H), 2.27 (m+s, 6H), 2.16 (m, 1H); ESI MS m/z 393 [M+H]; HPLC (Method A)>99% (AUC), t$_R$=14.51 min.

Example 59

Preparation of 2-(6-Fluoro-1H-indol-1-yl)sulfonyl-6,7,8,9,10-pentahydro-7,10-epiminocyclohepta[b]benzofuran hydrochloride

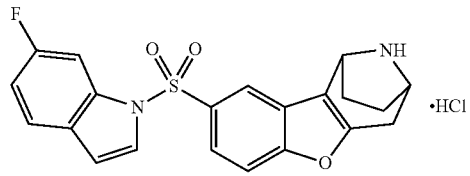 [SMILES: O=S(=O)(c1ccc2oc3c(c2c1)C1CCC(C3)N1)n1ccc2ccc(F)cc21 ; Cl]

Step A: The product of Example 58, step A and 6-fluoroindole were coupled following the procedure of Example 41, step C. Purification by combiflash (silica gel, hexane/ethyl acetate, 100:0 to 40:60) provided tert-butyl 2-(6-fluoro-1H-indol-1-yl)sulfonyl-6,7,8,9,10-pentahydro-7,10-epiminocyclohepta[b]benzofuran-carboxylate (56 mg, 50%) as a foam: $^1$H NMR (CDCl$_3$, 500 MHz) δ 8.07 (s, 1H), 7.71 (m, 2H), 7.58 (d, J=3.0 Hz, 1H), 7.43 (td, J=8.7, 2.4 Hz, 2H), 6.96 (dt, J=4.5, 2.1 Hz, 1H), 6.62 (d, J=3.7 Hz, 1H), 5.15 (d, J=36 Hz, 1H), 4.65 (d, J=46 Hz, 1H), 3.39 (d, J=46 Hz, 1H), 2.52 (d, J=17 Hz, 1H), 2.34 (m, 1H), 2.22 (m, 1H), 1.96 (t, J=9.6 Hz, 1H), 1.60 (m, 1H), 1.37 (2 x s, 9H).

Step B: The product of step A was deprotected and converted to the hydrochloride salt following the procedure of Example 29, step D to provide 2-(6-fluoro-1H-indol-1-yl)sulfonyl-6,7,8,9,10-pentahydro-7,10-epiminocyclohepta[b]benzofuran hydrochloride (13 mg, 27%) as a white solid: mp 184-187° C.; $^1$H NMR (DMSO-d$_6$, 500 MHz) δ 9.60 (s, 1H), 9.20 (s, 1H), 8.69 (d, J=3.4 Hz, 1H), 7.94 (dd, J=8.8, 2.0 Hz, 1H), 7.83 (d, J=3.7 Hz, 1H), 7.81 (d, J=8.8 Hz, 1H), 7.78 (dd, J=10, 2.5 Hz, 1H), 7.62 (d, J=8.8, 5.4 Hz, 1H), 7.12 (dt, J=4.5, 2.2 Hz, 1H), 6.85 (dd, J=3.7, 0.6 Hz, 1H), 5.34 (d, J=4.4 Hz, 1H), 4.49 (t, J=5.8 Hz, 1H), 3.38 (dd, J=18, 4.4 Hz, 1H), 2.99 (d, J=17 Hz, 1H), 2.24 (m, 3H), 1.85 (m, 1H); ESI MS m/z 397 [M+H]; HPLC (Method A)>99% (AUC), t$_R$=14.23 min.

Example 60

Preparation of 7-(Phenylsulfonyl)-1,2,3,4-tetrahydrobenzofuro[3,2-c]pyridine hydrochloride

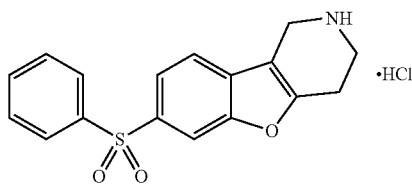 [SMILES: O=S(=O)(c1ccccc1)c1ccc2c3c(oc2c1)CCNC3 ; Cl]

Step A: To a mixture of 3-bromophenylboronic acid (246 mg, 1.23 mmol), 2-hydroxyisoindoline-1,3-dione (100 mg, 0.61 mmol), cupric acetate (223 mg, 1.23 mmol) and activated 4 Å molecular sieves (155 mg) in 1,2-dichloroethane (3 mL) under a nitrogen atmosphere was added pyridine (0.11 mL, 1.35 mmol). The reaction was stirred at ambient temperature for 24 h, concentrated in vacuo and purified by flash column chromatography (82:18 hexanes/ethyl acetate) to provide 2-(3-bromophenoxy)isoindoline-1,3-dione (102 mg, 52%) as a white solid: $^1$H NMR (CDCl$_3$, 300 MHz) δ 7.93 (dd, J=5.4, 3.0 Hz, 2H), 7.83 (dd, J=5.6, 3.0 Hz, 2H), 7.33 (t, J=2.1 Hz, 1H), 7.29 (dt, J=7.8, 2.0 Hz, 1H), 7.22 (t, J=8.1, 1H), 7.16-7.10 (m, 1H).

Step B: To a solution of 2-(3-bromophenoxy)isoindoline-1,3-dione (1.85 g, 5.82 mmol) in chloroform (50 mL) and methanol (5.6 mL) under a nitrogen atmosphere was added hydrazine hydrate (0.88 mL, 17.4 mmol). The reaction mixture was stirred at ambient temperature for 15 h and concentrated in vacuo to give the crude product which was purified by flash column chromatography (SiO$_2$, 70:30 hexanes/ethyl acetate). After removal of solvent in vacuo the free base was treated directly with 1.25M hydrochloric acid in methanol (25 mL). The resulting solution was concentrated in vacuo and the residue washed with ethyl acetate/hexane (5:95) to give O-(3-bromophenyl)hydroxylamine hydrochloride as a pale yellow solid: $^1$H NMR (CD$_3$OD, 300 MHz) δ 7.43-7.36 (m, 3H), 7.18 (dt, J=7.8, 1.8 Hz, 1H); ESI MS m/z 187 [M+H]$^+$ Step C: The product of step B was reacted with tert-butyl 4-oxopiperidine-1-carboxylate then Boc protected following the procedure of Example 29, step B to give tert-butyl 7-bromo-3,4-dihydrobenzofuro[3,2-c]pyridine-2(1H)-carboxylate (181 mg, 11%) as an off-white solid: $^1$H NMR (CDCl$_3$, 300 MHz) δ 7.59 (d, J=1.6 Hz, 1H), 7.34 (dd, J=8.3 Hz, 1.8 Hz, 1H), 7.26 (d, J=8.1 Hz, 1H), 4.53 (s, 2H), 3.82 (t, J=5.4 Hz, 2H), 2.83 (t, J=5.7 Hz, 2H), 1.52 (s, 9H); ESI MS m/z 352 [M+H]$^+$.

Step D: The product of step C was coupled with sodium benzenesulfinate following the procedure of Example 29, step C. Purification by flash column chromatography (SiO$_2$, 85:15 hexanes/ethyl acetate) provided tert-butyl 7-(phenylsulfonyl)-3,4-dihydrobenzofuro[3,2-c]pyridine-2(1H)-carboxylate (31 mg, 29%) as light yellow solid: $^1$H NMR (CDCl$_3$, 300 MHz) δ 8.06 (d, J=1.2 Hz, 1H), 7.98-7.91 (m, 2H), 7.81 (dd, J=8.1 Hz, 1.2 Hz, 1H), 7.56-7.45 (m, 4H), 4.54 (s, 2H), 3.82 (t, J=5.4 Hz, 2H), 2.88 (t, J=5.7 Hz, 2H), 1.49 (s, 9H).

Step E: The product of step D was deprotected using the procedure of Example 32, step B. Purification by flash column chromatography (SiO$_2$, 90:9:1 dichloromethane/methanol/ammonium hydroxide) provided 7-(phenylsulfonyl)-1,2,3,4-tetrahydrobenzofuro[3,2-c]pyridine (21 mg, 62%) as a white solid: $^1$H NMR (CDCl$_3$, 300 MHz) δ 8.04 (d, J=1.2 Hz, 1H), 7.98-7.91 (m, 2H), 7.78 (dd, J=8.1 Hz, 1.5 Hz, 1H), 7.57-7.42 (m, 4H), 3.96 (s, 2H), 3.24 (t, J=5.7 Hz, 2H), 2.86-2.77 (m, 2H); ESI MS m/z 314 [M+H]$^+$.

Step F: The product of step E was converted to the HCl salt using the procedure of Example 32, step C providing 7-(phenylsulfonyl)-1,2,3,4-tetrahydrobenzofuro[3,2-c]pyridine hydrochloride (22 mg, 94%, AUC HPLC 97.4%) as a white solid: mp 235-238° C.: $^1$H NMR (DMSO-d$_6$, 300 MHz) δ 9.69 (br s, 2H), 8.27 (s, 1H), 7.98 (d, J=6.9 Hz, 2H), 7.89-7.81 (m, 2H), 7.70-7.56 (m, 3H), 4.33 (s, 2H), 3.53 (t, J=6.0 Hz, 2H), 3.16-3.14 (m, 2H); ESI MS m/z 314 [M+H]$^+$.

Example 61

Preparation of 2-Methyl-7-(phenylsulfonyl)-1,2,3,4-tetrahydrobenzofuro[3,2-c]pyridine hydrochloride

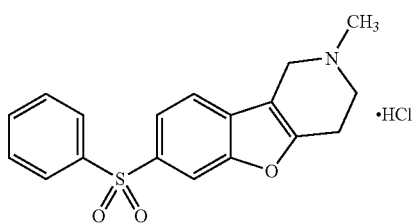 [SMILES: CN1CCc2oc3cc(S(=O)(=O)c4ccccc4)ccc3c2C1 ; Cl]

To a solution of the product of Example 60, step E (15 mg, 0.05 mmol) in 1,2-dichloroethane (0.5 mL) was added formaldehyde (12 µL, 37% in water). The reaction mixture was stirred at ambient temperature for 10 min before sodium triacetoxyborohydride (61 mg, 0.29 mmol) was added. The reaction mixture was stirred for 15 h, quenched with saturated sodium bicarbonate solution and extracted with chloroform. The organic layer was dried over sodium sulfate, filtered, and concentrated in vacuo. The residue was treated with 1.25 M HCl in methanol and the resulting solution concentrated in vacuo to afford 2-methyl-7-(phenylsulfonyl)-1,2,3,4-tetrahydrobenzofuro[3,2-c]pyridine hydrochloride (9.5 mg, 61%, AUC HPLC 95.7%) as a white solid: mp 242-245° C.; $^1$H NMR (CD$_3$OD, 300 MHz) δ 8.21-8.13 (m, 1H), 7.98 (d, J=7.2 Hz, 2H), 7.87 (dd, J=8.3 Hz, 1.2 Hz, 1H), 7.71 (d, J=8.1 Hz, 1H), 7.63-7.54 (m, 3H), 4.74-4.30 (br s, 2H), 3.96-3.60 (br s, 2H), 3.30 (br s, 2H), 3.13 (s, 3H); ESI MS m/z 328 [M+H]$^+$.

Example 62

Preparation of 7-(3-Chlorophenylsulfonyl)-1,2,3,4-tetrahydrobenzofuro[3,2-c]pyridine hydrochloride

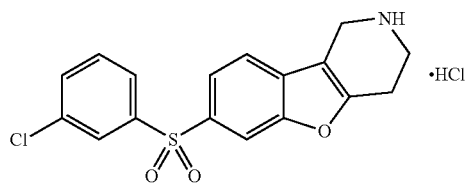 [SMILES: O=S(=O)(c1cccc(Cl)c1)c1ccc2c3c(oc2c1)CCNC3 ; Cl]

Step A: O-(3-bromophenyl)hydroxylamine (2.0 g, 8.9 mmol) was reacted with 4-piperidone hydrochloride following the procedure of Example 29, step B. The crude product was Boc protected following the procedure of Example 29, step B to provide tert-butyl 7-bromo-3,4-dihydrobenzofuro[3,2-c]pyridine-2(1H)-carboxylate (1.38 g, 44%) as an off-white solid: $^1$H NMR (CDCl$_3$, 300 MHz) δ 7.59 (s, 1H), 7.34 (d, J=8.2 Hz, 1H), 7.27 (d, J=7.8 Hz, 1H), 4.53 (br s, 2H), 3.82 (br s, 2H), 2.83 (br s, 2H), 1.50 (s, 9H).

Step B: The product of step A was coupled with sodium 3-chlorobenzenesulfinate following the procedure of Example 29, step C. Purification by flash column chromatography (SiO$_2$, 100:0 to 30:70 hexanes/ethyl acetate) provided tert-butyl 7-(3-chlorophenylsulfonyl)-3,4-dihydrobenzofuro[3,2-c]pyridine-2(1H)-carboxylate (66 mg, 52%) as an oil: $^1$H NMR (CDCl$_3$, 300 MHz) δ 8.06 (d, J=1.3 Hz, 1H), 7.92 (t, J=1.9 Hz, 1H), 7.83 (td, J=7.9, 1.4 Hz, 1H), 7.80 (d, J=8.0 Hz, 1H), 7.53 (d, J=8.2 Hz, 1H), 7.50 (m, 1H), 7.42 (t, J=7.9 Hz, 1H), 4.55 (br s, 2H), 3.83 (br s, 2H), 2.89 (br s, 2H), 1.49 (s, 9H).

Step C: The product of step B was deprotected using the procedure of Example 29, step D providing 7-(3-chlorophenylsulfonyl)-1,2,3,4-tetrahydrobenzofuro[3,2-c]pyridine hydrochloride (55 mg, 96%) as a white solid: mp 288-292° C.; $^1$H NMR (DMSO-d$_6$, 500 MHz) δ 9.65 (s, 2H), 8.36 (d, J=1.1 Hz, 1H), 8.06 (t, J=1.8 Hz, 1H), 7.96 (td, J=8.3, 1.6 Hz, 1H), 7.91 (d, J=1.5 Hz, 1H), 7.86 (d, J=8.3 Hz, 1H), 7.76 (m, 1H), 7.64 (t, J=7.9 Hz, 1H), 4.33 (br s, 2H), 3.53 (t, J=6.0 Hz, 2H), 3.15 (t, J=5.9 Hz, 2H); ESI MS m/z 348 [M+H]$^+$; HPLC (Method A)=96.8% (AUC), t$_R$=13.83 min.

Example 63

Preparation of 7-(3-Trifluoromethylphenylsulfonyl)-1,2,3,4-tetrahydrobenzofuro[3,2-c]pyridine hydrochloride

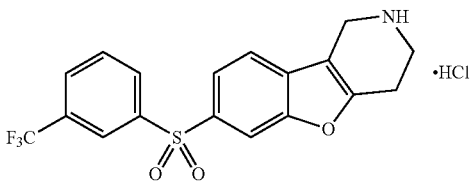 [SMILES: O=S(=O)(c1cccc(C(F)(F)F)c1)c1ccc2c3c(oc2c1)CCNC3 ; Cl]

Step A: The product of Example 62, step A (100 mg, 0.284 mmol) was coupled with sodium 3-chlorobenzenesulfinate following the procedure of Example 29, step C. Purification by flash column chromatography (silica gel, hexanes/EtOAc, 100:0 to 30:70) provided tert-butyl 7-(3-trifluoromethylphenylsulfonyl)-3,4-dihydrobenzofuro[3,2-c]pyridine-2(1H)-carboxylate (62 mg, 45%) as an oil: $^1$H NMR (CDCl$_3$, 300 MHz) δ 8.21 (s, 1H), 8.13 (d, J=7.9 Hz, 1H), 8.08 (d, J=1.2 Hz, 1H), 7.80 (t, J=7.9 Hz, 2H), 7.65 (t, J=7.9 Hz, 1H), 7.54 (d, J=8.2 Hz, 1H), 4.55 (br s, 2H), 3.83 (t, J=5.1 Hz, 2H), 2.90 (t, J=5.4 Hz, 2H), 1.49 (s, 9H).

Step B: The product of step A was deprotected using the procedure of Example 29, step D providing 7-(3-trifluoromethylphenylsulfonyl)-1,2,3,4-tetrahydrobenzofuro[3,2-c]pyridine hydrochloride (52 mg, 96%) as an off-white solid: mp 290-294° C.; $^1$H NMR (DMSO-d$_6$, 500 MHz) δ 9.57 (s, 2H), 8.42 (d, J=1.5 Hz, 1H), 8.31 (t, J=6.7 Hz, 2H), 8.08 (d, J=7.9 Hz, 1H), 7.97 (dd, J=8.2, 1.5 Hz, 1H), 7.87 (d, J=8.2 Hz, 2H), 4.34 (br s, 2H), 3.53 (t, J=6.2 Hz, 2H), 3.15 (t, J=5.8 Hz, 2H); ESI MS m/z 382 [M+H]$^+$; HPLC (Method A)=95.0% (AUC), $t_R$=13.80 min.

Example 64

Preparation of 3-(3-Trifluoromethylphenyl)sulfonyl-6,7,8,9,10-pentahydro-7,10-epiminocyclohepta[b]benzofuran hydrochloride

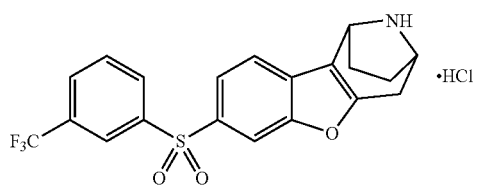 [SMILES: O=S(=O)(c1cccc(C(F)(F)F)c1)c1ccc2c3c(oc2c1)CC1CCC3N1 ; Cl]

Step A: The product of Example 60, step B was reacted with nortropinone following the procedure of Example 60, step D providing tert-butyl 3-bromo-6,7,8,9,10-pentahydro-7,10-epiminocyclohepta[b]benzofuran-carboxylate (730 mg, 18%) as a foam: $^1$H NMR (CDCl$_3$, 300 MHz) δ 7.58 (s, 1H), 7.33 (s, 2H), 5.12 (d, J=31 Hz, 1H), 4.65 (d, J=21 Hz, 1H), 3.39 (d, J=32 Hz, 1H), 2.51 (d, J=16 Hz, 1H), 2.34 (m, 1H), 2.19 (m, 1H), 1.96 (dt, J=5.8, 1.9 Hz, 1H), 1.66 (m, 1H), 1.40 (s, 9H).

Step B: The product of step A was coupled with sodium 3-trifluoromethylbenzenesulfinate following the procedure of Example 29, step C. Purification by flash column chromatography (silica gel, hexanes/EtOAc, 100:0 to 20:80) provided tert-butyl 3-(3-trifluoromethylphenyl)sulfonyl-6,7,8,9,10-pentahydro-7,10-epiminocyclohepta[b]benzofuran-carboxylate (50 mg, 41%) as an oil: $^1$H NMR (CDCl$_3$, 300 MHz) δ 8.22 (s, 1H), 8.13 (d, J=8.1 Hz, 1H), 8.05 (d, J=1.2 Hz, 1H), 7.80 (t, J=6.9 Hz, 2H), 7.64 (t, J=7.9 Hz, 2H), 5.15 (br s, 1H), 4.65 (br s, 1H), 3.42 (br s, 1H), 2.59 (d, J=17 Hz, 1H), 2.37 (m, 1H), 2.20 (m, 1H), 1.94 (dt, J=5.8, 2.0 Hz, 1H), 1.66 (m, 1H), 1.40 (s, 9H).

Step C: The product of step B was deprotected using the procedure of Example 29, step D providing 3-(3-trifluoromethylphenyl)sulfonyl-6,7,8,9,10-pentahydro-7,10-epiminocyclohepta[b]benzofuran hydrochloride (39 mg, 89%) as a pale yellow solid: mp 178-183° C.; $^1$H NMR (DMSO-d$_6$, 500 MHz) δ 9.62 (s, 1H), 9.31 (s, 1H), 8.42 (d, J=0.8 Hz, 1H), 8.32 (d, J=8.8 Hz, 2H), 8.08 (d, J=7.9 Hz, 1H), 7.97 (m, 2H), 7.86 (t, J=7.9 Hz, 1H), 5.25 (d, J=4.7 Hz, 1H), 4.50 (t, J=5.8 Hz, 1H), 3.43 (dd, J=18, 4.9 Hz, 1H), 3.04 (d, J=18 Hz, 1H), 2.24 (m, 3H), 1.86 (m, 1H); ESI MS m/z 408 [M+H]$^+$; HPLC (Method A)=98.3% (AUC), $t_R$=13.84 min.

Example 65

Preparation of 3-(3-Chlorophenyl)sulfonyl-6,7,8,9,10-pentahydro-7,10-epiminocyclohepta[b]benzofuran hydrochloride

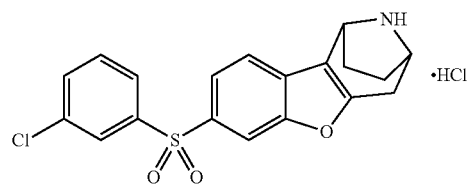 [SMILES: O=S(=O)(c1cccc(Cl)c1)c1ccc2c3c(oc2c1)CC1CCC3N1 ; Cl]

Step A: The product of Example 64, step A was coupled with sodium 3-chloromethylbenzenesulfinate following the procedure of Example 29, step C. Purification by flash column chromatography (silica gel, hexanes/EtOAc, 100:0 to 30:70) provided tert-butyl 3-(3-chlorophenyl)sulfonyl-6,7,8,9,10-pentahydro-7,10-epiminocyclohepta[b]benzofuran-carboxylate (29 mg, 25%) as an oil: $^1$H NMR (CDCl$_3$, 300 MHz) δ 8.03 (s, 1H), 7.92 (s, 1H), 7.81 (t, J=9.8 Hz, 2H), 7.58 (d, J=8.3 Hz, 1H), 7.46 (m, 2H), 5.17 (br s, 1H), 4.66 (br s, 1H), 3.40 (br s, 1H), 2.58 (d, J=17 Hz, 1H), 2.36 (m, 1H), 2.20 (m, 1H), 1.94 (dt, J=5.8, 2.1 Hz, 1H), 1.65 (m, 1H), 1.39 (s, 9H).

Step B: The product of step A was deprotected using the procedure of Example 29, step D. Purification by preparative HPLC followed by conversion to the HCl salt (2N HCl in ether) provided 3-(3-chlorophenyl)sulfonyl-6,7,8,9,10-pentahydro-7,10-epiminocyclohepta[b]benzofuran hydrochloride (11 mg, 48%) as a white solid: mp 193-197° C.; $^1$H NMR (DMSO-d$_6$, 500 MHz) δ 9.24 (s, 2H), 8.36 (s, 1H), 8.06 (t, J=1.8 Hz, 1H), 7.95 (m, 3H), 7.75 (dd, J=8.2, 1.3 Hz, 1H), 7.64 (t, J=7.9 Hz, 1H), 5.21 (d, J=4.7 Hz, 1H), 4.48 (t, J=5.7 Hz, 1H), 3.43 (dd, J=18, 4.4 Hz, 1H), 3.01 (d, J=18 Hz, 1H), 2.21 (m, 3H), 1.84 (m, 1H); ESI MS m/z 374 [M+H]$^+$; HPLC (Method A)>99% (AUC), $t_R$=13.34 min.

Example 66

Preparation of 3-(3-Fluorophenyl)sulfonyl-6,7,8,9,10-pentahydro-7,10-epiminocyclohepta[b]benzofuran hydrochloride

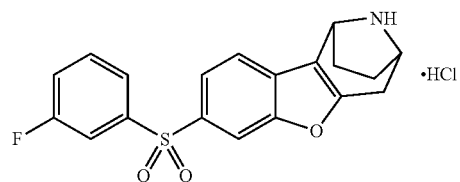 [SMILES: O=S(=O)(c1cccc(F)c1)c1ccc2c3c(oc2c1)CC1CCC3N1 ; Cl]

Step A: The product of Example 64, step A was coupled with sodium 3-fluorobenzenesulfinate following the procedure of Example 29, step C. Purification by flash column chromatography (silica gel, hexanes/EtOAc, 100:0 to 30:70) provided tert-butyl 3-(3-fluorophenyl)sulfonyl-6,7,8,9,10-pentahydro-7,10-epiminocyclohepta[b]benzofuran-carboxylate (68 mg, 61%) as an oil: $^1$H NMR (CDCl$_3$, 300 MHz)

δ 8.03 (s, 1H), 7.82 (d, J=6.3 Hz, 1H), 7.70 (s, 1H), 7.64 (d, J=8.7 Hz, 1H), 7.57 (d, J=8.3 Hz, 1H), 7.47 (m, 1H), 7.23 (t, J=8.4 Hz, 1H), 5.15 (d, J=46 Hz, 1H), 4.67 (d, J=54 Hz, 1H), 3.44 (d, J=56 Hz, 1H), 2.58 (d, J=17 Hz, 1H), 2.36 (m, 1H), 2.20 (m, 1H), 1.95 (t, J=9.7 Hz, 1H), 1.65 (m, 1H), 1.39 (2 x s, 9H).

Step B: The product of step A was deprotected using the procedure of Example 29, step D providing 3-(3-fluorophenyl)sulfonyl-6,7,8,9,10-pentahydro-7,10-epiminocyclohepta[b]benzofuran hydrochloride (26 mg, 46%) as a white solid: $^1$H NMR (DMSO-$d_6$, 500 MHz) δ 9.37 (s, 2H), 8.33 (d, J=1.0 Hz, 1H), 7.95 (m, 2H), 7.88 (td, J=8.7, 2.3 Hz, 1H), 7.84 (td, J=7.9, 1.1 Hz, 1H), 7.67 (m, 1H), 7.54 (dt, J=4.1, 2.5 Hz, 1H), 5.24 (d, J=5.9 Hz, 1H), 4.49 (t, J=5.8 Hz, 1H), 3.45 (dd, J=19, 5.2 Hz, 1H), 3.03 (d, J=17 Hz, 1H), 2.22 (m, 3H), 1.85 (m, 1H); ESI MS m/z 358 [M+H]$^+$; HPLC (Method A)>99% (AUC), $t_R$=12.78 min.

Example 67

Preparation of 3-(1H-indol-1-yl)sulfonyl-6,7,8,9,10-pentahydro-7,10-epiminocyclohepta[b]benzofuran hydrochloride

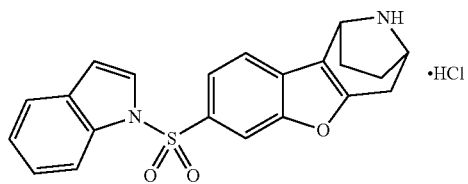 [SMILES: O=S(=O)(c1ccc2c3c(oc2c1)CC1CCC3N1)n1ccc2ccccc21 ; Cl]

Step A: The product of Example 64, step A (416 mg, 1.1 mmol) was sulfonylated following the procedure of Example 41, step A. The crude product was converted to the sulfonyl chloride following the procedure of Example 41, step B providing tert-butyl 3-chlorosulfonyl-6,7,8,9,10-pentahydro-7,10-epiminocyclohepta[b]benzofuran-carboxylate (76 mg, 17%) as a foamy solid: $^1$H NMR (CDCl$_3$, 300 MHz) δ 7.46 (m, 1H), 7.40 (m, 1H), 7.21 (m, 1H), 5.16 (d, J=29 Hz, 1H), 4.66 (d, J=27 Hz, 1H), 3.44 (d, J=17 Hz, 1H), 2.53 (m, J=17 Hz, 1H), 2.33 (m, 1H), 2.19 (m, 1H), 1.99 (dt, J=5.7, 2.0 Hz, 1H), 1.66 (m, 1H), 1.41 (s, 9H).

Step B: The product of step A (71 mg, 0.179 mmol) and indole were coupled following the procedure of Example 41, step C. Purification by combiflash (silica gel, hexane/ethyl acetate, 100:0 to 40:60) provided tert-butyl 3-(1H-indol-1-yl)sulfonyl-6,7,8,9,10-pentahydro-7,10-epiminocyclohepta[b]benzofuran-carboxylate (32 mg, 38%) as an oil: $^1$H NMR (CDCl$_3$, 300 MHz) δ 8.03 (d, J=8.2 Hz, 1H), 7.97 (s, 1H), 7.74 (d, J=8.3 Hz, 1H), 7.60 (d, J=3.6 Hz, 1H), 7.51 (d, J=8.0 Hz, 1H), 7.46 (d, J=8.3 Hz, 1H), 7.31 (t, J=7.3 Hz, 1H), 7.21 (t, J=7.2 Hz, 1H), 6.65 (d, J=3.6 Hz, 1H), 5.08 (d, J=25 Hz, 1H), 4.64 (d, J=27 Hz, 1H), 3.39 (br s, 1H), 2.53 (d, J=17 Hz, 1H), 2.32 (m, 1H), 2.15 (m, 1H), 1.88 (dt, J=5.8, 2.3 Hz, 1H), 1.61 (m, 1H), 1.39 (s, 9H).

Step C: The product of step B was deprotected using the procedure of Example 29, step D. Purification by preparative HPLC followed by conversion to the hydrochloride salt (2N HCl in ether) provided 3-(1H-indol-1-yl)sulfonyl-6,7,8,9,10-pentahydro-7,10-epiminocyclohepta[b]benzofuran hydrochloride (15 mg, 54%) as a pink solid: mp 192-196° C.; $^1$H NMR (DMSO-$d_6$, 500 MHz) δ 9.54 (s, 1H), 9.18 (s, 1H), 8.35 (s, 1H), 8.00 (d, J=8.4 Hz, 1H), 7.88 (s, 2H), 7.84 (d, J=3.7 Hz, 1H), 7.57 (d, J=7.8 Hz, 1H), 7.31 (t, J=7.7 Hz, 1H), 7.20 (t, J=7.7 Hz, 1H), 6.83 (d, J=3.7 Hz, 1H), 5.19 (d, J=5.0 Hz, 1H), 4.47 (t, J=6.3 Hz, 1H), 3.41 (dd, J=18, 4.6 Hz, 1H), 3.00 (d, J=18 Hz, 1H), 2.19 (m, 3H), 1.83 (m, 1H); ESI MS m/z 379 [M+H]$^+$; HPLC (Method A)=97.8% (AUC), $t_R$=14.15 min.

Example 68

Preparation of 8-(Phenylsulfonyl)-2,3,4,5-tetrahydro-1H-benzofuro[3,2-c]azepine hydrochloride

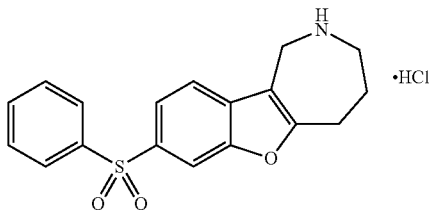 [SMILES: O=S(=O)(c1ccccc1)c1ccc2c3c(oc2c1)CCCNC3 ; Cl]

Step A: A mixture of the product of Example 60, step B (9.0 g, 40.1 mmol) and cyclohexane-1,3-dione (6.74 g, 60.1 mmol) in 10% H$_2$SO$_4$/acetic acid (100 mL) was heated at 110° C. for 12 h. After cooling to ambient temperature, the reaction mixture was diluted with water, basified by treating with 10 N NaOH and extracted with dichloromethane. The organic layer was washed with brine, dried over sodium sulfate, filtered and concentrated in vacuo to give the crude material which was purified by flash column chromatography (SiO$_2$, 90:10 hexanes/ethyl acetate) to provide 7-bromo-3,4-dihydrodibenzo[b,d]furan-1(2H)-one (6.8 g, 64%) as a pale yellow solid: $^1$H NMR (CDCl$_3$, 300 MHz) δ 7.91 (d, J=8.1 Hz, 1H), 7.65 (d, J=1.5 Hz, 1H), 7.45 (dd, J=8.1, 1.5 Hz, 1H), 3.03 (t, J=6.3 Hz, 2H), 2.61 (t, J=6.3 Hz, 2H), 2.35-2.24 (m, 2H).

Step B: A mixture of the product of step A (6.80 g, 25.7 mmol), sodium acetate (3.16 g, 38.5 mmol) and hydroxylamine hydrochloride (2.67 g, 38.5 mmol) in water (28 mL) and ethanol (14 mL) was heated to 85° C. for 7 h. After cooling to 5° C., the reaction mixture was filtered. The solid obtained was washed with cold water and dried in vacuo to give 7-bromo-3,4-dihydrodibenzo[b,d]furan-1(2H)-one oxime (1.05 g, 15%) as an off-white solid: $^1$H NMR (DMSO-$d_6$, 300 MHz) δ 10.95 (s, 1H), 7.88 (d, J=1.8 Hz, 1H), 7.74 (d, J=8.4 Hz, 1H), 7.47 (dd, J=8.4, 1.8 Hz, 1H), 2.87 (t, J=6.3 Hz, 2H), 2.69 (t, J=6.3 Hz, 2H), 2.03-1.89 (m, 2H).

Step C: A mixture of the product of step B (1.05 g, 3.74 mmol) and polyphosphoric acid (15 g) was heated to 110° C. for 5 h. After cooling to ambient temperature, the reaction mixture was diluted with water, basified with 10 N NaOH and filtered. The solid obtained was washed with water and dried in vacuo at 70° C. to give 8-bromo-2,3,4,5-tetrahydro-1H-benzofuro[3,2-c]azepin-1-one (858 mg, 82%) as a white solid: $^1$H NMR (DMSO-$d_6$, 300 MHz) δ 8.06-7.95 (m, 2H), 7.86 (d, J=1.8 Hz, 1H), 7.45 (dd, J=8.4, 1.8 Hz, 1H), 3.28-3.20 (m, 2H), 3.15 (t, J=6.6 Hz, 2H), 2.07-1.93 (m, 2H).

Step D: To a slurry of the product of step C (858 mg, 3.06 mmol) in anhydrous THF (6 mL) was added 1 M borane-THF complex (1 N in THF, 15.3 mL, 15.3 mmol) at ambient temperature. The reaction mixture was heated to 65° C. for 15 h. After cooling to ambient temperature, the reaction mixture was quenched with 1 M HCl and concentrated in vacuo. The residue was basified with 1 M NaOH and extracted with dichloromethane. The organic layer was dried over sodium sulfate, filtered, and concentrated in vacuo to give the crude material which was purified by flash column chromatography (SiO$_2$, 90:10 dichloromethane/methanol) to provide 8-bromo-2,3,4,5-tetrahydro-1H-benzofuro[3,2-c]azepine (369 mg, 45%) as a pale yellow solid: $^1$H NMR (CDCl$_3$, 300 MHz) δ 7.53 (d, J=1.8 Hz, 1H), 7.33-7.28 (m, 1H), 7.21 (d, J=8.4 Hz, 1H), 3.95 (s, 2H), 3.18 (td, J=3.9, 2.4 Hz, 2H), 3.00 (t, J=6.0 Hz, 2H), 1.94-1.84 (m, 2H), 1.57 (s, 1H).

Step E: A mixture of the product of step D (369 mg, 1.39 mmol), di-tert-butyl dicarbonate (365 mg, 1.67 mmol) and triethylamine (0.58 mL, 4.18 mmol) was dissolved in dichloromethane (10 mL). The reaction mixture was stirred at ambient temperature for 5 h and concentrated in vacuo to give the crude material which was purified with flash column chromatography (SiO$_2$, 80:20 hexanes/ethyl acetate) to provide tert-butyl 8-bromo-4,5-dihydro-1H-benzofuro[3,2-c]azepine-2(3H)-carboxylate (410 mg, 83%) as a pale yellow solid: $^1$H NMR (CDCl$_3$, 300 MHz) δ 7.54 (s, 1H), 7.39-7.27 (m, 2H), 4.63-4.49 (m, 2H), 3.67 (br s, 2H), 2.98 (t, J=6.0 Hz, 2H), 2.08-1.91 (m, 2H), 1.49-1.27 (m, 9H).

Step F: The product of step E was coupled with sodium benzenesulfinate following the procedure of Example 29, step C. Purification by flash column chromatography (SiO$_2$, 70:30 hexanes/ethyl acetate) provided tert-butyl 8-(phenylsulfonyl)-4,5-dihydro-1H-benzofuro[3,2-c]azepine-2(3H)-carboxylate (106 mg, 34%) as a pale yellow solid: $^1$H NMR (CDCl$_3$, 300 MHz) δ 8.04-7.87 (m, 3H), 7.83-7.72 (m, 1H), 7.60-7.41 (m, 4H), 4.64-4.61 (m, 2H), 3.67 (br s, 2H), 3.03 (t, J=6.3 Hz, 2H), 1.99 (br s, 2H), 1.53-1.25 (m, 9H).

Step G: The product of step F was deprotected using the procedure of Example 29, step D providing 8-(phenylsulfonyl)-2,3,4,5-tetrahydro-1H-benzofuro[3,2-c]azepine hydrochloride (81 mg, 90%, AUC HPLC 98.6%) as an off-white solid: mp 221-225° C.; $^1$H NMR (DMSO-d$_6$, 400 MHz) δ 9.38 (br s, 2H), 8.21 (d, J=1.6 Hz, 1H), 8.01-7.96 (m, 2H), 7.92 (d, J=8.4 Hz, 1H), 7.84 (dd, J=8.4, 1.6 Hz, 1H), 7.69-7.57 (m, 3H), 4.38 (s, 2H), 3.44 (t, J=5.2 Hz, 2H), 3.13 (t, J=6.0 Hz, 2H), 2.07 (br s, 2H); ESI MS m/z 328 [M+H]$^+$.

Example 69

Preparation of 9-(Phenylsulfonyl)-2,3,4,5-tetrahydro-1H-benzofuro[3,2-c]azepine hydrochloride

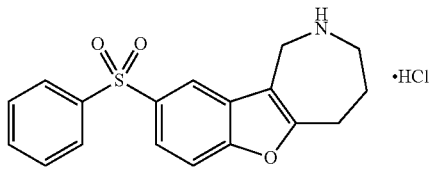 [SMILES: O=S(=O)(c1ccccc1)c1ccc2oc3c(c2c1)CNCCC3 ; Cl]

Step A: The product of Example 29, step A (1.0 g, 4.45 mmol) and cyclohexane-1,3-dione (750 mg, 6.68 mmol) were reacted following the procedure of Example 44, step A. Purification by flash column chromatography (SiO$_2$, 90:10 hexanes/ethyl acetate) provided 8-bromo-3,4-dihydrodibenzo[b,d]furan-1(2H)-one (410 mg, 35%) as a pale yellow solid: $^1$H NMR (CDCl$_3$, 300 MHz) δ 8.20 (d, J=1.8 Hz, 1H), 7.42 (dd, J=8.7, 2.1 Hz, 1H), 7.33 (dd, J=8.7, 2.7 Hz, 1H), 3.04 (t, J=6.3 Hz, 2H), 2.61 (t, J=6.0 Hz, 2H), 2.28 (m, 2H).

Step B: The product of step A was converted to the oxime using the procedure of Example 68, step B to provide 8-bromo-3,4-dihydrodibenzo[b,d]furan-1(2H)-one oxime (4.74 g, 64%) as an off-white solid: $^1$H NMR (DMSO-d$_6$, 300 MHz) δ 10.97 (s, 1H), 7.95 (d, J=2.1 Hz, 1H), 7.57 (d, J=8.4 Hz, 1H), 7.46 (dd, J=8.7, 2.1 Hz, 1H), 2.89 (t, J=6.0 Hz, 2H), 2.69 (t, J=6.6 Hz, 2H), 1.98 (t, J=6.3 Hz, 2H).

Step C: The product of step B was converted to the lactam using the procedure of Example 68, step C to give 9-bromo-2,3,4,5-tetrahydro-1H-benzofuro[3,2-c]azepin-1-one (1.0 g, 98%) as a white solid: $^1$H NMR (DMSO-d$_6$, 300 MHz) δ 8.24 (s, 1H), 8.02 (s, 1H), 7.55 (dd, J=5.1, 3.3 Hz, 1H), 7.46 (dd, J=8.7, 2.1 Hz, 1H), 3.29-3.20 (m, 2H), 3.17 (t, J=6.6 Hz, 2H), 2.04 (t, J=5.4 Hz, 2H).

Step D: The product of step C was reduced to the amine using the procedure of Example 68, step D to provide 9-bromo-2,3,4,5-tetrahydro-1H-benzofuro[3,2-c]azepine (75 mg, 9%) as a pale yellow solid: $^1$H NMR (CDCl$_3$, 300 MHz) δ 7.49-7.45 (m, 1H), 7.33-7.18 (m, 2H), 3.93 (s, 2H), 3.22-3.10 (m, 2H), 3.04-2.90 (m, 2H), 1.97-1.79 (m, 3H).

Step E: The product of step D was Boc protected using the procedure of Example 68, step E to provide tert-butyl 9-bromo-4,5-dihydro-1H-benzofuro[3,2-c]azepine-2(3H)-carboxylate (100 mg, 100%) as a pale yellow solid: $^1$H NMR (CDCl$_3$, 300 MHz) δ 7.61-7.49 (m, 1H), 7.34-7.18 (m, 2H), 4.66-4.33 (m, 2H), 3.68 (br s, 2H), 3.00 (t, J=6.0 Hz, 2H), 2.04-1.92 (m, 2H), 1.51-1.33 (m, 9H).

Step F: The product of step E was coupled with sodium benzenesulfinate following the procedure of Example 29, step C. Purification by flash column chromatography (SiO$_2$, 70:30 hexanes/ethyl acetate) provided tert-butyl 9-(phenylsulfonyl)-4,5-dihydro-1H-benzofuro[3,2-c]azepine-2(3H)-carboxylate (22 mg, 22%) as a light yellow solid: $^1$H NMR (CDCl$_3$, 300 MHz) δ 8.09 (br s, 1H), 8.00-7.91 (m, 2H), 7.86-7.77 (m, 1H), 7.58-7.37 (m, 4H), 4.68-4.38 (m, 2H), 3.70 (br s, 2H), 3.01 (t, J=6.0 Hz, 2H), 2.09-1.92 (m, 2H), 1.53-1.20 (m, 9H).

Step G: The product of step F (22 mg, 0.05 mmol) in 2N HCl diethyl ether solution (5 mL) was stirred at 0-5° C. for 2 h and then at ambient temperature for 4 h. After concentration in vacuo, the solid obtained was treated with saturated sodium bicarbonate solution and extracted with dichloromethane. The organic layer was dried over sodium sulfate, filtered, and concentrated in vacuo to give the crude material which was purified by flash column chromatography (SiO$_2$, 80:18:2 dichloromethane/methanol/ammonium hydroxide) followed by semi-preparative HPLC. After concentration in vacuo, the solid obtained was treated with 1.25M HCl methanol solution (0.5 mL) and lyophilized to yield 9-(phenylsulfonyl)-2,3,4,5-tetrahydro-1H-benzofuro[3,2-c]azepine hydrochloride (2.8 mg, 15%, AUC HPLC 98.8%) as a white solid: mp 211-216° C.; $^1$H NMR (CD$_3$OD, 300 MHz) δ 8.12 (s, 1H), 7.96 (dt, J=6.6, 1.8 Hz, 2H), 7.81 (dd, J=8.7, 1.8 Hz, 1H), 7.76-7.51 (m, 4H), 4.02 (s, 2H), 3.19 (br s, 2H), 3.05 (t, J=6.0 Hz, 2H), 1.95 (br s, 2H); ESI MS m/z 328 [M+H]$^+$.

Example 70

Preparation of 8-(1H-indol-5-ylsulfonyl)-6-methoxy-1,2,3,4-tetrahydrobenzofuro[3,2-c]pyridine hydrochloride

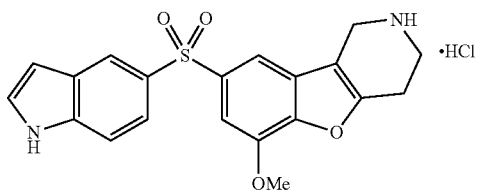 [SMILES: COc1cc(S(=O)(=O)c2ccc3[nH]ccc3c2)cc2c3c(oc12)CCNC3 ; Cl]

Step A: The product of Example 44, step B (250 mg, 0.63 mmol) was coupled with ethyl 5-iodo-1H-indole-1-carboxylate following the procedure of Example 50, step A. The crude product was purified by column chromatography (SiO$_2$, 3:1 hexanes/ethyl acetate) to give tert-butyl 6-chloro-8-((1-(ethoxycarbonyl)-1H-indol-5-yl)sulfonyl)-3,4-dihydrobenzofuro[3,2-c]pyridine-2(1H)-carboxylate (70 mg, 20%) as a white solid: $^1$H NMR (CDCl$_3$, 400 MHz) δ 8.31 (d, J=8.8 Hz, 1H), 8.24 (d, J=1.6 Hz, 1H), 7.99 (s, 1H), 7.88 (dd, J=8.8, 1.6 Hz, 1H), 7.84 (s, 1H), 7.74 (d, J=3.6 Hz, 1H), 6.73-6.68 (m, 1H), 4.56 (s, 2H), 4.51 (q, J=7.2 Hz, 2H), 3.82 (s, 2H), 2.89 (s, 2H), 1.50 (s, 9H), 1.47 (t, J=7.2 Hz, 3H).

Step B: The product of step A was converted to the phenol derivative using the procedure of Example 54, step A. Purification by flash column chromatography (SiO$_2$, 3:7 hexane/ethyl acetate) provided tert-butyl 8-((1H-indol-5-yl)sulfonyl)-6-hydroxy-3,4-dihydrobenzofuro[3,2-c]pyridine-2(1H)-carboxylate (90 mg, 65%) as a yellow solid: $^1$H NMR (CDCl$_3$, 400 MHz) δ 8.98 (s, 1H), 8.22 (s, 1H), 7.77-7.17 (m, 4H), 6.51 (s, 1H), 4.49 (s, 2H), 3.80-3.67 (m, 2H), 2.80-2.63 (m, 2H), 1.49 (s, 9H).

Step C: A mixture of the product of step B (90 mg, 0.19 mmol), sodium hydroxide (31 mg, 0.76 mmol) tetrabutylammonium hydrogen sulfate (13 mg, 0.04 mmol) and water (2 drops) in dichloromethane (10 mL) was stirred at ambient temperature for 5 min under an argon atmosphere before addition of ethyl chloroformate (24 μL, 0.25 mmol). The reaction mixture was stirred for 2 h before quenching with aqueous ammonium chloride (15 mL) and extracted with dichloromethane. The organic extract was washed with brine, dried over sodium sulfate and concentrated in vacuo. The residue was purified by flash column chromatography (SiO$_2$, 30:70 hexane/ethyl acetate) to give tert-butyl 8-((1-(ethoxycarbonyl)-1H-indol-5-yl)sulfonyl)-6-hydroxy-3,4-dihydrobenzofuro[3,2-c]pyridine-2(1H)-carboxylate (30 mg, 29%) as a yellow solid: $^1$H NMR (CDCl$_3$, 400 MHz) δ 8.25 (d, J=8.8 Hz, 1H), 8.20 (s, 1H), 7.85 (d, J=8.4 Hz, 1H), 7.78-7.52 (m, 2H), 7.43 (d, J=1.6 Hz, 1H), 6.70-6.63 (m, 1H), 4.54 (s, 2H), 4.50 (q, J=7.2 Hz, 2H), 3.89-3.72 (m, 2H), 2.91-2.77 (m, 2H), 1.51 (s, 9H), 1.46 (t, J=7.2 Hz, 3H).

Step D: The product of step C was converted to the methyl ether derivative following the procedure of Example 54, step B. Purification by flash column chromatography (SiO$_2$, 75:25 hexane/ethyl acetate) provided tert-butyl 8-((1-(ethoxycarbonyl)-1H-indol-5-yl)sulfonyl)-6-methoxy-3,4-dihydrobenzofuro[3,2-c]pyridine-2(1H)-carboxylate (25 mg, 82%) as a colorless oil: $^1$H NMR (CDCl$_3$, 300 MHz) δ 8.30 (d, J=8.7 Hz, 1H), 8.23 (d, J=1.8 Hz, 1H), 7.88 (dd, J=8.7, 1.8 Hz, 1H), 7.73 (d, J=3.6 Hz, 2H), 7.35 (s, 1H), 6.69 (d, J=3.6 Hz, 1H), 4.60-4.45 (m, 4H), 4.03 (s, 3H), 3.88-3.74 (m, 2H), 2.95-2.75 (m, 2H), 1.50 (s, 9H), 1.47 (t, J=7.2 Hz, 3H).

Step E: A mixture of the product of step D (25 mg, 0.04 mmol), lithium hydroxide (14 mg, 0.32 mmol) in tetrahydrofuran (1.25 mL), methanol (0.62 mL) and water (0.31 mL) was stirred at ambient temperature for 8 h. The reaction was quenched with aqueous ammonium chloride (15 mL) and extracted with dichloromethane. The organic extract was washed with brine, dried over sodium sulfate and concentrated in vacuo. The residue was purified by flash column chromatography (SiO$_2$, 3:2 hexane/ethyl acetate) to give tert-butyl 8-((1H-indol-5-yl)sulfonyl)-6-methoxy-3,4-dihydrobenzofuro[3,2-c]pyridine-2(1H)-carboxylate (18 mg, 83%) as a white solid: $^1$H NMR (CDCl$_3$, 300 MHz) δ 8.62 (s, 1H), 8.33 (s, 1H), 7.77-7.62 (m, 2H), 7.75 (d, J=8.4 Hz, 1H), 7.36 (s, 1H), 7.35-7.30 (m, 1H), 6.70-6.64 (m, 1H), 4.53 (s, 2H), 4.02 (s, 3H), 3.80 (t, J=5.4 Hz, 2H), 2.92-2.76 (m, 2H), 1.50 (s, 9H).

Step F: The product of step E was Boc deprotected following the procedure of Example 29, step D. Purification by flash column chromatography (SiO$_2$, 95:5 dichloromethane/methanol) provided 8-((1H-indol-5-yl)sulfonyl)-6-methoxy-1,2,3,4-tetrahydrobenzofuro[3,2-c]pyridine (10 mg, 70%) as a white solid: $^1$H NMR (CDCl$_3$, 400 MHz) δ 8.55 (s, 1H), 8.35-8.30 (m, 1H), 7.72 (dd, J=8.4, 1.6 Hz, 1H), 7.68 (d, J=1.6 Hz, 1H), 7.44 (d, J=8.4 Hz, 1H), 7.34 (d, J=1.6 Hz, 1H), 7.33-7.30 (m, 1H), 6.69-6.63 (m, 1H), 4.02 (s, 3H), 3.96 (t, J=2.0 Hz, 2H), 3.22 (t, J=6.0 Hz, 2H), 2.83-2.74 (m, 2H).

Step G: The product obtained in step D (10 mg, 0.02 mmol) was converted to hydrochloride salt by dissolving in dichloromethane and treating with 1.25 M HCl in methanol. The reaction mixture was concentrated in vacuo to give 8-((1H-indol-5-yl)sulfonyl)-6-methoxy-1,2,3,4-tetrahydrobenzofuro[3,2-c]pyridine hydrochloride (7 mg, 64%, AUC HPLC 97.6%) as a white solid: mp <<MP data>>; $^1$H NMR (DMSO-d$_6$, 400 MHz) δ 11.64 (s, 1H), 9.20 (br s, 2H), 8.27 (d, J=2.0 Hz, 1H), 7.93 (d, J=1.6 Hz, 1H), 7.66 (dd, J=8.8, 2.0 Hz, 1H), 7.59-7.51 (m, 2H), 7.43 (d, J=1.6 Hz, 1H), 6.67-6.61 (m, 1H), 4.35 (s, 2H), 4.00 (s, 3H), 3.49 (t, J=6.0 Hz, 2H), 3.11-3.02 (m, 2H); ESI MS m/z 383 [M+H]$^+$.

Example 71

Preparation of 6-chloro-8-(3-(tetrahydrofuran-3-yl)phenylsulfonyl)-1,2,3,4-tetrahydrobenzofuro[3,2-c]pyridine hydrochloride

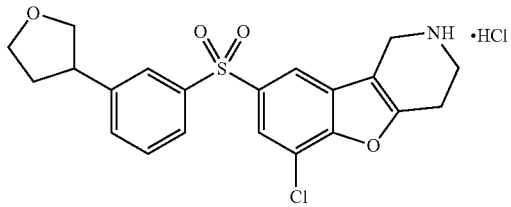 [SMILES: O=S(=O)(c1cccc(C2CCOC2)c1)c1cc(Cl)c2oc3c(c2c1)CNCC3 ; Cl]

Step A: A solution of 1,3-diiodobenzene (3.0 g, 9.09 mmol) in dry THF (40 mL) was cooled to −78° C. under a nitrogen before addition of n-butyl lithium (1.6 M in hexane, 5.6 mL, 9.09 mmol) dropwise over 10 min. The reaction mixture was stirred for 30 min and then a solution of dihydrofuran-3(2H)-one (782 mg, 9.09 mmol) in THF (3 mL) added over 5 min. The reaction mixture was stirred for 1 h at −78° C. then poured into saturated NH₄Cl solution. The mixture was extracted with ethyl acetate and the organic layer dried over Na₂SO₄ and concentrated in vacuo. The residue was purified by flash column chromatography (SiO₂, 9:1 hexanes/ethyl acetate) to give 3-(3-iodophenyl)tetrahydrofuran-3-ol (2.0 g, 76%) as a colorless liquid: ¹H NMR (CDCl₃, 300 MHz) δ 7.87 (t, J=1.8 Hz, 1H), 7.64 (td, J=7.8 Hz, 1H), 7.45 (td, J=7.8 Hz, 1H), 7.10 (t, J=8.1 Hz, 1H), 4.26-4.06 (m, 2H), 3.98-3.82 (m, 2H), 2.46-2.32 (m, 1H), 2.30-2.21 (m, 1H).

Step B: A solution of the product of step A (2.0 g, 3.79 mmol) in dichloromethane (15 mL) was cooled to 0° C. under a nitrogen atmosphere before addition of triethylsilane (5.0 mL, 31.38 mmol), TFA (4.4 mL, 55.74 mmol) and borontrifluoride-diethyletherate complex (7.0 mL, 55.74 mmol). The reaction mixture was stirred for 48 h at ambient temperature, then poured into K₂CO₃ (aq.) solution and extracted with dichloromethane. The combined organic layer was dried over Na₂SO₄, concentrated and the residue purified by flash column chromatography (SiO₂, 98:2 hexanes/ethyl acetate) to give 3-(3-iodophenyl)tetrahydrofuran (0.89 g, 86%) as a colorless liquid: ¹H NMR (CDCl₃, 300 MHz) δ 7.60 (t, J=1.8 Hz, 1H), 7.56 (td, J=7.8 Hz, 1H), 7.22 (d, J=7.8 Hz, 1H), 7.04 (t, J=7.8 Hz, 1H), 4.15-4.00 (m, 2H), 3.96-3.84 (m, 1H), 3.76-3.66 (m, 1H), 3.33 (p, J=7.8 Hz, 1H), 2.43-2.29 (m, 1H), 2.04-1.89 (m, 1H). Step C: The product of step B was coupled with lithium 2-(tert-butoxycarbonyl)-6-chloro-1,2,3,4-tetrahydrobenzofuro[3,2-c]pyridine-8-sulfinate following the procedure of Example 50, step A. The crude product was purified by flash column chromatography (SiO₂, 4:1 hexanes/ethyl acetate) to give tert-butyl 6-chloro-8-(3-(tetrahydrofuran-3-yl)phenylsulfonyl)-3,4-dihydrobenzofuro[3,2-c]pyridine-2(1H)-carboxylate (55 mg, 8%) as an off-white solid: ¹H NMR (CDCl₃, 300 MHz) δ 8.02-7.91 (m, 1H), 7.87-7.76 (m, 3H), 7.51-7.44 (m, 2H), 4.57 (s, 2H), 4.18-4.02 (m, 2H), 3.97-3.78 (m, 3H), 3.77-3.67 (m, 1H), 3.46 (p, J=7.5 Hz, 1H), 2.98-2.84 (m, 2H), 2.49-2.34 (m, 1H), 2.06-1.89 (m, 1H), 1.50 (s, 9H); APCI MS m/z 418 [(M+H)—C₅H₉O₂]⁺.

Step D: The product obtained in step C was Boc deprotected and converted to the hydrochloride salt following the procedure of Example 29, step D to give 6-chloro-8-(3-(tetrahydrofuran-3-yl)phenylsulfonyl)-1,2,3,4-tetrahydrobenzofuro[3,2-c]pyridine hydrochloride (15 mg, 75%, AUC HPLC 98.2%) as an off-white solid: mp <<MP data>> dec.; ¹H NMR (DMSO-d₆, 300 MHz) δ 9.71-9.54 (m, 2H), 8.42 (s, 1H), 8.05 (d, J=1.2 Hz, 1H), 7.96-7.81 (m, 2H), 7.67-7.50 (m, 2H), 4.39 (s, 2H), 4.08-3.89 (m, 2H), 3.80 (q, J=7.8 Hz, 1H), 3.68-3.45 (m, 4H), 3.23-3.08 (m, 2H), 2.43-2.22 (m, 1H), 2.00-1.80 (m, 1H); APCI MS m/z 418 [M+H]⁻.

Example 72

Preparation of (4-((6-chloro-1,2,3,4-tetrahydrobenzofuro[3,2-c]pyridin-8-yl)sulfonyl)phenyl)methanol hydrochloride

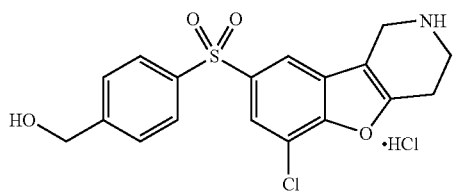 [SMILES: O=S(=O)(c1ccc(CO)cc1)c1cc(Cl)c2oc3c(c2c1)CNCC3 ; Cl]

Step A: To a solution of 4-iodobenzyl alcohol (2.0 g, 8.54 mmol) in dry dichloromethane (15 mL) was added 3,4-dihydro-2H-pyran (0.92 mL, 10.25 mmol) followed by p-toluenesulfonic acid (147 mg, 0.85 mmol). The reaction mixture was stirred at ambient temperature for 2 h under a nitrogen atmosphere before partitioning between water and dichloromethane. The organic layer was washed with water followed by brine solution then dried over Na₂SO₄. After concentration in vacuo the residue was purified by flash column chromatography (SiO₂, 9:1 hexanes/ethyl acetate) to give 2-(4-iodobenzyloxy)tetrahydro-2H-pyran (2.0 g, 74%) as a colorless liquid: ¹H NMR (CDCl₃, 400 MHz) δ 8.12 (d, J=8.4 Hz, 2H), 7.12 (d, J=8.4 Hz, 2H), 4.76-4.65 (m, 2H), 4.46 (d, J=12.0 Hz, 1H), 3.94-3.84 (m, 1H), 3.59-3.49 (m, 1H), 1.91-1.49 (m, 6H).

Step B: The product of step A was coupled with lithium 2-(tert-butoxycarbonyl)-6-chloro-1,2,3,4-tetrahydrobenzofuro[3,2-c]pyridine-8-sulfinate following the procedure of Example 50, step A. The crude product was purified by flash column chromatography (SiO₂, 7:3 hexanes/ethyl acetate) to give tert-butyl 6-chloro-8-((4-(hydroxymethyl)phenyl)sulfonyl)-3,4-dihydrobenzofuro[3,2-c]pyridine-2(1H)-carboxylate (30 mg, 7%) as an off-white solid: ¹H NMR (CDCl₃, 300 MHz) δ 8.02-7.89 (m, 3H), 7.82 (s, 1H), 7.53 (d, J=8.1 Hz, 2H), 4.77 (d, J=5.4 Hz, 2H), 4.56 (s, 2H), 3.83 (t, J=5.7 Hz, 2H), 2.97-2.85 (m, 2H) 1.50 (s, 9H).

Step C: The product of step B was Boc deprotected and converted to the hydrochloride salt following the procedure of Example 29, step D to give (4-(6-chloro-1,2,3,4-tetrahydrobenzofuro[3,2-c]pyridin-8-ylsulfonyl)phenyl)methanol hydrochloride (12 mg, 47%, AUC HPLC 96.8%) as a white solid: mp <<MP data>> dec; ¹H NMR (CD₃OD, 400 MHz) δ 8.12 (d, J=1.6 Hz, 1H), 7.97 (d, J=8.0 Hz, 2H), 7.87 (d, J=1.6 Hz, 1H), 7.56 (d, J=8.4 Hz, 2H), 4.65 (s, 2H), 4.15 (s, 2H), 3.39 (t, J=5.6 Hz, 2H), 3.04-2.97 (m, 2H); APCI MS m/z 378 [M+H]⁺.

Example 73

Preparation of 8-(3-fluorophenylsulfonyl)-1,2,3,4-tetrahydrobenzofuro[3,2-c]pyridine-6-carbonitrile hydrochloride

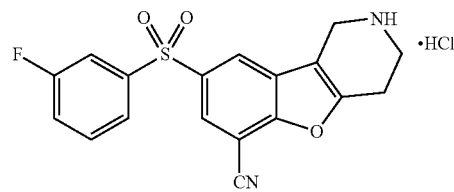 [SMILES: N#Cc1cc(S(=O)(=O)c2cccc(F)c2)cc2c3c(oc12)CCNC3 ; Cl]

Step A: The product of Example 44, step B and sodium 3-fluorobenzenesulfinate were coupled using the procedure of Example 29, step C. Purification by flash column chromatography (SiO₂, 80:20 hexane/ethyl acetate) provided tert-butyl 6-chloro-8-((3-fluorophenyl)sulfonyl)-3,4-dihydrobenzofuro[3,2-c]pyridine-2(1H)-carboxylate (172 mg, 37%) as a white solid: ¹H NMR (CDCl₃, 400 MHz) δ 8.01-7.91 (m, 1H), 7.83 (s, 1H), 7.80-7.73 (m, 1H), 7.70-7.62 (m, 1H), 7.60-7.45 (m, 2H), 4.57 (s, 2H), 3.84 (s, 2H), 2.91 (s, 2H), 1.51 (s, 9H).

Step B: A mixture of the product of step A (43 mg, 0.09 mmol), zinc-dust (1.2 mg, 0.02 mmol), zinc(II) cyanide (7 mg, 0.06 mmol), 1,1'-Bis(diphenylphosphino)ferrocene (5 mg, 0.01 mmol) and di-palladium-tris(dibenzylideneacetone) (25 mg, 0.02 mmol) were suspended in anhydrous dimethylacetamide (3 mL) in a sealed tube. The sealed tube was purged with argon, capped and heated at 120° C. for 16 h. The reaction mixture was cooled to ambient temperature, diluted with water and extracted with ethyl acetate. The organic extract was dried over sodium sulfate, filtered and concentrated in vacuo. The residue was purified by flash column chromatography (SiO$_2$, 75:25 hexane/ethyl acetate) to give tert-butyl 6-chloro-8-((3-fluorophenyl)sulfonyl)-3,4-dihydrobenzofuro[3,2-c]pyridine-2(1H)-carboxylate (20 mg, 47%) as a white solid: $^1$H NMR (CDCl$_3$, 300 MHz) δ 8.25 (s, 1H), 8.10 (d, J=1.5 Hz, 1H), 7.76 (d, J=8.1 Hz, 1H), 7.70-7.62 (m, 1H), 7.60-7.48 (m, 1H), 7.36-7.24 (m, 1H), 4.60 (s, 2H), 3.85 (t, J=5.7 Hz, 2H), 3.02-2.87 (m, 2H), 1.51 (s, 9H).

Step C: To a solution of the product from step B (20 mg, 0.04 mmol) in tetrahydrofuran (2.5 mL) was added concentrated HCl (0.5 mL) at 0° C. The reaction mixture was slowly allowed to reach to ambient temperature. After stirring overnight the reaction mixture was quenched with 10% sodium bicarbonate solution (10 mL) and extracted with dichloromethane. The organic extract was dried over sodium sulfate, filtered and concentrated in vacuo. The residue was purified by flash column chromatography (SiO$_2$, 94:6 dichloromethane/methanol) to give 8-((3-fluorophenyl)sulfonyl)-1,2,3,4-tetrahydrobenzofuro[3,2-c]pyridine-6-carbonitrile (13 mg, 83%) as a white solid: $^1$H NMR (CDCl$_3$, 400 MHz) δ 8.21 (d, J=1.6 Hz, 1H), 8.07 (d, J=1.6 Hz, 1H), 7.79-7.73 (m, 1H), 7.68-7.62 (m, 1H), 7.57-7.49 (m, 1H), 7.33-7.26 (m, 1H), 4.02 (t, J=2.0 Hz, 2H), 3.27 (t, J=5.6 Hz, 2H), 2.93-2.83 (m, 2H).

Step D: The product obtained in step C (13 mg, 0.03 mmol) was converted to hydrochloride salt by dissolving in dichloromethane and treating with 1.25 M HCl in methanol. The reaction mixture was concentrated in vacuo to give 8-((3-fluorophenyl)sulfonyl)-1,2,3,4-tetrahydrobenzofuro[3,2-c]pyridine-6-carbonitrile hydrochloride (13.5 mg, 95%, AUC HPLC>99%) as a white solid: mp <<MP data>>; $^1$H NMR (DMSO-d$_6$, 400 MHz) δ 9.25 (br s, 2H), 8.76 (d, J=2.0 Hz, 1H), 8.59 (d, J=2.0 Hz, 1H), 7.97-7.86 (m, 2H), 7.75-7.66 (m, 1H), 7.64-7.55 (m, 1H), 4.39 (s, 2H), 3.53 (t, J=6.0 Hz, 2H), 3.22-3.12 (m, 2H); APCI MS m/z 357 [M+H]$^+$.

Example 74

Preparation of (8-(phenylsulfonyl)-1,2,3,4-tetrahydrobenzofuro[3,2-c]pyridin-6-yl)methanol hydrochloride

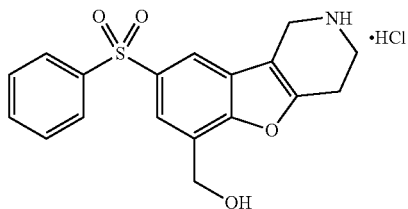 [SMILES: O=S(=O)(c1ccccc1)c1cc(CO)c2oc3c(c2c1)CNCC3 ; Cl]

Step A: To a solution of 4-bromophenol (25 g, 144.5 mmol) in 25% aqueous ammonia solution (350 mL) was added a solution of potassium iodide (72 g, 433.5 mmol) and iodine (36.7 g, 144.5 mmol) in water (288 mL). The reaction mixture was stirred at ambient temperature for 2 h and quenched with 250 mL of water. The reaction was acidified by addition of concentrated HCl (350 mL) and extracted with dichloromethane. The combined organic extracts were dried over Na$_2$SO$_4$ and concentrated in vacuo to give the crude product which was purified by column chromatography (SiO$_2$, 9:1 hexanes/ethyl acetate) providing 4-bromo-2-iodophenol (33 g, 77%) as a pink solid: $^1$H NMR (CDCl$_3$, 300 MHz) δ 7.78-7.75 (m, 1H), 7.37-7.31 (m, 1H), 6.88 (d, J=8.7 Hz, 1H).

Step B: To a solution of product of step A (10.0 g, 33.4 mmol) in methanol (100 mL) at 0° C. was added potassium tert-butoxide (2.59 g, 23.1 mmol) portionwise and the mixture stirred for 40 min. The reaction mixture was concentrated in vacuo, and suspended in dichloromethane. To the suspension was added a solution of O-(mesitylsulfonyl)hydroxylamine (5.53 g, 33.4 mmol) in dichloromethane at 0° C. and the reaction stirred for 1 h. The mixture was then washed with cold 5% KOH solution and dried over anhydrous sodium sulfate. The organic layer was treated with methanesulfonic acid (1.75 mL, 26.72 mmol) then concentrated in vacuo to give crude O-(4-bromo-2-iodophenyl)hydroxylamine methanesulfonic acid salt (8.0 g, 58%) as a brown solid. CAUTION: This compound has potential to be shock sensitive and may be susceptible to decomposition. It should be handled with care and used directly without storage.

Step C: A mixture of the product of step B (7.0 g, 17.0 mmol) and tert-butyl 4-oxopiperidine-1-carboxylate (3.73 g, 18.7 mmol) was suspended in a mixture of glacial acetic acid (63 mL) and methanesulfonic acid (7 mL). The suspension was heated to 110° C. for 3 h. After cooling to ambient temperature the reaction mixture was concentrated in vacuo, cooled to 0° C., quenched with 5% KOH solution and suspended in 2-propanol (100 mL) followed by addition of di-tert-butyl dicarbonate (4.45 g, 20.4 mmol). After stirring for 12 h, the mixture was concentrated in vacuo and extracted with dichloromethane. The organic layer was concentrated in vacuo and the residue purified by flash column chromatography (SiO$_2$, 95:5 hexanes/ethyl acetate) to give tert-butyl 8-bromo-6-iodo-3,4-dihydrobenzofuro[3,2-c]pyridine-2 (1H)-carboxylate (1.0 g, 9%) as a yellow brown solid: $^1$H NMR (CDCl$_3$, 300 MHz) δ 7.71 (d, J=1.8 Hz, 1H), 7.50 (br s, 1H), 4.49 (br s, 2H), 3.87-3.78 (m, 2H), 2.94-2.87 (m, 2H), 1.50 (s, 9H).

Step D: To a solution of the product of step C (300 mg, 0.62 mmol) in tetrahydrofuran (1.5 mL) was added isopropylmagnesium chloride (1 M in tetrahydrofuran) (0.75 mL, 0.75 mmol) dropwise under an argon atmosphere at −20° C. over 5 min. The reaction mixture was stirred at −15° C. to −10° C. for 1 h before dry CO$_2$ gas was bubbled through the reaction mixture over 15 min. The reaction mixture was slowly allowed to reach to ambient temperature and stirred overnight. The mixture was quenched with aqueous saturated ammonium chloride solution (10 mL) and extracted with dichloromethane. The organic extract was dried over sodium sulfate, filtered and concentrated in vacuo to give 8-bromo-2-(tert-butoxycarbonyl)-1,2,3,4-tetrahydrobenzofuro[3,2-c]pyridine-6-carboxylic acid (125 mg, 50%) as a white solid. The crude product was directly used for the next step.

Step E: To a solution of the product of step D (125 mg, 0.31 mmol) in tetrahydrofuran (3 mL) was added borane-tetrahydrofuran complex (1 M in tetrahydrofuran; 0.41 mL, 0.41 mmol) dropwise under an argon atmosphere at 0° C. over 5 min. The reaction mixture was slowly allowed to reach ambient temperature and stirred for 6 h. The reaction mixture was quenched with aqueous sodium bicarbonate solution (10 mL) and extracted with ethyl acetate. The organic extract was dried over sodium sulfate, filtered and concentrated in vacuo. The residue was purified by flash column chromatography (SiO$_2$, 65:35 hexane/ethyl acetate) to give tert-butyl 8-bromo-6-(hydroxymethyl)-3,4-dihydrobenzofuro[3,2-c]pyridine-2(1H)-carboxylate (65 mg, 54%) as a white solid: $^1$H NMR (CDCl$_3$, 300 MHz) δ 7.46 (s, 1H), 7.40 (s, 1H), 4.94 (d, J=6.3 Hz, 2H), 4.49 (s, 2H), 3.81 (t, J=5.4 Hz, 2H), 2.85 (t, J=5.7 Hz, 2H), 2.08 (t, J=6.0 Hz, 1H), 1.50 (s, 9H).

Step F: The product of step E and sodium benzenesulfinate were coupled using the procedure of Example 29, step C. Purification by flash column chromatography (SiO$_2$, 1:1 hexane/ethyl acetate) provided tert-butyl 6-(hydroxymethyl)-8-(phenylsulfonyl)-3,4-dihydrobenzofuro[3,2-c]pyridine-2(1H)-carboxylate (33 mg, 44%) as a colorless oil: $^1$H NMR (CDCl$_3$, 400 MHz) δ 8.03 (s, 1H), 7.99-7.93 (m, 2H), 7.88 (d, J=1.6 Hz, 1H), 7.58-7.46 (m, 3H), 4.99 (d, J=6.0 Hz, 2H), 4.56 (s, 2H), 3.82 (s, 2H), 2.87 (s, 2H), 2.13 (t, J=6.0 Hz, 1H), 1.51 (s, 9H).

Step G: The product of step F was Boc deprotected using the procedure of Example 29, step D. Purification by flash column chromatography (SiO$_2$, 9:1 dichloromethane/methanol) provided (8-(phenylsulfonyl)-1,2,3,4-tetrahydrobenzofuro[3,2-c]pyridin-6-yl)methanol (14 mg, 55%) as a white solid: $^1$H NMR (CDCl$_3$, 400 MHz) δ 8.01-7.93 (m, 3H), 7.85 (d, J=1.6 Hz, 1H), 7.57-7.45 (m, 3H), 4.98 (s, 2H), 3.98 (t, J=1.6 Hz, 2H), 3.24 (t, J=5.6 Hz, 2H), 2.85-2.77 (m, 2H).

Step H: The product obtained in step G (14 mg, 0.04 mmol) was converted to the hydrochloride salt by dissolving in dichloromethane and treating with 1.25 M HCl in methanol. The reaction mixture was concentrated in vacuo to give (8-(phenylsulfonyl)-1,2,3,4-tetrahydrobenzofuro[3,2-c]pyridin-6-yl)methanol hydrochloride (15 mg, 97%, AUC HPLC>99%) as a white solid: mp <<MP data>>; $^1$H NMR (DMSO-d$_6$, 400 MHz) δ 9.32 (br s, 2H), 8.30 (d, J=1.2 Hz, 1H), 7.99-7.87 (m, 3H), 7.71-7.57 (m, 3H), 5.58 (t, J=5.6 Hz, 1H), 4.81 (d, J=5.6 Hz, 2H), 4.38 (s, 2H), 3.52 (t, J=6.0 Hz, 2H), 3.17-3.05 (m, 2H); ESI MS m/z 344 [M+H]$^+$.

Example 75

Preparation of 6-((1H-pyrazol-1-yl)methyl)-8-(phenylsulfonyl)-1,2,3,4-tetrahydrobenzofuro[3,2-c]pyridine hydrochloride

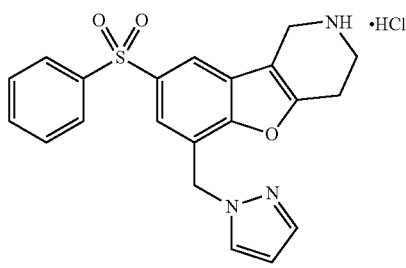 [SMILES: O=S(=O)(c1ccccc1)c1cc(Cn2cccn2)c2oc3c(c2c1)CNCC3 ; Cl]

Step A: To a mixture of the product of Example 74, step E (300 mg, 0.78 mmol) in dichloromethane (4 mL) at 0° C. was added triethylamine (93 mg, 0.92 mmol) followed by methanesulfonyl chloride (100 mg, 0.88 mmol). The reaction mixture was allowed to warm to ambient temperature over 2 h, then treated with saturated sodium bicarbonate solution and extracted with dichloromethane. The organic extracts were dried over sodium sulphate, filtered, and concentrated in vacuo. Purification by flash chromatography (SiO$_2$, 95:5 hexanes/ethyl acetate) provided tert-butyl 8-bromo-6-((methylsulfonyloxy)methyl)-3,4-dihydrobenzofuro[3,2-c]pyridine-2(1H)-carboxylate (340 mg, 94%) as a yellow solid: $^1$H NMR (CDCl$_3$, 300 MHz) δ 7.59 (s, 1H), 7.44 (s, 1H), 5.47 (s, 2H), 4.52 (s, 2H), 3.83 (t, J=5.1 Hz, 2H), 3.02 (s, 3H), 2.88 (s, 2H), 1.51 (s, 9H).

Step B: To a solution of 1H-pyrazole (20 mg, 0.52 mmol) in tetrahydrofuran (3 mL) at 0° C. was added sodium hydride (60% dispersion in oil, 26 mg, 0.39 mmol). After stirring the mixture for 1 h the product of step A (120 mg, 0.26 mmol) was added and the reaction warmed to ambient temperature over 2 h. The reaction mixture was quenched with 5% sodium bicarbonate solution and then extracted with ethyl acetate (3×20 mL). The combined organic layer was washed with brine, dried over sodium sulfate, filtered, and concentrated in vacuo. The crude product was purified by flash column chromatography (95:5 hexanes/ethyl acetate) to give tert-butyl 6-((1H-pyrazol-1-yl)methyl)-8-bromo-3,4-dihydrobenzofuro[3,2-c]pyridine-2(1H)-carboxylate (40 mg, 35%) as a yellow solid: $^1$H NMR (CDCl$_3$, 300 MHz) δ 7.55 (d, J=1.5 Hz, 1H), 7.48 (d, J=1.8 Hz, 2H), 7.14 (d, J=1.5 Hz, 1H), 6.28 (t, J=2.1 Hz, 1H), 5.55 (s, 2H), 4.50 (s, 2H), 3.82 (t, J=5.4 Hz, 2H), 2.87 (t, J=5.4 Hz, 2H), 1.50 (s, 9H).

Step C: The product of step B and sodium benzenesulfinate were coupled using the procedure of Example 29, step C. Purification by flash chromatography (SiO$_2$, 80:20 hexanes/ethyl acetate) provided tert-butyl 6-((1H-pyrazol-1-yl)methyl)-8-(phenylsulfonyl)-3,4-dihydrobenzofuro[3,2-c]pyridine-2(1H)-carboxylate (18 mg, 39%) as a yellow solid: $^1$H NMR (CDCl$_3$, 300 MHz) δ 8.05-7.96 (m, 1H), 7.95-7.85 (m, 2H), 7.62-7.40 (m, 6H), 6.32-6.25 (m, 1H), 5.60 (s, 2H), 4.56 (s, 2H), 3.83 (t, J=5.1 Hz, 2H), 2.95-2.80 (m, 2H), 1.51 (s, 9H).

Step D: The product of step C was Boc deprotected and converted to the hydrochloride salt following the procedure of Example 29, step D to provide 6-((1H-pyrazol-1-yl)methyl)-8-(phenylsulfonyl)-1,2,3,4-tetrahydrobenzofuro[3,2-c]pyridine hydrochloride (13 mg, 82%, AUC HPLC>99%) as a white solid: mp 145-148° C.; $^1$H NMR (DMSO-d$_6$, 400 MHz) δ 9.45 (br s, 2H), 8.35 (d, J=2.0 Hz, 1H), 7.93-7.86 (m, 3H), 7.71-7.56 (m, 4H), 7.48-7.44 (m, 1H), 6.30 (t, J=2.0 Hz, 1H), 5.68 (s, 2H), 4.39 (s, 2H), 3.59-3.50 (m, 2H), 3.16-3.05 (m, 2H); APCI MS m/z 394 [M+H]$^+$.

Example 76

Preparation of 8-(phenylsulfonyl)-6-(1H-pyrazol-1-yl)-1,2,3,4-tetrahydrobenzofuro[3,2-c]pyridine hydrochloride

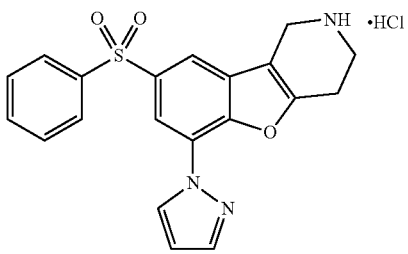 [SMILES: O=S(=O)(c1ccccc1)c1cc(-n2cccn2)c2oc3c(c2c1)CNCC3 ; Cl]

Step A: To a solution of tert-butyl 6-hydroxy-8-phenylsulfonyl-3,4-dihydrobenzofuro[3,2-c]pyridine-2(1H)-carboxylate (275 mg, 0.64 mmol) in dichloromethane (16 mL) under an argon atmosphere was added pyridine (266 µL, 3.3 mmol) followed by trifluoromethanesulfonic anhydride (134 µL, 0.77 mmol) at 0° C. The reaction mixture was allowed to reach to ambient temperature and stirred for a further 3 h before concentrating in vacuo. The residue was purified by flash column chromatography (SiO$_2$, 30:70 hexane/ethyl acetate) providing tert-butyl 8-(phenylsulfonyl)-6-((((trifluoromethyl)sulfonyl)oxy)-3,4-dihydrobenzofuro[3,2-c]pyridine-2(1H)-carboxylate (232 mg, 64%) as a yellow solid: $^1$H NMR (CDCl$_3$, 400 MHz) δ 8.13-7.91 (m, 3H), 7.77 (s, 1H), 7.64-7.48 (m, 3H), 4.58 (s, 2H), 3.84 (s, 2H), 2.91 (s, 2H), 1.50 (s, 9H).

Step B: A mixture of the product of step A (100 mg, 0.17 mmol), (R/S) BINAP (11 mg, 0.02 mmol), benzophenone hydrazine (39 mg, 0.19 mmol) and cesium carbonate (74 mg, 0.26 mmol) in anhydrous toluene (3 mL) was stirred at ambient temperature for 5 min under an argon atmosphere before the addition of palladium(II) acetate (1.3 mg, 0.006 mmol). The reaction flask was purged with argon, sealed, and heated to 110° C. for 5 h. The reaction mixture was cooled to ambient temperature, diluted with aqueous ammonium chloride (15 mL), and extracted with dichloromethane. The organic extract was washed with brine, dried over sodium sulfate, and concentrated in vacuo. The residue was purified by flash column chromatography (SiO$_2$, 15:85 hexane/ethyl acetate) to give tert-butyl 6-(2-(diphenylmethylene)hydrazinyl)-8-(phenylsulfonyl)-3,4-dihydrobenzofuro[3,2-c]pyridine-2(1H)-carboxylate (65 mg, 60%) as a yellow solid: $^1$H NMR (CDCl$_3$, 300 MHz) δ 8.07-7.98 (m, 3H), 7.91 (s, 1H), 7.67-7.46 (m, 9H), 7.41-7.32 (m, 5H), 4.51 (s, 2H), 3.85-3.68 (m, 2H), 2.80-2.66 (m, 2H), 1.49 (s, 9H).

Step C: A mixture of the product of step B (65 mg, 0.10 mmol), 1,1,3,3-tetramethoxypropane (18 µL, 0.11 mmol) and concentrated HCl (0.25 mL) was dissolved in ethanol (5 mL). The reaction flask was purged with argon, sealed and heated at 100° C. for 5 h. The reaction mixture was cooled to ambient temperature, quenched with 10% sodium bicarbonate solution, and extracted with dichloromethane. The organic extract was washed with brine, dried over sodium sulfate, and concentrated in vacuo. The residue was purified by flash column chromatography (SiO$_2$, 93:7 dichloromethane/methanol) to give 8-(phenylsulfonyl)-6-(1H-pyrazol-1-yl)-1,2,3,4-tetrahydrobenzofuro[3,2-c]pyridine (23 mg, 56%) as a white solid: $^1$H NMR (CDCl$_3$, 400 MHz) δ 8.48 (dd, J=2.8, 0.4 Hz, 1H), 8.43 (d, J=1.6 Hz, 1H), 8.03-7.97 (m, 2H), 7.93 (d, J=1.6 Hz, 1H), 7.82-7.77 (m, 1H), 7.58-7.45 (m, 3H), 6.53 (dd, J=2.4, 2.0 Hz, 1H), 4.01 (t, J=2.0 Hz, 2H), 3.27 (t, J=5.6 Hz, 2H), 2.90-2.81 (m, 2H).

Step D: The product obtained in step C (23 mg, 0.06 mmol) was converted to the hydrochloride salt by dissolving in dichloromethane and treating with 1.25 M HCl in methanol. The reaction mixture was concentrated in vacuo to give 8-(phenylsulfonyl)-6-(1H-pyrazol-1-yl)-1,2,3,4-tetrahydrobenzofuro[3,2-c]pyridine hydrochloride (24 mg, 96%, AUC HPLC 98.6%) as a white solid: mp <<MP data>>; $^1$H NMR (DMSO-d$_6$, 400 MHz) δ 9.35 (br s, 2H), 8.69-8.65 (m, 1H), 8.36 (d, J=2.0 Hz, 1H), 8.30 (d, J=1.6 Hz, 1H), 8.05-7.99 (m, 2H), 7.92 (d, J=1.6 Hz, 1H), 7.74-7.59 (m, 3H), 6.89 (d, J=2.0 Hz, 1H), 4.43 (s, 2H), 3.55 (t, J=6.0 Hz, 2H), 3.17 (t, J=6.0 Hz, 2H); ESI MS m/z 380 [M+H]$^+$.

Example 77

Preparation of 8-(phenylsulfonyl)-6-(1H-pyrazol-4-yl)-1,2,3,4-tetrahydrobenzofuro[3,2-c]pyridine hydrochloride

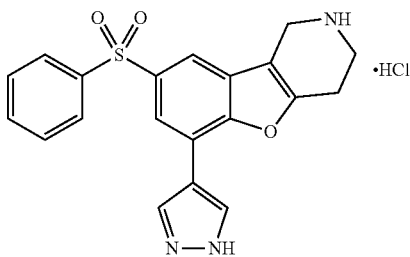 [SMILES: O=S(=O)(c1ccccc1)c1cc(-c2cn[nH]c2)c2oc3c(c2c1)CNCC3 ; Cl]

Step A: A mixture of the product of Example 76, step A (75 mg, 0.13 mmol) and tetrakis(triphenylphosphine)palladium (8.0 mg, 0.006 mmol) in dioxane (3 mL) was stirred at ambient temperature for 30 min under an argon atmosphere before the addition of aqueous sodium bicarbonate (1.2 mL) followed by a solution of (1H-pyrazol-4-yl)boronic acid (23 mg, 0.20 mmol) in ethanol (1.2 mL). The reaction flask was purged with argon, sealed, and heated to 120° C. for 3 h. After cooling to ambient temperature, the mixture was diluted with aqueous ammonium chloride (15 mL) and extracted with dichloromethane. The organic extract was washed with brine, dried over sodium sulfate, and concentrated in vacuo. The residue was purified by flash column chromatography (SiO$_2$, 15:85 hexane/ethyl acetate) to give tert-butyl 8-(phenylsulfonyl)-6-(1H-pyrazol-4-yl)-3,4-dihydrobenzofuro[3,2-c]pyridine-2(1H)-carboxylate (31 mg, 60%) as a white solid: $^1$H NMR (CDCl$_3$, 300 MHz) δ 8.24 (s, 2H), 8.06-7.88 (m, 4H), 7.59-7.43 (m, 4H), 4.59 (s, 2H), 3.86 (t, J=5.1 Hz, 2H), 2.98-2.86 (m, 2H), 1.52 (s, 9H).

Step B: To a solution of the product from step A (36 mg, 0.07 mmol) in tetrahydrofuran (2.5 mL) was added concentrated HCl (0.5 mL) at 0° C. The reaction mixture was slowly allowed to reach ambient temperature and stirred overnight. The precipitate was filtered, washed with tetrahydrofuran, and dried overnight in vacuo at 45° C. to give 8-(phenylsulfonyl)-6-(1H-pyrazol-4-yl)-1,2,3,4-tetrahydrobenzofuro[3,2-c]pyridine hydrochloride (18 mg, 58%, AUC HPLC>99%) as a white solid: mp <<MP data>>; $^1$H NMR (DMSO-d$_6$, 400 MHz) δ 9.46 (br s, 2H), 8.42 (s, 2H), 8.19 (d, J=1.6 Hz, 1H), 8.16 (d, J=2.0 Hz, 1H), 8.08-8.01 (m, 2H), 7.71-7.57 (m, 3H), 4.41 (s, 2H), 3.64 (br s, 2H); 3.22-3.12 (m, 2H); APCI MS m/z 380 [M+H]$^+$.

Example 78

Preparation of N-methyl-8-(phenylsulfonyl)-1,2,3,4-tetrahydrobenzofuro[3,2-c]pyridine-6-carboxamide hydrochloride

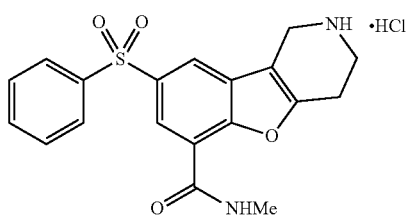 [SMILES: CNC(=O)c1cc(S(=O)(=O)c2ccccc2)cc2c3c(oc12)CCNC3 ; Cl]

Step A: To a solution of the product of Example 74, step D (75 mg, 0.19 mmol) in dichloromethane (3 mL) under an argon atmosphere at ambient temperature was added oxalyl chloride (48 µL, 0.56 mmol) followed by DMF (2 drops). After stirring overnight the reaction mixture was concentrated in vacuo. The residue was dissolved in ethyl acetate (4 mL) before addition of methyl amine (40% aqueous solution, 1 mL) at ambient temperature. After stirring for 2 h at ambient temperature the reaction mixture was diluted with water (20 mL) and extracted with dichloromethane. The organic extract was dried over sodium sulfate, filtered, and concentrated in vacuo. Purification by flash column chromatography (SiO$_2$, 9:1 dichloromethane/ethyl acetate) provided tert-butyl 8-bromo-6-(methylcarbamoyl)-3,4-dihydrobenzofuro[3,2-c]pyridine-2(1H)-carboxylate (52 mg, 67%) as a yellow solid: $^1$H NMR (CDCl$_3$, 400 MHz) δ 8.12 (d, J=2.0 Hz, 1H), 7.62 (s, 1H), 7.30 (s, 1H), 4.52 (s, 2H), 3.94-3.78 (m, 2H), 3.10 (d, J=4.8 Hz, 3H), 2.98-2.83 (m, 2H), 1.51 (s, 9H).

Step B: The product of step A and sodium benzenesulfinate were coupled using the procedure of Example 29, step C. Purification by flash column chromatography (SiO$_2$, 1:4 dichloromethane/ethyl acetate) provided tert-butyl 6-(methylcarbamoyl)-8-(phenylsulfonyl)-3,4-dihydrobenzofuro[3,2-c]pyridine-2(1H)-carboxylate (41 mg, 68%) as a yellow oil: $^1$H NMR (CDCl$_3$, 400 MHz) δ 8.54 (d, J=2.0 Hz, 1H), 8.18 (s, 1H), 7.97 (d, J=7.2 Hz, 2H), 7.59-7.44 (m, 3H), 7.28 (s, 1H), 4.59 (s, 2H), 3.87 (t, J=5.2 Hz, 2H), 3.10 (d, J=4.8 Hz, 3H), 3.00-2.88 (m, 2H), 1.51 (s, 9H).

Step C: To a solution of the product from step B (41 mg, 0.08 mmol) in tetrahydrofuran (2.5 mL) was added concentrated HCl (0.5 mL) at 0° C. The reaction mixture was slowly allowed to reach to ambient temperature. After stirring overnight at ambient temperature the precipitate was filtered, washed with tetrahydrofuran, and dried overnight in vacuo at 45° C. to give N-methyl-8-(phenylsulfonyl)-1,2,3,4-tetrahydrobenzofuro[3,2-c]pyridine-6-carboxamide hydrochloride (21 mg, 59%, AUC HPLC>99%) as a white solid: mp <<MP data>>; $^1$H NMR (DMSO-d$_6$, 400 MHz) δ 9.35 (br s, 2H), 8.56-8.47 (m, 2H), 8.14 (d, J=2.0 Hz, 1H), 8.03-7.95 (m, 2H), 7.72-7.58 (m, 3H), 4.41 (s, 2H), 3.54 (t, J=6.0 Hz, 2H), 3.14 (t, J=6.0 Hz, 2H), 2.86 (d, J=4.8 Hz, 3H); APCI MS m/z 371 [M+H]$^+$.

Example 79

Preparation of 2-(8-(phenylsulfonyl)-1,2,3,4-tetrahydrobenzofuro[3,2-c]pyridin-6-yl)ethanol hydrochloride

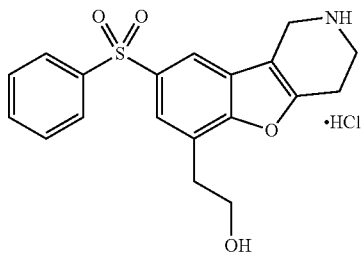 [SMILES: O=S(=O)(c1ccccc1)c1cc(CCO)c2oc3c(c2c1)CNCC3 ; Cl]

Step A: A mixture of tert-butyl 8-(phenylsulfonyl)-6-(((trifluoromethyl)sulfonyl)oxy)-3,4-dihydrobenzofuro[3,2-c]pyridine-2(1H)-carboxylate (200 mg, 0.45 mmol), tributyl (vinyl)stannane (0.11 mL, 0.48 mmol), lithium chloride (45 mg, 1.34 mmol) and palladium tetrakis(triphenylphosphine) (8 mg, 0.01 mmol) was suspended in anhydrous 1,4-dioxane (5 mL). The flask was purged with argon, sealed, and heated to 100° C. for 3 h. The reaction mixture was cooled to ambient temperature, diluted with water, and extracted with ethyl acetate. The organic extract was dried over sodium sulfate, filtered, and concentrated in vacuo. The residue was purified by flash column chromatography (SiO$_2$, 9:1 hexanes/ethyl acetate) to give tert-butyl 8-(phenylsulfonyl)-6-vinyl-3,4-dihydrobenzofuro[3,2-c]pyridine-2(1H)-carboxylate (120 mg, 77%) as a white solid: $^1$H NMR (CDCl$_3$, 300 MHz) δ 8.00-7.90 (m, 3H), 7.86 (s, 1H), 7.61-7.45 (m, 3H), 7.00-6.84 (m, 1H), 6.23 (d, J=17.4 Hz, 1H), 5.60 (d, J=17.4 Hz, 1H), 4.57 (s, 2H), 3.84 (t, J=5.7 Hz, 2H), 2.88 (br s, 2H), 1.51 (s, 9H).

Step B: To a suspension of 4,4,5,5-tetramethyl-1,3,2-dioxaborolane (0.05 mL, 0.33 mmol) and Rh(CO)(PPh$_3$)$_2$Cl (2 mg, 2.7 mmol) in dichloromethane (4 mL) at ambient temperature was added tert-butyl 8-(phenylsulfonyl)-6-vinyl-3,4-dihydrobenzofuro[3,2-c]pyridine-2(1H)-carboxylate (120 mg, 0.27 mmol). The reaction mixture was stirred for 4 h then diluted with water and extracted with dichloromethane. The organic extract was dried over sodium sulfate, filtered, and concentrated in vacuo. The residue was purified by flash column chromatography (SiO$_2$, 7:3 hexanes/ethyl acetate) to give tert-butyl 8-(phenylsulfonyl)-6-(2-(4,4,5,5-tetramethyl-1,3,2-dioxaborolan-2-yl)ethyl)-3,4-dihydrobenzofuro[3,2-c]pyridine-2(1H)-carboxylate (85 mg, 55%) as a white solid: $^1$H NMR (CDCl$_3$, 400 MHz) δ 8.01-7.92 (m, 3H), 7.72 (br s, 1H), 7.58-7.46 (m, 3H), 4.56 (s, 2H), 3.97 (q, J=6.4 Hz, 2H), 3.83 (br s, 2H), 3.16 (t, J=6.4 Hz, 2H), 2.86 (br s, 2H), 1.51 (s, 9H), 1.39-1.19 (m, 12H).

Step C: To a solution of tert-butyl 8-(phenylsulfonyl)-6-(2-(4,4,5,5-tetramethyl-1,3,2-dioxaborolan-2-yl)ethyl)-3,4-dihydrobenzofuro[3,2-c]pyridine-2(1H)-carboxylate (85 mg, 0.15 mmol) in THF (3 mL) was added sodium hydroxide (3 N aqueous solution, 0.08 mL, 0.22 mmol) followed by hydrogen peroxide (30% aqueous solution, 0.07 mL, 0.60 mmol). The reaction mixture was stirred at ambient temperature for 2 h then diluted with water and extracted with dichloromethane. The organic extract was dried over sodium sulfate, filtered, and concentrated in vacuo. The resultant solid was Boc-protected and converted to the hydrochloride salt following the procedure of Example 29, step D to give 2-(8-(phenylsulfonyl)-1,2,3,4-tetrahydrobenzofuro[3,2-c]pyridin-6-yl)ethanol hydrochloride (30 mg, 43%, AUC HPLC 99.5%) as a white solid: mp 239-240° C.; $^1$H NMR (DMSO-d$_6$, 400 MHz) δ 9.35 (br s, 2H), 8.22 (s, 1H), 7.96 (d, J=7.2 Hz, 2H), 7.81 (s, 1H), 7.70-7.58 (m, 3H), 4.76 (br s, 1H), 4.38 (br s, 2H), 3.72 (br s, 2H), 3.52 (br s, 2H), 3.11 (br s, 2H), 3.04 (t, J=6.4 Hz, 2H); APCI MS m/z 358 [M+H]$^+$.

Example 80

Preparation of 1-(8-(phenylsulfonyl)-1,2,3,4-tetrahydrobenzofuro[3,2-c]pyridin-6-yl)propan-2-ol hydrochloride

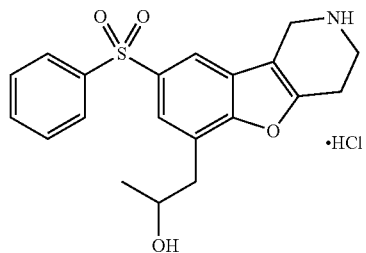 [SMILES: CC(O)Cc1cc(S(=O)(=O)c2ccccc2)cc2c3c(oc12)CCNC3 ; Cl]

Step A: To a solution of tert-butyl 8-bromo-6-iodo-3,4-dihydrobenzofuro[3,2-c]pyridine-2(1H)-carboxylate (200 mg, 0.42 mmol) in anhydrous THF (2 mL) at −78° C. was added isopropylmagnesium bromide (2 M solution in THF, 0.4 mL, 0.84 mmol). The reaction mixture was stirred at −40° C. for 1 h and Cu(I) iodide (96 mg, 0.50 mmol) was added. The reaction mixture was stirred at −40° C. for a further 30 min then 2-methyloxirane (0.29 mL, 4.18 mmol) was added. After 1 h, the reaction was quenched with saturated ammonium chloride and extracted with ethyl acetate. The organic extract was dried over sodium sulfate, filtered, and concentrated in vacuo. The residue was purified by flash column chromatography (SiO$_2$, 7:3 hexanes/ethyl acetate) to give tert-butyl 8-bromo-6-(2-hydroxypropyl)-3,4-dihydrobenzofuro[3,2-c]pyridine-2(1H)-carboxylate (110 mg, 17%) as a colorless oil: $^1$H NMR (CDCl$_3$, 300 MHz) δ 7.42 (d, J=1.5 Hz, 1H), 7.22 (d, J=1.5 Hz, 1H), 4.50 (s, 2H), 4.30-4.16 (m, 1H), 3.82 (br s, 2H), 3.05-2.91 (m, 2H), 2.85 (br s, 2H), 1.50 (s, 9H), 1.27 (d, J=6.3 Hz, 3H).

Step B: A mixture of tert-butyl 8-bromo-6-(2-hydroxypropyl)-3,4-dihydrobenzofuro[3,2-c]pyridine-2(1H)-carboxylate (110 mg, 0.27 mmol), sodium benzenesulfinate (53 mg, 0.32 mmol), di-palladium-tris(dibenzylideneacetone) (24 mg, 0.03 mmol), cesium carbonate (131 mg, 0.40 mmol) and xantphos (31 mg, 0.06 mmol) was suspended in anhydrous toluene (8 mL). The flask was purged with argon, sealed, and heated to 120° C. for 14 h. The reaction mixture was cooled, diluted with dichloromethane, and filtered through a celite bed. The filtrate was concentrated in vacuo to give the crude product which was purified by flash column chromatography (SiO$_2$, 4:1 hexanes/ethyl acetate) to give tert-butyl 6-(2-hydroxypropyl)-8-(phenylsulfonyl)-3,4-dihydrobenzofuro[3,2-c]pyridine-2(1H)-carboxylate (50 mg, 44%) as a white solid: $^1$H NMR (CDCl$_3$, 300 MHz) δ 8.00-7.92 (m, 3H), 7.71 (s, 1H), 7.58-7.45 (m, 3H), 4.56 (br s, 2H), 4.26-4.17 (m, 1H), 3.83 (s, 2H), 3.04 (t, J=3.9 Hz, 2H), 2.86 (br s, 2H), 1.51 (s, 9H), 1.25 (d, J=4.8 Hz, 3H).

Step C: The product of step B was Boc-protected and converted to the hydrochloride salt following the procedure of Example 29, step D to give 1-(8-(phenylsulfonyl)-1,2,3,4-tetrahydrobenzofuro[3,2-c]pyridin-6-yl)propan-2-ol hydrochloride (21 mg, 49%, AUC HPLC 99.6%) as a white solid: mp 283-284° C.; $^1$H NMR (DMSO-d$_6$, 400 MHz) δ 9.52 (br s, 2H), 8.21 (s, 1H), 7.96-7.92 (m, 2H), 7.79 (s, 1H), 7.69-7.57 (m, 3H), 4.71 (s, 1H), 4.37 (s, 2H), 4.05-3.95 (m, 1H), 3.52 (d, J=5.6 Hz, 2H), 3.11 (d, J=5.6 Hz, 2H), 2.94 (d, J=6.4 Hz, 2H), 1.07 (d, J=6.0 Hz, 3H); APCI MS m/z 372 [M+H]$^+$.

Example 81

Preparation of 6-chloro-1-methyl-8-(phenylsulfonyl)-1,2,3,4-tetra hydrobenzofuro[3,2-c]pyridine hydrochloride and 6-chloro-3-methyl-8-(phenylsulfonyl)-1,2,3,4-tetrahydrobenzofuro[3,2-c]pyridine hydrochloride

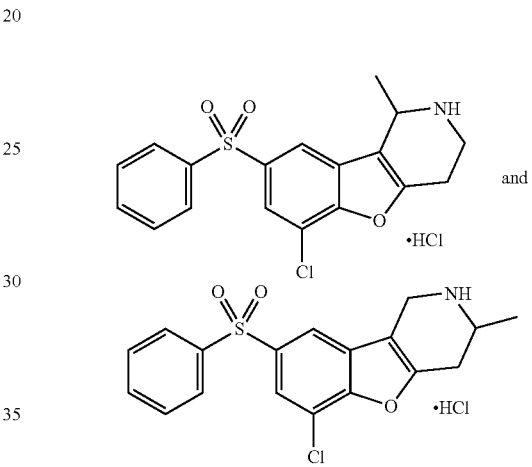

Step A: To a stirred solution of aluminum chloride (6.8 g, 51 mmol) in dichloromethane (10 mL) at −35° C. under a nitrogen atmosphere was added slowly a solution of 2-trans-crotonyl chloride (5.0 mL, 50 mmol) in dichloromethane (10 mL) while maintaining the reaction temperature at −35° C. After stirring for 15 minutes, a solution of vinyltrimethylsilane chloride (7.5 mL, 51 mmol) in dichloromethane (30 mL) was added over 30 minutes at the same temperature. After stirring for another 30 minutes, the solution was cooled to at −50° C. and a cold solution of potassium carbonate (36 g, 260 mmol) in water (85 mL) was added cautiously. After 5 minutes, the reaction was allowed to warm to ambient temperature and stirred vigorously for another 20 minutes. The two layers were separated and the aqueous phase was further extracted with dichloromethane (3×50 mL). The combined organic extracts were washed with water (100 mL), dried over Na$_2$SO$_4$ and filtered. The filtrate was concentrated in vacuo to yield crude (E)-hexa-1,4-dien-3-one (3.46 g, 72%) as brown oil which was sufficiently pure for the next step.

Step B: To a stirred solution of benzylamine (5.2 mL, 47 mmol) in acetonitrile (30 mL) was added aqueous NaHCO$_3$ solution (20 mL, 1.8 M, 36 mmol). After cooling to 16° C., the crude product obtained in step A (3.46 g, 32.9 mmol) dissolved in acetonitrile (30 mL) was added slowly over 40 minutes. After addition, the solution was heated to reflux for 1 h. The solvent was evaporated in vacuo to approximate 25 mL volume and ethyl acetate (60 mL) added. The resulting solution was stirred for 15 minutes. The organic layer was separated, washed with water (60 mL), dried over Na$_2$SO$_4$ and filtered. The filtrate was concentrated in vacuo and the residue purified by flash column chromatography (SiO$_2$, 8:1 to 7:3 hexanes/ethyl acetate) to give 1-benzyl-2-methylpiperidin-4-one (3.9 g, 54%) as a brown oil: $^1$H NMR (CDCl$_3$, 300 MHz) δ 7.39-7.26 (m, 5H), 3.96 (d, J=13.5 Hz, 1H), 3.45 (d, J=13.2 Hz, 1H), 3.03-2.95 (m, 2H), 2.56-2.51 (m, 2H), 2.39-2.31 (m, 2H), 2.28-2.24 (m, 1H), 1.17 (d, J=6.3 Hz, 3H).

Step C: To a solution of the product of step B (3.8 g, 18.7 mmol) in acetic acid (20 mL) was added Pd/C 10% (380 mg) cautiously. The resulting mixture was hydrogenated at 50 psi H2 for 3 h. The reaction mixture was filtered through celite and washed with acetic acid (20 mL). The filtrate was concentrated in vacuo to yield 2-methylpiperidin-4-one acetate as a brown oil (2.98 g, >99%) which was sufficiently pure for the next step: $^1$H NMR (CD$_3$OD, 400 MHz) δ 3.24-3.19 (m, 1H), 2.86-2.81 (m, 1H), 2.74-2.67 (m, 1H), 2.51-2.49 (m, 2H), 2.37-2.28 (m, 2H), 2.22-2.18 (m, 1H), 2.12-2.02 (m, 2H), 1.08 (d, J=6.4 Hz, 3H).

Step D: The product obtained from step C (3.8 g, 18.7 mmol) was reacted with O-(4-bromo-2-chlorophenyl)hydroxylamine hydrochloride following the procedure of Example 29 step B. Purification by column chromatography (SiO$_2$, 49:1 to 19:1 hexanes/ethyl acetate) afforded a 1:2 inseparable mixture of tert-butyl 8-bromo-6-chloro-1-methyl-3,4-dihydrobenzofuro[3,2-c]pyridine-2(1H)-carboxylate and tert-butyl 8-bromo-6-chloro-3-methyl-3,4-dihydrobenzofuro[3,2-c]pyridine-2(1H)-carboxylate (3.0 g, 40%) as a colorless oil: $^1$H NMR (CDCl$_3$, 300 MHz) δ 7.46 (d, J=2.1 Hz, 1H), 7.39 (d, J=1.8 Hz, 1H), 4.90 (br s, 1H), 4.08-4.02 (m, 1H), 3.71 (s, 1H), 3.20-2.90 (m, 1H), 2.78-2.60 (m, 1H), 1.56-1.44 (m, 9H), 1.35-1.18 (m, 3H).

Step E: The product mixture obtained from step D (2.0 g, 5.0 mmol) and sodium benzenesulfinate were coupled using the procedure of Example 29 step D. Purification by flash column chromatography (SiO$_2$, 6:1 to 7:3, hexanes/ethyl acetate) afforded a 1:2 inseparable mixture of tert-butyl 6-chloro-1-methyl-8-(phenylsulfonyl)-3,4-dihydrobenzofuro[3,2-c]pyridine-2(1H)-carboxylate and tert-butyl 6-chloro-3-methyl-8-(phenylsulfonyl)-3,4-dihydrobenzofuro[3,2-c]pyridine-2(1H)-carboxylate (1.03 g, 43%) as a yellow oil which was used directly in the next step.

Step F: The mixture of isomers from step E were Boc deprotected using the procedure of Example 29, step D. Purification by flash column chromatography (SiO$_2$, 19:1 to 4:1, dichloromethane/methanol) afforded 6-chloro-1-methyl-8-(phenylsulfonyl)-1,2,3,4-tetrahydrobenzofuro[3,2-c]pyridine (202 mg, 26%) as a brown oil: $^1$H NMR (CDCl$_3$, 400 MHz) δ 8.01-7.94 (m, 3H), 7.81 (d, J=1.6 Hz, 1H), 7.57-7.49 (m, 3H), 4.23-4.18 (m, 1H), 3.43-3.37 (m, 1H), 3.14-3.07 (m, 1H), 2.86-2.78 (m, 2H), 1.52 (d, J=6.8 Hz, 3H); and 6-chloro-3-methyl-8-(phenylsulfonyl)-1,2,3,4-tetrahydrobenzofuro[3,2-c]pyridine (395 mg, 49%) as a brown oil: $^1$H NMR (CDCl$_3$, 400 MHz) δ 7.96-7.94 (m, 3H), 7.80 (d, J=1.6 Hz, 1H), 7.57-7.49 (m, 3H), 4.07-3.97 (m, 1H), 3.19-3.14 (m, 1H), 2.90-2.84 (m, 1H), 2.57-2.49 (m, 1H), 1.34 (d, J=6.4 Hz, 3H).

Step G: 6-chloro-1-methyl-8-(phenylsulfonyl)-1,2,3,4-tetrahydrobenzofuro[3,2-c]pyridine (100 mg, 0.3 mmol) was converted to the hydrochloride salt by dissolving in methanol and treating with 1.25 M HCl in methanol. The reaction mixture was concentrated in vacuo to give 6-chloro-1-methyl-8-(phenylsulfonyl)-1,2,3,4-tetrahydrobenzofuro[3,2-c] pyridine hydrochloride (81a, 110 mg, 97%, AUC HPLC>99%): mp <<MP data>>; $^1$H NMR (DMSO-d$_6$, 400 MHz) δ 9.55 (br s, 2H), 8.35 (d, J=1.6 Hz, 1H), 8.07-8.03 (m, 3H), 7.70-7.61 (m, 3H), 4.87-4.82 (m, 1H), 3.65-3.59 (m, 1H), 3.49-3.43 (m, 1H), 3.16-3.13 (m, 2H), 1.66 (d, J=6.8 Hz, 3H); ESI MS m/z 403 [M+H+CH$_3$CN]$^+$.

Step H: 6-chloro-3-methyl-8-(phenylsulfonyl)-1,2,3,4-tetrahydrobenzofuro[3,2-c]pyridine (100 mg, 0.3 mmol) was converted to the hydrochloride salt by dissolving in methanol and treating with 1.25 M HCl in methanol. The reaction mixture was concentrated in vacuo to give 6-chloro-3-methyl-8-(phenylsulfonyl)-1,2,3,4-tetra hydrobenzofuro[3,2-c] pyridine hydrochloride (81b, 108 mg, 96%, AUC HPLC 98.1%): mp <<MP data>>; $^1$H NMR (DMSO-d$_6$, 400 MHz) δ 9.62 (br, 2H), 8.41 (d, J=1.6 Hz, 1H), 8.04-8.02 (m, 3H), 7.71-7.62 (m, 3H), 4.51-4.32 (m, 2H), 3.77-3.72 (m, 1H), 3.26-3.24 (m, 1H), 2.98-2.91 (m, 1H), 1.44 (d, J=6.4 Hz, 3H); ESI MS m/z 403 [M+H+CH$_3$CN]$^+$.

Example 82

Preparation of (+) 6-chloro-1-methyl-8-(phenylsulfonyl)-1,2,3,4-tetra hydrobenzofuro[3,2-c]pyridine hydrochloride and (−) 6-chloro-1-methyl-8-(phenylsulfonyl)-1,2,3,4-tetrahydrobenzofuro[3,2-c]pyridine hydrochloride Enantiomer A

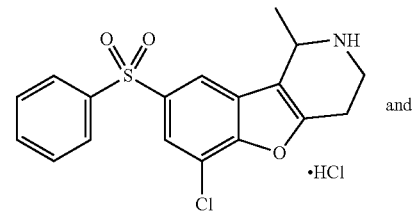

and

Enantiomer B

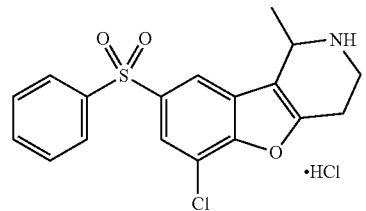

Step A: The racemate of Example 81, step G (270 mg) was separated into single enantiomers using a Chiralpak AD preparative HPLC column (90:10 to 80:20 heptane/2-propanol+0.1% diethylamine): Enantiomer A [(+)-enantiomer] (120 mg, 44%) was recovered as a white solid: [α]$^{20}_D$=+87.5° (c=0.34, CH$_2$Cl$_2$); chiral phase HPLC>99% (AUC, Chiralpak AD column), t$_R$=14.9 min.; Enantiomer B [(−)-enantiomer] (124 mg, 45%) was recovered as a white solid: [α]$^{20}_D$=−67.0° (c=0.14, CH$_2$Cl$_2$); chiral phase HPLC>99% (AUC, Chiralpak AD column), t$_R$=20.5 min.

Step B: Enantiomer A from step A (45 mg, 0.13 mmol) was converted to the hydrochloride salt by dissolving in methanol and treating with 1.25 M HCl in methanol. The reaction mixture was concentrated in vacuo to give (+)-6-chloro-1-methyl-8-(phenylsulfonyl)-1,2,3,4-tetrahydrobenzofuro[3, 2-c]pyridine hydrochloride (82a, 50 mg, 99%, AUC HPLC 98.7%) as a white solid: [α]$^{20}_D$ (c=0.8, methanol)=+16.0°; mp 295° C. dec.; chiral phase HPLC>99% (Chiralpak AD column, heptane/2-propanol 80:20+0.1% diethylamine, t$_R$=14.9 min); $^1$H NMR (DMSO-d$_6$, 300 MHz) δ 9.65 (br s, 2H), 8.36 (d, J=1.8 Hz, 1H), 8.08-8.04 (m, 3H), 7.71-7.60 (m, 3H), 4.87-4.82 (m, 1H), 3.65-3.59 (m, 1H), 3.48-3.43 (m, 1H), 3.16-3.14 (m, 2H), 1.67 (d, J=6.9 Hz, 3H); ESI MS m/z 362 [M+H]+.

Step C: To a solution of enantiomer B from step A (120 mg, 0.3 mmol) in methanol (1 mL) and dichloromethane (1 mL) was added 2 M HCl in diethyl ether solution (5 mL). The precipitated solid was isolated by filtration to afford (+6-chloro-1-methyl-8-(phenylsulfonyl)-1,2,3,4-tetrahydrobenzofuro[3,2-c]pyridine hydrochloride (82b, 86 mg, 77%, AUC HPLC>99%) as a white solid: $[\alpha]^{20}_D$ (c=1.0, methanol)=−14.0°; mp>295° C.; chiral phase HPLC 98.4% (Chiralpak AD column, heptane/2-propanol 80:20+0.1% diethylamine, $t_R$=20.5 min); 1H NMR (DMSO-$d_6$, 300 MHz) δ 9.83 (br s, 2H), 8.36 (d, J=1.5 Hz, 1H), 8.08-8.04 (m, 3H), 7.71-7.61 (m, 3H), 4.87-4.85 (m, 1H), 3.66-3.58 (m, 1H), 3.50-3.33 (m, 1H), 3.15 (t, J=5.7 Hz, 2H), 1.67 (d, J=6.9 Hz, 3H); ESI MS m/z 362 [M+H]+.

Example 83

Preparation of (−) 6-chloro-3-methyl-8-(phenyl sulfonyl)-1,2,3,4-tetra hydrobenzofuro[3,2-c]pyridine hydrochloride and (+) 6-chloro-3-methyl-8-(phenylsulfonyl)-1,2,3,4-tetrahydrobenzofuro[3,2-c]pyridine hydrochloride

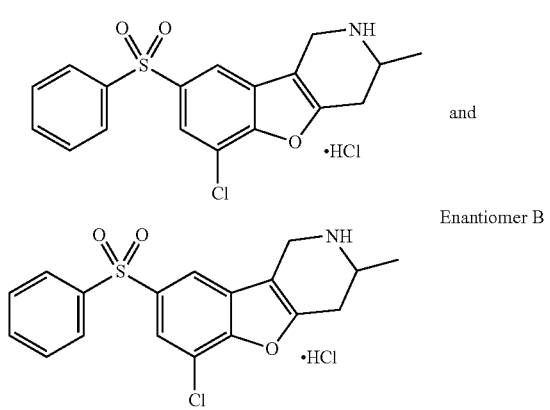

Enantiomer A and

Enantiomer B

Step A: The racemate of Example 81, step H (470 mg) was separated into single enantiomers using a Chiralpak AD preparative HPLC column (90:10 to 80:20 heptane/2-propanol+0.1% diethylamine): Enantiomer A [(−)-enantiomer] (220 mg, 47%) was recovered as a white solid; $[\alpha]^{20}_D$ ($CH_2Cl_2$, 0.22)=−63.6°; chiral phase HPLC>99% (AUC, Chiralpak AD column), $t_R$=20.5 min.; Enantiomer B [(+)-enantiomer] (224 mg, 48%) was recovered as a white solid; $[\alpha]^{20}_D$ ($CH_2Cl_2$, 0.22)=+44.6°; chiral phase HPLC>99% (AUC, Chiralpak AD column), $t_R$=28.9 min.

Step B: To enantiomer A from step A (220 mg, 0.6 mmol) in methanol (1 mL) and dichloromethane (1 mL) was added 2 M HCl in diethyl ether solution (5 mL). The precipitated solid was isolated by filtration to afford (−) 6-chloro-3-methyl-8-(phenylsulfonyl)-1,2,3,4-tetrahydrobenzofuro[3,2-c]pyridine hydrochloride (83a, 216 mg, 87%, AUC HPLC>99%) as a white solid: $[\alpha]^{20}_D$ (c=0.9, methanol)=−23.0°; mp 293° C. dec.; chiral phase HPLC>99% (Chiralpak AD column, heptane/2-propanol 80:20+0.1% diethylamine, $t_R$=20.5 min); 1H NMR (DMSO-$d_6$, 300 MHz) δ 9.83 (br s, 2H), 8.42 (d, J=1.8 Hz, 1H), 8.04-8.02 (m, 3H), 7.71-7.61 (m, 3H), 4.51-4.31 (m, 2H), 3.78-3.72 (m, 1H), 3.34-3.24 (m, 1H), 3.01-2.92 (m, 1H), 1.45 (d, J=6.6 Hz, 3H); ESI MS m/z 362 [M+H]+.

Step C: Enantiomer B from step A (55 mg, 0.16 mmol) was converted to the hydrochloride salt by dissolving in methanol and treating with 1.25 M HCl in methanol. The reaction mixture was concentrated in vacuo to give (+)-6-chloro-3-methyl-8-(phenylsulfonyl)-1,2,3,4-tetra hydrobenzofuro[3,2-c]pyridine hydrochloride (83b, 60 mg, 99%, AUC HPLC>99%) as a white solid: $[\alpha]^{20}_D$ (c=1.0, methanol)=+27.2°; mp 288-290° C.; chiral phase HPLC>99% (Chiralpak AD column, heptane/2-propanol 80:20+0.1% diethylamine, $t_R$=28.9 min); 1H NMR (DMSO-$d_6$, 300 MHz) δ 9.71 (br s, 2H), 8.42 (d, J=1.8 Hz, 1H), 8.05-8.02 (m, 3H), 7.71-7.61 (m, 3H), 4.52-4.32 (m, 2H), 3.79-3.72 (m, 1H), 3.32-3.24 (m, 1H), 3.00-2.91 (m, 1H), 1.45 (d, J=6.3 Hz, 3H); ESI MS m/z 362 [M+H]+.

Example 84

Preparation of 6-chloro-1,1-dimethyl-8-(phenylsulfonyl)-1,2,3,4-tetrahydrobenzofuro[3,2-c]pyridine hydrochloride

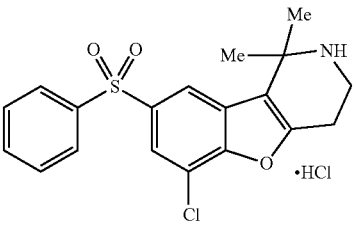 [SMILES: CC1(C)NCCc2oc3c(Cl)cc(S(=O)(=O)c4ccccc4)cc3c21 ; Cl]

Step A: To a solution of 4-bromo-2-chlorophenol (10 g, 48.2 mmol) in 25% aqueous ammonia solution (140 mL) was added a solution of potassium iodide (24 g, 144.6 mmol) and iodine (12.2 g, 48.2 mmol) in water (125 mL). The reaction mixture was stirred at ambient temperature for 4 h and quenched with 100 mL of water. The reaction was acidified by addition of concentrated HCl (150 mL) and extracted with ethyl acetate (3×40 mL). The combined organic extracts were dried over $Na_2SO_4$ and concentrated in vacuo to give the crude product which was purified by column chromatography ($SiO_2$, 9:1 hexanes/ethyl acetate) providing 4-bromo-2-chloro-6-iodophenol (14 g, 89%) as an off-white solid: 1H NMR (CDCl3, 400 MHz) δ 7.74 (d, J=2.0 Hz, 1H), 7.47 (d, J=2.0 Hz, 1H), 5.93 (s, 1H).

Step B: The product of step A (14.0 g, 42.76 mmol) was added to a mixture of but-3-yn-1-ol (3.24 mL, 42.79 mmol), copper(II)oxide (3.67 g, 25.67 mmol), pyridine (21.3 mL) and N-methylpyrrolidone (85.0 mL). The reaction mixture was heated to 70° C. for 12 h then 100° C. for a further 2.5 h. The mixture was diluted with MTBE (200 mL), washed successively with 5% aq $NH_4OH$ (200 mL), 0.5 M NaOH (200 mL) and saturated brine solution (200 mL) and extracted with ethyl acetate (3×75 mL). The combined organic extracts were dried over $Na_2SO_4$ and concentrated in vacuo to give the crude product which was purified by column chromatography ($SiO_2$, 4:1 hexanes/ethyl acetate) providing 2-(5-bromo-7-chlorobenzofuran-2-yl)ethanol (7.8 g, 66%) as an off-white solid: 1H NMR (CDCl3, 400 MHz) δ 7.52 (d, J=1.6 Hz, 1H), 7.37 (d, J=2.0 Hz, 1H), 6.52-6.51 (m, 1H), 4.02 (q, J=6.0 Hz, 2H), 3.09 (t, J=6.2 Hz, 2H), 1.65 (t, J=5.6 Hz, 1H).

Step C: To a solution of the product of step B (3.5 g, 12.7 mmol) in dichloromethane (30 mL) was added triethylamine (3.7 mL, 25.4 mmol) followed by p-toluenesulfonyl chloride (3.6 mL, 19.05 mmol) at 0° C. The reaction mixture was stirred at ambient temperature for 12 h and concentrated in vacuo. The reaction mixture was quenched with saturated sodium bicarbonate solution, washed with 0.5 N HCl and extracted with ethyl acetate (2×20 mL). The combined organic extracts were dried over $Na_2SO_4$ and concentrated in vacuo to give the crude product which was purified by column chromatography ($SiO_2$, 4:1 hexanes/ethyl acetate) providing 2-(5-bromo-7-chlorobenzofuran-2-yl)ethyl 4-methylbenzenesulfonate (5.1 g, 95%) as an off-white solid: $^1$H NMR ($CDCl_3$, 400 MHz) δ 7.66-7.62 (m, 2H), 7.49 (d, J=2.0 Hz, 1H), 7.36 (d, J=1.6 Hz, 1H), 7.18-7.14 (m, 2H), 6.43 (s, 1H), 4.39 (t, J=6.4 Hz, 2H), 3.14 (t, J=6.0 Hz, 2H), 2.37 (s, 3H).

Step D: To a solution of the product of step C (2.3 g, 5.35 mmol) in dimethylformamide (11 mL) was added sodium azide (1.2 g, 18.73 mmol) at ambient temperature. The reaction mixture was heated at 70° C. for 2 h, cooled and quenched with water then extracted with ethyl acetate (2×15 mL). The combined organic extracts were dried over $Na_2SO_4$ and concentrated in vacuo to give the crude product which was purified by column chromatography ($SiO_2$, 4:1 hexanes/ethyl acetate) providing 2-(2-azidoethyl)-5-bromo-7-chlorobenzofuran (1.2 g, 75%) as an off-white solid: $^1$H NMR ($CDCl_3$, 400 MHz) δ 7.52-7.49 (m, 1H), 7.37-7.35 (m, 1H), 6.50 (s, 1H), 3.67 (t, J=6.8 Hz, 2H), 3.07 (t, J=6.8 Hz, 2H).

Step E: To a solution of the product of step D (500 mg, 1.66 mmol) in THF (8 mL) was added triphenylphosphine (72 mg, 3.32 mmol) followed by water (3 mL). The reaction mixture was heated to 65° C. for 4 h and concentrated in vacuo. Purification by column chromatography ($SiO_2$, 95:5 dichloromethane/methanol) provided 2-(5-bromo-7-chlorobenzofuran-2-yl)ethanamine (388 mg, 85%) as a colorless liquid: $^1$H NMR ($CDCl_3$, 400 MHz) δ 7.51 (t, J=2.4 Hz, 1H), 7.36 (t, J=2.4 Hz, 1H), 6.45 (s, 1H), 3.12 (t, J=8.4 Hz, 2H), 2.94 (t, J=8.8 Hz, 2H).

Step F: A mixture of the product of step E (75 mg, 0.27 mmol), acetone (3 mL) and titanium tetra-isopropoxide (93 mg, 0.32 mmol), was heated at 90° C. under an argon atmosphere. After 3 h, the reaction mixture was cooled to 0° C. and a solution of formic acid (1.03 mL, 27.3 mmol) and acetic anhydride (4.21 mL, 54.6 mmol) was added. After heating the reaction mixture to 90° C. for 2 h, trifluoroacetic acid was added and the reaction was maintained at 90° C. for 16 h. The reaction mixture was cooled to ambient temperature, quenched with methanol (10 mL) and diluted with 20% methanol/dichloromethane (120 mL). The mixture was passed through a short silica gel column and the filtrate concentrated in vacuo. The residue was dissolved in ethanol (6 mL) and 20% aqueous sodium hydroxide (6 mL) was added. After refluxing for 15 h, the reaction mixture was cooled, diluted with water (30 mL), and extracted with dichloromethane (2×10 mL). The combined organic extracts were dried over $Na_2SO_4$ and concentrated in vacuo to give the crude product which was purified by column chromatography ($SiO_2$, 95:5 dichloromethane/methanol) providing 8-bromo-6-chloro-1,1-dimethyl-1,2,3,4-tetrahydrobenzofuro[3,2-c]pyridine (45 mg, 52%) as an off-white solid: $^1$H NMR ($CDCl_3$, 400 MHz) δ 7.49 (d, J=2.0 Hz, 1H), 7.36 (d, J=1.6 Hz, 1H), 3.24 (t, J=5.6 Hz, 2H), 2.77 (t, J=5.6 Hz, 2H), 1.49 (s, 6H).

Step G: A mixture of the product of step F (34 mg, 0.11 mmol), sodium benzenesulfinate (26 mg, 0.16 mmol), dipalladium-tris(dibenzylideneacetone) (4.9 mg, 0.005 mmol), cesium carbonate (51 mg, 1.5 mmol) and xantphos (6.24 mg, 0.01 mmol) was suspended in anhydrous toluene (3 mL). The reaction flask was purged with argon and heated to 110° C. for 20 h. After cooling, the reaction mixture was diluted with dichloromethane and filtered through a celite bed. The filtrate was concentrated in vacuo and the residue purified by flash column chromatography ($SiO_2$, 95:5 dichloromethane/methanol) to give 6-chloro-1,1-dimethyl-8-(phenylsulfonyl)-1,2,3,4-tetrahydrobenzofuro[3,2-c]pyiridine (4 mg, 7%) as an off-white solid: $^1$H NMR ($CDCl_3$, 400 MHz) δ 8.03 (d, J=1.6 Hz, 1H), 7.98-7.94 (m, 2H), 7.79 (d, J=1.6 Hz, 1H), 7.59-7.49 (m, 3H), 3.25 (t, J=6.0 Hz, 2H), 2.78 (t, J=5.6 Hz, 2H), 1.52 (s, 6H).

Step H: The product of step G (4 mg, 0.01 mmol) was converted to the hydrochloride salt by dissolving in methanol and treating with 1.25 M HCl in methanol. The reaction mixture was concentrated in vacuo to give 6-chloro-1,1-dimethyl-8-(phenylsulfonyl)-1,2,3,4-tetrahydrobenzofuro[3,2-c]pyridine hydrochloride (4 mg, 97%, AUC HPLC 95%) as an off-white solid: mp 282-287° C. dec; $^1$H NMR (DMSO-$d_6$, 400 MHz) δ 8.27-8.21 (m, 2H), 8.13-8.07 (m, 2H), 7.99 (s, 1H), 7.74-7.58 (m, 4H), 3.01-2.91 (m, 2H), 2.74-2.71 (m, 1H), 2.29-2.24 (m, 1H), 1.68-1.58 (br s, 6H); APCI MS m/z 376 $[M+H]^+$.

Example 85

Preparation of (6-chloro-8-(phenylsulfonyl)-1,2,3,4-tetrahydrobenzofuro[3,2-c]pyridin-1-yl)methanol hydrochloride

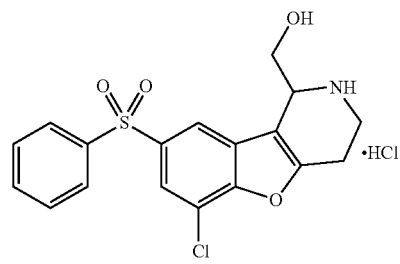 [SMILES: O=S(=O)(c1ccccc1)c1cc(Cl)c2oc3c(c2c1)C(CO)NCC3 ; Cl]

Step A: To a stirred mixture of trifluoroacetic acid (1 mL) in toluene (100 mL) was added the product of Example 84, step E (910 mg, 3.35 mmol) followed by ethyl glyoxalate (0.73 mL, 3.68 mmol). The resulting solution was heated to reflux for 3 h. The solvents were removed in vacuo and the residue was treated with aqueous sodium bicarbonate (25 mL). The resulting solution was extracted with ethyl acetate (3×20 mL). The combined organic extracts were dried over anhydrous $Na_2SO_4$, filtered and the filtrate concentrated in vacuo to give a crude residue which was purified by column chromatography ($SiO_2$, 4:1 to 3:1, hexanes/ethyl acetate) to afford ethyl 8-bromo-6-chloro-1,2,3,4-tetrahydro benzofuro [3,2-c]pyridine-1-carboxylate (850 mg, 71%) as a colorless oil: $^1$H NMR ($CDCl_3$, 400 MHz) δ 7.71 (d, J=1.6 Hz, 1H), 7.38 (d, J=2.0 Hz, 1H), 4.71 (s, 1H), 4.27-4.22 (m, 2H), 3.42-3.35 (m, 1H), 3.27-3.21 (m, 1H), 2.91-2.86 (m, 1H), 2.83-2.77 (m, 1H), 1.32 (t, J=7.2 Hz, 3H).

Step B: To a stirred solution of the product of step A (850 mg, 2.37 mmol) in ethanol was added triethylamine (0.9 mL, 6.40 mmol) followed by di-tert-butyl dicarbonate (880 mg, 4.00 mmol). The resulting solution was stirred at ambient temperature for 3 h. The solvents were removed in vacuo to afford a brown residue which was purified by flash column chromatography (SiO$_2$, 10:1 to 5:1, hexanes/ethyl acetate) providing 2-tert-butyl 1-ethyl 8-bromo-6-chloro-3,4-dihydrobenzofuro[3,2-c]pyridine-1,2(1H)-dicarboxylate (920 mg, 84%) as a colorless oil: $^1$H NMR (CDCl$_3$, 400 MHz) δ 7.83 (t, J=1.5 Hz, 1H), 7.40 (s, 1H), 5.76 (s, 0.4H), 5.54 (s, 0.6H), 4.65-4.42 (m, 1H), 4.28-4.20 (m, 2H), 3.60-3.35 (m, 1H), 3.05-2.78 (m, 2H), 1.49 (s, 9H), 1.32-1.30 (m, 3H).

Step C: The product of step B and sodium benzenesulfinate were coupled using the procedure of Example 29 step C. Purification by flash column chromatography (SiO$_2$, 9:1 to 7:3, hexanes/ethyl acetate) afforded 2-tert-butyl 1-ethyl-6-chloro-8-(phenylsulfonyl)-3,4-dihydrobenzofuro[3,2-c]pyridine-1,2(1H)-dicarboxylate (270 mg, 60%) as a white solid: $^1$H NMR (CDCl$_3$, 300 MHz) δ 8.36-8.29 (m, 1H), 7.99-7.86 (m, 3H), 7.58-7.49 (m, 3H), 5.83 (s, 0.4H), 5.61 (s, 0.6H), 4.67-4.43 (m, 1H), 4.31-4.09 (m, 2H), 3.60-3.38 (m, 1H), 3.10-2.77 (m, 2H), 1.50 (s, 9H), 1.32-1.26 (m, 3H).

Step D: To a stirred solution of the product of step C (60 mg, 0.12 mmol) in dichloromethane (2 mL) was added 4M HCl in dioxane (2 mL). The resulting solution was stirred at ambient temperature for 3 h. The solvents were removed in vacuo to afford a brown residue which was treated with saturated aqueous sodium bicarbonate (15 mL). The resulting solution was extracted with ethyl acetate (3×15 mL). The combined organic extracts were dried over anhydrous Na$_2$SO$_4$, filtered and the filtrate was concentrated in vacuo. The residue was purified by flash column chromatography (SiO$_2$, 4:2 to 3:7, hexanes/ethyl acetate) to afford ethyl 6-chloro-8-(phenylsulfonyl)-1,2,3,4-tetrahydrobenzofuro[3,2-c]pyridine-1-carboxylate (51 mg, 99%) as a brown oil: $^1$H NMR (CDCl$_3$, 300 MHz) δ 8.23 (d, J=1.8 Hz, 1H), 7.97-7.85 (m, 2H), 7.70-7.57 (m, 4H), 4.76 (s, 1H), 4.27-4.17 (m, 2H), 3.77-3.63 (m, 2H), 3.42-3.22 (m, 1H), 2.98-2.76 (m, 1H), 1.28 (t, J=7.2 Hz, 3H).

Step E: To a stirred solution of the product of step D (51 mg, 0.12 mmol) in ethanol (5 mL) was added lithium borohydride (44 mg, 2.00 mmol) at ambient temperature. After 3 h, water (2 mL) was added and the mixture was extracted with dichloromethane (3×10 mL). The combined organic extracts were dried over anhydrous Na$_2$SO$_4$, filtered and the filtrate concentrated in vacuo. The residue was purified by flash column chromatography (SiO$_2$, 8:2 hexanes/ethyl acetate to ethyl acetate) to afford (6-chloro-8-(phenylsulfonyl)-1,2,3,4-tetrahydrobenzofuro[3,2-c]pyridin-1-yl)methanol (30 mg, 64%) as a brown oil: $^1$H NMR (CDCl$_3$, 400 MHz) δ 8.01-7.94 (m, 3H), 7.82 (d, J=1.6 Hz, 1H), 7.57-7.50 (m, 3H), 4.23 (dd, J=4.0, 2.0 Hz, 1H), 3.95 (dd, J=11.2, 4.0 Hz, 1H), 3.77 (dd, J=10.8, 7.8 Hz, 1H), 3.31-3.17 (m, 2H), 2.84-2.81 (m, 2H).

Step F: The product of step E (30 mg, 0.08 mmol) was converted to the hydrochloride salt by dissolving in methanol and treating with 1.25 M HCl in methanol. The reaction solution was concentrated in vacuo to afford (6-chloro-8-(phenylsulfonyl)-1,2,3,4-tetrahydrobenzofuro[3,2-c]pyridin-1-yl)methanol hydrochloride (7 mg, 70%, AUC HPLC 98.5%) as a white solid: mp 185-187° C.; $^1$H NMR (DMSO-d$_6$, 400 MHz) δ 9.75 (br s, 2H), 8.38 (d, J=2.0 Hz, 1H), 8.06-8.03 (m, 3H), 7.71-7.63 (m, 3H), 5.61 (t, J=4.8 Hz, 1H), 4.81 (s, 1H), 4.04-4.00 (m, 2H), 3.63-3.60 (m, 1H), 3.49-3.46 (m, 1H), 3.16 (br s, 2H); APCI MS m/z 378 [M+H]$^+$.

Example 86

Preparation of (6-chloro-8-(phenylsulfonyl)-1,2,3,4-tetrahydrobenzofuro[3,2-c]pyridin-3-yl)methanol hydrochloride

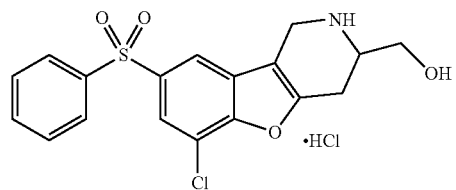 [SMILES: O=S(=O)(c1ccccc1)c1cc(Cl)c2oc3c(c2c1)CNC(CO)C3 ; Cl]

Step A: To a solution of benzylamine (100 mL, 0.9 mol) and 4-bromobut-1-ene (25 g, 0.18 mmol) in ethanol (250 mL) was added sodium iodide (1.0 g, 6.7 mmol). The reaction mixture was degassed via argon bubbling for 20 min then heated to 75° C. for 4 h. After cooling, the reaction mixture was diluted with dichloromethane (1 L) and 1M KOH (500 mL) was added. The two phases were separated and the aqueous layer was further extracted with dichloromethane (3×200 mL). The combined organic layers were dried over Na$_2$SO$_4$, filtered, and concentrated in vacuo. Purification by flash chromatography (SiO$_2$, ethyl acetate to 10:1 ethyl acetate/triethylamine) provided N-benzylbut-3-en-1-amine (24.5 g, 84%) as a colorless oil: $^1$H NMR (CDCl$_3$, 400 MHz) δ 7.31-7.28 (m, 3H), 7.24-7.21 (m, 2H), 5.82-5.72 (m, 1H), 5.10-5.00 (m, 2H), 3.77 (s, 2H), 2.68 (t, J=6.8 Hz, 2H), 2.29-2.23 (m, 2H), 1.36 (br s, 1H).

Step B: The product of step A (24.5 g, 0.15 mol) was dissolved in acetonitrile/water (1:1, 500 mL) and treated with glyoxylic acid monohydrate (15.3 g, 0.17 mol). The resulting solution was allowed to stir at ambient temperature for 12 h. The reaction mixture was concentrated in vacuo, made basic via addition of 1 M NaOH (500 mL) and extracted with dichloromethane (3×200 mL). The combined organic extracts were dried over Na$_2$SO$_4$, filtered, and concentrated in vacuo to afford crude 1-benzyl-4-hydroxypiperidine-2-carboxylic acid (24 g, 69%) as a colorless oil which was used without further purification: $^1$H NMR (CDCl$_3$, 400 MHz) δ 7.38-7.27 (m, 5H), 4.82 (t, J=5.2 Hz, 1H), 3.73-3.59 (m, 2H), 3.30 (d, J=4.8 Hz, 1H), 3.03 (dd, J=12.0, 6.4 Hz, 1H), 2.50-2.43 (m, 1H), 2.29-2.19 (m 1H), 2.08-1.98 (m, 1H), 1.97-1.88 (m, 2H).

Step C: To a stirred solution of the product of step B (600 mg, 2.4 mmol) in methanol (15 mL) was added 10% palladium on carbon (60 mg) and ammonium formate (1.26 g, 20.0 mmol). The reaction mixture was heated to reflux for 2 h, cooled to ambient temperature then filtered through Celite. The filtrate was concentrated in vacuo to afford methyl 4-hydroxypiperidine-2-carboxylate (470 mg, 95%) as a colorless oil which was carried forward without purification: $^1$H NMR (CDCl$_3$, 400 MHz) δ 3.76-3.74 (m, 4H), 3.44-3.41 (m, 1H), 3.26-3.21 (m, 1H), 2.70-2.63 (m, 1H), 2.33-2.28 (m 1H), 1.91-1.90 (m, 1H), 1.50-1.40 (m, 2H).

Step D: To a stirred solution of the product of step C (470 mg, 2.9 mmol) in methanol (10 mL) was added triethylamine (1.0 mL, 7.0 mmol) followed by di-tert-butyl dicarbonate (1.18 g, 5.7 mmol). The resulting solution was stirred at ambient temperature for 4 h then concentrated in vacuo. The residue was purified by column chromatography (SiO₂, 4:1 to 3:1, hexanes/ethyl acetate) to afford 1-tert-butyl 2-methyl 4-hydroxypiperidine-1,2-dicarboxylate (481 mg, 64%) as a colorless oil: $^1$H NMR (CDCl₃, 400 MHz) δ 5.01-4.65 (m, 1H), 4.14 (s, 1H), 3.91-3.78 (m, 1H), 3.73 (s, 3H), 3.40-3.36 (br s, 1H), 2.42 (d, J=14.4 Hz, 1H), 1.94-1.88 (m, 1H), 1.70-1.62 (m, 2H), 1.46 (s, 9H).

Step E: To a stirred solution of the alcohol from step D (3.8 g, 15.0 mmol) in anhydrous dichloromethane (50 mL) was added dihydropyran (7.5 mL, 88.6 mmol) followed by p-toluenesulfonic acid monohydrate (71 mg, 0.4 mmol). After 3 h, triethylamine (0.42 mL, 3.0 mmol) was added and the reaction mixture was concentrated in vacuo. Ethyl acetate (100 mL) was added and the resulting solution was washed with brine (3×50 mL), dried over Na₂SO₄ and filtered. The filtrate was concentrated in vacuo and the residue purified by column chromatography (SiO₂, 9:1 to 7:3, hexanes/ethyl acetate) to afford 1-tert-butyl 2-methyl 4-((tetrahydro-2H-pyran-2-yl)oxy)piperidine-1,2-dicarboxylate (5.0 g, 96%) as a colorless oil: $^1$H NMR (CDCl₃, 400 MHz) δ 5.00-4.62 (m, 2H), 4.15-4.02 (m, 1H), 3.71 (t, J=7.2 Hz, 3H), 3.50-3.47 (m, 1H), 2.49 (br s, 1H), 1.95-1.70 (m, 4H), 1.60-1.42 (m, 13H), 1.27-1.24 (m, 4H).

Step F: To a solution of the product of step E (5.0 g, 14.6 mmol) in tetrahydrofuran (50 mL) at −20° C. was added lithium aluminum hydride (1.14 g, 30 mmol). After stirring at −20° C. for 1 h, the reaction was quenched by slow addition of water (10 mL). The resulting suspension was filtered through Celite and the filtrate concentrated in vacuo to dryness. Water (60 mL) was added and the aqueous phase was extracted with ethyl acetate (3×30 mL). The combined organic extracts were dried over anhydrous Na₂SO₄, filtered, and concentrated in vacuo. Purification by flash column chromatography (SiO₂, 4:1 to 7:3, hexanes/ethyl acetate) afforded tert-butyl 2-(hydroxymethyl)-4-((tetrahydro-2H-pyran-2-yl)oxy)piperidine-1-carboxylate (4.1 g, 81%) as a colorless oil: $^1$H NMR (CDCl₃, 400 MHz) δ 4.73-4.63 (m, 1H), 4.44-4.23 (m, 1H), 4.02-4.00 (m, 1H), 3.90-3.70 (m, 4H), 3.50-3.48 (m, 1H), 3.21-2.42 (m, 1H), 2.09-1.93 (m, 1H), 1.82-1.71 (m, 5H), 1.54 (br s, 5H), 1.47 (s, 9H).

Step G: To a solution of the product of step F (1.0 g, 3.7 mmol) in dichloromethane (20 mL) at 0° C. was added diisopropylethylamine (1.0 mL, 5.7 mmol) followed by acetyl chloride (0.32 mL, 4.4 mmol). The solution was stirred for 10 min at 0° C. followed by 45 min at ambient temperature. The reaction mixture was washed with NaHCO₃ solution (3×15 mL) then NaCl solution (2×10 mL) and dried over Na₂SO₄. The mixture was filtered and the filtrate concentrated in vacuo to afford the crude product which was purified by flash column chromatography (SiO₂, 19:1 to 4:1, hexanes/ethyl acetate) to give tert-butyl 2-(acetoxymethyl)-4-((tetrahydro-2H-pyran-2-yl)oxy)piperidine-1-carboxylate (701 mg, 68%) as a colorless oil: $^1$H NMR (CDCl₃, 300 MHz) δ 4.69-4.51 (m, 3H), 4.22-3.83 (m, 5H), 3.53-3.48 (m, 3H), 3.23-3.18 (m, 1H), 2.05-2.03 (m, 3H), 1.84-1.55 (m, 7H), 1.41 (s, 9H).

Step H: To a solution of the product of step G (710 mg, 2.3 mmol) in methanol (20 mL) was added p-toluenesulfonic acid monohydrate (20 mg, 0.1 mmol). After stirring at ambient temperature for 4 h the solution was concentrated in vacuo to afford the crude product. Purification by flash column chromatography (SiO₂, 19:1 to 7:3, hexanes/ethyl acetate) afforded tert-butyl 2-(acetoxymethyl)-4-hydroxypiperidine-1-carboxylate (506 mg, 83%) as a colorless oil: $^1$H NMR (CDCl₃, 300 MHz) δ 4.49-4.41 (m, 2H), 4.33-4.05 (m, 3H), 3.94-3.88 (m, 1H), 3.29-3.21 (s, 1H), 2.05 (s, 3H), 1.89-1.80 (m, 1H), 1.76-1.69 (m, 2H), 1.46 (s, 9H).

Step I: To a solution of the product of step H (506 mg, 1.9 mmol) in dichloromethane (15 mL) at 0° C. was added pyridinium chlorochromate (4.0 g, 19 mmol). The reaction was allowed to warm to ambient temperature and stirred for a further 2 h. The reaction mixture was filtered through celite and the filtrate was concentrated in vacuo to afford the crude product which was purified by flash column chromatography (SiO₂, 19:1 to 4:1, hexanes/ethyl acetate) to afford tert-butyl 2-(acetoxymethyl)-4-oxopiperidine-1-carboxylate (220 mg, 43%) as a colorless oil: $^1$H NMR (CDCl₃, 400 MHz) δ 4.57 (br s, 1H), 4.03-3.99 (m, 2H), 3.91-3.87 (m, 1H), 3.28-3.21 (s, 1H), 2.52-2.46 (m, 1H), 2.35-2.31 (m, 1H), 2.26-2.18 (m, 2H), 1.83 (s, 3H), 1.50 (s, 9H).

Step J: The product obtained from step I (1.33 g, 4.9 mmol) was reacted with O-(4-bromo-2-chlorophenyl)hydroxylamine hydrochloride following the procedure of Example 29 step B. Purification by column chromatography (SiO₂, 49:1 to 19:1 hexanes/ethyl acetate) afforded tert-butyl 3-(acetoxymethyl)-8-bromo-6-chloro-1,4,4a,9b-tetrahydrobenzofuro[3,2-c]pyridine-2(3H)-carboxylate (203 mg, 8%) as a colorless oil: $^1$H NMR (CDCl₃, 300 MHz) δ 7.43 (s, 1H), 7.38 (d, J=1.8 Hz, 1H), 5.14 (br s, 2H), 4.10-4.07 (m, 3H), 3.16-3.14 (m, 1H), 2.80 (d, J=17.4 Hz, 1H), 2.04 (s, 3H), 1.52 (s, 9H).

Step K: The product from step J and sodium benzenesulfinate were coupled following the procedure of Example 29 step C. The crude product was purified by flash column chromatography (SiO₂, 9:1 to 7:3, hexanes/ethyl acetate) to give tert-butyl 3-(acetoxymethyl)-6-chloro-8-(phenylsulfonyl)-3,4-dihydrobenzofuro[3,2-c]pyridine-2(1H)-carboxylate (110 mg, 84%) as a white solid: $^1$H NMR (CDCl₃, 300 MHz) δ 7.98-7.95 (m, 3H), 7.86 (s, 1H), 7.58-7.49 (m, 3H), 5.10 (br s, 2H), 4.20-4.04 (m, 3H), 3.22-3.14 (m, 1H), 2.81 (d, J=17.4 Hz, 1H), 2.04 (s, 3H), 1.53 (s, 9H).

Step L: To the crude product of step K (110 mg, 0.22 mmol) in methanol (5 mL) and water (5 mL) at 0° C. was added lithium hydroxide monohydrate (92 mg, 2.2 mmol). The solution was stirred at ambient temperature for 2 h then concentrated in vacuo. Water (10 mL) was added and the mixture extracted with ethyl acetate (3×10 mL). The combined organic extracts were dried over Na₂SO₄, filtered, and concentrated in vacuo to give the crude product. Purification by flash column chromatography (SiO₂, 9:1 to 7:3, hexanes/ethyl acetate) afforded tert-butyl 6-chloro-3-(hydroxymethyl)-8-(phenylsulfonyl)-3,4-dihydrobenzofuro[3,2-c]pyridine-2(1H)-carboxylate (85 mg, 80%) as a colorless oil: $^1$H NMR (CDCl₃, 300 MHz) δ 7.98-7.95 (m, 3H), 7.84 (d, J=1.5 Hz, 1H), 7.56-7.51 (m, 3H), 4.93 (br s, 2H), 4.13-4.10 (m, 1H), 3.64-3.61 (m, 2H), 3.17-3.08 (m, 1H), 2.88 (d, J=17.4 Hz, 1H), 1.85 (br s, 1H), 1.53 (s, 9H).

Step M: The product obtained from step L (85 mg, 0.18 mmol) was Boc de-protected and converted to hydrochloride salt using the general procedure of Example 29 step D to afford (6-chloro-8-(phenylsulfonyl)-1,2,3,4-tetrahydrobenzofuro[3,2-c]pyridin-3-yl)methanol hydrochloride (60 mg, 88%, AUC HPLC 98%) as an off-white solid: mp <<MP data>> dec.; $^1$H NMR (DMSO-d₆, 400 MHz) δ 9.58 (br s, 2H), 8.44 (d, J=1.6 Hz, 1H), 8.04-8.01 (m, 3H), 7.70-7.63 (m, 3H), 5.66-5.64 (m, 1H), 4.49-3.36 (m, 2H), 3.85-3.83 (m, 1H), 3.72-3.69 (m, 2H), 3.17-3.16 (m, 1H), 3.09-3.06 (m, 1H); ESI MS m/z 378 [M+H]+.

Example 87

Preparation of 6-chloro-1-fluoromethyl-8-phenylsulfonyl-1,2,3,4-tetrahydrobenzofuro[3,2-c]pyridine hydrochloride

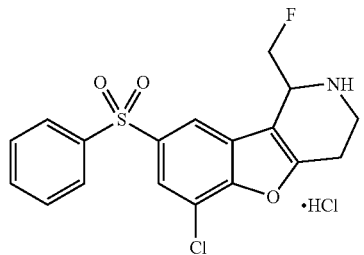 [SMILES: O=S(=O)(c1ccccc1)c1cc(Cl)c2oc3c(c2c1)C(CF)NCC3 ; Cl]

Step A: To a solution of the product of Example 84, step D (250 mg, 0.6 mmol) in 1,2-dichloroethane (10 mL) at ambient temperature was added 4-methoxybenzaldehyde (136 mg, 1.0 mmol) followed by NaHB(OAc)$_3$ (424 mg, 2.0 mmol). After stirring for 12 h, aqueous saturated NaHCO$_3$ solution (20 mL) was added and the solution was extracted with dichloromethane (2×10 mL). The combined organic extracts were dried over MgSO$_4$, filtered, and the filtrate concentrated in vacuo to give the crude product. Purification by flash column chromatography (SiO$_2$, 9:1 to 7:3 hexanes/ethyl acetate) gave ethyl 6-chloro-2-(4-methoxybenzyl)-8-(phenylsulfonyl)-1,2,3,4-tetrahydrobenzofuro[3,2-c]pyridine-1-carboxylate (269 mg, 83%) as a colorless oil: $^1$H NMR (CDCl$_3$, 400 MHz) δ 8.10 (d, J=1.6 Hz, 1H), 7.95-7.93 (m, 3H), 7.83 (d, J=1.6 Hz, 1H), 7.56-7.47 (m, 3H), 7.27-7.25 (m, 2H), 6.89-6.86 (m, 2H), 4.19-4.09 (m, 3H), 3.90 (s, 2H), 3.82 (s, 3H), 3.64-3.61 (m, 1H), 3.08-3.04 (m, 2H), 2.79 (d, J=2.8 Hz, 1H), 1.26 (t, J=7.2 Hz, 3H).

Step B: The product obtained from step A (269 mg, 0.50 mmol) was dissolved in ethanol (10 mL) at 0° C. Lithium borohydride (220 mg, 10.0 mmol) was added slowly and the reaction mixture was stirred at ambient temperature for 2 h. Water (10 mL) was added and the mixture was extracted with dichloromethane (2×20 mL). The combined organic extracts were dried over MgSO$_4$, filtered, and the filtrate concentrated in vacuo. Purification by flash column chromatography (SiO$_2$, 9:1 to 7:3 hexanes/ethyl acetate) afforded (6-chloro-2-(4-methoxybenzyl)-8-(phenylsulfonyl)-1,2,3,4-tetrahydrobenzofuro[3,2-c]pyridin-1-yl)methanol (149 mg, 60%) as a colorless oil: $^1$H NMR (CDCl$_3$, 300 MHz) δ 8.05-7.94 (m, 3H), 7.86-7.83 (m, 1H), 7.57-7.48 (m, 3H), 7.26-7.21 (m, 3H), 6.92-6.87 (m, 2H), 4.02-3.98 (m, 1H), 3.82 (s, 3H), 3.83-3.80 (m, 1H), 3.72 (s, 2H), 3.64-3.57 (m, 1H), 3.29-3.19 (m, 1H), 3.12-2.98 (m, 2H), 2.68-2.60 (m, 1H).

Step C: DAST (0.4 mL, 3.20 mmol) was slowly added to a stirred solution of the product of step B (180 mg, 0.36 mmol) in anhydrous dichloromethane (12 mL) at 0° C. The resulting solution was allowed to warm to ambient temperature for 3 h then quenched by slow addition of aqueous sodium bicarbonate solution (10 mL). The organic layer was separated and the aqueous solution was further extracted with dichloromethane (2×20 mL). The combined organic extracts were dried over anhydrous Na$_2$SO$_4$, filtered, and the filtrate concentrated in vacuo. The residue was purified by flash column chromatography (SiO$_2$, 9:1 to 7:3 hexanes/ethyl acetate) to give 6-chloro-1-(fluoromethyl)-2-(4-methoxybenzyl)-8-(phenylsulfonyl)-1,2,3,4-tetrahydrobenzofuro[3,2-c]pyridine (90 mg, 51%) as a colorless oil: $^1$H NMR (CDCl$_3$, 300 MHz) δ 8.14 (d, J=1.2 Hz, 1H), 7.97-7.94 (m, 2H), 7.85 (d, J=1.5 Hz, 1H), 7.61-7.48 (m, 3H), 7.30-7.28 (m, 2H), 6.89-6.86 (m, 2H), 5.76-5.58 (m, 1H), 3.87 (s, 2H), 3.81 (s, 3H), 3.48-3.38 (m, 1H), 3.31-2.89 (m, 5H).

Step D: A solution of ceric ammonium nitrate (800 mg, 1.46 mmol) in water (1 mL) was added to a solution of the product obtained in step C (90 mg, 0.18 mmol) in acetone (10 mL). The resulting red solution was stirred at ambient temperature for 1.5 h, diluted with ethyl acetate, washed sequentially with saturated aqueous NaHCO$_3$ and brine then dried over anhydrous MgSO$_4$. The solution was filtered and the filtrate concentrated in vacuo to give the crude product which was purified by flash column chromatography (SiO$_2$, 9:1 to 1:1 hexanes/ethyl acetate) providing 6-chloro-1-(fluoromethyl)-8-(phenylsulfonyl)-1,2,3,4-tetrahydrobenzofuro[3,2-c]pyridine (8 mg, 12%) as a colorless oil: $^1$H NMR (CDCl$_3$, 300 MHz) δ 8.14 (d, J=1.5 Hz, 1H), 7.98-7.95 (m, 2H), 7.85 (d, J=1.8 Hz, 1H), 7.57-7.48 (m, 3H), 5.72-5.54 (m, 1H), 3.68-3.58 (m, 1H), 3.42-3.28 (m, 2H), 3.26-3.18 (m, 1H), 3.13-3.00 (m, 2H).

Step E: The product of step D (8 mg, 0.02 mmol) was converted to the hydrochloride salt by dissolving in methanol and treating with 1.25 M HCl in methanol. The reaction was concentrated in vacuo to afford 6-chloro-1-(fluoromethyl)-8-(phenyl sulfonyl)-1,2,3,4-tetrahydrobenzofuro[3,2-c]pyridine hydrochloride (6 mg, 71%, AUC HPLC 96%) as a white solid: mp <<MP data>>; $^1$H NMR (DMSO-d$_6$, 400 MHz) δ 9.51 (br s, 2H), 8.49 (d, J=1.6 Hz, 1H), 8.08-8.04 (m, 3H), 7.73-7.62 (m, 3H), 6.52-6.40 (m, 1H), 4.02-3.95 (m, 1H), 3.71-3.34 (m, 5H); APCI MS m/z 402 [M+Na]+.

Example 88

Preparation of 6-chloro-N,N-dimethyl-8-(phenylsulfonyl)-1,2,3,4-tetrahydrobenzofuro[3,2-c]pyridine-1-carboxamide hydrochloride

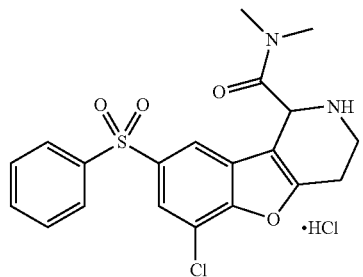 [SMILES: CN(C)C(=O)C1NCCc2oc3c(Cl)cc(S(=O)(=O)c4ccccc4)cc3c21 ; Cl]

Step A: To a stirred solution of the product of Example 85, step C (80 mg, 0.12 mmol) in water (5 mL) and tetrahydrofuran (5 mL) was added lithium hydroxide monohydrate (84 mg, 2.0 mmol) at ambient temperature. After 2 h, 1 M HCl solution (3 mL) was added. The mixture was extracted with dichloromethane (2×10 mL) and the combined organic extracts were dried over anhydrous Na$_2$SO$_4$ and filtered. The filtrate was concentrated in vacuo to give 2-(tert-butoxycarbonyl)-6-chloro-8-(phenylsulfonyl)-1,2,3,4-tetrahydrobenzofuro[3,2-c]pyridine-1-carboxylic acid (80 mg, 99%) as a colorless oil which was used directly in the next step.

Step B: To a solution of the product obtained from step A (80 mg, 0.16 mmol) in anhydrous acetonitrile (1.5 mL) was added triethylamine (45 µL, 0.32 mmol) followed by dimethylamine hydrochloride (20 mg, 0.24 mmol) and benzotriazole-1-yl-oxy-tris-(dimethylamino)-phosphonium-hexafluorophosphate (106 mg, 0.24 mmol). After stirring at ambient temperature for 12 h, the resulting solution was concentrated to dryness in vacuo. The reaction mixture was diluted with ethyl acetate (20 mL), washed sequentially with saturated aqueous NaHCO$_3$ (10 mL) and brine (10 mL), and dried over anhydrous MgSO$_4$. After filtration, the filtrate was concentrated in vacuo to give the crude product which was purified by flash column chromatography (SiO$_2$, 9:1 to 3:2 hexanes/ethyl acetate) to afford tert-butyl 6-chloro-1-(dimethylcarbamoyl)-8-(phenylsulfonyl)-3,4-dihydrobenzofuro[3,2-c]pyridine-2(1H)-carboxylate (60 mg, 71%) as a colorless oil: $^1$H NMR (CDCl$_3$, 400 MHz) δ 7.93-7.77 (m, 4H), 7.57-7.48 (m, 3H), 6.19 (s, 1H), 4.53-4.27 (m, 1H), 3.76-3.62 (m, 2H), 3.43 (s, 3H), 3.02 (s, 3H), 2.85-2.80 (m, 1H), 1.49 (s, 9H).

Step C: The product of step B was Boc deprotected using the procedure of Example 29, step D. Purification by flash column chromatography (SiO$_2$, 19:1 to 4:1, dichloromethane/methanol) afforded 6-chloro-N,N-dimethyl-8-(phenylsulfonyl)-1,2,3,4-tetrahydrobenzofuro[3,2-c]pyridine-1-carboxamide (60 mg, 78%) as a white solid; ESI MS m/z 419 [M+H]$^+$.

Step D: The product of step C (60 mg, 0.12 mmol) was converted to the hydrochloride salt by dissolving in methanol and treating with 1.25 M HCl in methanol. The reaction mixture was concentrated in vacuo to give 6-chloro-N,N-dimethyl-8-(phenylsulfonyl)-1,2,3,4-tetrahydrobenzofuro[3,2-c]pyridine-1-carboxamide hydrochloride (60 mg, 94%, AUC HPLC>99%) as an off-white solid: mp <<MP data>>; $^1$H NMR (CD$_3$OD, 400 MHz) δ 7.92-7.90 (m, 3H), 7.77-7.76 (m, 1H), 7.56-7.48 (m, 3H), 5.03 (s, 1H), 3.52-3.46 (m, 1H), 3.40 (s, 3H), 3.18-3.12 (m, 1H), 3.08 (s, 3H), 2.93-2.77 (m, 2H); ESI MS m/z 419 [M+H]$^+$.

Example 89

Preparation of 6-chloro-4-methyl-8-(phenylsulfonyl)-1,2,3,4-tetrahydrobenzofuro[3,2-c]pyridine hydrochloride

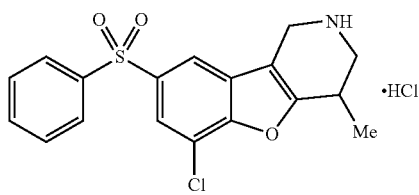 [SMILES: CC1CNCc2c1oc1c(Cl)cc(S(=O)(=O)c3ccccc3)cc21 ; Cl]

Step A: To a solution of tert-butyl 4-oxopiperidine-1-carboxylate (10.0 g, 50.2 mmol) in tetrahydrofuran (50 mL) was added lithium diisopropylamide (2.0 M in THF, 1.5 mL, 3.01 mmol) at −78° C. After 1 h, iodomethane (0.19 mL, 3.01 mmol) was added and the reaction mixture was allowed to warm to ambient temperature over 48 h before being quenched with 1M ammonium chloride and extracted with ethyl acetate. The organic layer was concentrated in vacuo and the residue purified by flash column chromatography (SiO$_2$, 9:1 hexanes/ethyl acetate) to give tert-butyl 3-methyl-4-oxopiperidine-1-carboxylate (4.1 g, 38%) as a yellow solid: $^1$H NMR (CDCl$_3$, 300 MHz) δ 4.24-4.12 (m, 2H), 3.32-3.20 (m, 1H), 2.94-2.75 (m, 1H), 2.61-2.38 (m, 3H), 1.50 (s, 9H), 1.05 (d, J=6.9 Hz, 3H).

Step B: The product of step A (4.0 g, 18.78 mmol) and O-(4-bromo-2-chlorophenyl)hydroxylamine hydrochloride (4.42 g, 17.07 mmol) were suspended in a mixture of sulphuric acid (10 mL) and glacial acetic acid (90 mL) and heated to 110° C. for 6 h. After cooling, the mixture was concentrated in vacuo and basified with 10% sodium hydroxide solution. 2-propanol was added followed by di-tert-butyl dicarbonate (4.47 g, 20.48 mmol) and the reaction stirred for 3 h, diluted with water and extracted with dichloromethane. The combined extracts were concentrated in vacuo and the residue purified by flash column chromatography (SiO$_2$, 95:5 hexanes/ethyl acetate) to give tert-butyl 8-bromo-6-chloro-4-methyl-3,4-dihydrobenzofuro[3,2-e]pyridine-2(1H)-carboxylate (560 mg, 8%) as a light brown solid: $^1$H NMR (CDCl$_3$, 300 MHz) δ 7.44 (s, 1H), 7.38 (d, J=1.5 Hz, 1H), 4.58-4.45 (m, 2H), 4.08-3.74 (m, 1H), 3.54-3.42 (m, 1H), 3.21-3.09 (m, 1H), 1.58 (s, 9H), 1.33 (d, J=6.9 Hz, 3H).

Step C: A mixture of the product of step B (560 mg, 1.39 mmol), sodium benzenesulfinate (275 mg, 1.67 mmol), dipalladium-tris(dibenzylideneacetone) (179 mg, 0.19 mmol), cesium carbonate (683 mg, 2.09 mmol) and xantphos (225 mg, 0.39 mmol) were suspended in anhydrous toluene (20 mL). The reaction flask was purged with argon and heated to 110° C. for 6 h. After cooling to ambient temperature, the reaction was diluted with dichloromethane and filtered through a celite bed. The filtrate was concentrated in vacuo and the residue purified by flash column chromatography (SiO$_2$, 4:1 hexanes/ethyl acetate) to give tert-butyl 6-chloro-4-methyl-8-(phenylsulfonyl)-3,4-dihydrobenzofuro[3,2-e]pyridine-2(1H)-carboxylate (190 mg, 29%) as an off-white solid: $^1$H NMR (CDCl$_3$, 300 MHz) δ 8.01-7.93 (m, 3H), 7.84 (s, 1H), 7.61-7.47 (m, 3H), 4.63-4.47 (m, 2H), 4.08-3.75 (m, 1H), 3.58-3.27 (m, 1H), 3.21-3.08 (m, 1H), 1.51 (s, 9H), 1.33 (d, J=6.9 Hz, 3H).

Step D: To a solution of the product of step C (190 mg, 0.41 mmol) in tetrahydrofuran (10 mL) was added conc. hydrochloric acid (1.2 mL, 12.34 mmol) at ambient temperature. After 15 h, the reaction was basified with 10% NaOH solution and extracted with dichloromethane. The organic layer was concentrated in vacuo and the residue purified by flash column chromatography (SiO$_2$, 95:5 dichloromethane/methanol) to provide the free base which was converted directly to the hydrochloride salt by dissolving in methanol and treating with 1.25 M HCl in methanol. Concentration in vacuo afforded 6-chloro-4-methyl-8-(phenylsulfonyl)-1,2,3,4-tetrahydrobenzofuro[3,2-c]pyridine hydrochloride (70 mg, 48%, AUC HPLC 96.8%) as a white solid: mp 291-292° C. dec; $^1$H NMR (DMSO-d$_6$, 400 MHz) δ 9.72 (br s, 2H), 8.43 (s, 1H), 8.09-7.99 (m, 3H), 7.74-7.59 (m, 3H), 4.49-4.28 (m, 2H), 3.71-3.44 (m, 2H), 3.19-3.11 (m, 1H), 1.35 (d, J=4.8 Hz, 3H); APCI MS m/z 362 [M+H]⁺.

Example 90

Preparation of 7-chloro-9-(phenylsulfonyl)-2,3,4,5-tetrahydro-1H-benzofuro[2,3-d]azepine hydrochloride

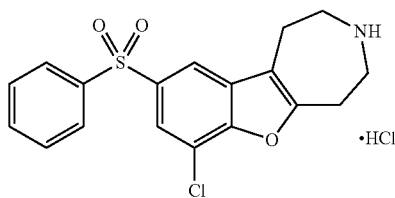 [SMILES: O=S(=O)(c1ccccc1)c1cc(Cl)c2oc3c(c2c1)CCNCC3 ; Cl]

Step A: To a solution of the product of Example 84, step C (2.0 g, 4.65 mmol) in dioxane (10 mL) was added 2,2-dimethoxyethanamine (1.47 g, 13.95 mmol). The reaction mixture was heated to 90° C. for 3 h, cooled to ambient temperature, treated with water (20 mL) and extracted with dichloromethane (3×20 mL). The combined organic extracts were washed with brine, dried over $Na_2SO_4$, filtered, and the filtrate concentrated in vacuo. Purification by flash column chromatography ($SiO_2$, hexanes/ethyl acetate) gave N-(2-(5-bromo-7-chlorobenzofuran-2-yl)ethyl)-2,2-dimethoxyethanamine (1.27 g, 75%) as a colorless oil: ¹H NMR (CDCl₃, 400 MHz) δ 7.49 (d, J=1.8 Hz, 1H), 7.33 (d, J=1.8 Hz, 1H), 6.44 (s, 1H), 4.48 (t, J=5.5 Hz, 2H), 3.38 (s, 6H), 3.09-2.94 (m, 4H), 2.78 (d, J=5.4 Hz, 2H).

Step B: To a solution of the product obtained from step A (640 mg, 1.76 mmol) in dichloromethane (5 mL) at 0° C. was added diisopropylethylamine (0.61 mL, 3.53 mmol) followed by ethyl chloroformate (0.34 mL, 3.53 mmol). The reaction mixture was allowed to warm to ambient temperature over 2 h before addition of water (10 mL). The mixture was extracted with dichloromethane (2×20 mL) and the combined organic extracts washed with brine, dried over $Na_2SO_4$, filtered and the filtrate concentrated in vacuo. Purification by flash column chromatography ($SiO_2$, 9:1 to 1:1 hexanes/ethyl acetate) afforded ethyl 2-(5-bromo-7-chlorobenzofuran-2-yl)ethyl(2,2-dimethoxyethyl)carbamate (685 mg, 89%) as a colorless oil: ¹H NMR (CDCl₃, 300 MHz) δ 7.51 (s, 1H), 7.37 (s, 1H), 6.50-6.39 (m, 1H), 4.53-4.38 (m, 1H), 4.21-3.98 (m, 2H), 3.75-3.64 (m, 2H), 3.47-3.35 (m, 6H), 3.34-3.22 (m, 2H), 3.13-2.99 (m, 2H), 1.30-1.11 (m, 3H).

Step C: To a stirred solution of the product of step B (660 mg, 1.52 mmol) in anhydrous dichloromethane (8 mL) at 0° C. was added $AlCl_3$ (810 mg, 6.07 mmol) and the reaction mixture was allowed to warm to ambient temperature over 3 h before being quenched by addition of aqueous sodium bicarbonate solution. The organic layer was separated and the aqueous solution further extracted with dichloromethane (2×20 mL). The combined organic extracts were dried over anhydrous $Na_2SO_4$, filtered and the filtrate concentrated in vacuo. The residue was purified by flash column chromatography ($SiO_2$, 9:1 to 1:1 hexanes/ethyl acetate) to give ethyl 9-bromo-7-chloro-4,5-dihydro-3H-benzofuro[2,3-d]azepine-3-carboxylate (50 mg, 9%) as an off-white solid: ¹H NMR (CDCl₃, 300 MHz) δ 7.56 (d, J=1.7 Hz, 1H), 7.39 (d, J=1.6 Hz, 1H), 7.08-6.82 (m, 1H), 5.88-5.70 (m, 1H), 4.38 (q, J=7.1 Hz, 2H), 3.90 (t, J=5.1 Hz, 2H), 3.26 (t, J=5.0 Hz, 2H), 1.34 (t, J=7.0 Hz, 3H).

Step D: To a solution of the product of step C (50 mg, 0.13 mmol) and trifluoroacetic acid (0.75 mL) at 0° C. was added triethylsilane (64 μL, 0.40 mmol). The reaction was allowed to warm to ambient temperature over 14 h then quenched by addition of aqueous sodium bicarbonate solution. The mixture was extracted with dichloromethane (2×20 mL) and the combined organic extracts dried over anhydrous $Na_2SO_4$, filtered, and the filtrate concentrated in vacuo. The residue was purified by flash column chromatography ($SiO_2$, 9:1 to 1:1 hexanes/ethyl acetate) to give ethyl 9-bromo-7-chloro-4,5-dihydro-1H-benzofuro[2,3-d]azepine-3(2H)-carboxylate (48 mg, 96%) as a colorless oil: ¹H NMR (CDCl₃, 300 MHz) δ 7.45-7.38 (m, 1H), 7.35 (d, J=1.4 Hz, 1H), 4.20 (q, J=7.1 Hz, 2H), 3.78-3.67 (m, 4H), 3.20-3.10 (m, 2H), 2.88-2.75 (m, 2H), 1.29 (t, J=7.0 Hz, 3H).

Step E: The product of step D and sodium benzenesulfinate were coupled using the procedure of Example 29 step C. Purification by flash column chromatography ($SiO_2$, 9:1 to 1:1 hexanes/ethyl acetate) afforded ethyl 7-chloro-9-(phenylsulfonyl)-4,5-dihydro-1H-benzofuro[2,3-d]azepine-3(2H)-carboxylate (35 mg, 62%) as a white solid: ¹H NMR (CDCl₃, 300 MHz) δ 8.00-7.92. (m, 3H), 7.80 (s, 1H), 7.62-7.48 (m, 3H), 4.20 (q, J=7.1 Hz, 2H), 3.80-3.68 (m, 4H), 3.22-3.11 (m, 2H), 2.96-2.82 (m, 2H), 1.29 (t, J=7.1 Hz, 3H).

Step F: The product of step E (35 mg, 0.08 mmol) was dissolved in a mixture of ethylene glycol (0.5 mL) and DME (0.5 mL) then treated with 20% KOH solution (0.5 mL). The reaction mixture was heated to 100° C. for 36 h. After cooling to ambient temperature, the reaction mixture was diluted with water (5 mL) and extracted with dichloromethane (3×20 mL). The combined organic extracts were washed with brine, dried over $Na_2SO_4$, filtered, and concentrated in vacuo. The crude product was purified by semi-preparative HPLC to give the free base which was treated directly with 1.25 M HCl in methanol solution. Concentration in vacuo afforded 7-chloro-9-(phenylsulfonyl)-2,3,4,5-tetrahydro-1H-benzofuro[2,3-d]azepine hydrochloride (5 mg, 15%, AUC HPLC>99%) as a white solid: ¹H NMR (CD₃OD, 300 MHz) δ 8.18 (d, J=2.0 Hz, 1H), 8.00 (d, J=7.4 Hz, 2H), 7.90 (d, J=1.7 Hz, 1H), 7.68-7.52 (m, 3H), 3.60-3.51 (m, 4H), 3.42-3.35 (m, 2H), 3.23-3.15 (m, 2H); APCI MS m/z 362 [M+H]⁺.

Example 91

Preparation of 6-chloro-8-(phenylthio)-1,2,3,4-tetrahydrobenzofuro[3,2-c]pyridine hydrochloride

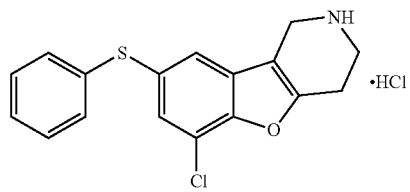 [SMILES: Clc1cc(Sc2ccccc2)cc2c3c(oc12)CCNC3 ; Cl]

Step A: A mixture of tert-butyl 8-bromo-6-chloro-3,4-dihydrobenzofuro[3,2-c]pyridine-2(1H)-carboxylate (1.00 g, 2.58 mmol), benzenethiol (0.40 mL, 3.87 mmol), di-palladium-tris(dibenzylideneacetone) (118 mg, 0.13 mmol), N,N-diisopropylethylamine (0.9 mL, 5.16 mmol) and xantphos (149 mg, 0.26 mmol) were suspended in anhydrous dioxane (10 mL). The reaction flask was purged with argon and the mixture heated to 110° C. for 14 h. After cooling, the reaction mixture was diluted with dichloromethane and filtered through a celite bed. The filtrate was concentrated in vacuo and the residue purified by flash column chromatography (SiO$_2$, 9:1 hexanes/ethyl acetate) to give tert-butyl 6-chloro-8-(phenylthio)-3,4-dihydrobenzofuro[3,2-c]pyridine-2(1H)-carboxylate (1.10 g, 91%) as an off-white solid: $^1$H NMR (CDCl$_3$, 400 MHz) δ 7.47-7.38 (m, 1H), 7.34 (d, J=1.2 Hz, 1H), 7.31-7.27 (m, 1H), 7.26-7.25 (m, 2H), 7.24-7.19 (m, 2H), 4.50 (s, 2H), 3.86-3.79 (m, 2H), 2.92-2.87 (m, 2H), 1.50 (s, 9H).

Step B: The product of step A (100 mg, 0.24 mmol) was Boc deprotected and converted to the hydrochloride salt following the procedure of Example 29, step D to provide 6-chloro-8-(phenylthio)-1,2,3,4-tetrahydrobenzofuro[3,2-e]pyridine hydrochloride (75 mg, 88%, AUC HPLC>99%) as a brown solid: mp 241-248° C. dec; $^1$H NMR (DMSO-d$_6$, 400 MHz) δ 9.59 (br s, 2H), 7.81 (s, 1H), 7.46 (s, 1H), 7.39-7.33 (m, 2H), 7.31-7.25 (m, 3H), 4.30 (s, 2H), 3.53 (t, J=5.8 Hz, 2H), 3.18-3.12 (m, 2H); APCI MS m/z 316 [M+H]$^+$.

Example 92

Preparation of 6-methoxy-8-phenoxy-1,2,3,4-tetrahydrobenzofuro[3,2-c]pyridine hydrochloride

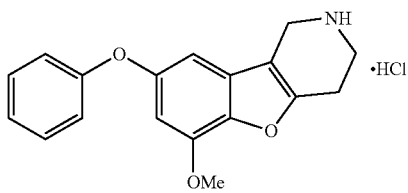 [SMILES: COc1cc(Oc2ccccc2)cc2c3c(oc12)CCNC3 ; Cl]

Step A: A mixture of the product of Example 29, step C (400 mg, 1.03 mmol), copper(I) iodide (10 mg, 0.05 mmol), trans-N,N'-dimethylcyclohexane-1,2-diamine (16 mg, 0.10 mmol) and sodium iodide (310 mg, 2.06 mmol) were suspended in anhydrous m-xylene (5 mL) and diglyme (1.6 mL). The reaction flask was purged with argon, sealed, and heated to 135° C. for 48 h. The reaction mixture was cooled to ambient temperature, diluted with water, and extracted with ethyl acetate. The organic extract was dried over sodium sulfate, filtered, and concentrated in vacuo. The residue was purified by flash column chromatography (SiO$_2$, 9:1 hexane/ethyl acetate) to give tert-butyl 6-chloro-8-iodo-3,4-dihydrobenzofuro[3,2-c]pyridine-2(1H)-carboxylate (370 mg, 82%) as a yellow solid: $^1$H NMR (CDCl$_3$, 400 MHz) δ 7.44 (s, 1H), 7.39 (d, J=1.6 Hz, 1H), 4.50 (s, 2H), 3.82 (s, 2H), 2.89 (s, 2H), 1.50 (s, 9H).

Step B: A mixture of the product of step A (100 mg, 0.23 mmol), copper (I) iodide (9 mg, 0.04 mmol), phenol (54 mg, 0.57 mmol), N,N-dimethylglycine (5 mg, 0.04 mmol) and potassium phosphate (171 mg, 0.80 mmol) in dimethylacetamide (1.5 mL) in a microwave tube was purged with argon and heated in a microwave reactor at 150° C. for 3 h. The reaction mixture was cooled to ambient temperature, diluted with water, and extracted with ethyl acetate. The organic extract was dried over sodium sulfate, filtered, and concentrated in vacuo. The residue was purified by flash column chromatography (SiO$_2$, 9:1 hexane/ethyl acetate) to give (45 mg, 49%) as a white solid: $^1$H NMR (CDCl$_3$, 300 MHz) δ 7.27-7.18 (m, 3H), 6.95-6.80 (m, 4H), 4.47 (s, 2H), 3.90-3.75 (m, 2H), 2.95-2.83 (m, 2H), 1.51 (s, 9H).

Step C: The product of step B was converted to the phenol derivative using the procedure of Example 54, step A. Purification by flash column chromatography (SiO$_2$, 1:1 hexane/ethyl acetate) provided tert-butyl 6-hydroxy-8-phenoxy-3,4-dihydrobenzofuro[3,2-c]pyridine-2(1H)-carboxylate (25 mg, 58%) as a white solid: $^1$H NMR (CDCl$_3$, 400 MHz) δ 7.34-7.26 (m, 2H), 7.11-6.91 (m, 3H), 6.83-6.76 (m, 1H), 6.63-6.53 (m, 1H), 4.45 (s, 2H), 3.90-3.74 (m, 2H), 2.89-2.76 (m, 2H), 1.50 (s, 9H).

Step D: The product of step C was converted to the methyl ether derivative following the procedure of Example 54, step B. Purification by flash column chromatography (SiO$_2$, 17:3 hexane/ethyl acetate) provided tert-butyl 6-methoxy-8-phenoxy-3,4-dihydrobenzofuro[3,2-c]pyridine-2(1H)-carboxylate (20 mg, 78%) as a colorless oil: $^1$H NMR (CDCl$_3$, 400 MHz) δ 7.36-7.29 (m, 2H), 7.11-7.04 (m, 1H), 7.02-6.95 (m, 2H), 6.63 (s, 1H), 6.56 (d, J=2.0 Hz, 1H), 4.46 (s, 2H), 4.00 (s, 3H), 3.82 (s, 2H), 2.86 (s, 2H), 1.50 (s, 9H).

Step E: The product of step D was Boc deprotected following the procedure of Example 29, step D. Purification by flash column chromatography (SiO$_2$, 9:1 dichloromethane/methanol) provided 6-methoxy-8-phenoxy-1,2,3,4-tetrahydrobenzofuro[3,2-c]pyridine (5 mg, 34%) as a white solid: $^1$H NMR (CDCl$_3$, 400 MHz) δ 7.36-7.28 (m, 2H), 7.10-7.03 (m, 1H), 7.01-6.94 (m, 2H), 6.61 (d, J=2.0 Hz, 1H), 6.55 (d, J=2.0 Hz, 1H), 3.95 (s, 3H), 3.89 (t, J=2.0 Hz, 2H), 3.23 (d, J=6.0 Hz, 2H), 2.85-2.77 (m, 2H).

Step F: The product obtained from step E (5 mg, 0.01 mmol) was converted to the hydrochloride salt by dissolving in dichloromethane and treating with 1.25 M HCl in methanol. The reaction mixture was concentrated in vacuo to give 6-methoxy-8-phenoxy-1,2,3,4-tetrahydrobenzofuro[3,2-c]pyridine hydrochloride (5.5 mg, 97%, AUC HPLC 95.9%) as a white solid: mp <<MP data>>; $^1$H NMR (DMSO-d$_6$, 400 MHz) δ 8.97 (br s, 2H), 7.41-7.33 (m, 2H), 7.13-7.07 (m, 1H), 7.00-6.94 (m, 2H), 6.82 (d, J=2.4 Hz, 1H), 6.76 (d, J=2.0 Hz, 1H), 4.20 (s, 2H), 3.90 (s, 3H), 3.54-3.45 (m, 2H), 3.09-3.00 (m, 2H); APCI MS m/z 296 [M+H]$^+$.

Example 93

Preparation of 6-chloro-8-(phenylsulfinyl)-1,2,3,4-tetrahydrobenzofuro[3,2-c]pyridine hydrochloride

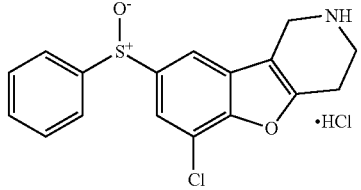 [SMILES: [O-][S+](c1ccccc1)c1cc(Cl)c2oc3c(c2c1)CNCC3 ; Cl]

Step A: To a solution of the product of Example 91, step A (50 mg, 0.12 mmol) in dichloromethane (2.0 mL) at −10° C. was added a solution of m-chloroperoxybenzoic acid (18 mg, 0.108 mmol) in dichloromethane (1.0 mL) drop wise. The reaction mixture was stirred at ambient temperature for 2 h, concentrated in vacuo and purified by column chromatography (SiO$_2$, 4:1 hexanes/ethyl acetate) providing tert-butyl 6-chloro-8-(phenylsulfinyl)-3,4-dihydrobenzofuro[3,2-c]pyridine-2(1H)-carboxylate (30 mg, 58%) as an off-white solid: $^1$H NMR (CDCl$_3$, 400 MHz) δ 7.68-7.63 (m, 3H), 7.51-7.45 (m, 4H), 4.55 (s, 2H), 3.86-3.77 (m, 2H), 2.93-2.85 (m, 2H), 1.50 (s, 9H).

Step B: The product of step A (30 mg, 0.07 mmol) was Boc deprotected and converted to the hydrochloride salt following the procedure of Example 29, step D to provide 6-chloro-8-(phenylsulfinyl)-1,2,3,4-tetrahydrobenzofuro[3,2-c]pyridine (12 mg, 60%, AUC HPLC 95%) as an off-white solid: mp 264-272° C. dec; $^1$H NMR (DMSO-d$_6$, 400 MHz) δ 9.61-9.45 (m, 2H), 8.12 (s, 1H), 7.81-7.73 (m, 3H), 7.58-7.49 (m, 3H), 4.36 (s, 2H), 3.57-3.48 (m, 2H), 3.19-3.10 (m, 2H); ESI MS m/z 332 [M+H]$^+$.

Example 94

Preparation of (6-chloro-1,2,3,4-tetrahydrobenzofuro[3,2-c]pyridin-8-yl)(phenyl)methanol hydrochloride

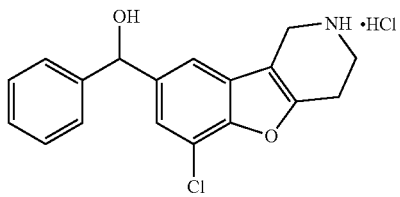 [SMILES: OC(c1ccccc1)c1cc(Cl)c2oc3c(c2c1)CNCC3 ; Cl]

Step A: A solution of the product of Example 29 step B (1.0 g, 2.58 mmol) in dry THF (15 mL) was cooled to −78° C. under a nitrogen atmosphere and n-butyl lithium (1.6 M in hexane, 1.0 mL, 1.54 mmol) was added dropwise over 10 min. The reaction mixture was stirred for 20 min and a solution of benzaldehyde (137 mg, 1.29 mmol) in THF (1 mL) was added over 5 min. The reaction was stirred for 1 h at −78° C., poured into saturated NH$_4$Cl solution and extracted with ethyl acetate. The organic layer was dried over Na$_2$SO$_4$, concentrated in vacuo and the residue purified by flash column chromatography (SiO$_2$, 85:15 hexanes/ethyl acetate) to afford tert-butyl 6-chloro-8-(hydroxy(phenyl)methyl)-3,4-dihydrobenzofuro[3,2-c]pyridine-2(1H)-carboxylate (0.6 g, 56%) as a white solid: $^1$H NMR (CDCl$_3$, 300 MHz) δ 7.42-7.26 (m, 7H), 5.91 (d, J=3.3 Hz, 1H), 4.51 (s, 2H), 3.87-3.75 (m, 2H), 2.93-2.83 (m, 2H), 2.28 (d, J=3.3 Hz, 1H), 1.49 (s, 9H).

Step B: To a solution of the product of step A (50.0 mg, 0.12 mmol) in dichloromethane (4 mL) was added trifluoroacetic acid (0.4 mL). After stirring for 2 h at ambient temperature the reaction mixture was quenched with 10% sodium bicarbonate solution (15 mL) and extracted with dichloromethane. The organic extract was dried over sodium sulphate and concentrated in vacuo. The residue was purified by flash column chromatography (SiO$_2$, 9:1 dichloromethane/methanol). The product was converted to hydrochloride salt by dissolving in dichloromethane and treating with 2 M HCl in diethyl ether at 0° C. After stirring for 20 min the reaction mixture was concentrated in vacuo to give (6-chloro-1,2,3,4-tetrahydrobenzofuro[3,2-c]pyridin-8-yl)(phenyl)methanol hydrochloride (18 mg, 47%, AUC HPLC 97.1%) as a white solid: mp 260° C. dec.; $^1$H NMR (CD$_3$OD, 300 MHz) δ 7.46 (s, 1H), 7.41-7.20 (m, 6H), 5.85 (br s, 1H), 4.40 (s, 2H), 3.68 (t, J=6 Hz, 2H), 3.25-3.15 (m, 2H); APCI MS m/z 314 [M+H]$^+$.

Example 95

Preparation of 6-chloro-8-(1-phenylethyl)-1,2,3,4-tetrahydrobenzofuro[3,2-c]pyridine hydrochloride

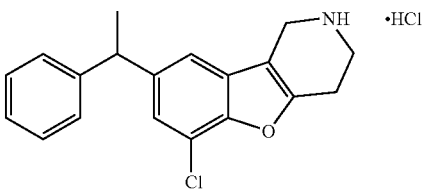 [SMILES: CC(c1ccccc1)c1cc(Cl)c2oc3c(c2c1)CNCC3 ; Cl]

Step A: tert-Butyl 8-benzoyl-6-chloro-3,4-dihydrobenzofuro[3,2-c]pyridine-2(1H)-carboxylate was converted to the alcohol derivative following the procedure of Example 94, step A. The crude product was purified by flash column chromatography (SiO$_2$, 9:1 hexanes/ethyl acetate) affording tert-butyl 6-chloro-8-(1-hydroxy-1-phenylethyl)-3,4-dihydrobenzofuro[3,2-c]pyridine-2(1H)-carboxylate (60 g, 64%) as an off-white solid: $^1$H NMR (CDCl$_3$, 400 MHz) δ 7.45-7.39 (m, 3H), 7.37-7.30 (m, 3H), 7.27 (t, J=1.2 Hz, 1H), 4.50 (s, 2H), 3.88-3.75 (m, 2H), 2.93-2.82 (m, 2H), 2.25 (s, 1H), 1.99 (s, 3H), 1.49 (s, 9H).

Step B: To a solution of the product of step A (60.0 mg, 0.14 mmol) in dichloromethane (6 mL) was added trifluoroacetic acid (0.5 mL). After stirring for 2 h at ambient temperature the reaction mixture was quenched with 10% sodium bicarbonate solution (15 mL) and extracted with dichloromethane. The organic extract was dried over sodium sulphate and concentrated in vacuo. The residue was purified by flash column chromatography (SiO$_2$, 9:1 dichloromethane/methanol) affording 6-chloro-8-(1-phenylvinyl)-1,2,3,4-tetrahydrobenzofuro[3,2-c]pyridine (40 mg, 74%) as a white solid: $^1$H NMR (CDCl$_3$, 300 MHz) δ 7.36-7.31 (m, 5H), 7.24-7.20 (m, 2H), 5.47 (d, J=11.4 Hz, 2H), 3.92 (t, J=1.8 Hz, 2H), 3.24 (t, J=5.7 Hz, 2H), 2.84 (t, J=5.7 Hz, 2H)

Step C: To the product obtained in step B (40.0 mg, 0.12 mmol) was added triethylsilane (0.5 mL, 3.22 mmol), trifluoroacetic acid (0.35 mL, 4.51 mmol) and boron trifluoride-diethylether complex (0.65 mL, 4.51 mmol) at 0° C. The reaction mixture was stirred at ambient temperature for 24 h under a nitrogen atmosphere, quenched with 20% potassium carbonate solution (15 mL) and extracted with dichloromethane. The organic extract was washed with water followed by brine, dried over sodium sulphate and concentrated in vacuo. The residue was purified by flash column chromatography (SiO$_2$, 9:1 dichloromethane/methanol). The product was converted to hydrochloride salt by dissolving in dichloromethane and treating with 2 M HCl in diethyl ether at 0° C. After stirring for 20 min the reaction mixture was concentrated in vacuo to give 6-chloro-8-(1-phenylethyl)-1,2,3,4-tetrahydrobenzofuro[3,2-c]pyridine hydrochloride (32 mg, 90%, AUC HPLC 96.5%) as an off-white solid: mp 245-255° C. dec.; $^1$H NMR (CD$_3$OD, 400 MHz) δ 7.38 (d, J=0.8 Hz, 1H), 7.31-7.20 (m, 5H), 7.20-7.14 (m, 1H), 4.39 (s, 2H), 4.27

(q, J=7.2 Hz, 1H), 3.67 (t, J=6.0 Hz, 2H), 3.18 (t, J=6.0 Hz, 2H), 1.67 (d, J=7.2 Hz, 3H); APCI MS m/z 312 [M+H]+

Example 96

Preparation of 8-benzyl-6-methoxy-1,2,3,4-tetrahydrobenzofuro[3,2-c]pyridine hydrochloride

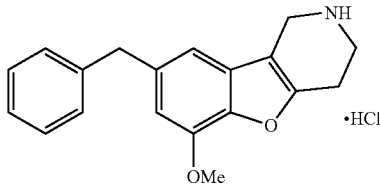 [SMILES: COc1cc(Cc2ccccc2)cc2c3c(oc12)CCNC3 ; Cl]

Step A: To a solution of tert-butyl 8-bromo-6-chloro-3,4-dihydrobenzofuro[3,2-c]pyridine-2(1H)-carboxylate (400 mg, 1.03 mmol) in tetrahydrofuran (6 mL) was added n-butyllithium (1.6 M in hexanes, 0.94 mL, 1.23 mmol) at −78° C., under argon. After stirring the reaction mixture for 30 min at this temperature, benzaldehyde (0.1 mL, 1.03 mmol) was added and the reaction stirred for 1 h before quenching with saturated ammonium chloride solution. The mixture was extracted with ethyl acetate and the organic layer concentrated in vacuo. The residue was purified by flash column chromatography (SiO₂, 4:1 hexanes/ethyl acetate) to give tert-butyl 6-chloro-8-(hydroxy)(phenyl)methyl)-3,4-dihydrobenzofuro[3,2-c]pyridine-2(1H)-carboxylate (300 mg, 70%) as a white solid: ¹H NMR (CDCl₃, 300 MHz) δ 7.42-7.28 (m, 7H), 5.91 (d, J=3.3 Hz, 1H), 4.51 (s, 2H), 3.86-3.76 (m, 2H), 2.93-2.83 (m, 2H), 1.50 (s, 9H).

Step B: To a solution of product of step A (170 mg, 0.41 mmol) in dichloromethane (3 mL) at 0° C. was added triethylsilane (0.05 mL, 0.32 mmol) and trifluoroacetic acid (0.5 mL, 6.97 mmol). After stirring for 4 h, the reaction mixture was quenched with saturated sodium bicarbonate solution and extracted with dichloromethane. The organic layer was concentrated in vacuo and the residue purified by flash column chromatography (SiO₂, 95:5 dichloromethane/methanol) to give 8-bromo-6-chloro-1,2,3,4-tetrahydrobenzofuro[3,2-c]pyridine (150 mg, 98%) as a white solid: ¹H NMR (CDCl₃, 300 MHz) δ 7.32-7.16 (m, 7H), 4.01 (s, 2H), 3.93 (s, 2H), 3.24 (t, J=5.7 Hz, 2H), 2.84-2.79 (m, 2H).

Step C: To a suspension of the product of step B (150 mg, 0.50 mmol) in 2-propanol (5 mL) and water (5 mL) at 0° C. was added potassium carbonate (104 mg) and di-tert-butyl dicarbonate (131 mg, 0.6 mmol). After 2 h the reaction mixture was concentrated in vacuo and extracted with dichloromethane. The organic layer was concentrated in vacuo and the residue purified by flash column chromatography (SiO₂, 95/5 hexanes/ethyl acetate) to give tert-butyl 8-benzyl-6-chloro-3,4-dihydrobenzofuro[3,2-c]pyridine-2(1H)-carboxylate (150 mg, 75%) as a white solid: ¹H NMR (CDCl₃, 300 MHz) δ 7.33-7.22 (m, 3H), 7.21-7.16 (m, 2H), 7.13-7.08 (m, 2H), 4.50 (br s, 2H), 4.03 (s, 2H), 3.81 (t, J=5.4 Hz, 2H), 2.87 (t, J=5.4 Hz, 2H), 1.53 (s, 9H).

Step D: The product of step C (150 mg, 0.37 mmol) was converted to the phenol derivative following the procedure of Example 54, step A. The crude product was purified by column chromatography (SiO₂, 4:1 hexanes/ethyl acetate) providing tert-butyl 8-benzyl-6-hydroxy-3,4-dihydrobenzofuro[3,2-c]pyridine-2(1H)-carboxylate (100 mg, 71%) as an off-white solid which was converted directly to the methyl ether derivative following the procedure of Example 54, step B. Purification by column chromatography (SiO₂, 85:15 hexanes/ethyl acetate) provided tert-butyl 8-benzyl-6-methoxy-3,4-dihydrobenzofuro[3,2-c]pyridine-2(1H)-carboxylate (80 mg, 58%) as a white solid: ¹H NMR (CDCl₃, 300 MHz) δ 7.32-7.27 (m, 2H), 7.23-7.16 (m, 3H), 6.84 (br s, 1H), 6.61 (s, 1H), 4.50 (br s, 2H), 4.04 (s, 2H), 3.95 (s, 3H), 3.80 (t, J=5.4 Hz, 2H), 2.88-2.81 (m, 2H), 1.49 (s, 9H).

Step E: The product of step D (80 mg, 0.20 mmol) was Boc deprotected and converted to the hydrochloride salt following the procedure of Example 29, step D to provide 8-benzyl-6-methoxy-1,2,3,4-tetrahydrobenzofuro[3,2-c]pyridine hydrochloride (40 mg, 61%, AUC HPLC>99%) as an off-white solid: mp 263-265° C.; ¹H NMR (DMSO-d₆, 300 MHz) δ 9.43 (br s, 2H), 7.32-7.22 (m, 4H), 7.21-7.14 (m, 1H), 7.02-6.99 (m, 1H), 6.87 (d, J=1.2 Hz, 1H), 4.26 (s, 2H), 4.00 (s, 2H), 3.89 (s, 3H), 3.50 (t, J=6 Hz, 2H), 3.05 (t, J=5.7 Hz, 2H); APCI MS m/z 294 [M+H]+.

Example 97

Preparation of 6-chloro-8-(phenylsulfonyl)-1,2,3,4-tetrahydrodibenzo[b,d]furan-2-ol

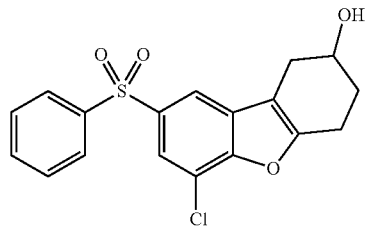 [SMILES: O=S(=O)(c1ccccc1)c1cc(Cl)c2oc3c(c2c1)CC(O)CC3]

Step A: A mixture of cyclohexane-1,4-dione (2.70 g, 10.50 mmol) and the product of example 29 step A (1.30 g, 11.60 mmol) was suspended in a mixture of glacial acetic acid (17.4 mL) and methanesulfonic acid (2.6 mL). The reaction was heated at 110° C. for 2.5 h, cooled, quenched with 5% NaOH solution, and extracted with dichloromethane. The organic layer was concentrated in vacuo and the residue purified by flash column chromatography (SiO₂, 9:1 hexanes/ethyl acetate) to give 8-bromo-6-chloro-3,4-dihydrobenzo[b,d]furan-2(1H)-one (300 mg, 9%) as a white solid: ¹H NMR (CDCl₃, 300 MHz) δ 7.42 (s, 2H), 3.46 (t, J=1.8 Hz, 2H), 3.27-3.21 (m, 2H), 2.84 (t, J=6.9 Hz, 2H).

Step B: The product of step A (300 mg, 1.01 mmol) was suspended in methanol (20 mL) and cooled to 0° C. Sodium borohydride (76 mg, 2.01 mmol) was added portionwise and the reaction mixture stirred at ambient temperature for 2.5 h. The reaction mixture was concentrated in vacuo and the residue purified by flash column chromatography (SiO₂, 2:1 hexanes/ethyl acetate) to give 8-bromo-6-chloro-1,2,3,4-tetrahydrodibenzo[b,d]furan-2-ol (280 mg, 92%) as a white solid: ¹H NMR (CDCl₃, 300 MHz) δ 7.42 (d, J=1.8 Hz, 1H), 7.34 (d, J=1.8 Hz, 1H), 4.35-4.26 (m, 1H), 3.02-2.79 (m, 3H), 2.66-2.57 (m, 1H), 2.14-2.05 (m, 2H), 1.71-1.61 (m, 1H).

Step C: A mixture of the product of step B (120 mg, 0.39 mmol), sodium benzenesulfinate (77 mg, 0.47 mmol), di-palladium-tris(dibenzylideneacetone) (36 mg, 0.04 mmol), cesium carbonate (190 mg, 0.58 mmol) and xantphos (45 mg, 0.08 mmol) was suspended in anhydrous toluene (5.0 mL). The reaction flask was purged with argon and heated to 110° C. for 1 h. After cooling to ambient temperature, the reaction mixture was diluted with dichloromethane and filtered through a celite bed. The filtrate was concentrated in vacuo and the residue purified by flash column chromatography (SiO$_2$, 9:1 hexanes/ethyl acetate) and triturated with MTBE to give 6-chloro-8-(phenylsulfonyl)-1,2,3,4-tetrahydrodibenzo[b,d]furan-2-ol (40 mg, 27%, AUC HPLC 97.1%) as a white solid: mp 236-240° C.; $^1$H NMR (DMSO-d$_6$, 400 MHz) δ 8.15 (d, J=1.6 Hz, 1H), 8.05-8.01 (m, 2H), 7.89 (d, J=1.6 Hz, 1H), 7.71-7.66 (m, 1H), 7.64-7.59 (m, 2H), 4.92 (d, J=4.0 Hz, 1H), 4.11-4.04 (m, 1H), 2.94-2.76 (m, 3H), 2.60-2.52 (m, 1H), 2.00-1.87 (m, 2H); ESI MS m/z 363 [M+H]$^+$.

Example 98

Preparation of (−)-6-chloro-8-(phenylsulfonyl)-1,2,3,4-tetrahydrodibenzo[b,d]furan-2-ol

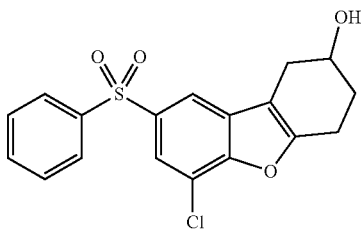 [SMILES: O=S(=O)(c1ccccc1)c1cc(Cl)c2oc3c(c2c1)CC(O)CC3]

Step A: A mixture of the racemic alcohol obtained from Example 97, step B (520 mg, 1.7 mmol), *Candida antarctica* lipase B (20 mg) and vinyl acetate (2.1 mL, 3.5 mmol) in hexanes (21 mL) was warmed to 32° C. for 2 h. The reaction mixture was concentrated in vacuo and the residue purified by flash column chromatography (SiO$_2$, 2:1 hexanes/ethyl acetate) to give a single enantiomer of the acetate derivative 8-bromo-6-chloro-1,2,3,4-tetrahydrodibenzo[b,d]furan-2-yl acetate (240 mg, 42%) as a white solid: $^1$H NMR (CDCl$_3$, 300 MHz) δ 7.41 (d, J=1.8 Hz, 1H), 7.36 (d, J=1.8 Hz, 1H), 5.36-5.27 (m, 1H), 3.01-2.85 (m, 3H), 2.77-2.67 (m, 1H), 2.28-2.08 (m, 2H), 2.05 (s, 3H).

Step B: A mixture of the product of step A (150 mg, 0.43 mmol), sodium benzenesulfinate (86 mg, 0.52 mmol), di-palladium-tris(dibenzylideneacetone) (39 mg, 0.04 mmol), cesium carbonate (210 mg, 0.64 mmol) and xantphos (50 mg, 0.09 mmol) was suspended in anhydrous toluene (8 mL). The reaction flask was purged with argon and heated at 110° C. for 5 h. After cooling to ambient temperature, the reaction mixture was diluted with dichloromethane and filtered through a celite bed. The filtrate was concentrated in vacuo and the residue purified by flash column chromatography (SiO$_2$, 7:3 hexanes/ethyl acetate) to give a single enantiomer of 6-chloro-8-(phenylsulfonyl)-1,2,3,4-tetrahydrodibenzo[b,d]furan-2-yl acetate (120 mg, 30%) as a white solid: $^1$H NMR (CDCl$_3$, 300 MHz) δ 8.01-7.92 (m, 3H), 7.83 (d, J=1.5 Hz, 1H), 7.60-7.47 (m, 3H), 5.36-5.28 (m, 1H), 3.06-2.73 (m, 4H), 2.28-2.07 (m, 2H), 2.05 (s, 3H).

Step C: To a solution of the product of step B (180 mg, 0.44 mmol) in tetrahydrofuran (30 mL) and methanol (15 mL) was added a solution of lithium hydroxide monohydrate (56 mg, 1.32 mmol) in water (7.5 mL) and the reaction mixture was stirred at ambient temperature for 1 h. The mixture was concentrated in vacuo and the residue purified by flash column chromatography (SiO$_2$, 1:1 hexanes/ethyl acetate) then (SiO$_2$, 95:5 dichloromethane/methanol) to give (−)-8-bromo-6-chloro-1,2,3,4-tetrahydrodibenzo[b,d]furan-2-ol (32 mg, 20%, AUC HPLC 95.5%) chiral phase HPLC>99% (Chiralpak AD column, 70:30 heptane/2-propanol+0.1% DEA), as a white solid: mp 236-240° C.; [α]$^{25}_D$ −80°; $^1$H NMR (DMSO-d$_6$, 300 MHz) δ 8.15 (d, J=1.5 Hz, 1H), 8.06-8.00 (m, 2H), 7.89 (d, J=1.6 Hz, 1H), 7.72-7.58 (m, 3H), 4.92 (d, J=6.0 Hz, 1H), 4.11-4.05 (m, 1H), 2.96-2.72 (m, 3H), 2.62-2.56 (m, 1H), 2.02-1.84 (m, 2H); ESI MS m/z 363 [M+H]$^+$.

Example 99

Preparation of (+)-6-chloro-8-(phenylsulfonyl)-1,2,3,4-tetrahydrodibenzo[b,d]furan-2-ol

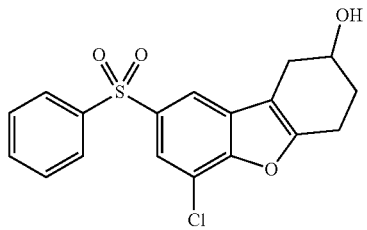 [SMILES: O=S(=O)(c1ccccc1)c1cc(Cl)c2oc3c(c2c1)CC(O)CC3]

Step A: The residual alcohol derivative obtained in Example 98 step A was separated into single enantiomers using a Chiralpak AD preparative HPLC column, (heptane/2-propanol, 98:2+0.1% diethylamine) to elute Enantiomer A followed by Enantiomer B (desired enantiomer) as white solids.

Step B: To a solution of separated Enantiomer B from step A (200 mg, 0.66 mmol) in dichloromethane (2.5 mL) was added triethylamine (0.32 mL, 2.64 mmol), 4-dimethylaminopyridine (7 mg, 0.06 mmol) and acetic anhydride (0.27 mL, 3.30 mmol) at 0° C. The reaction mixture was stirred at ambient temperature for 2 h, concentrated in vacuo and the residue purified by flash column chromatography (SiO$_2$, 9:1 hexanes/ethyl acetate) to give a single enantiomer of 8-bromo-6-chloro-1,2,3,4-tetrahydrodibenzo[b,d]furan-2-yl acetate (230 mg, 98%) as a white solid: $^1$H NMR (CDCl$_3$, 300 MHz) δ 7.40 (s, 1H), 7.36 (s, 1H), 5.35-5.27 (m, 1H), 3.01-2.84 (m, 3H), 2.77-2.64 (m, 1H), 2.27-2.07 (m, 2H), 2.05 (m, 3H).

Step C: A mixture of the product of step B (230 mg, 0.66 mmol), sodium benzenesulfinate (132 mg, 0.80 mmol), di-palladium-tris(dibenzylideneacetone) (60 mg, 0.07 mmol), cesium carbonate (322 mg, 0.99 mmol) and xantphos (76 mg, 0.13 mmol) was suspended in anhydrous toluene (4 mL). The reaction flask was purged with argon and heated at 110° C. for 5 h. After cooling, the reaction mixture was diluted with dichloromethane and filtered through a celite bed. The filtrate was concentrated in vacuo and the residue purified by flash column chromatography (SiO$_2$, 7:3 hexanes/ethyl acetate) to give a single enantiomer of 6-chloro-8-(phenylsulfonyl)-1,2,3,4-tetrahydrodibenzo[b,d]furan-2-yl acetate (150 mg, 56%) as a white solid: $^1$H NMR (CDCl$_3$, 300 MHz) δ 8.01-7.92 (m, 3H), 7.83 (d, J=1.8 Hz, 1H), 7.61-7.48 (m, 3H), 5.36-5.28 (m, 1H), 3.06-2.73 (m, 4H), 2.28-2.09 (m, 2H), 2.05 (s, 3H).

Step D: To a solution of the product of step C (150 mg, 0.37 mmol) in tetrahydrofuran (24 mL) and methanol (12 mL) was added a solution of lithium hydroxide monohydrate (47 mg, 1.11 mmol) in water (6.0 mL) and the reaction mixture was stirred at ambient temperature for 1 h. The reaction mixture was concentrated in vacuo and the residue purified by flash column chromatography (SiO$_2$, 1:1 hexanes/ethyl acetate) then (SiO$_2$, 95:5 dichloromethane/methanol) to give (+)-8-bromo-6-chloro-1,2,3,4-tetrahydrodibenzo[b,d]furan-2-ol (35 mg, 21%, AUC HPLC 95.1%) chiral phase HPLC>99%

(Chiralpak AD column, 80:20 heptane/2-propanol+0.1% DEA) as a white solid: mp 238-242° C.; [α]$^{25}_D$ +40°; $^1$H NMR (DMSO-d$_6$, 300 MHz) δ 8.15 (d, J=1.5 Hz, 1H), 8.06-8.01 (m, 2H), 7.89 (d, J=1.6 Hz, 1H), 7.72-7.58 (m, 3H), 4.92 (d, J=3.9 Hz, 1H), 4.13-4.02 (m, 1H), 2.95-2.79 (m, 3H), 2.61-2.54 (m, 1H), 2.00-1.86 (m, 2H); ESI MS m/z 363 [M+H]$^+$.

By methods as described above, the compounds listed in TABLE 1 were synthesized.

TABLE 1

| Ex. No. | Structure | Mass Spec [M + H]$^+$ | $^1$H NMR Data |
|---|---|---|---|
| 100 | 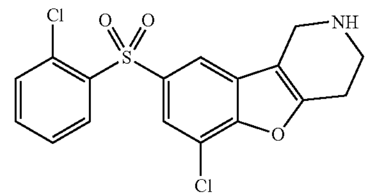 | 382 | $^1$H NMR (DMSO-d$_6$, 300 MHz) δ 9.52 (br s, 2 H), 8.38 (d, J = 1.8 Hz, 1 H), 8.33 (dd, J = 7.8, 2.1 Hz, 1 H), 7.94 (d, J = 1.8 Hz, 1 H), 7.80-7.67 (m, 2 H), 7.64 (dd, J = 7.5, 1.5 Hz, 1 H), 4.40 (s, 2 H), 3.54 (t, J = 6.0 Hz, 2 H), 3.23-3.13 (m, 2 H). |
| 101 | 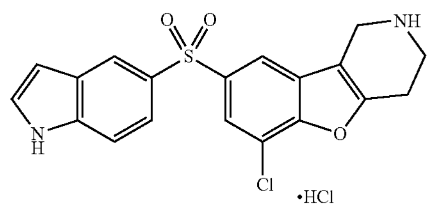 [SMILES: O=S(=O)(c1ccc2[nH]ccc2c1)c1cc(Cl)c2oc3c(c2c1)CNCC3 ; Cl] | 387 | $^1$H NMR (DMSO-d$_6$, 400 MHz) δ 11.71 (s, 1 H), 9.47 (br s, 2 H), 8.37 (s, 1 H), 8.30 (s, 1 H), 7.96 (s, 1 H), 7.69-7.53 (m, 3 H), 6.66 (s, 1 H), 4.38 (s, 2 H), 3.51 (t, J = 6.0 Hz, 2 H), 3.14 (t, J = 6.0 Hz, 2 H). |
| 102 | 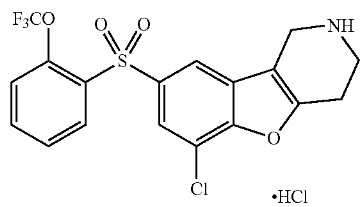 [SMILES: O=S(=O)(c1cc(Cl)c2oc3c(c2c1)CNCC3)c1ccccc1OC(F)(F)F ; Cl] | 432 | $^1$H NMR (DMSO-d$_6$, 400 MHz) δ 9.52 (br s, 2 H), 8.35-8.24 (m, 2 H), 7.98-7.84 (m, 2 H), 7.75-7.67 (m, 1 H), 7.58-7.51 (m, 1 H), 4.37 (s, 2 H), 3.54 (br s, 2 H), 3.19 (s, 2 H). |
| 103 | 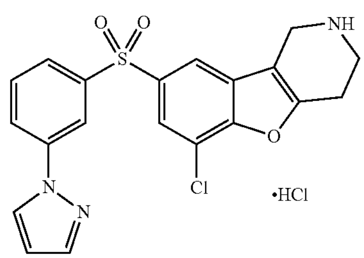 [SMILES: O=S(=O)(c1cccc(-n2cccn2)c1)c1cc(Cl)c2oc3c(c2c1)CNCC3 ; Cl] | 414 | $^1$H NMR (DMSO-d$_6$, 300 MHz) δ 9.66 (br s, 2 H), 8.68 (d, J = 2.7 Hz, 1 H), 8.48 (d, J = 1.8 Hz, 1 H), 8.43 (t, J = 1.8 Hz, 1 H), 8.21-8.10 (m, 2 H), 7.97-7.90 (m, 1 H), 7.82 (d, J = 1.5 Hz, 1 H), 7.75 (t, J = 8.1 Hz, 1 H), 6.61 (t, J = 2.4 Hz, 1 H), 4.40 (s, 2 H), 3.60-3.45 (m, 2 H), 3.22-3.10 (m, 2 H). |
| 104 | 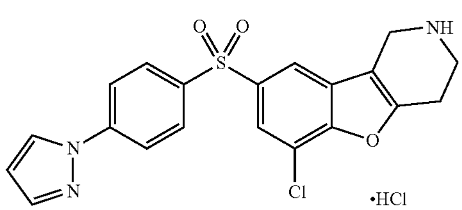 [SMILES: O=S(=O)(c1ccc(-n2cccn2)cc1)c1cc(Cl)c2oc3c(c2c1)CNCC3 ; Cl] | 414 | $^1$H NMR (DMSO-d$_6$, 400 MHz) δ 9.30 (br s, 2 H), 8.65 (d, J = 2.4 Hz, 1 H), 8.42 (d, J = 1.6 Hz, 1 H), 8.18-8.02 (m, 5 H), 7.83 (d, J = 1.6 Hz, 1 H), 6.65-6.58 (m, 1 H), 4.38 (s, 2 H), 3.52 (t, J = 5.2 Hz, 2 H), 3.19-3.10 (m, 2 H). |
| 105 | 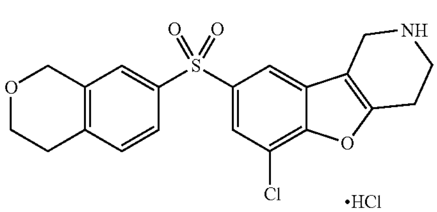 [SMILES: O=S(=O)(c1ccc2c(c1)COCC2)c1cc(Cl)c2oc3c(c2c1)CNCC3 ; Cl] | 404 | $^1$H NMR (DMSO-d$_6$, 400 MHz) δ 9.52 (br s, 2 H), 8.38 (d, J = 1.6 Hz, 1 H), 7.99 (d, J = 1.6 Hz, 1 H), 7.78 (d, J = 8.4 Hz, 1 H), 7.74 (s, 1 H), 7.38 (d, J = 8.0 Hz, 1 H), 4.74 (s, 2 H), 4.40 (br s, 2 H), 3.86 (t, J = 6.0 Hz, 2 H), 3.57-3.52 (m, 2 H), 3.19-3.13 (m, 2 H), 2.83 (t, J = 5.6 Hz, 2 H). |

TABLE 1-continued

| Ex. No. | Structure | Mass Spec [M + H]+ | ¹H NMR Data |
|---|---|---|---|
| 106 | 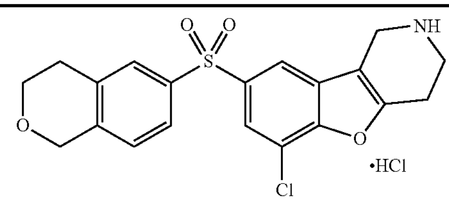 | 404 | ¹H NMR (DMSO-d₆, 400 MHz) δ 9.36-9.52 (m, 2 H), 8.39 (d, J = 1.6 Hz, 1 H), 8.01 (d, J = 1.6 Hz, 1 H), 7.81 (br s, 1 H), 7.79 (dd, J = 8.0, 1.6 Hz, 1 H), 7.28 (d, J = 8.4 Hz, 1 H), 4.71 (s, 2 H), 4.39 (s, 2 H), 3.86 (t, J = 5.6 Hz, 2 H), 3.53 (t, J = 6.0 Hz, 2 H), 3.16 (t, J = 6.0 Hz, 2 H), 2.86 (t, J = 5.6 Hz, 2 H). |
| 107 | 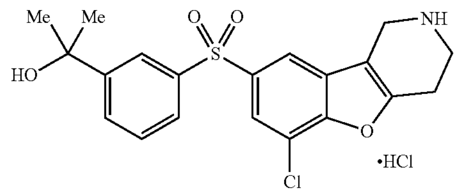 [SMILES: CC(C)(O)c1cccc(S(=O)(=O)c2cc(Cl)c3oc4c(c3c2)CNCC4)c1 ; Cl] | 406 | ¹H NMR (CD₃OD, 400 MHz) δ 8.21 (d, J = 1.6 Hz, 1 H), 8.16 (t, J = 1.6 Hz, 1 H), 7.94 (d, J = 1.6 Hz, 1 H), 7.89-7.84 (m, 1 H), 7.76-7.71 (m, 1 H), 7.53 (t, J = 7.6 Hz, 1 H), 4.40-4.30 (m, 2 H), 3.75-3.51 (m, 2 H), 3.25-3.09 (m, 2 H), 1.51 (s, 6 H). |
| 108 | 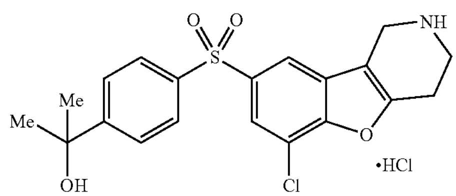 [SMILES: CC(C)(O)c1ccc(S(=O)(=O)c2cc(Cl)c3oc4c(c3c2)CNCC4)cc1 ; Cl] | 406 | ¹H NMR (CD₃OD, 400 MHz) δ 8.22 (d, J = 1.6 Hz, 1 H), 7.99-7.91 (m, 3 H), 7.71 (d, J = 8.8 Hz, 2 H), 4.48 (s, 2 H), 3.69 (t, J = 6.4 Hz, 2 H), 3.23 (t, J = 6.0 Hz, 2 H), 1.50 (s, 6 H). |
| 109 | 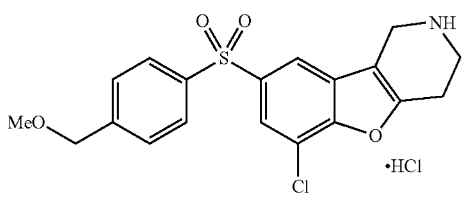 [SMILES: COCc1ccc(S(=O)(=O)c2cc(Cl)c3oc4c(c3c2)CNCC4)cc1 ; Cl] | 392 | ¹H NMR (CD₃OD, 400 MHz) δ 8.12 (d, J = 1.6 Hz, 1 H), 7.98 (d, J = 8.4 Hz, 2 H), 7.89 (d, J = 1.6 Hz, 1 H), 7.54 (d, J = 8.4 Hz, 2 H), 4.50 (s, 2 H), 4.16 (s, 2 H), 3.45-3.35 (m, 5 H), 3.01 (t, J = 6 Hz, 2 H). |
| 110 | 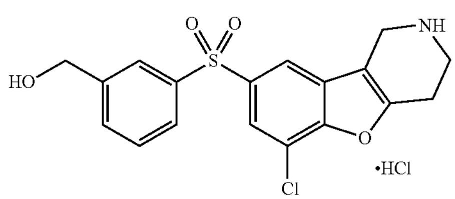 [SMILES: O=S(=O)(c1cccc(CO)c1)c1cc(Cl)c2oc3c(c2c1)CNCC3 ; Cl] | 378 | ¹H NMR (DMSO-d₆, 300 MHz) δ 9.68-9.56 (m, 2 H), 8.41 (d, J = 1.5 Hz, 1 H), 8.00 (d, J = 1.5 Hz, 1 H), 7.95 (s, 1 H), 7.93-7.86 (m, 1 H), 7.65-7.54 (m, 2 H), 5.52-5.35 (m, 1 H), 4.56 (s, 2 H), 4.40 (s, 2 H), 3.53 (t, J = 5.7 Hz, 2 H), 3.21-3.11 (m, 2 H). |
| 111 | 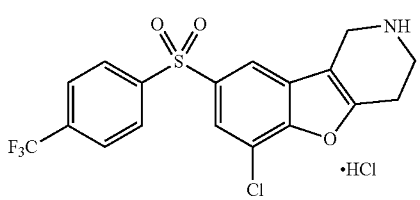 [SMILES: O=S(=O)(c1ccc(C(F)(F)F)cc1)c1cc(Cl)c2oc3c(c2c1)CNCC3 ; Cl] | 416 | ¹H NMR (DMSO-d₆, 400 MHz) δ 9.57-9.50 (m, 2 H), 8.46 (d, J = 2.0 Hz, 1 H), 8.25 (d, J = 8.4 Hz, 2 H), 8.11 (d, J = 1.6 Hz, 1 H), 8.02 (d, J = 8.4 Hz, 2 H), 4.39 (s, 2 H), 3.53 (t, J = 6.0 Hz, 2 H), 3.16 (t, J = 5.6 Hz, 2 H). |
| 112 | 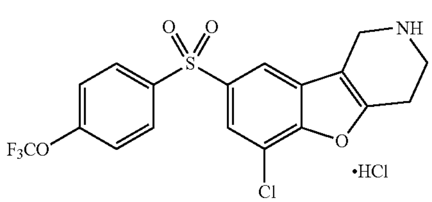 [SMILES: O=S(=O)(c1ccc(OC(F)(F)F)cc1)c1cc(Cl)c2oc3c(c2c1)CNCC3 ; Cl] | 432 | ¹H NMR (DMSO-d₆, 300 MHz) δ 9.68-9.56 (m, 2 H), 8.43 (d, J = 1.8 Hz, 1 H), 8.19 (d, J = 9.0 Hz, 2 H), 8.08 (d, J = 1.5 Hz, 1 H), 7.62 (d, J = 8.4 Hz, 2 H), 4.39 (s, 2 H), 3.53 (t, J = 5.7 Hz, 2 H), 3.22-3.10 (m, 2 H). |
| 113 | 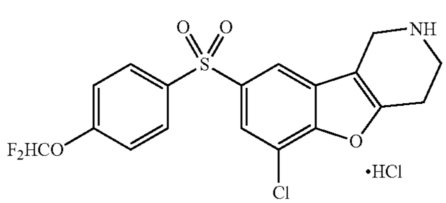 [SMILES: O=S(=O)(c1ccc(OC(F)F)cc1)c1cc(Cl)c2oc3c(c2c1)CNCC3 ; Cl] | 414 | ¹H NMR (DMSO-d₆, 400 MHz) δ 9.77-9.67 (m, 2 H), 8.42 (d, J = 1.2 Hz, 1 H), 8.10 (d, J = 7.2 Hz, 2 H), 8.04 (d, J = 1.6 Hz, 1 H), 7.43-7.35 (m, 3 H), 4.38 (s, 2 H), 3.53 (t, J = 6.0 Hz, 2 H), 3.17 (t, J = 5.2 Hz, 2 H). |

TABLE 1-continued

| Ex. No. | Structure | Mass Spec [M + H]+ | 1H NMR Data |
|---|---|---|---|
| 114 | 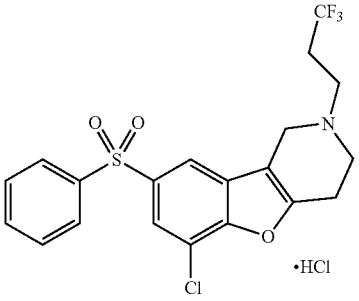 [SMILES: O=S(=O)(c1ccccc1)c1cc(Cl)c2oc3c(c2c1)CN(CCC(F)(F)F)CC3 ; Cl] | 444 | 1H NMR (CD3OD, 300 MHz) δ 8.21-8.19 (m, 1 H), 8.04-7.95 (m, 3 H), 7.68-7.55 (m, 3 H), 7.67-7.55 (m, 3 H), 4.52 (br s, 2 H), 3.72 (br s, 2 H), 3.60 (br s, 2 H), 3.40 (br s, 2 H), 2.97-2.82 (m, 2 H). |
| 115 | 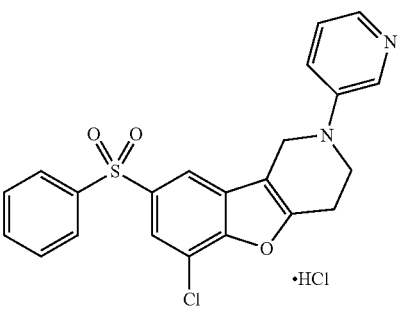 [SMILES: O=S(=O)(c1ccccc1)c1cc(Cl)c2oc3c(c2c1)CN(c1cccnc1)CC3 ; Cl] | 425 | 1H NMR (CD3OD, 300 MHz) δ 8.53 (d, J = 3.0 Hz, 1 H), 8.26-8.17 (m, 2 H), 8.16-8.12 (m, 1 H), 8.05-7.97 (m, 2 H), 7.92 (d, J = 3.0 Hz, 1 H), 7.89-7.82 (m, 1 H), 7.68-7.56 (m, 3 H), 4.67 (s, 2 H), 4.01 (t, J = 6.0 Hz, 2 H), 3.12 (t, J = 6.0 Hz, 2 H). |
| 116 | 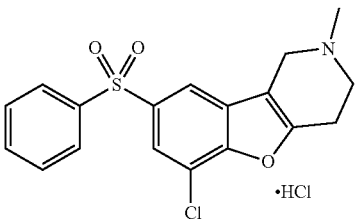 [SMILES: CN1CCc2oc3c(Cl)cc(S(=O)(=O)c4ccccc4)cc3c2C1 ; Cl] | 362 | 1H NMR (DMSO-d6, 400 MHz) δ 10.63 (br s, 1 H), 8.36 (s, 1 H), 8.09-7.98 (m, 2 H), 7.78-7.57 (m, 4 H), 4.49 (br s, 2 H), 3.70 (br s, 2 H), 3.23 (br s, 2 H), 2.93 (s, 3 H). |
| 117 | 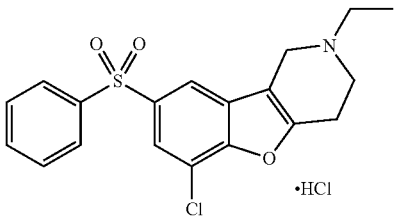 [SMILES: CCN1CCc2oc3c(Cl)cc(S(=O)(=O)c4ccccc4)cc3c2C1 ; Cl] | 376 | 1H NMR (DMSO-d6, 300 MHz) δ 10.41 (br s, 1 H), 8.39 (s, 1 H), 8.04-8.01 (m, 3 H), 7.73-7.62 (m, 3 H), 4.76 (br s, 1 H), 4.34 (br s, 1 H), 3.87 (br s, 1 H), 3.50-3.39 (m, 5 H), 3.26 (br s, 2 H), 1.34 (br s, 3 H). |
| 118 | 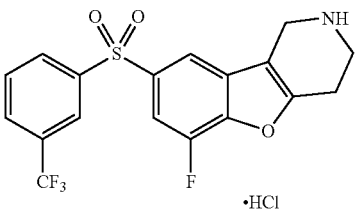 [SMILES: O=S(=O)(c1cccc(C(F)(F)F)c1)c1cc(F)c2oc3c(c2c1)CNCC3 ; Cl] | 400 | 1H NMR (DMSO-d6, 300 MHz) δ 9.37 (br s, 2 H), 8.40-8.30 (m, 3 H), 8.14-8.03 (m, 2 H), 7.89 (t, J = 9.0 Hz, 1 H), 4.40 (s, 2 H), 3.54 (t, J = 3.0 Hz, 2 H), 3.20-3.10 (m, 2 H). |
| 119 | 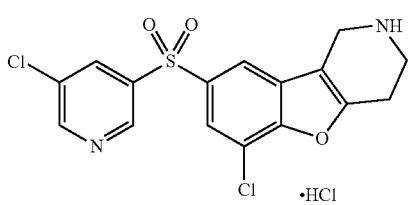 [SMILES: O=S(=O)(c1cncc(Cl)c1)c1cc(Cl)c2oc3c(c2c1)CNCC3 ; Cl] | 383 | 1H NMR (DMSO-d6, 400 MHz) δ 9.55-9.47 (m, 2 H), 9.15 (d, J = 2.0 Hz, 1 H), 8.95 (t, J = 2.0 Hz, 1 H), 8.62 (t, J = 2.0 Hz, 1 H), 8.52 (d, J = 1.6 Hz, 1 H), 8.22 (t, J = 1.6 Hz, 1 H), 4.34 (s, 2 H), 3.58-3.52 (m, 2 H), 3.21-3.14 (m, 2 H). |

TABLE 1-continued

| Ex. No. | Structure | Mass Spec [M + H]+ | 1H NMR Data |
|---|---|---|---|
| 120 | 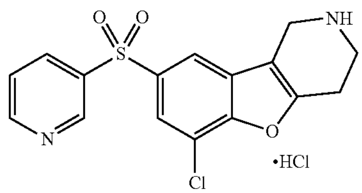 [SMILES: O=S(=O)(c1cccnc1)c1cc(Cl)c2oc3c(c2c1)CNCC3 ; Cl] | 349 | 1H NMR (DMSO-d6, 400 MHz) δ 9.65-9.57 (m, 2 H), 9.21 (d, J = 2.0 Hz, 1 H), 8.87 (t, J = 3.2 Hz, 1 H), 8.48 (d, J = 2.0 Hz, 1 H), 8.45-8.41 (m, 1 H), 8.16-8.13 (m, 1 H), 7.70-7.65 (m, 1 H), 4.40 (s, 2 H), 3.54-3.50 (m, 2 H), 3.21-3.12 (m, 2 H). |
| 121 | 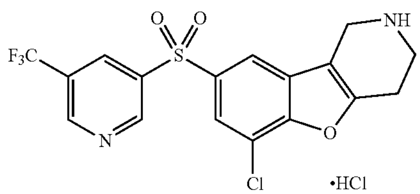 [SMILES: O=S(=O)(c1cncc(C(F)(F)F)c1)c1cc(Cl)c2oc3c(c2c1)CNCC3 ; Cl] | 417 | 1H NMR (DMSO-d6, 400 MHz) δ 9.52-9.38 (m, 3 H), 9.31 (d, J = 1.2 Hz, 1 H), 8.83-8.81 (m, 1 H), 8.57 (d, J = 2.0 Hz, 1 H), 8.29 (d, J = 1.6 Hz, 1 H), 4.40 (br s, 2 H), 3.58-3.53 (m, 2 H), 3.19-3.15 (m, 2 H). |
| 122 | 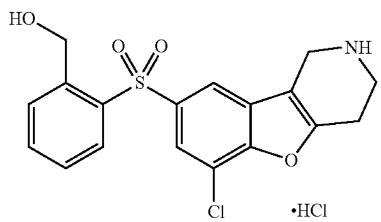 [SMILES: O=S(=O)(c1cc(Cl)c2oc3c(c2c1)CNCC3)c1ccccc1CO ; Cl] | 378 | 1H NMR (DMSO-d6, 400 MHz) δ 9.35-9.19 (m, 2 H), 8.35 (d, J = 1.2 Hz, 1 H), 8.12 (d, J = 7.6 Hz, 1 H), 7.87 (d, J = 1.6 Hz, 1 H), 7.81-7.73 (m, 2 H), 7.61-7.55 (m, 1 H), 5.39 (t, J = 6.0 Hz, 1 H), 4.74 (d, J = 5.6 Hz, 2 H), 4.38 (s, 2 H), 3.52 (t, J = 5.2 Hz, 2 H), 3.19-3.12 (m, 2 H). |
| 123 | 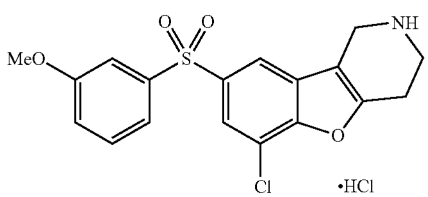 [SMILES: COc1cccc(S(=O)(=O)c2cc(Cl)c3oc4c(c3c2)CNCC4)c1 ; Cl] | 378 | 1H NMR (DMSO-d6, 400 MHz) δ 9.83-9.47 (m, 2 H), 8.43 (s, 1 H), 8.06 (s, 1 H), 7.60-7.49 (m, 3 H), 7.26 (d, J = 7.6 Hz, 1 H), 4.39 (s, 2 H), 3.84 (s, 3 H), 3.52 (t, J = 5.6 Hz, 2 H), 3.16 (t, J = 5.6 Hz, 2 H). |
| 124 | 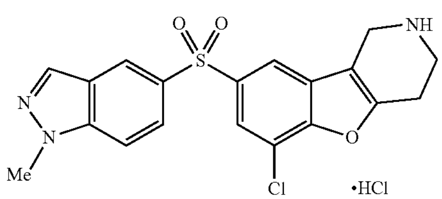 [SMILES: Cn1ncc2cc(S(=O)(=O)c3cc(Cl)c4oc5c(c4c3)CNCC5)ccc21 ; Cl] | 402 | 1H NMR (CD3OD, 300 MHz) δ 8.57 (s, 1 H), 8.22 (d, J = 7.5 Hz, 2 H), 7.99 (d, J = 1.5 Hz, 1 H), 7.93 (dd, J = 8.7, 1.5 Hz, 1 H), 7.71 (d, J = 8.7 Hz, 1 H), 4.48 (s, 2 H), 4.09 (s, 3 H), 3.69 (t, J = 6.0 Hz, 2 H), 3.23 (t, J = 6.0 Hz, 2 H). |
| 125 | 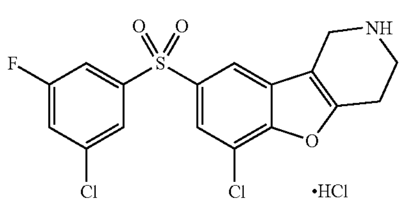 [SMILES: O=S(=O)(c1cc(F)cc(Cl)c1)c1cc(Cl)c2oc3c(c2c1)CNCC3 ; Cl] | 400 | 1H NMR (DMSO-d6, 300 MHz) δ 9.50 (br s, 2 H), 8.48 (d, J = 1.5 Hz, 1 H), 8.18 (d, J = 1.5 Hz, 1 H), 8.03-7.94 (m, 2 H), 7.88-7.82 (m, 1 H), 4.39 (s, 2 H), 3.53 (s, 2 H), 3.16 (s, 2 H). |
| 126 | 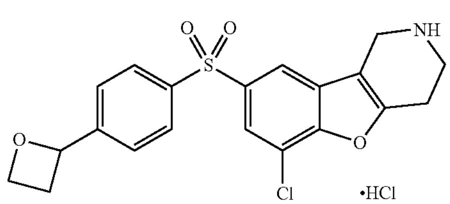 [SMILES: O=S(=O)(c1ccc(C2CCO2)cc1)c1cc(Cl)c2oc3c(c2c1)CNCC3 ; Cl] | 404 | 1H NMR (CD3OD, 300 MHz) δ 8.24-8.18 (m, 1 H), 8.05-7.95 (m, 3 H), 7.68-7.60 (m, 2 H), 5.23-5.14 (m, 1 H), 4.47 (s, 2 H), 3.76-3.63 (m, 3 H), 3.60-3.49 (m, 1 H), 3.27-3.14 (m, 2 H), 2.31-2.08 (m, 2 H). |

TABLE 1-continued

| Ex. No. | Structure | Mass Spec [M + H]⁺ | ¹H NMR Data |
|---|---|---|---|
| 127 | 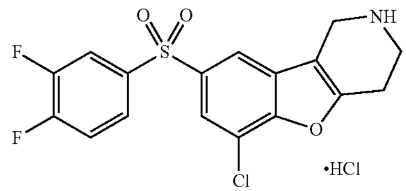 [SMILES: O=S(=O)(c1ccc(F)c(F)c1)c1cc(Cl)c2oc3c(c2c1)CNCC3 ; Cl] | 384 | ¹H NMR (CD₃OD, 300 MHz) δ 8.26 (s, 1 H), 8.11-7.82 (m, 3 H), 7.59-7.44 (m, 1 H), 4.49 (s, 2 H), 3.70 (s, 2 H), 3.26-3.18 (m, 2 H). |
| 128 | 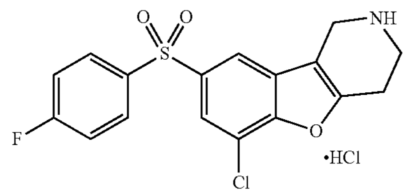 [SMILES: O=S(=O)(c1ccc(F)cc1)c1cc(Cl)c2oc3c(c2c1)CNCC3 ; Cl] | 366 | ¹H NMR (DMSO-d₆, 300 MHz) δ 9.64-9.42 (m, 2 H), 8.41 (d, J = 1.8 Hz, 1 H), 8.16-8.07 (m, 2 H), 8.05 (d, J = 1.5 Hz, 1 H), 7.54-7.42 (m, 2 H), 4.39 (s, 2 H), 3.53 (t, J = 6.0 Hz, 2 H), 3.21-3.11 (m, 2 H). |
| 129 | 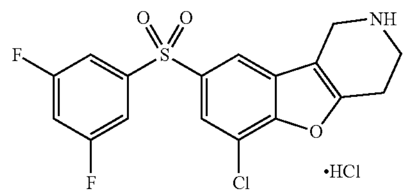 [SMILES: O=S(=O)(c1cc(F)cc(F)c1)c1cc(Cl)c2oc3c(c2c1)CNCC3 ; Cl] | 384 | ¹H NMR (DMSO-d₆, 400 MHz) δ 9.61 (br s, 2 H), 8.48 (s, 1 H), 8.16 (s, 1 H), 7.88-7.78 (m, 2 H), 7.68 (t, J = 9.2 Hz, 1 H), 4.39 (s, 2 H), 3.6-3.42 (m, 2 H), 3.23-3.10 (m, 2 H). |
| 130 | 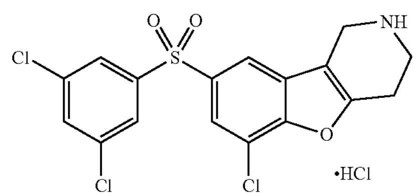 [SMILES: O=S(=O)(c1cc(Cl)cc(Cl)c1)c1cc(Cl)c2oc3c(c2c1)CNCC3 ; Cl] | 416 | ¹H NMR (DMSO-d₆, 400 MHz) δ 9.50 (br s, 2 H), 8.50 (d, J = 1.6 Hz, 1 H), 8.21 (d, J = 1.6 Hz, 1 H), 8.10 (d, J = 1.6 Hz, 2 H), 8.04-7.97 (m, 1 H), 4.40 (s, 2 H), 3.54 (t, J = 6.0 Hz, 2 H), 3.21-3.13 (m, 2 H). |
| 131 | 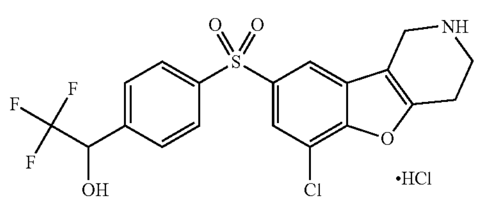 [SMILES: O=S(=O)(c1ccc(C(O)C(F)(F)F)cc1)c1cc(Cl)c2oc3c(c2c1)CNCC3 ; Cl] | 446 | ¹H NMR (DMSO-d₆, 400 MHz) δ 9.61 (br s, 2 H), 8.42 (d, J = 1.6 Hz, 1 H), 8.12-8.02 (m, 3 H), 7.74 (d, J = 8.4 Hz, 2 H), 7.10 (d, J = 6.0 Hz, 1 H), 5.40-5.28 (m, 1 H), 4.39 (s, 2 H), 3.56-3.47 (m, 2 H), 3.22-3.13 (m, 2 H). |
| 132 | 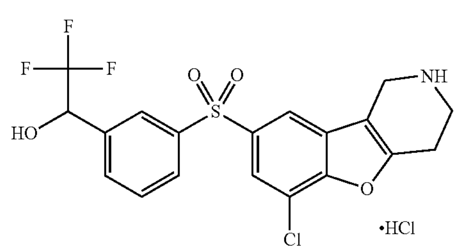 [SMILES: O=S(=O)(c1cccc(C(O)C(F)(F)F)c1)c1cc(Cl)c2oc3c(c2c1)CNCC3 ; Cl] | 446 | ¹H NMR (DMSO-d₆, 400 MHz) δ 9.41 (br s, 2 H), 8.42 (d, J = 2.0 Hz, 1 H), 8.15 (s, 1 H), 8.09-8.05 (m, 1 H), 8.02 (d, J = 1.6 Hz, 1 H), 7.81 (d, J = 8.0 Hz, 1 H), 7.69 (t, J = 8.0 Hz, 1 H), 7.12 (d, J = 5.6 Hz, 1 H), 5.44-5.30 (m, 1 H), 4.40 (s, 2 H), 3.60-3.50 (m, 2 H), 3.20-3.10 (m, 2 H). |
| 133 | 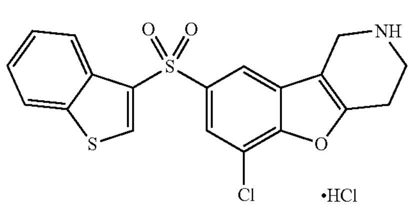 [SMILES: O=S(=O)(c1cc(Cl)c2oc3c(c2c1)CNCC3)c1csc2ccccc12 ; Cl] | 404 | ¹H NMR (DMSO-d₆, 400 MHz) δ 9.58 (br s, 2 H), 8.94 (s, 1 H), 8.56 (d, J = 1.6 Hz, 1 H), 8.23-8.10 (m, 2 H), 8.07 (d, J = 1.6 Hz, 1 H), 7.57-7.44 (m, 2 H), 4.41 (s, 2 H), 3.53 (t, J = 6.0 Hz, 2 H), 3.20-3.10 (m, 2 H). |

TABLE 1-continued

| Ex. No. | Structure | Mass Spec [M + H]+ | 1H NMR Data |
|---|---|---|---|
| 134 | 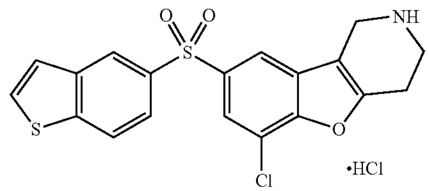 [SMILES: O=S(=O)(c1ccc2sccc2c1)c1cc(Cl)c2oc3c(c2c1)CNCC3 ; Cl] | 404 | 1H NMR (DMSO-d6, 400 MHz) δ 9.54 (br s, 2 H), 8.62 (d, J = 1.6 Hz, 1 H), 8.43 (d, J = 1.6 Hz, 1 H), 8.27 (d, J = 8.4 Hz, 1 H), 8.06 (d, J = 1.6 Hz, 1 H), 8.01 (d, J = 5.6 Hz, 1 H), 7.91 (dd, J = 8.8, 2.0 Hz, 1 H), 7.67 (d, J = 5.6 Hz, 1 H), 4.39 (s, 2 H), 3.52 (t, J = 6.0 Hz, 2 H), 3.20-3.10 (m, 2 H). |
| 135 | 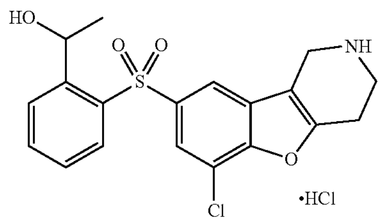 [SMILES: CC(O)c1ccccc1S(=O)(=O)c1cc(Cl)c2oc3c(c2c1)CNCC3 ; Cl] | 392 | 1H NMR (CD3OD, 300 MHz) δ 8.11 (d, J = 7.2 Hz, 2 H), 7.78 (d, J = 7.2 Hz, 2 H), 7.69 (t, J = 7.2 Hz, 1 H), 7.51 (t, J = 7.2 Hz, 1 H), 5.56 (q, J = 6.3 Hz, 1 H), 4.39 (s, 2 H), 3.61 (t, J = 6.0 Hz, 2 H), 3.22-3.11 (m, 2 H), 1.22 (d, J = 6.3 Hz, 3 H). |
| 136 | 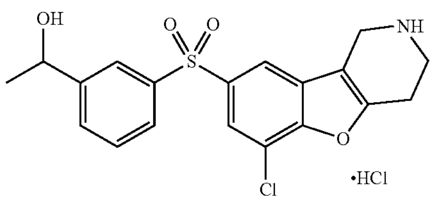 [SMILES: CC(O)c1cccc(S(=O)(=O)c2cc(Cl)c3oc4c(c3c2)CNCC4)c1 ; Cl] | 392 | 1H NMR (CD3OD, 400 MHz) δ 8.23 (s, 1 H), 8.02 (s, 1 H), 7.95 (s, 1 H), 7.89 (d, J = 8.0 Hz, 1 H), 7.64 (d, J = 7.6 Hz, 1 H), 7.54 (t, J = 7.6 Hz, 1 H), 4.96-4.85 (m, 1 H), 4.49 (s, 2 H), 3.76-3.66 (m, 2 H), 3.28-3.19 (m, 2 H), 1.42 (d, J = 6.4 Hz, 3 H). |
| 137 | 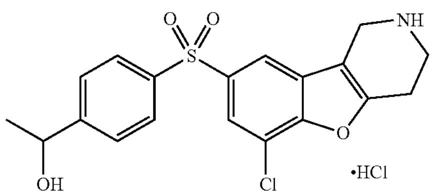 [SMILES: CC(O)c1ccc(S(=O)(=O)c2cc(Cl)c3oc4c(c3c2)CNCC4)cc1 ; Cl] | 392 | 1H NMR (CD3OD, 400 MHz) δ 8.22 (d, J = 1.6 Hz, 1 H), 7.99-7.94 (m, 3 H), 7.59 (d, J = 8.4 Hz, 2 H), 4.92-4.83 (m, 1 H), 4.48 (s, 2 H), 3.69 (t, J = 6.4 Hz, 2 H), 3.23 (t, J = 6.0 Hz, 2 H), 1.40 (d, J = 6.8 Hz, 3 H). |
| 138 | [α]20D -10° | 392 | 1H NMR (DMSO-d6, 400 MHz) 9.85-9.73 (m, 2 H), 8.42 (d, J = 1.6 Hz, 1 H), 8.00 (d, J = 1.6 Hz, 1 H), 7.99 (s, 1 H), 7.89 (d, J = 7.6 Hz, 1 H), 7.65 (d, J = 8.0 Hz, 1 H), 7.57 (t, J = 7.6 Hz, 1 H), 4.81 (q, J = 6.4, 1 H), 4.39 (s, 2 H), 3.60-3.43 (m, 2 H), 3.22-3.11 (m, 2 H), 1.32 (d, J = 6.4, 3 H). |
| 139 | [α]20D +10° | 392 | 1H NMR (DMSO-d6, 400 MHz) 9.75-9.65 (m, 2 H), 8.42 (d, J = 1.2 Hz, 1 H), 8.0 (d, J = 6.6 Hz, 2 H), 7.89 (d, J = 7.2 Hz, 1 H), 7.65 (d, J = 7.6 Hz, 1 H), 7.57 (t, J = 7.6 Hz, 1 H), 4.87-4.50 (m, 1 H), 4.40 (s, 2 H), 3.58-3.48 (m, 2 H), 3.21-3.13 (m, 2 H), 1.32 (d, J = 6.4 Hz, 3 H). |
| 140 | [α]20D -14° | 392 | 1H NMR (DMSO-d6, 400 MHz) 9.62-9.50 (m, 2 H), 8.40 (d, J = 1.2 Hz, 1 H), 8.01 (d, J = 1.2 Hz, 1 H), 7.97 (d, J = 8.0 Hz, 2 H), 7.58 (d, J = 8.4 Hz, 2 H), 5.38 (d, J = 4.0 Hz, 1 H), 4.84-4.73 (m, 1 H), 4.39 (s, 2 H), 3.53 (t, J = 5.6 Hz, 2 H), 3.22-3.10 (m, 2 H), 1.29 (d, J = 6.4 Hz, 3 H). |

TABLE 1-continued

| Ex. No. | Structure | Mass Spec [M + H]+ | 1H NMR Data |
|---|---|---|---|
| 141 | 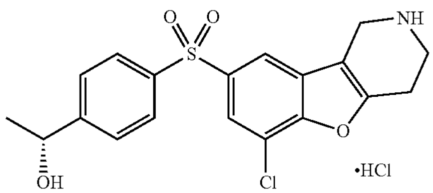 | 392 | 1H NMR (CD3OD, 400 MHz) 8.22 (d, J = 1.6 Hz, 1 H), 7.99-7.94 (m, 3 H), 7.59 (d, J = 8.0 Hz, 2 H), 4.88 (q, J = 6.4 Hz, 1 H), 4.47 (t, J = 1.6 Hz, 2 H), 3.69 (t, J = 6.4 Hz, 2 H), 3.23 (t, J = 6.0 Hz, 2 H), 1.40 (d, J = 6.4 Hz, 3 H). |
| 142 | 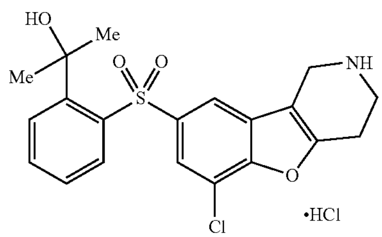 [SMILES: CC(C)(O)c1ccccc1S(=O)(=O)c1cc(Cl)c2oc3c(c2c1)CNCC3 ; Cl] | 406 | 1H NMR (CD3OD, 400 MHz) 8.38 (d, J = 7.4 Hz, 1 H), 7.95 (d, J = 1.6 Hz, 1 H), 7.73 (d, J = 1.6 Hz, 1 H), 7.70-7.58 (m, 2 H), 7.52 (t, J = 7.6 Hz, 1 H), 4.28 (s, 2 H), 3.54 (t, J = 6.0 Hz, 2 H), 3.17-3.08 (m, 2 H), 1.63 (s, 6 H). |
| 143 | 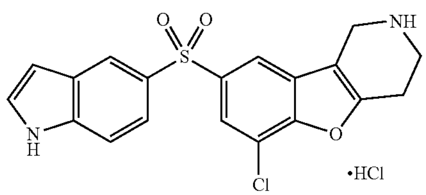 [SMILES: O=S(=O)(c1ccc2[nH]ccc2c1)c1cc(Cl)c2oc3c(c2c1)CNCC3 ; Cl] | 387 | 1H NMR (DMSO-d6, 400 MHz) δ 11.71 (s, 1 H), 9.47 (br s, 2 H), 8.37 (s, 1 H), 8.30 (s, 1 H), 7.96 (s, 1 H), 7.69-7.53 (m, 3 H), 6.66 (s, 1 H), 4.38 (s, 2 H), 3.51 (t, J = 6.0 Hz, 2 H), 3.14 (t, J = 6.0 Hz, 2 H). |
| 144 | 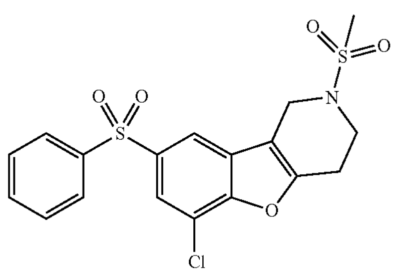 [SMILES: CS(=O)(=O)N1CCc2oc3c(Cl)cc(S(=O)(=O)c4ccccc4)cc3c2C1] | 426 | 1H NMR (CDCl3, 300 MHz) δ 7.98-7.96 (m, 1 H), 7.95 (d, J = 2.4 Hz, 1 H), 7.89 (d, J = 2.4 Hz, 1 H), 7.62-7.49 (m, 3 H), 4.51 (s, 2 H), 3.76 (t, J = 6.0 Hz, 2 H), 3.05 (t, J = 6.0 Hz, 2 H), 2.92 (s, 3 H). |
| 145 | 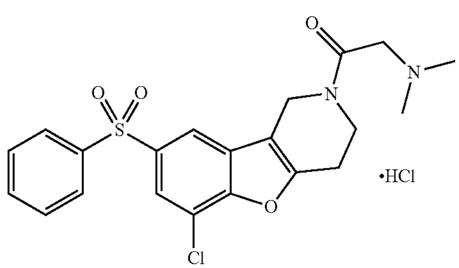 [SMILES: CN(C)CC(=O)N1CCc2oc3c(Cl)cc(S(=O)(=O)c4ccccc4)cc3c2C1 ; Cl] | 433 | 1H NMR (DMSO-d6, 300 MHz) δ 9.70 (br s, 1 H), 8.43-8.28 (m, 1 H), 8.10-8.01 (m, 3 H), 7.73-7.58 (m, 3 H), 4.79-4.67 (m, 2 H), 4.32-4.30 (m, 2 H), 4.00-3.72 (m, 2 H), 3.10-2.90 (m, 2 H), 2.81 (s, 6 H). |
| 146 | 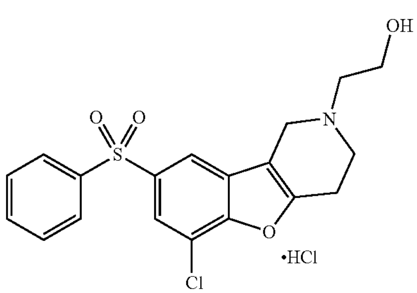 [SMILES: O=S(=O)(c1ccccc1)c1cc(Cl)c2oc3c(c2c1)CN(CCO)CC3 ; Cl] | 392 | 1H NMR (DMSO-d6, 400 MHz) δ 10.82 (br s, 1 H), 8.39 (s, 2 H), 7.76-7.50 (m, 5 H), 5.41 (br s, 2 H), 4.71 (br s, 2 H), 4.45 (br s, 2 H), 3.86 (br s, 2 H), 3.60 (br s, 2 H), 2.55, br s, 1 H). |

TABLE 1-continued
| Ex. No. | Structure | Mass Spec [M + H]+ | 1H NMR Data |
|---|---|---|---|
| 147 | 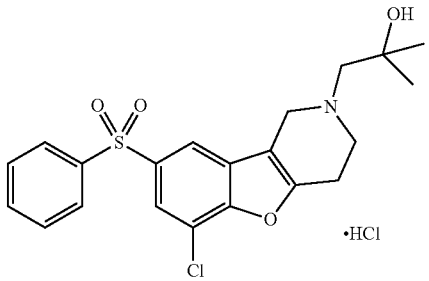 [SMILES: CC(C)(O)CN1CCc2oc3c(Cl)cc(S(=O)(=O)c4ccccc4)cc3c2C1 ; Cl] | 420 | 1H NMR (DMSO-d6, 400 MHz) δ 10.50 (br s, 1 H), 8.39 (s, 1 H), 8.08-7.99 (m, 3 H), 7.75-7.58 (m, 3 H), 5.39 (br s, 1 H), 4.75-4.50 (m, 2 H), 3.83-3.60 (m, 2 H), 3.30 (br s, 2 H), 3.17 (br s, 2 H), 1.30 (s, 6 H). |
| 148 | 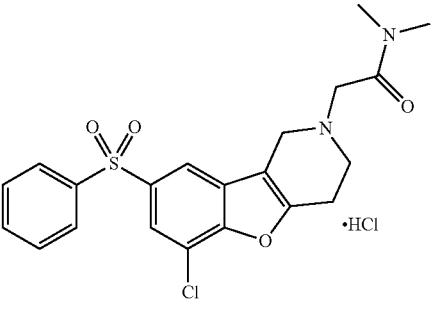 [SMILES: CN(C)C(=O)CN1CCc2oc3c(Cl)cc(S(=O)(=O)c4ccccc4)cc3c2C1 ; Cl] | 433 | 1H NMR (DMSO-d6, 400 MHz) δ 10.55 (br s, 1 H), 8.41 (s, 1 H), 8.06-7.95 (m, 3 H), 7.71-7.57 (m, 3 H), 4.72-4.43 (m, 2 H), 4.38 (s, 2 H), 3.69 (br s, 2 H), 3.29 (br s, 2 H), 2.93 (s, 3 H), 2.91 (s, 3 H). |
| 149 | 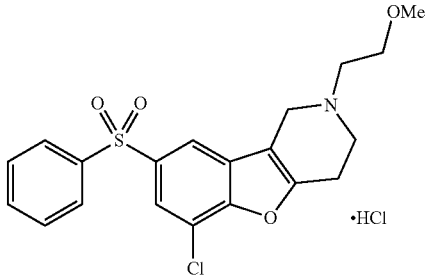 [SMILES: COCCN1CCc2oc3c(Cl)cc(S(=O)(=O)c4ccccc4)cc3c2C1 ; Cl] | 406 | 1H NMR (DMSO-d6, 400 MHz) δ 10.57 (br s, 1 H), 8.36 (s, 1 H), 8.10-7.98 (m, 3 H), 7.72-7.58 (m, 3 H), 4.51 (br s, 2 H), 3.96-3.62 (m, 4 H), 3.47 (br s, 2 H), 3.36 (s, 3 H), 3.26 (br s, 2 H). |
| 150 | 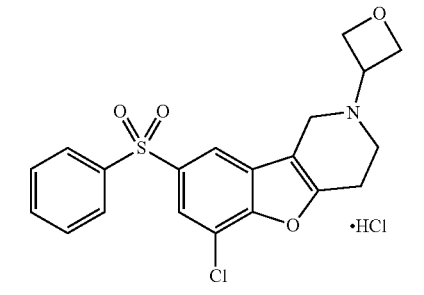 [SMILES: O=S(=O)(c1ccccc1)c1cc(Cl)c2oc3c(c2c1)CN(C1COC1)CC3 ; Cl] | 404 | 1H NMR (DMSO-d6, 400 MHz) δ 12.53 (br s, 1 H), 8.13 (s, 1 H), 8.07-8.00 (m, 3 H), 7.74-7.58 (m, 3 H), 4.90 (br s, 2 H), 4.75 (br s, 2 H), 4.68-4.40 (m, 2 H), 4.21-4.25 (m, 1 H), 4.00-3.81 (m, 2 H), 3.24 (br s, 2 H). |
| 151 | 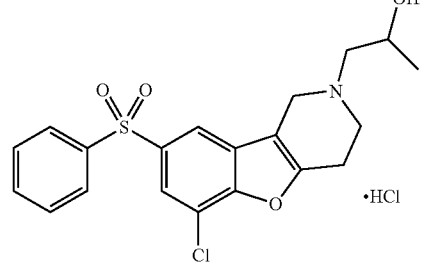 | 406 | 1H NMR (DMSO-d6, 400 MHz) δ 10.72 (br s, 1 H), 8.39 (br s, 1 H), 8.07-7.97 (m, 3 H), 7.70-7.57 (m, 3 H), 5.52 (s, 1 H), 4.81-4.60 (m, 1 H), 4.46 (br s, 1 H), 4.24 (br s, 1 H), 3.90-3.71 (m, 2 H), 3.17-3.09 (m, 4 H), 1.15 (d, J = 6.0 Hz, 3 H). |

| Ex. No. | Structure | Mass Spec [M + H]+ | 1H NMR Data |
|---|---|---|---|
| 152 | 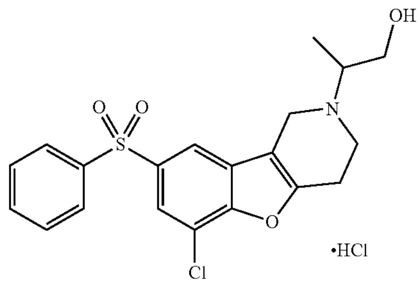 [SMILES: CC(CO)N1CCc2oc3c(Cl)cc(S(=O)(=O)c4ccccc4)cc3c2C1 ; Cl] | 406 | 1H NMR (DMSO-d6, 400 MHz) δ 10.77 (br s, 1 H), 8.40 (s, 1 H), 8.05-7.98 (m, 3 H), 7.72-7.57 (m, 3 H), 5.62-5.49 (m, 1 H), 4.63 (br s, 2 H), 3.88-3.76 (m, 3 H), 3.64 (br s, 2 H), 3.20 (brs, 2 H), 1.48-1.36 (m, 3 H). |
| 153 | 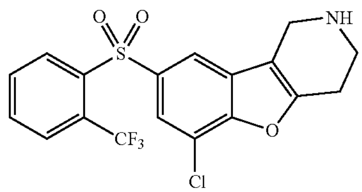 [SMILES: O=S(=O)(c1cc(Cl)c2oc3c(c2c1)CNCC3)c1ccccc1C(F)(F)F] | 416 | 1H NMR (CD3OD, 400 MHz) δ 8.51 (d, J = 7.6 Hz, 1 H), 8.06 (s, 1 H), 7.98-7.81 (m, 3 H), 7.76 (s, 1 H), 4.16 (s, 2 H), 3.41 (t, J = 5.8 Hz, 2 H), 3.03 (t, J = 5.8 Hz, 2 H). |
| 154 | 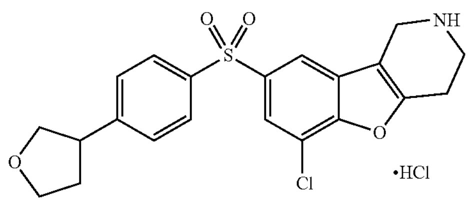 [SMILES: O=S(=O)(c1ccc(C2CCOC2)cc1)c1cc(Cl)c2oc3c(c2c1)CNCC3 ; Cl] | 418 | 1H NMR (DMSO-d6, 300 MHz) 9.71-9.55 (m, 2 H), 8.40 (d, J = 1.2 Hz, 1 H), 8.01 (d, J = 1.2 Hz, 1 H), 7.96 (d, J = 8.4 Hz, 2 H), 7.53 (d, J = 8.1 Hz, 2 H), 4.39 (s, 2 H), 4.06-3.87 (m, 2 H), 3.78 (q, J = 7.8 Hz, 1 H), 3.61-3.40 (m, 4 H), 3.22-3.10 (m, 2 H), 2.39-2.22 (m, 1 H), 1.97-1.80 (m, 1 H). |
| 155 | 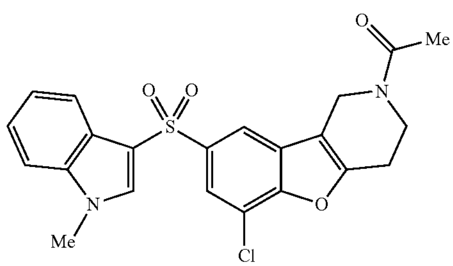 [SMILES: CC(=O)N1CCc2oc3c(Cl)cc(S(=O)(=O)c4cn(C)c5ccccc45)cc3c2C1] | 443 | 1H NMR (DMSO-d6, 400 MHz) δ 8.32 (d, J = 1.6 Hz, 1 H), 8.28 (s, 1 H), 7.94-7.81 (m, 2 H), 7.61-7.54 (m, 1 H), 7.35-7.22 (m, 2 H), 4.73 (s, 0.9 H), 4.66 (s, 1.1 H), 3.93-3.76 (m, 5 H), 3.02-2.93 (m, 1.1 H), 2.90-2.80 (m, 0.9 H), 2.13 (s, 3 H). |
| 156 | 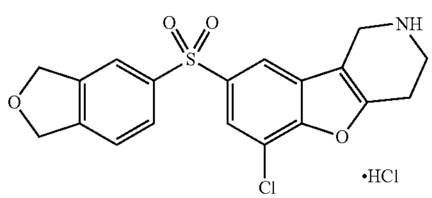 [SMILES: O=S(=O)(c1ccc2c(c1)COC2)c1cc(Cl)c2oc3c(c2c1)CNCC3 ; Cl] | 390 | 1H NMR (DMSO-d6, 400 MHz) δ 9.31 (br s, 2 H), 8.39 (d, J = 1.6 Hz, 1 H), 8.01 (d, J = 2.0 Hz, 1 H), 7.99-7.90 (m, 2 H), 7.55 (d, J = 8.0 Hz, 1 H), 5.03 (s, 4 H), 4.38 (s, 2 H), 3.52 (t, J = 6.0 Hz, 2 H), 3.14 (t, J = 6.0 Hz, 2 H). |
| 157 | 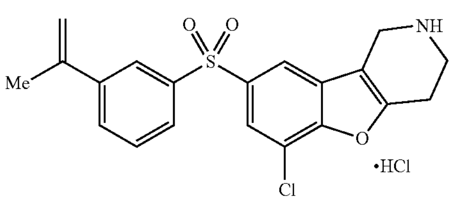 [SMILES: C=C(C)c1cccc(S(=O)(=O)c2cc(Cl)c3oc4c(c3c2)CNCC4)c1 ; Cl] | 388 | 1H NMR (DMSO-d6, 400 MHz) δ 9.23 (br s, 2 H), 8.45 (d, J = 1.6 Hz, 1 H), 8.10 (d, J = 1.6 Hz, 1 H), 8.06 (t, J = 1.6 Hz, 1 H), 7.97-7.91 (m, 1 H), 7.85-7.78 (m, 1 H), 7.61 (t, J = 6.0 Hz, 1 H), 5.56 (s, 1 H), 5.25 (t, J = 1.2 Hz, 1 H), 4.38 (s, 2 H), 3.52 (t, J = 2.0 Hz, 2 H), 3.14 (t, J = 1.6 Hz, 2 H), 2.14 (d, J = 0.4 Hz, 3 H). |
| 158 | 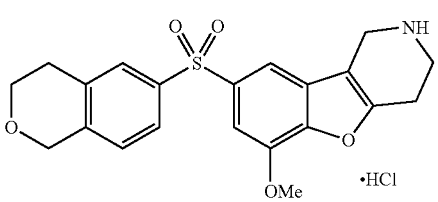 [SMILES: COc1cc(S(=O)(=O)c2ccc3c(c2)CCOC3)cc2c3c(oc12)CCNC3 ; Cl] | 400 | 1H NMR (DMSO-d6, 400 MHz) δ 9.36-9.25 (m, 2 H), 7.96 (d, J = 1.6 Hz, 1 H), 7.81-7.74 (m, 2 H), 7.43 (d, J = 1.6 Hz, 1 H), 7.26 (d, J = 8.0 Hz, 1 H), 4.71 (s, 2 H), 4.36 (s, 2 H), 4.02 (s, 3 H), 3.86 (t, J = 5.6 Hz, 2 H), 3.51 (t, J = 5.6 Hz, 2 H), 3.13-3.05 (m, 2 H), 2.86 (t, J = 5.6 Hz, 2 H). |

TABLE 1-continued

| Ex. No. | Structure | Mass Spec [M + H]+ | 1H NMR Data |
|---|---|---|---|
| 159 | 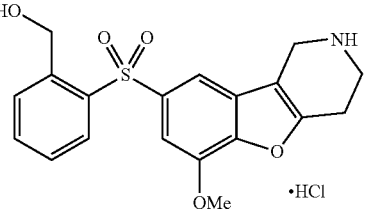 | 374 | 1H NMR (DMSO-d6, 400 MHz) δ 9.50-9.48 (m, 2 H), 8.06 (dd, J = 8.0, 1.2 Hz, 1 H), 7.91 (d, J = 1.6 Hz, 1 H), 7.80-7.76 (m, 1 H), 7.74-7.69 (m, 1 H), 7.57-7.52 (m, 1 H), 7.33 (d, J = 1.6 Hz, 1 H), 5.39 (t, J = 5.6 Hz, 1 H), 4.74 (d, J = 13.6 Hz, 2 H), 4.36 (s, 2 H), 3.98 (s, 3 H), 3.52 (t, J = 6.4 Hz, 2 H), 3.14-3.07 (m, 2 H). |
| 160 | 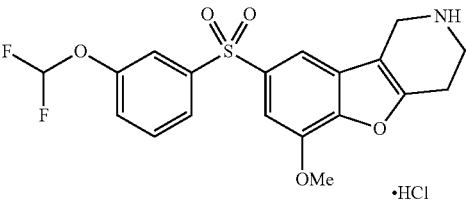 [SMILES: COc1cc(S(=O)(=O)c2cccc(OC(F)F)c2)cc2c3c(oc12)CCNC3 ; Cl] | 410 | 1H NMR (CD3OD, 300 MHz) δ 7.89-7.83 (m, 2 H), 7.75 (br s, 1 H), 7.61 (t, J = 8.1 Hz, 1 H), 7.48-7.37 (m, 2 H), 6.93 (t, J = 73.2 Hz, 1 H), 4.46 (s, 2 H), 4.05 (s, 3 H), 3.68 (t, J = 6.0 Hz, 2 H), 3.19 (t, J = 6.0 Hz, 2 H). |
| 161 | 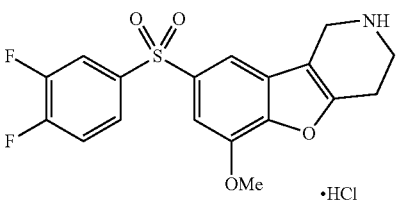 [SMILES: COc1cc(S(=O)(=O)c2ccc(F)c(F)c2)cc2c3c(oc12)CCNC3 ; Cl] | 380 | 1H NMR (CD3OD, 300 MHz) δ 8.03-7.93 (m, 1 H), 7.91-7.82 (m, 2 H), 7.54-7.42 (m, 2 H), 4.46 (s, 2 H), 3.69 (t, J = 6.0 Hz, 2 H), 3.31 (s, 3 H), 3.20 (t, J = 6.0 Hz, 2 H). |
| 162 | 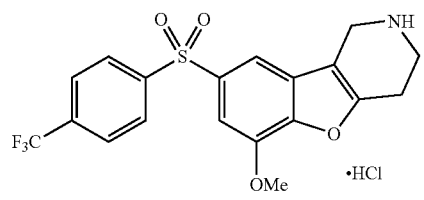 [SMILES: COc1cc(S(=O)(=O)c2ccc(C(F)(F)F)cc2)cc2c3c(oc12)CCNC3 ; Cl] | 412 | 1H NMR (DMSO-d6, 300 MHz) δ 9.40 (br s, 2 H), 8.22 (d, J = 8.1 Hz, 2 H), 8.04 (d, J = 1.5 Hz, 1 H), 8.00 (d, J = 8.4 Hz, 2 H), 7.50 (d, J = 1.5 Hz, 1 H), 4.36 (s, 2 H), 4.04 (s, 3 H), 3.52 (t, J = 5.7 Hz, 2 H), 3.05-3.15 (m, 2 H). |
| 163 | 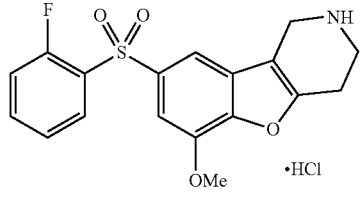 [SMILES: COc1cc(S(=O)(=O)c2ccccc2F)cc2c3c(oc12)CCNC3 ; Cl] | 362 | 1H NMR (DMSO-d6, 300 MHz) δ 9.46 (br s, 2 H), 8.12-8.02 (m, 1 H), 7.97 (s, 1 H), 7.83-7.72 (m, 1 H), 7.50 (t, J = 6.0 Hz, 1 H), 7.45-7.34 (m, 2 H), 4.37 (s, 2 H), 4.00 (s, 3 H), 3.58-3.49 (m, 2 H), 3.18-3.06 (m, 2 H). |
| 164 | 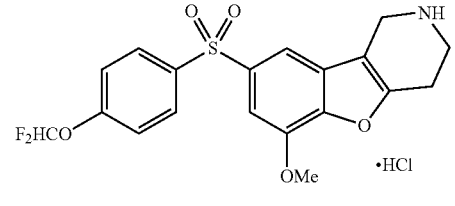 [SMILES: COc1cc(S(=O)(=O)c2ccc(OC(F)F)cc2)cc2c3c(oc12)CCNC3 ; Cl] | 410 | 1H NMR (DMSO-d6, 300 MHz) δ 9.52 (br s, 2 H), 8.12-8.04 (m, 2 H), 7.98 (d, J = 1.8 Hz, 1 H), 7.66-7.10 (m, 4 H), 4.36 (br s, 2 H), 4.03 (s, 3 H), 3.56-3.46 (m, 2 H), 3.15-3.05 (m, 2 H). |
| 165 | 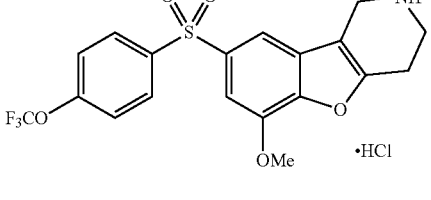 | 428 | 1H NMR (DMSO-d6, 300 MHz) δ 9.55 (br s, 2 H), 8.17 (d, J = 8.7 Hz, 2 H), 8.02 (s, 1 H), 7.62 (d, J = 8.4 Hz, 2 H), 7.48 (d, J = 1.5 Hz, 1 H), 4.36 (s, 2 H), 4.04 (s, 3 H), 3.52 (t, J = 6.0 Hz, 2 H), 3.11 (s, 2 H). |

TABLE 1-continued

| Ex. No. | Structure | Mass Spec [M + H]+ | 1H NMR Data |
|---|---|---|---|
| 166 | 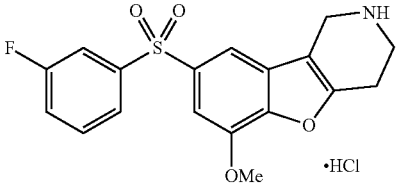 [SMILES: COc1cc(S(=O)(=O)c2cccc(F)c2)cc2c3c(oc12)CCNC3 ; Cl] | 362 | 1H NMR (DMSO-d6, 400 MHz) δ 9.14 (br s, 2 H), 8.02 (d, J = 1.6 Hz, 1 H), 7.90-7.85 (m, 2 H), 7.70-7.65 (m, 1 H), 7.57-7.53 (m, 1 H), 7.49 (d, J = 1.6 Hz, 1 H), 4.34 (s, 2 H), 4.03 (s, 3 H), 3.50 (s, 2 H), 3.07 (s, 2 H). |
| 167 | 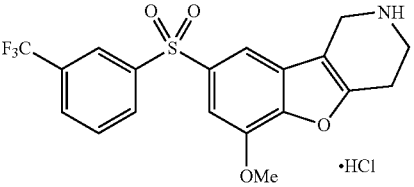 [SMILES: COc1cc(S(=O)(=O)c2cccc(C(F)(F)F)c2)cc2c3c(oc12)CCNC3 ; Cl] | 412 | 1H NMR (DMSO-d6, 300 MHz) δ 9.73 (br s, 2 H), 8.36-8.31 (m, 2 H), 8.09-8.07 (m, 2 H), 7.87 (t, J = 7.7 Hz, 1 H), 7.55 (s, 1 H), 4.36 (s, 2 H), 4.04 (s, 3 H), 3.53 (s, 2 H), 3.11 (s, 2 H). |
| 168 | 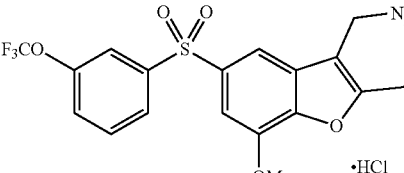 | 428 | 1H NMR (DMSO-d6, 300 MHz) δ 9.31 (br s, 2 H), 8.05-8.01 (m, 3 H), 7.80-7.70 (m, 2 H), 7.52 (d, J = 1.5 Hz, 1 H), 4.37 (s, 2 H), 4.03 (s, 3 H), 3.54 (s, 2 H), 3.10 (s, 2 H). |
| 169 | 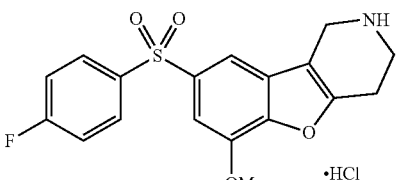 | 362 | 1H NMR (DMSO-d6, 300 MHz) δ 9.35 (br s, 2 H), 8.11-8.06 (m, 2 H), 7.98 (d, J = 0.9 Hz, 1 H), 7.48-7.42 (m, 3 H), 4.35 (br s, 2 H), 4.02 (s, 3 H), 3.51 (m, 2 H), 3.09 (s, 2 H). |
| 170 | 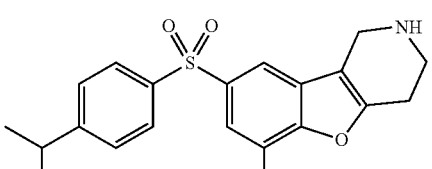 | 388 | 1H NMR (DMSO-d6, 300 MHz) 9.68-9.55 (m, 2 H), 8.02-7.89 (m, 3 H), 7.56 (d, J = 8.1 Hz, 2 H), 7.44 (s, 1 H), 5.37 (d, J = 3.6 Hz, 1 H), 4.84-4.70 (m, 1 H), 4.35 (s, 2 H), 4.02 (s, 3 H), 3.59-3.44 (m, 2 H), 3.15-3.02 (m, 2 H), 1.30 (d, J = 6.6 Hz, 3 H). |
| 171 | 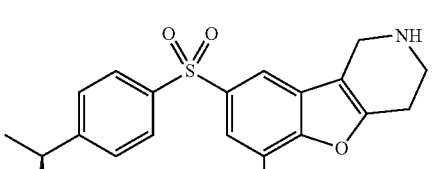 [α]20D -12° | 388 | 1H NMR (CD3OD, 300 MHz) 7.96 (d, J = 8.4 Hz, 2 H), 7.84 (d, J = 1.2 Hz, 1 H), 7.57 (d, J = 8.1 Hz, 2 H), 7.44 (d, J = 1.2 Hz, 1 H), 4.94-4.75 (m, 1 H), 4.44 (s, 2 H), 4.03 (s, 3 H), 3.67 (t, J = 6.3 Hz, 2 H), 3.18 (t, J = 6.0 Hz, 2 H), 1.40 (d, J = 6.6 Hz, 3 H). |
| 172 | 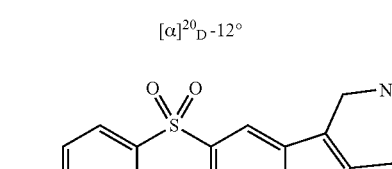 [α]20D +12° | 388 | 1H NMR (DMSO-d6, 300 MHz) 9.52-9.40 (m, 2 H), 8.00-7.90 (m, 3 H), 7.56 (d, J = 8.4 Hz, 2 H), 7.44 (d, J = 1.2 Hz, 1 H), 5.36 (d, J = 4.2 Hz, 1 H), 4.83-4.71 (m, 1 H), 4.36 (s, 2 H), 4.02 (s, 3 H), 3.51 (t, J = 6.0 Hz, 2 H), 3.16-3.04 (m, 2 H), 1.30 (d, J = 6.6 Hz, 3 H). |

TABLE 1-continued

| Ex. No. | Structure | Mass Spec [M + H]+ | 1H NMR Data |
|---|---|---|---|
| 173 | 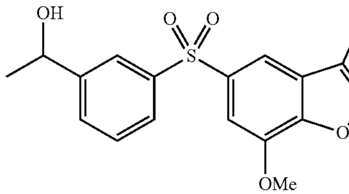 | 388 | 1H NMR (CD3OD, 400 MHz) 8.02 (t, J = 1.6 Hz, 1 H), 7.90-7.85 (m, 2 H), 7.61 (d, J = 7.6 Hz, 1 H), 7.52 (t, J = 7.6 Hz, 1 H), 7.44 (d, J = 1.6 Hz, 1 H), 4.89 (q, J = 6.4 Hz, 1 H), 4.45 (s, 2 H), 4.03 (s, 3 H), 3.68 (t, J = 6.4 Hz, 2 H), 3.20-3.18 (t, J = 6.0 Hz, 2 H), 1.42 (d, J = 6.4, 3 H). |
| 174 | [a]20D +8.8° | 388 | 1H NMR (DMSO-d6, 300 MHz) δ 9.46 (br s, 2 H), 7.98 (d, J = 1.5 Hz, 2 H), 7.86 (d, J = 7.8 Hz, 1 H), 7.63-7.52 (m, 2 H), 7.44 (d, J = 1.5 Hz, 1 H), 5.39 (d, J = 4.2 Hz, 1 H), 4.84-4.76 (m, 1 H), 4.36 (s, 2 H), 4.02 (s, 3 H), 3.51 (t, J = 6.0 Hz, 2 H), 3.09 (m, 2 H), 1.32 (d, J = 6.6 Hz, 3 H). |
| 175 | [α]20D -8.0° | 388 | 1H NMR (DMSO-d6, 300 MHz) δ 9.30 (br s, 2 H), 7.97-7.95 (m, 2 H), 7.85-7.82 (m, 1 H), 7.62 (d, J = 7.8 Hz, 1 H), 7.54 (t, J = 7.5 Hz, 1 H), 7.43 (d, J = 1.5 Hz, 1 H), 5.28 (d, J = 5.2 Hz, 1 H), 4.81-4.79 (m, 1 H), 4.36 (s, 2 H), 4.02 (s, 3 H), 3.52 (t, J = 6.3 Hz, 2 H), 3.09 (t, J = 6.0 Hz, 2 H), 1.32 (d, J = 6.6 Hz, 3 H). |
| 176 | 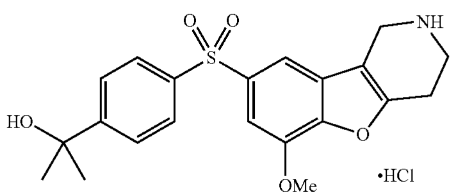 [SMILES: COc1cc(S(=O)(=O)c2ccc(C(C)(C)O)cc2)cc2c3c(oc12)CCNC3 ; Cl] | 402 | 1H NMR (DMSO-d6, 300 MHz) δ 9.50 (br s, 2 H), 7.98-7.92 (m, 3 H), 7.67 (d, J = 8.7 Hz, 2 H), 7.45 (d, J = 1.8 Hz, 1 H), 5.20 (br s, 1 H), 4.36 (s, 2 H), 4.02 (s, 3 H), 3.51 (br s, 2 H), 3.10 (m, 2 H), 1.40 (s, 6 H). |
| 177 | 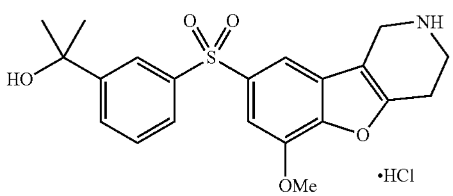 [SMILES: COc1cc(S(=O)(=O)c2cccc(C(C)(C)O)c2)cc2c3c(oc12)CCNC3 ; Cl] | 402 | 1H NMR (DMSO-d6, 400 MHz) δ 9.45 (br s, 2 H), 8.12 (t, J = 1.6 Hz, 1 H), 7.99 (d, J = 1.6 Hz, 1 H), 7.83 (d, J = 7.6 Hz, 1 H), 7.72 (d, J = 8.0 Hz, 1 H), 7.53 (t, J = 7.6 Hz, 1 H), 7.45 (d, J = 1.6 Hz, 1 H), 5.28 (s, 1 H), 4.37 (s, 2 H), 4.02 (s, 3 H), 3.52 (t, J = 5.6 Hz, 2 H), 3.15-3.05 (m, 2 H), 1.43 (s, 6 H). |
| 178 | 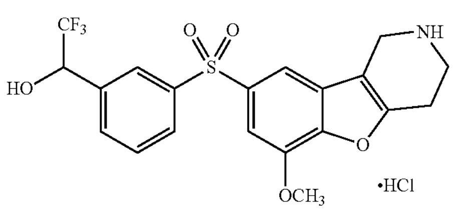 [SMILES: COc1cc(S(=O)(=O)c2cccc(C(O)C(F)(F)F)c2)cc2c3c(oc12)CCNC3 ; Cl] | 442 | 1H NMR (DMSO-d6, 400 MHz) δ 9.40 (br s, 2 H), 8.22 (d, J = 8.1 Hz, 2 H), 8.04 (d, J = 1.5 Hz, 1 H), 8.00 (d, J = 8.4 Hz, 2 H), 7.50 (d, J = 1.5 Hz, 1 H), 7.11 (d, J = 7.0 Hz, 1 H), 5.37 (m, 1 H), 4.36 (s, 2 H), 4.04 (s, 3 H), 3.52 (t, J = 5.7 Hz, 2 H), 3.05-3.15 (m, 2 H). |
| 179 | 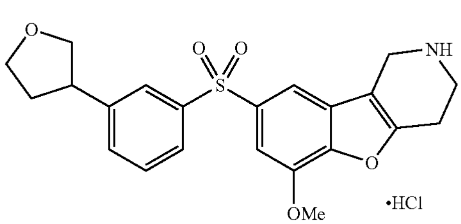 [SMILES: COc1cc(S(=O)(=O)c2cccc(C3CCOC3)c2)cc2c3c(oc12)CCNC3 ; Cl] | 414 | 1H NMR (CD3OD, 400 MHz) 7.89 (t, J = 1.6 Hz, 1 H), 7.86 (d, J = 1.6 Hz, 1 H), 7.83 (t, J = 1.6 Hz, 1 H), 7.59-7.54 (m, 1 H), 7.51 (t, J = 7.6 Hz, 1 H), 7.45 (d, J = 1.2 Hz, 1 H), 4.45 (s, 2 H), 4.11-4.01 (m, 5 H), 3.89 (q, J = 7.6 Hz, 1 H), 3.72-3.64 (m, 3 H), 3.52 (p, J = 7.6 Hz, 1 H), 3.18 (t, J = 6.0 Hz, 2 H), 2.47-2.36 (m, 1 H), 2.02-1.91 (m, 1 H). |

TABLE 1-continued

| Ex. No. | Structure | Mass Spec [M + H]+ | 1H NMR Data |
|---|---|---|---|
| 180 | 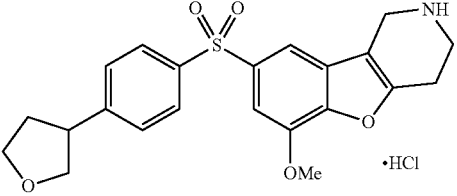 [SMILES: COc1cc(S(=O)(=O)c2ccc(C3CCOC3)cc2)cc2c3c(oc12)CCNC3 ; Cl] | 414 | 1H NMR (CD3OD, 300 MHz) 7.93 (d, J = 8.4 Hz, 2 H), 7.83 (d, J = 1.2 Hz, 1 H), 7.49 (d, J = 8.1 Hz, 2 H), 7.43 (s, 1 H), 4.45 (s, 2 H), 4.12-3.98 (m, 5 H), 3.88 (q, J = 7.5 Hz, 1 H), 3.74-3.62 (m, 3 H), 3.50 (p, J = 7.5 Hz, 1 H), 3.24-3.14 (m, 2 H), 2.47-2.32 (m, 1 H), 2.05-1.89 (m, 1 H). |
| 181 | 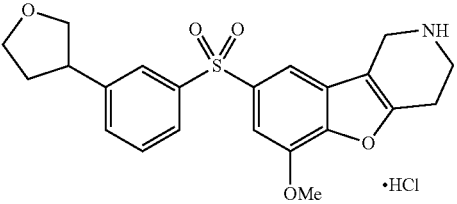 [α]20D -22.4° | 414 | 1H NMR (DMSO-d6, 400 MHz) 9.46-9.36 (br s, 2 H), 7.99 (d, J = 1.6 Hz, 1 H), 7.91-7.89 (m, 1 H), 7.86-7.83 (m, 1 H), 7.61-7.52 (m, 2 H), 7.47 (d, J = 1.6 Hz, 1 H), 4.36 (s, 2 H), 4.04-4.00 (m, 4 H), 3.98-3.92 (m, 1 H), 3.83-3.76 (m, 1 H), 3.59-3.46 (m, 4 H), 3.09 (t, J = 5.6 Hz, 2 H), 2.38-2.28 (m, 1 H), 1.95-1.85 (m, 1 H). |
| 182 | 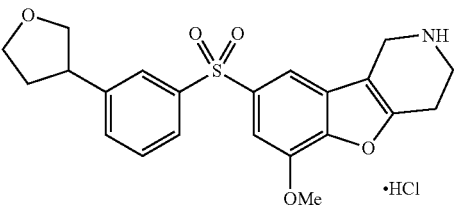 [α]20D +24° | 414 | 1H NMR (DMSO-d6, 400 MHz) δ 9.41-9.34 (br s, 2 H), 7.99 (d, J = 1.6 Hz, 1 H), 7.92-7.89 (m, 1 H), 7.85-7.82 (m, 1 H), 7.61-7.52 (m, 2 H), 7.47 (d, J = 1.6 Hz, 1 H), 4.37 (s, 2 H), 4.05-3.99 (m, 4 H), 3.98-3.92 (m, 1 H), 3.82-3.76 (m, 1 H), 3.59-3.46 (m, 4 H), 3.09 (t, J = 5.6 Hz, 2 H), 2.38-2.28 (m, 1 H), 1.95-1.85 (m, 1 H). |
| 183 | 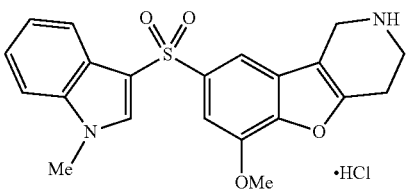 [SMILES: COc1cc(S(=O)(=O)c2cn(C)c3ccccc23)cc2c3c(oc12)CCNC3 ; Cl] | 397 | 1H NMR (DMSO-d6, 400 MHz) δ 9.20 (br s, 2 H), 8.23 (s, 1 H), 7.98 (d, J = 1.6 Hz, 1 H), 7.86 (d, J = 8.0 Hz, 1 H), 7.56 (d, J = 8.0 Hz, 1 H), 7.44 (d, J = 1.6 Hz, 1 H), 7.34-7.19 (m, 2 H), 4.35 (s, 2 H), 3.98 (s, 3 H), 3.87 (s, 3 H), 3.49 (t, J = 6.0 Hz, 2 H), 3.10-3.00 (m, 2 H). |
| 184 | 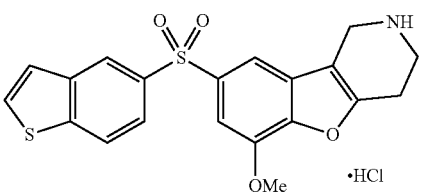 [SMILES: COc1cc(S(=O)(=O)c2ccc3sccc3c2)cc2c3c(oc12)CCNC3 ; Cl] | 400 | 1H NMR (DMSO-d6, 400 MHz) δ 9.47 (br s, 2 H), 8.59 (s, 1 H), 8.25 (d, J = 8.8 Hz, 1 H), 8.06-7.95 (m, 2 H), 7.90 (d, J = 8.0 Hz, 1 H), 7.66 (d, J = 5.2 Hz, 1 H), 7.48 (s, 1 H), 4.35 (s, 2 H), 4.02 (m, 3 H), 3.57-3.44 (m, 2 H), 3.15-3.03 (m, 2 H). |
| 185 | 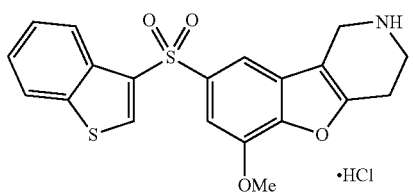 [SMILES: COc1cc(S(=O)(=O)c2csc3ccccc23)cc2c3c(oc12)CCNC3 ; Cl] | 400 | 1H NMR (DMSO-d6, 300 MHz) δ 9.50 (br s, 2 H), 8.88 (s, 1 H), 8.24-8.08 (m, 3 H), 7.56-7.44 (m, 3 H), 4.37 (s, 2 H), 4.00 (s, 3 H), 3.55-3.46 (m, 2 H), 3.13-3.04 (m, 2 H). |
| 186 | 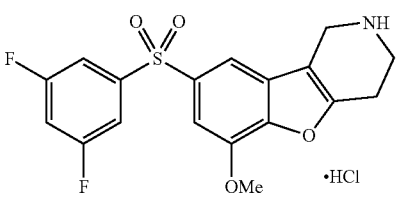 [SMILES: COc1cc(S(=O)(=O)c2cc(F)cc(F)c2)cc2c3c(oc12)CCNC3 ; Cl] | 380 | 1H NMR (DMSO-d6, 400 MHz) δ 9.55 (br s, 2 H), 8.06 (d, J = 1.6 Hz, 1 H), 7.83-7.77 (m, 1 H), 7.70-7.62 (m, 2 H), 7.53 (d, J = 2.0 Hz, 1 H), 4.36 (s, 2 H), 4.05 (s, 3 H), 3.52 (t, J = 4.5 Hz, 2 H), 3.11 (d, J = 4.5 Hz, 2 H). |

TABLE 1-continued

| Ex. No. | Structure | Mass Spec [M + H]+ | ¹H NMR Data |
|---|---|---|---|
| 187 | 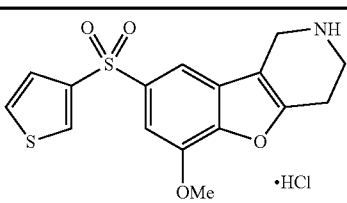 | 350 | ¹H NMR (DMSO-d₆, 400 MHz) δ 9.26 (br s, 2 H), 8.47-8.42 (m, 1 H), 7.97 (d, J = 1.2 Hz, 1 H), 7.76 (dd, J = 5.2, 2.8 Hz, 1 H), 7.53-7.49 (m, 1 H), 7.46 (d, J = 1.6 Hz, 1 H), 4.36 (s, 2 H), 4.02 (s, 3 H), 3.51 (t, J = 6.0 Hz, 2 H), 3.14-3.05 (m, 2 H). |
| 188 | 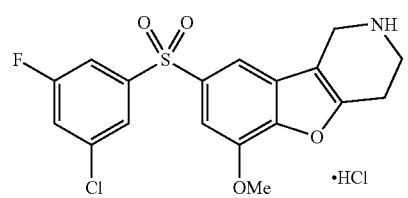 [SMILES: COc1cc(S(=O)(=O)c2cc(F)cc(Cl)c2)cc2c3c(oc12)CCNC3 ; Cl] | 396 | ¹H NMR (DMSO-d₆, 400 MHz) δ 9.18 (br s, 2 H), 8.07 (d, J = 1.6 Hz, 1 H), 7.96-7.90 (m, 2 H), 7.86-7.80 (m, 1 H), 7.54 (d, J = 1.6 Hz, 1 H), 4.36 (s, 2 H), 4.04 (s, 3 H), 3.52 (t, J = 6.0 Hz, 2 H), 3.14-3.04 (m, 2 H). |
| 189 | 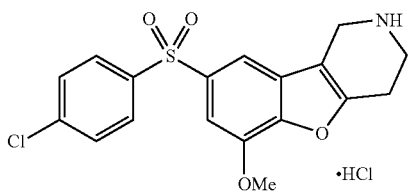 [SMILES: COc1cc(S(=O)(=O)c2ccc(Cl)cc2)cc2c3c(oc12)CCNC3 ; Cl] | 378 | ¹H NMR (DMSO-d₆, 400 MHz) δ 9.02 (br s, 2 H), 8.04-7.99 (m, 2 H), 7.98 (d, J = 1.6 Hz, 1 H), 7.72-7.67 (m, 2 H), 7.45 (d, J = 1.6 Hz, 1 H), 4.34 (s, 2 H), 4.02 (s, 3 H), 3.50 (t, J = 6.0 Hz, 2 H), 3.12-3.02 (m, 2 H). |
| 190 | 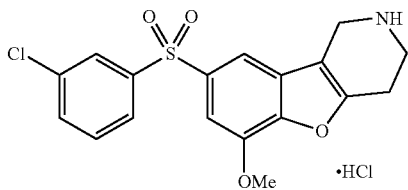 [SMILES: COc1cc(S(=O)(=O)c2cccc(Cl)c2)cc2c3c(oc12)CCNC3 ; Cl] | 378 | ¹H NMR (DMSO-d₆, 400 MHz) δ 9.07 (br s, 2 H), 8.06 (t, J = 1.6 Hz, 1 H), 8.03 (d, J = 1.6 Hz, 1 H), 8.01-7.95 (m, 1 H), 7.78-7.74 (m, 1 H), 7.68-7.61 (m, 1 H), 7.50 (d, J = 1.6 Hz, 1 H), 4.35 (s, 2 H), 4.03 (s, 3 H), 3.50 (t, J = 6.0 Hz, 2 H), 3.12-3.03 (m, 2 H). |
| 191 | 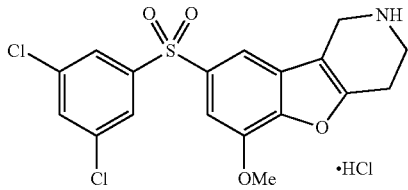 [SMILES: COc1cc(S(=O)(=O)c2cc(Cl)cc(Cl)c2)cc2c3c(oc12)CCNC3 ; Cl] | 412 | ¹H NMR (DMSO-d₆, 400 MHz) δ 9.18 (br s, 2 H), 8.09 (d, J = 1.6 Hz, 1 H), 8.07 (d, J = 2.0 Hz, 2 H), 7.98 (t, J = 2.0 Hz, 1 H), 7.56 (d, J = 1.6 Hz, 1 H), 4.36 (s, 2 H), 4.04 (s, 3 H), 3.51 (t, J = 6.0 Hz, 2 H), 3.14-3.04 (m, 2 H). |
| 192 | 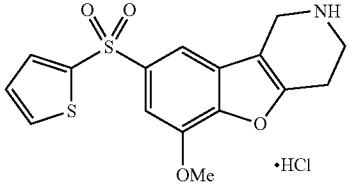 [SMILES: COc1cc(S(=O)(=O)c2cccs2)cc2c3c(oc12)CCNC3 ; Cl] | 350 | ¹H NMR (DMSO-d₆, 400 MHz) δ 9.49 (br s, 2 H), 8.06 (dd, J = 4.8, 1.6 Hz, 1 H), 7.99 (d, J = 1.6 Hz, 1 H), 7.89 (dd, J = 4.0, 1.6 Hz, 1 H), 7.45 (d, J = 1.6 Hz, 1 H), 7.22 (dd, J = 4.8, 4.0 Hz, 1 H), 4.37 (s, 2 H), 4.02 (s, 3 H), 3.56-3.47 (m, 2 H), 3.15-3.05 (m, 2 H). |
| 193 | 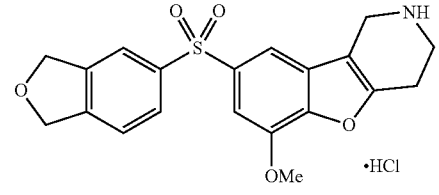 [SMILES: COc1cc(S(=O)(=O)c2ccc3c(c2)COC3)cc2c3c(oc12)CCNC3 ; Cl] | 386 | ¹H NMR (DMSO-d₆, 400 MHz) δ 9.01 (br s, 2 H), 7.98-7.89 (m, 3 H), 7.53 (d, J = 8.0 Hz, 1 H), 7.43 (d, J = 1.6 Hz, 1 H), 5.02 (s, 4 H), 4.33 (s, 2 H), 4.02 (s, 3 H), 3.49 (t, J = 6.0 Hz, 2 H), 3.11-3.02 (m, 2 H). |
| 194 | 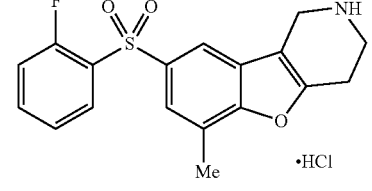 | 346 | ¹H NMR (CD₃OD, 400 MHz) δ 8.15-8.12 (m, 1 H), 8.11 (s, 1 H), 7.76 (s, 1 H), 7.72-7.66 (m, 1 H), 7.43 (dt, J = 7.6, 0.8 Hz, 1 H), 7.24-7.17 (m, 1 H), 4.47 (t, J = 2.0 Hz, 2 H), 3.69 (t, J = 6.4 Hz, 2 H), 3.22 (t, J = 6.4 Hz, 2 H), 2.56 (s, 3 H). |

TABLE 1-continued

| Ex. No. | Structure | Mass Spec [M + H]+ | 1H NMR Data |
|---|---|---|---|
| 195 | 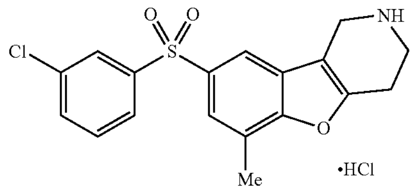 [SMILES: Cc1cc(S(=O)(=O)c2cccc(Cl)c2)cc2c3c(oc12)CCNC3 ; Cl] | 362 | 1H NMR (CD3OD, 400 MHz) δ 8.12 (d, J = 1.6 Hz, 1 H), 7.97 (d, J = 2.0 Hz, 1 H), 7.91 (dd, J = 7.6, 1.2 Hz, 1 H), 7.78 (s, 1 H), 7.63 (dd, J = 8.0, 1.2 Hz, 1 H), 7.55 (t, J = 8.0 Hz, 1 H), 4.47 (t, J = 2.0 Hz, 2 H), 3.69 (t, J = 6.0 Hz, 2 H), 3.21 (t, J = 6.0 Hz, 2 H), 2.56 (s, 3 H). |
| 196 | 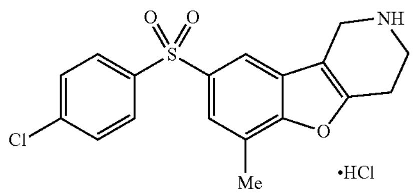 | 362 | 1H NMR (CD3OD, 400 MHz) δ 8.09 (d, J = 1.6 Hz, 1 H), 7.96 (dd, J = 8.8, 2.0 Hz, 2 H), 7.76 (t, J = 0.8 Hz, 1 H), 7.58 (dd, J = 8.8, 2.0 Hz, 2 H), 4.46 (t, J = 2.0 Hz, 2 H), 3.68 (t, J = 6.0 Hz, 2 H), 3.20 (t, J = 6.0 Hz, 2 H), 2.55 (s, 3 H). |
| 197 | 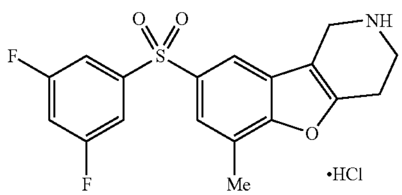 [SMILES: Cc1cc(S(=O)(=O)c2cc(F)cc(F)c2)cc2c3c(oc12)CCNC3 ; Cl] | 364 | 1H NMR (CD3OD, 300 MHz) δ 8.14 (d, J = 1.5 Hz, 1 H), 7.81 (d, J = 0.6 Hz, 1 H), 7.67-7.58 (m, 2 H), 7.29 (t, J = 9.0 Hz, 1 H), 4.47 (s, 2 H), 3.69 (t, J = 6.0 Hz, 2 H), 3.21 (t, J = 6.0 Hz, 2 H), 2.57 (s, 3 H). |
| 198 | 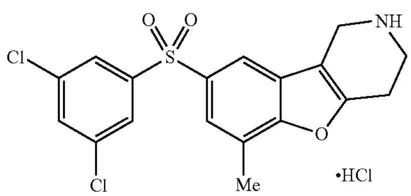 [SMILES: Cc1cc(S(=O)(=O)c2cc(Cl)cc(Cl)c2)cc2c3c(oc12)CCNC3 ; Cl] | 396 | 1H NMR (CD3OD, 300 MHz) δ 8.14 (d, J = 1.5 Hz, 1 H), 7.93 (d, J = 1.8 Hz, 2 H), 7.81 (br s, 1 H), 7.73 (t, J = 1.8 Hz, 1 H), 4.46 (s, 2 H), 3.68 (t, J = 6.0 Hz, 2 H), 3.20 (t, J = 6.0 Hz, 2 H), 2.57 (s, 3 H). |
| 199 | 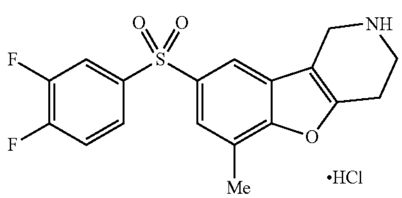 [SMILES: Cc1cc(S(=O)(=O)c2ccc(F)c(F)c2)cc2c3c(oc12)CCNC3 ; Cl] | 364 | 1H NMR (CD3OD, 300 MHz) δ 8.12 (s, 1 H), 8.01-7.92 (m, 1 H), 7.90-7.81 (m, 1 H), 7.79 (s, 1 H), 7.49 (q, J = 8.7 Hz, 1 H), 4.47 (s, 2 H), 3.69 (t, J = 6.0 Hz, 2 H), 3.21 (t, J = 6.0 Hz, 2 H), 2.56 (s, 3 H). |
| 200 | 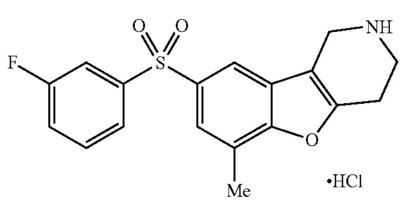 [SMILES: Cc1cc(S(=O)(=O)c2cccc(F)c2)cc2c3c(oc12)CCNC3 ; Cl] | 346 | 1H NMR (DMSO-d6, 300 MHz) δ 9.47 (br s, 2 H), 8.26 (d, J = 1.8 Hz, 1 H), 7.87-7.77 (m, 3 H), 7.71-7.63 (m, 1 H), 7.59-7.50 (m, 1 H), 4.37 (s, 2 H), 3.52 (t, J = 5.7 Hz, 2 H), 3.17-3.07 (m, 2 H), 2.52 (s, 3 H). |
| 201 | 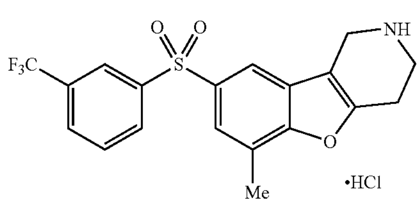 [SMILES: Cc1cc(S(=O)(=O)c2cccc(C(F)(F)F)c2)cc2c3c(oc12)CCNC3 ; Cl] | 396 | 1H NMR (CD3OD, 300 MHz) δ 8.29-8.21 (m, 2 H), 8.16 (s, 1 H), 7.98-7.92 (m, 1 H), 7.84-7.75 (m, 2 H), 4.47 (s, 2 H), 3.69 (t, J = 6.0 Hz, 2 H), 3.21 (t, J = 6.0 Hz, 2 H), 2.56 (s, 3 H). |

TABLE 1-continued

| Ex. No. | Structure | Mass Spec [M + H]+ | 1H NMR Data |
|---|---|---|---|
| 202 | 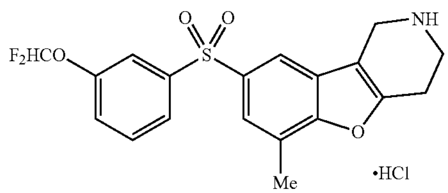 [SMILES: Cc1cc(S(=O)(=O)c2cccc(OC(F)F)c2)cc2c3c(oc12)CCNC3 ; Cl] | 394 | 1H NMR (CD3OD, 300 MHz) δ 8.11 (s, 1 H), 7.88-7.70 (m, 3 H), 7.60 (t, J = 8.1 Hz, 1 H), 7.46-7.37 (m, 1 H), 6.93 (t, J = 73.2 Hz, 1 H), 4.47 (s, 2 H), 3.69 (t, J = 6.0 Hz, 2 H), 3.26-3.17 (m, 2 H), 2.56 (s, 3 H). |
| 203 | 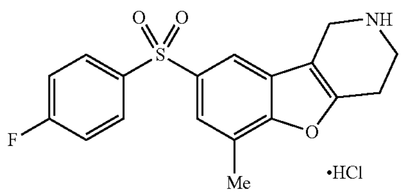 [SMILES: Cc1cc(S(=O)(=O)c2ccc(F)cc2)cc2c3c(oc12)CCNC3 ; Cl] | 346 | 1H NMR (CD3OD, 400 MHz) δ 8.10-8.01 (m, 3 H), 7.76 (s, 1 H), 7.32-7.27 (m, 2 H), 4.46 (s, 2 H), 3.68 (t, J = 6.0 Hz, 2 H), 3.20 (t, J = 6.0 Hz, 2 H), 2.55 (s, 3 H). |
| 204 | 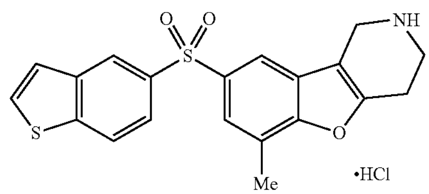 [SMILES: Cc1cc(S(=O)(=O)c2ccc3sccc3c2)cc2c3c(oc12)CCNC3 ; Cl] | 384 | 1H NMR (DMSO-d6, 400 MHz) δ 9.48 (br s, 2 H), 8.56 (s, 1 H), 8.30-8.18 (m, 2 H), 8.05-7.78 (m, 3 H), 7.67-7.60 (m, 1 H), 4.37 (s, 2 H), 3.51 (br s, 2 H), 3.20 (s, 3 H), 3.11 (br s, 2 H). |
| 205 | 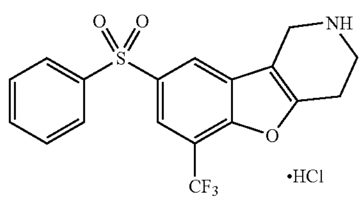 [SMILES: O=S(=O)(c1ccccc1)c1cc(C(F)(F)F)c2oc3c(c2c1)CNCC3 ; Cl] | 382 | 1H NMR (DMSO-d6, 400 MHz) δ 9.31 (br s, 2 H), 8.76 (d, J = 1.6 Hz, 1 H), 8.16 (d, J = 0.8 Hz, 1 H), 8.10-8.02 (m, 2 H), 7.75-7.61 (m, 3 H), 4.41 (s, 2 H), 3.53 (t, J = 5.6 Hz, 2 H), 3.16 (t, J = 5.6 Hz, 2 H). |
| 206 | 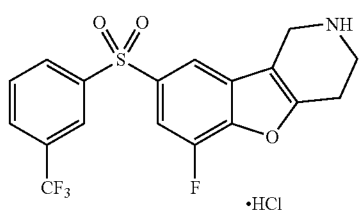 [SMILES: O=S(=O)(c1cccc(C(F)(F)F)c1)c1cc(F)c2oc3c(c2c1)CNCC3 ; Cl] | 400 | 1H NMR (DMSO-d6, 300 MHz) δ 9.37 (br s, 2 H), 8.40-8.30 (m, 3 H), 8.14-8.03 (m, 2 H), 7.89 (t, J = 9.0 Hz, 1 H), 4.40 (s, 2 H), 3.54 (t, J = 3.0 Hz, 2 H), 3.20-3.10 (m, 2 H). |
| 207 | 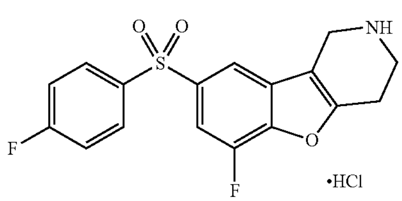 [SMILES: O=S(=O)(c1ccc(F)cc1)c1cc(F)c2oc3c(c2c1)CNCC3 ; Cl] | 350 | 1H NMR (DMSO-d6, 300 MHz) δ 9.73 (br s, 2 H), 8.29 (d, J = 1.5 Hz, 1 H), 8.15-8.04 (m, 2 H), 7.92 (dd, J = 10.2, 1.5 Hz, 1 H), 7.54-7.43 (m, 2 H), 4.39 (s, 2 H), 3.53 (t, J = 6.0 Hz, 2 H), 3.20-3.11 (m, 2 H). |
| 208 | 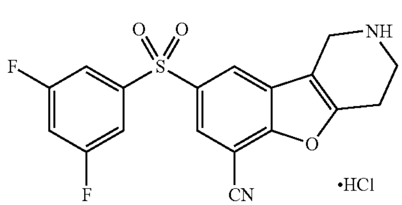 [SMILES: N#Cc1cc(S(=O)(=O)c2cc(F)cc(F)c2)cc2c3c(oc12)CCNC3 ; Cl] | 375 | 1H NMR (DMSO-d6, 300 MHz) δ 9.48 (br s, 2 H), 8.79 (d, J = 1.8 Hz, 1 H), 8.62 (d, J = 1.8 Hz, 1 H), 7.88-7.78 (m, 2 H), 7.75-7.65 (m, 1 H), 4.42 (s, 2 H), 3.55 (t, J = 6.0 Hz, 2 H), 3.25-3.15 (m, 2 H). |

TABLE 1-continued

| Ex. No. | Structure | Mass Spec [M + H]+ | ¹H NMR Data |
|---|---|---|---|
| 209 | 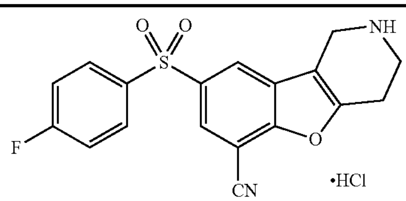 | 357 | ¹H NMR (DMSO-d₆, 300 MHz) δ 9.66-9.54 (m, 2 H), 8.75 (d, J = 1.8 Hz, 1 H), 8.54 (d, J = 2.1 Hz, 1 H), 8.18-8.08 (m, 2 H), 7.44-7.55 (m, 2 H), 4.41 (s, 2 H), 3.54 (t, J = 6.0 Hz, 2 H), 3.25-3.14 (m, 2 H). |
| 210 | 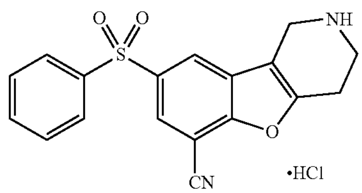 [SMILES: N#Cc1cc(S(=O)(=O)c2ccccc2)cc2c3c(oc12)CCNC3 ; Cl] | 339 | ¹H NMR (DMSO-d₆, 400 MHz) δ 9.06 (br s, 2 H), 8.73 (d, J = 2.0 Hz, 1 H), 8.53 (d, J = 2.0 Hz, 1 H), 8.09-8.01 (m, 2 H), 7.76-7.60 (m, 3 H), 4.37 (s, 2 H), 3.50 (t, J = 5.6 Hz, 2 H), 3.20-3.10 (m, 2 H). |
| 211 | 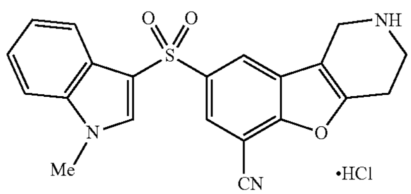 [SMILES: Cn1cc(S(=O)(=O)c2cc(C#N)c3oc4c(c3c2)CNCC4)c2ccccc21 ; Cl] | 392 | ¹H NMR (DMSO-d₆, 400 MHz) δ 9.05 (br s, 2 H), 8.73 (d, J = 2.0 Hz, 1 H), 8.42 (d, J = 1.6 Hz, 1 H), 8.29 (s, 1 H), 7.90-7.82 (m, 1 H), 7.58 (d, J = 8.4 Hz, 1 H), 7.36-7.20 (m, 2 H), 4.37 (s, 2 H), 3.88 (s, 3 H), 3.49 (t, J = 6.0 Hz, 2 H), 3.17-3.07 (m, 2 H). |
| 212 | 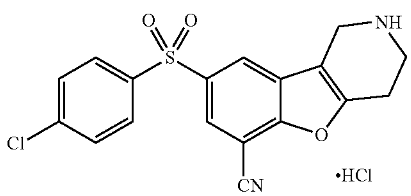 [SMILES: N#Cc1cc(S(=O)(=O)c2ccc(Cl)cc2)cc2c3c(oc12)CCNC3 ; Cl] | 373 | ¹H NMR (DMSO-d₆, 400 MHz) δ 9.28 (br s, 2 H), 8.74 (d, J = 2.0 Hz, 1 H), 8.55 (d, J = 1.6 Hz, 1 H), 8.09-8.02 (m, 2 H), 7.76-7.69 (m, 2 H), 4.39 (s, 2 H), 3.52 (t, J = 6.0 Hz, 2 H), 3.22-3.12 (m, 2 H). |
| 213 | 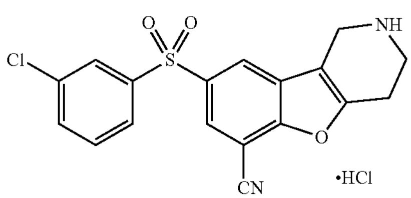 [SMILES: N#Cc1cc(S(=O)(=O)c2cccc(Cl)c2)cc2c3c(oc12)CCNC3 ; Cl] | 373 | ¹H NMR (DMSO-d₆, 400 MHz) δ 9.39 (br s, 2 H), 8.78 (d, J = 2.0 Hz, 1 H), 8.61 (d, J = 2.0 Hz, 1 H), 8.14-8.10 (m, 1 H), 8.04-7.98 (m, 1 H), 7.83-7.77 (m, 1 H), 7.71-7.64 (m, 1 H), 4.41 (s, 2 H), 3.53 (t, J = 6.0 Hz, 2 H), 3.23-3.13 (m, 2 H). |
| 214 | 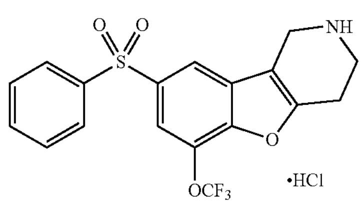 | 398 | ¹H NMR (DMSO-d₆, 400 MHz) δ 9.36 (br s, 2 H), 8.50 (d, J = 1.6 Hz, 1 H), 8.07-7.95 (m, 3 H), 7.75-7.60 (m, 3 H), 4.41 (s, 2 H), 3.53 (t, J = 6.0 Hz, 2 H), 3.15 (t, J = 6.0 Hz, 2 H). |
| 215 | 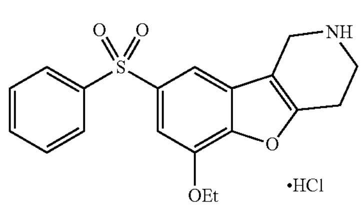 [SMILES: CCOc1cc(S(=O)(=O)c2ccccc2)cc2c3c(oc12)CCNC3 ; Cl] | 358 | ¹H NMR (DMSO-d₆, 400 MHz) δ 9.41 (br s, 2 H), 8.01-7.96 (m, 3 H), 7.69-7.59 (m, 3 H), 7.43 (d, J = 1.6 Hz, 1 H), 4.36 (s, 2 H), 4.28 (dd, J = 14.8, 6.8 Hz, 2 H), 3.51 (t, J = 6.0 Hz, 2 H), 3.10 (t, J = 6.0 Hz, 2 H), 1.40 (t, J = 6.8 Hz, 3 H). |
| 216 | 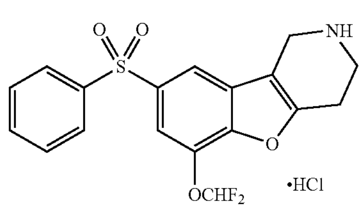 | 380 | ¹H NMR (DMSO-d₆, 400 MHz) δ 9.31 (br s, 2 H), 8.31 (d, J = 1.6 Hz, 1 H), 8.01-8.00 (m, 2 H), 7.76-7.61 (m, 4 H), 7.55 (t, J = 72.8 Hz, 1 H), 4.37 (s, 2 H), 3.50 (t, J = 6.0 Hz, 2 H), 3.12 (t, J = 5.8 Hz, 2 H). |

TABLE 1-continued

| Ex. No. | Structure | Mass Spec [M + H]⁺ | ¹H NMR Data |
|---|---|---|---|
| 217 | 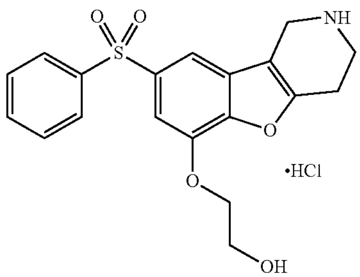 [SMILES: O=S(=O)(c1ccccc1)c1cc(OCCO)c2oc3c(c2c1)CNCC3 ; Cl] | 374 | ¹H NMR (CD₃OD, 300 MHz) δ 8.00 (s, 1 H), 7.98 (s, 1 H), 7.87-7.83 (m, 1 H), 7.67-7.52 (m, 3 H), 7.49 (s, 1 H), 4.45 (s, 2 H), 4.32 (t, J = 4.5 Hz, 2 H), 3.95 (t, J = 4.5 Hz, 2 H), 3.67 (t, J = 6.0 Hz, 2 H), 3.18 (t, J = 5.7 Hz, 2 H). |
| 218 | 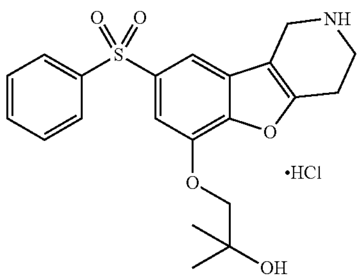 [SMILES: CC(C)(O)COc1cc(S(=O)(=O)c2ccccc2)cc2c3c(oc12)CCNC3 ; Cl] | 402 | ¹H NMR (CD₃OD, 300 MHz) δ 8.03-7.96 (m, 2 H), 7.88-7.84 (m, 1 H), 7.67-7.52 (m, 3 H), 7.47 (s, 1 H), 4.46 (s, 2 H), 4.05 (s, 2 H), 3.68 (t, J = 6.0 Hz, 2 H), 3.20 (t, J = 6.0 Hz, 2 H), 1.36 (s, 6 H). |
| 219 | 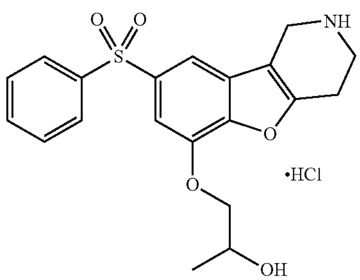 [SMILES: CC(O)COc1cc(S(=O)(=O)c2ccccc2)cc2c3c(oc12)CCNC3 ; Cl] | 402 | ¹H NMR (CD₃OD, 300 MHz) δ 8.02-7.92 (m, 2 H), 7.92-7.83 (m, 1 H), 7.71-7.51 (m, 3 H), 7.47 (s, 1 H), 4.45 (s, 2 H), 4.20-4.09 (m, 3 H), 3.73-3.63 (m, 2 H), 3.23-3.15 (m, 2 H), 1.31 (d, J = 6.0 Hz, 3 H). |
| 220 | 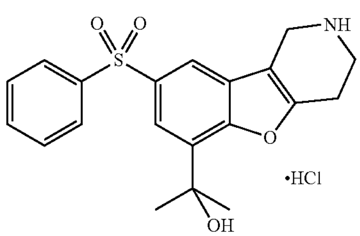 [SMILES: CC(C)(O)c1cc(S(=O)(=O)c2ccccc2)cc2c3c(oc12)CCNC3 ; Cl] | 354 [M + H − H₂O]⁺ | ¹H NMR (DMSO-d₆, 400 MHz) δ 8.95 (br s, 2 H), 8.25 (d, J = 1.6 Hz, 1 H), 8.04 (d, J = 2.0 Hz, 1 H), 7.98-7.91 (m, 2 H), 7.72-7.58 (m, 3 H), 4.33 (s, 2 H), 3.49 (t, J = 5.4 Hz, 2 H), 3.13-3.02 (m, 2 H), 1.58 (s, 6 H). |
| 221 | 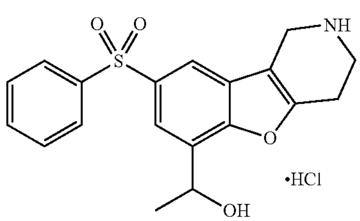 [SMILES: CC(O)c1cc(S(=O)(=O)c2ccccc2)cc2c3c(oc12)CCNC3 ; Cl] | 358 | ¹H NMR (DMSO-d₆, 400 MHz) δ 9.27 (br s, 2 H), 8.27 (d, J = 2.0 Hz, 1 H), 7.98-7.91 (m, 3 H), 7.71-7.58 (m, 3 H), 5.64 (d, J = 4.8 Hz, 1 H), 5.24-5.13 (m, 1 H), 4.37 (s, 2 H), 3.51 (t, J = 6.0 Hz, 2 H), 3.15-3.05 (m, 2 H), 1.43 (d, J = 6.4 Hz, 3 H). |
| 222 | 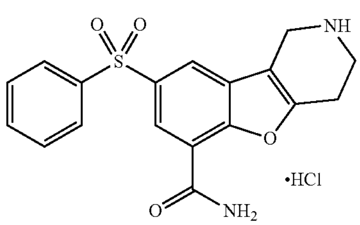 [SMILES: NC(=O)c1cc(S(=O)(=O)c2ccccc2)cc2c3c(oc12)CCNC3 ; Cl] | 357 | ¹H NMR (DMSO-d₆, 400 MHz) δ 9.38 (br s, 2 H), 8.53 (d, J = 2.0 Hz, 1 H), 8.18 (d, J = 2.0 Hz, 1 H), 8.04-7.94 (m, 4 H), 7.73-7.58 (m, 3 H), 4.41 (s, 2 H), 3.53 (t, J = 6.0 Hz, 2 H), 3.14 (t, J = 6.0 Hz, 2 H). |

TABLE 1-continued

| Ex. No. | Structure | Mass Spec [M + H]+ | 1H NMR Data |
|---|---|---|---|
| 223 | 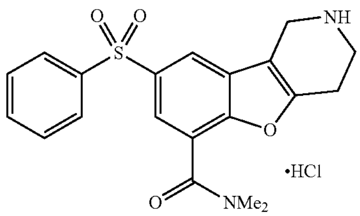 [SMILES: CN(C)C(=O)c1cc(S(=O)(=O)c2ccccc2)cc2c3c(oc12)CCNC3 ; Cl] | 385 | 1H NMR (DMSO-d6, 400 MHz) δ 9.15 (br s, 2 H), 8.46 (d, J = 1.6 Hz, 1 H), 8.05-7.97 (m, 2 H), 7.88 (d, J = 2.0 Hz, 1 H), 7.74-7.59 (m, 3 H), 4.40 (s, 2 H), 3.59-3.49 (m, 2 H), 3.15-3.06 (m, 2 H), 3.05 (s, 3 H), 2.79 (s, 3 H). |
| 224 | 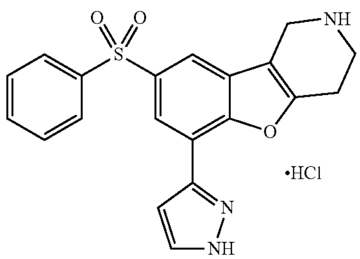 [SMILES: O=S(=O)(c1ccccc1)c1cc(-c2cc[nH]n2)c2oc3c(c2c1)CNCC3 ; Cl] | 380 | 1H NMR (DMSO-d6, 400 MHz) δ 9.48 (br s, 2 H), 8.37 (d, J = 2.0 Hz, 1 H), 8.33 (d, J = 2.0 Hz, 1 H), 8.03-7.96 (m, 2 H), 7.91 (d, J = 2.4 Hz, 1 H), 7.72-7.58 (m, 3 H), 7.03 (d, J = 2.0 Hz, 1 H), 4.42 (s, 2 H), 3.63-3.50 (m, 2 H), 3.18 (t, J = 5.6 Hz, 2 H). |
| 225 | 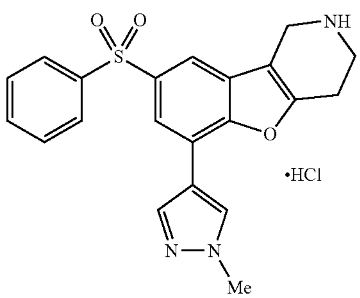 [SMILES: Cn1cc(-c2cc(S(=O)(=O)c3ccccc3)cc3c4c(oc23)CCNC4)cn1 ; Cl] | 394 | 1H NMR (DMSO-d6, 400 MHz) δ 9.39 (br s, 2 H), 8.53 (s, 1 H), 8.22 (d, J = 0.8 Hz, 1 H), 8.20 (d, J = 1.6 Hz, 1 H), 8.12 (d, J = 2.0 Hz, 1 H), 8.07-8.0 (m, 2 H), 7.71-7.58 (m, 3 H), 4.41 (s, 2 H), 3.94 (s, 3 H), 3.59 (br s, 2 H); 3.23-3.12 (m, 2 H). |
| 226 | 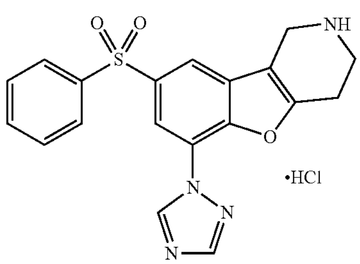 [SMILES: O=S(=O)(c1ccccc1)c1cc(-n2cncn2)c2oc3c(c2c1)CNCC3 ; Cl] | 381 | 1H NMR (DMSO-d6, 400 MHz) δ 9.40 (s, 1 H), 9.05 (br s, 2 H), 8.47 (d, J = 1.6 Hz, 1 H), 8.40 (s, 1 H), 8.28 (d, J = 2.0 Hz, 1 H), 8.07-8.00 (m, 2 H), 7.74-7.60 (m, 3 H), 4.41 (s, 2 H), 3.52 (t, J = 6.0 Hz, 2 H), 3.19-3.09 (m, 2 H). |
| 227 | 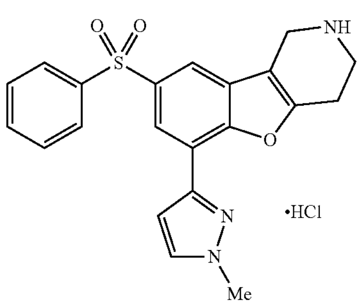 [SMILES: Cn1ccc(-c2cc(S(=O)(=O)c3ccccc3)cc3c4c(oc23)CCNC4)n1 ; Cl] | 394 | 1H NMR (DMSO-d6, 400 MHz) δ 9.55 (br s, 2 H), 8.36-8.29 (m, 2 H), 8.02-7.95 (m, 2 H), 7.90 (d, J = 2.4 Hz, 1 H), 7.72-7.57 (m, 3 H), 7.00 (d, J = 2.4 Hz, 1 H), 4.41 (s, 2 H), 3.97 (s, 3 H), 3.61-3.48 (m, 2 H), 3.18 (t, J = 6.0 Hz, 2 H). |

TABLE 1-continued

| Ex. No. | Structure | Mass Spec [M + H]+ | 1H NMR Data |
|---|---|---|---|
| 228 | 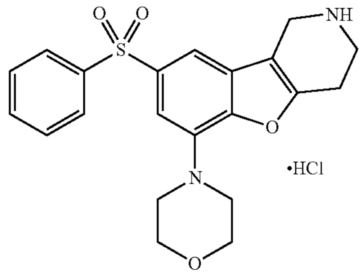 [SMILES: O=S(=O)(c1ccccc1)c1cc(N2CCOCC2)c2oc3c(c2c1)CNCC3 ; Cl] | 399 | 1H NMR (DMSO-d6, 400 MHz) δ 9.99-9.97 (m, 2 H), 7.98 (d, J = 6.9 Hz, 2 H), 7.90 (d, J = 1.5 Hz, 1 H), 7.71-7.56 (m, 3 H), 7.24 (s, 1 H), 4.33 (s, 2 H), 3.86-3.73 (m, 4 H), 3.54-3.42 (m, 2 H), 3.38-3.24 (m, 4 H), 3.17-3.04 (m, 2 H). |
| 229 | 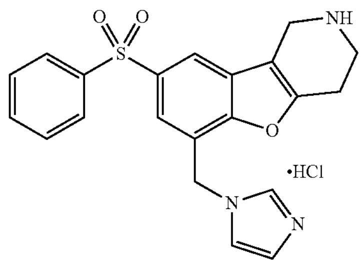 [SMILES: O=S(=O)(c1ccccc1)c1cc(Cn2ccnc2)c2oc3c(c2c1)CNCC3 ; Cl] | 394 | 1H NMR (DMSO-d6, 400 MHz) δ 9.73 (br s, 2 H), 9.27 (s, 1 H), 8.45 (d, J = 2.0 Hz, 1 H), 8.00 (d, J = 2.0 Hz, 1 H), 7.98-7.92 (m, 2 H), 7.82-7.75 (m, 1 H), 7.72-7.58 (m, 4 H), 5.78 (s, 2 H), 4.37 (br s, 2 H), 3.56-3.48 (m, 2 H), 3.10 (t, J = 1.6 Hz, 2 H). |
| 230 | 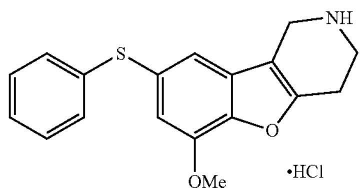 [SMILES: COc1cc(Sc2ccccc2)cc2c3c(oc12)CCNC3 ; Cl] | 312 | 1H NMR (DMSO-d6, 400 MHz) δ 9.69-9.54 (m, 2 H), 7.39 (d, J = 1.6 Hz, 1 H), 7.35-7.29 (m, 2 H), 7.25-7.17 (m, 3 H), 7.04 (d, J = 1.2 Hz, 1 H), 4.26 (s, 2 H), 3.91 (s, 3 H), 3.51 (t, J = 6.0 Hz, 2 H), 3.13-3.06 (m, 2 H). |
| 231 | [a]20D -12 | 332 | 1H NMR (DMSO-d6, 400 MHz) δ 9.27 (br s, 2 H), 8.11 (d, J = 1.2 Hz, 1 H), 7.79-7.74 (m, 3 H), 7.58-7.49 (m, 3 H), 4.36 (s, 2 H), 3.52 (t, J = 6.0 Hz, 2 H), 3.26-3.11 (m, 2 H). |
| 232 | [a]20D +13° | 332 | 1H NMR (DMSO-d6, 400 MHz) δ 9.21 (br s, 2 H), 8.11 (d, J = 1.2 Hz, 1 H), 7.81-7.74 (m, 3 H), 7.57-7.50 (m, 3 H), 4.36 (s, 2 H), 3.53 (t, J = 6.0 Hz, 2 H), 3.12 (t, J = 5.6 Hz, 2 H). |
| 233 | 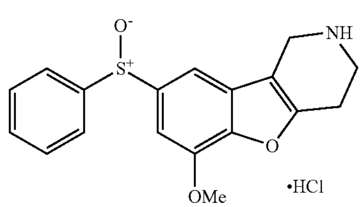 [SMILES: COc1cc([S+]([O-])c2ccccc2)cc2c3c(oc12)CCNC3 ; Cl] | 328 | 1H NMR (DMSO-d6, 400 MHz) δ 9.71 (br s, 2 H), 8.19-8.14 (m, 2 H), 8.11 (s, 1 H), 7.98-7.92 (m, 3 H), 7.71 (s, 1 H), 4.76 (s, 2 H), 4.39 (s, 3 H), 3.94 (t, J = 5.6 Hz, 2 H), 3.54-3.46 (m, 2 H). |

TABLE 1-continued

| Ex. No. | Structure | Mass Spec [M + H]+ | 1H NMR Data |
|---|---|---|---|
| 234 | [a]20D +70° •HCl | 328 | 1H NMR (DMSO-d6, 300 MHz) δ 9.73 (br s, 2 H), 7.80-7.64 (m, 3 H), 7.59-7.45 (m, 3 H), 7.32-7.25 (m, 1 H), 4.32 (s, 2 H), 3.96 (s, 3 H), 3.56-3.44 (m, 2 H), 3.16-3.04 (m, 2 H). |
| 235 | [a]20D −15° •HCl | 328 | 1H NMR (CD3OD, 400 MHz) δ 7.73-7.69 (m, 2 H), 7.58 (d, J = 1.6 Hz, 1 H), 7.56-7.50 (m, 3 H), 7.20 (d, J = 1.2 Hz, 1 H), 4.39 (t, J = 2.0 Hz, 2 H), 3.98 (s, 3 H), 3.63 (t, J = 6.0 Hz, 2 H), 3.18-3.13 (m, 2 H). |
| 236 | •HCl | 298 | 1H NMR (DMSO-d6, 300 MHz) δ 9.50 (br s, 2 H), 7.48 (d, J = 1.5 Hz, 1 H), 7.33-7.15 (m, 6 H), 4.30 (s, 2 H), 4.03 (s, 2 H), 3.53 (t, J = 5.7 Hz, 2 H), 3.11 (t, J = 5.7 Hz, 2 H). |
| 237 | •HCl | 296 | 1H NMR (DMSO-d6, 400 MHz) δ 8.97 (br s, 2 H), 7.41-7.33 (m, 2 H), 7.13-7.07 (m, 1 H), 7.00-6.94 (m, 2 H), 6.82 (d, J = 2.4 Hz, 1 H), 6.76 (d, J = 2.0 Hz, 1 H), 4.20 (s, 2 H), 3.90 (s, 3 H), 3.54-3.45 (m, 2 H), 3.09-3.00 (m, 2 H). |
| 238 | [a]20D +16° | 359 | 1H NMR (DMSO-d6, 300 MHz, AUC HPLC 98.6%) δ 8.03-7.97 (m, 2 H), 7.73 (d, J = 1.8 Hz, 1 H), 7.69-7.56 (m, 3 H), 7.35 (d, J = 1.5 Hz, 1 H), 4.88 (d, J = 4.2 Hz, 1 H), 4.09-4.01 (m, 1 H), 3.99 (s, 3 H), 2.91-2.68 (m, 3 H), 2.01-1.79 (m, 2 H). |
| 239 | 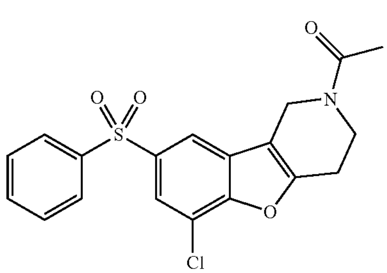 [SMILES: CC(=O)N1CCc2oc3c(Cl)cc(S(=O)(=O)c4ccccc4)cc3c2C1] | 390 | 1H NMR (DMSO-d6, 400 MHz) δ 8.37-8.33 (m, 1 H), 8.06-8.02 (m, 2 H), 7.98-7.94 (m, 1 H), 7.70-7.60 (m, 3 H), 4.71 (s, J = 19.6 Hz, 2 H), 3.88-3.81 (m, 2 H), 3.00 (s, 1 H), 2.87 (s, 1 H), 2.14 (s, 3 H). |

Example 240

Binding Assay Procedures

The relative affinities of the various compounds for the 5-HT$_6$ receptor were measured in a radioligand binding assay, using a scintillation proximity assay (SPA) format. Test compounds were dissolved to 10 mM in 100% DMSO, then serially diluted at 4× assay concentrations into assay buffer containing 16% DMSO in 96-well poly-propylene plates.

For binding analysis vs. the human receptor, samples were incubated in 50 mM Tris-HCl, pH 7.5, 5 mM MgCl$_2$, 1 mM EDTA (4% DMSO final) with 10 nM [N-methyl-$^3$H]-LSD (Perkin Elmer), 2.5 ng of human 5-HT$_6$ receptor membranes (Millipore) and 50 µg SPA beads (PVT-PEI-WGA, GE Healthcare) per well in a final volume of 0.2 mL. For binding analysis vs. the rat receptor, samples were incubated in the same buffer with 3.5 nM [N-methyl-$^3$H]-LSD, 50 µg of rat 5-HT$_6$ receptor membranes (Perkin Elmer) and 0.4 mg SPA beads (PVT-PEI-WGA Type B, GE Healthcare) per well also in a final volume of 0.2 mL. Binding reactions were performed in PicoPlate96 microtiter plates (Perkin Elmer) by consecutively adding 50 µL of each competing compound or buffer, SPA beads, radioligand and 5-HT$_6$ receptor membranes. After an overnight incubation at room temperature on a Nutator mixer, plates were centrifuged for 15 min at 1,500 rpm, followed by incubation in the dark for 10 min. Radioactivity was counted in either a TopCountNXT microplate counter (Perkin Elmer) or a Wallac Trilux 1450 Microbeta microplate reader (Perkin Elmer) for 5 min per well. Total binding control contained compound dilution buffer only; nonspecific binding is determined in the presence of 100 µM 5-hydroxytryptamine. Specific binding was determined by subtracting nonspecific binding from total binding.

All experiments were performed in duplicate using ten concentrations of competing ligand, with clozapine included as a control in every run. IC$_{50}$ values were determined from specific binding data using XLfit4.1 curve fitting software from IDBS Ltd. The inhibition constant (K$_i$) was calculated using the Cheng-Prusoff equation: $K_i=IC_{50}/(1+(L/K_D))$, where L=concentration of radioligand in the assay, and K$_D$=affinity of the radioligand for the receptor.

Example 241

Cell-Based Functional Assay Procedures

The functional activities of the various compounds on the 5-HT6 receptor were determined in a cell-based functional assay by measuring the production of cAMP using HTRF™ assay technology. (CisBio International) Test compounds were dissolved to 10 mM in 100% DMSO, then serially diluted at 1000× assay concentrations into 100% DMSO in 96-well polypropylene plates. Compounds were further diluted to 4× assay concentrations with serum free media containing IBMX. For functional analysis vs. both the human and rat 5-HT$_6$ receptor expressing cell lines, samples were incubated in serum free DMEM with 1 mM IBMX (0.25% DMSO final) with 60,000 cells/well in a final volume of 100 µL for a total of 30 minutes at room temperature.

Antagonist activity was determined after a 20 minute incubation by the addition of a 5-hydroxytryptamine challenge at the EC$_{80}$ (30 nM 5-HT) and an additional incubation of 10 minutes. Cells were lysed by addition of HTRF™ reagents (CisBio International) and after another 30 minute incubation, the plates were read on an AnalystGT (MDS) or SynergyHT (BioTek) microplate reader. Basal cAMP accumulation levels were measured in the presence of 0.25% DMSO only. Antagonist activity was expressed as the ratio of cAMP produced in a test well to the average cAMP produced in the EC$_{80}$ challenge control wells.

Agonist activity was determined after a full 30 minutes of incubation at room temperature, using 10 µM 5-HT as the E$_{max}$ control. Cells were lysed by addition of HTRF™ reagents (CisBio International) and after another 30 minute incubation, the plates were read on an AnalystGT (MDS) or SynergyHT (BioTek) microplate reader. Basal cAMP accumulation levels were measured in the presence of 0.25% DMSO only. Agonist activity was expressed as the ratio of cAMP produced in a test well to the average cAMP produced in the E$_{max}$ control wells.

All cell-based experiments were performed in duplicate using ten concentrations of test compound with 5-HT (agonist mode) or a known antagonist (antagonist mode) included as additional controls in every run. IC$_{50}$/EC$_{50}$ values were determined using XLfit4.1 curve fitting software from IDBS Ltd. For antagonists, the apparent dissociation constant (K$_b$) was calculated using a modified Cheng-Prusoff equation: $K_b=IC_{50}/(1+(A/EC_{50,A}))$, where A=concentration of reference agonist in the assay and EC$_{50}$A=EC$_{50}$ value of the reference agonist.

TABLE 1

Biological activity of the compounds of the present invention.

| Compound | human 5HT$_6$ Ki (nm) |
| --- | --- |
| Compound of Example 27 | 6.5 |
| Compound of Example 28 | 19 |
| Compound of Example 29 | 16 |
| Compound of Example 30 | 6.2 |
| Compound of Example 31 | 43 |
| Compound of Example 32 | 38 |
| Compound of Example 33 | 100 |
| Compound of Example 34 | 1320 |
| Compound of Example 35 | 38 |
| Compound of Example 36 | 40 |
| Compound of Example 37 | 339 |
| Compound of Example 38 | 17 |
| Compound of Example 39 | 5.0 |
| Compound of Example 40 | 21 |
| Compound of Example 41 | 0.58 |
| Compound of Example 42 | 1.5 |
| Compound of Example 43 | 0.42 |
| Compound of Example 44 | 0.55 |
| Compound of Example 45 | 0.48 |
| Compound of Example 46 | 0.35 |
| Compound of Example 47 | 0.39 |
| Compound of Example 48 | 12 |
| Compound of Example 49 | 1.9 |
| Compound of Example 50 | 0.17 |
| Compound of Example 51 | 0.20 |
| Compound of Example 52 | 5.1 |
| Compound of Example 53 | 0.22 |
| Compound of Example 54 | 0.12 |
| Compound of Example 55 | 53 |
| Compound of Example 56 | 31 |
| Compound of Example 57 | 133 |
| Compound of Example 58 | 16 |
| Compound of Example 59 | 17 |
| Compound of Example 60 | 9.8 |
| Compound of Example 61 | 18 |
| Compound of Example 62 | 1.7 |
| Compound of Example 63 | 2.1 |
| Compound of Example 64 | 116 |
| Compound of Example 65 | 154 |
| Compound of Example 66 | 533 |
| Compound of Example 67 | 34 |
| Compound of Example 68 | 132 |
| Compound of Example 69 | 571 |
| Compound of Example 70 | 0.083 |
| Compound of Example 71 | 2.0 |

TABLE 1-continued

Biological activity of the compounds of the present invention.

| Compound | human 5HT$_6$ Ki (nm) |
|---|---|
| Compound of Example 72 | 12 |
| Compound of Example 73 | 4.3 |
| Compound of Example 74 | 13 |
| Compound of Example 75 | 124 |
| Compound of Example 76 | 9.3 |
| Compound of Example 77 | 28 |
| Compound of Example 78 | 607 |
| Compound of Example 79 | 4.3 |
| Compound of Example 80 | 19 |
| Compound of Example 81a | 0.35 |
| Compound of Example 81b | 19 |
| Compound of Example 82a | 56 |
| Compound of Example 82b | 0.15 |
| Compound of Example 83a | 25 |
| Compound of Example 83b | 16 |
| Compound of Example 84 | 27 |
| Compound of Example 85 | 1.6 |
| Compound of Example 86 | 522 |
| Compound of Example 87 | 4.0 |
| Compound of Example 88 | 252 |
| Compound of Example 89 | 110 |
| Compound of Example 90 | 0.25 |
| Compound of Example 91 | 12 |
| Compound of Example 92 | 645 |
| Compound of Example 93 | 10 |
| Compound of Example 94 | 143 |
| Compound of Example 95 | 7.5 |
| Compound of Example 96 | 4.9 |
| Compound of Example 97 | 1.7 |
| Compound of Example 98 | 46 |
| Compound of Example 99 | 1.0 |
| Compound of Example 100 | 0.77 |
| Compound of Example 101 | 0.13 |
| Compound of Example 102 | 3.3 |
| Compound of Example 103 | 2.2 |
| Compound of Example 104 | 26 |
| Compound of Example 105 | 13 |
| Compound of Example 106 | 2.5 |
| Compound of Example 107 | 0.79 |
| Compound of Example 108 | 1.3 |
| Compound of Example 109 | 14 |
| Compound of Example 110 | 4.4 |
| Compound of Example 111 | 3.3 |
| Compound of Example 112 | 4.9 |
| Compound of Example 113 | 2.2 |
| Compound of Example 114 | 19 |
| Compound of Example 115 | 123 |
| Compound of Example 116 | 1.0 |
| Compound of Example 117 | 1.2 |
| Compound of Example 118 | 5.9 |
| Compound of Example 119 | 20 |
| Compound of Example 120 | 26 |
| Compound of Example 121 | 29 |
| Compound of Example 122 | 5.4 |
| Compound of Example 123 | 1.2 |
| Compound of Example 124 | 37 |
| Compound of Example 125 | 2.3 |
| Compound of Example 126 | 10 |
| Compound of Example 127 | 4.0 |
| Compound of Example 128 | 3.0 |
| Compound of Example 129 | 9.9 |
| Compound of Example 130 | 6.0 |
| Compound of Example 131 | 7.6 |
| Compound of Example 132 | 3.3 |
| Compound of Example 133 | 0.26 |
| Compound of Example 134 | 0.55 |
| Compound of Example 135 | 20 |
| Compound of Example 136 | 3.0 |
| Compound of Example 137 | 5.6 |
| Compound of Example 138 | 5.1 |
| Compound of Example 139 | 2.7 |
| Compound of Example 140 | 16 |
| Compound of Example 141 | 3.1 |
| Compound of Example 142 | 25 |
| Compound of Example 143 | 0.13 |
| Compound of Example 144 | 492 |
| Compound of Example 145 | 66 |
| Compound of Example 146 | 1.6 |
| Compound of Example 147 | 1.2 |
| Compound of Example 148 | 45 |
| Compound of Example 149 | 1.6 |
| Compound of Example 150 | 76 |
| Compound of Example 151 | 1.7 |
| Compound of Example 152 | 3.4 |
| Compound of Example 153 | 6.1 |
| Compound of Example 154 | 5.6 |
| Compound of Example 155 | 167 |
| Compound of Example 156 | 7.6 |
| Compound of Example 157 | 0.66 |
| Compound of Example 158 | 0.48 |
| Compound of Example 159 | 1.5 |
| Compound of Example 160 | 0.11 |
| Compound of Example 161 | 0.32 |
| Compound of Example 162 | 0.49 |
| Compound of Example 163 | 0.19 |
| Compound of Example 164 | 0.40 |
| Compound of Example 165 | 1.9 |
| Compound of Example 166 | 0.20 |
| Compound of Example 167 | 0.13 |
| Compound of Example 168 | 0.19 |
| Compound of Example 169 | 0.75 |
| Compound of Example 170 | 2.9 |
| Compound of Example 171 | 8.6 |
| Compound of Example 172 | 1.9 |
| Compound of Example 173 | 0.60 |
| Compound of Example 174 | 0.69 |
| Compound of Example 175 | 1.2 |
| Compound of Example 176 | 0.74 |
| Compound of Example 177 | 0.35 |
| Compound of Example 178 | 0.32 |
| Compound of Example 179 | 0.41 |
| Compound of Example 180 | 2.2 |
| Compound of Example 181 | 0.36 |
| Compound of Example 182 | 0.49 |
| Compound of Example 183 | 0.16 |
| Compound of Example 184 | 0.16 |
| Compound of Example 185 | 0.10 |
| Compound of Example 186 | 0.33 |
| Compound of Example 187 | 0.27 |
| Compound of Example 188 | 0.11 |
| Compound of Example 189 | 0.28 |
| Compound of Example 190 | 0.050 |
| Compound of Example 191 | 0.23 |
| Compound of Example 192 | 0.17 |
| Compound of Example 193 | 0.80 |
| Compound of Example 194 | 0.39 |
| Compound of Example 195 | 0.28 |
| Compound of Example 196 | 1.1 |
| Compound of Example 197 | 1.3 |
| Compound of Example 198 | 1.2 |
| Compound of Example 199 | 2.0 |
| Compound of Example 200 | 0.50 |
| Compound of Example 201 | 0.22 |
| Compound of Example 202 | 0.30 |
| Compound of Example 203 | 1.5 |
| Compound of Example 204 | 0.23 |
| Compound of Example 205 | 2.1 |
| Compound of Example 206 | 5.9 |
| Compound of Example 207 | 44 |
| Compound of Example 208 | 50 |
| Compound of Example 209 | 18 |
| Compound of Example 210 | 4.2 |
| Compound of Example 211 | 0.40 |
| Compound of Example 212 | 8.8 |
| Compound of Example 213 | 1.9 |
| Compound of Example 214 | 0.88 |
| Compound of Example 215 | 0.11 |
| Compound of Example 216 | 0.33 |
| Compound of Example 217 | 1.6 |
| Compound of Example 218 | 507 |
| Compound of Example 219 | 7.7 |
| Compound of Example 220 | 55 |

TABLE 1-continued

Biological activity of the compounds of the present invention.

| Compound | human $5HT_6$ Ki (nm) |
|---|---|
| Compound of Example 221 | 5.7 |
| Compound of Example 222 | 307 |
| Compound of Example 223 | 1110 |
| Compound of Example 224 | 4.5 |
| Compound of Example 225 | 11 |
| Compound of Example 226 | 106 |
| Compound of Example 227 | 60 |
| Compound of Example 228 | 47 |
| Compound of Example 229 | 64 |
| Compound of Example 230 | 1.9 |
| Compound of Example 231 | 3.1 |
| Compound of Example 232 | 29 |
| Compound of Example 233 | 2.4 |
| Compound of Example 234 | 7.4 |
| Compound of Example 235 | 1.1 |
| Compound of Example 236 | 24 |
| Compound of Example 237 | 645 |
| Compound of Example 238 | 0.59 |
| Compound of Example 239 | 9.5 |

This table illustrates representative compounds tested for $5HT_6$ affinity in the human binding assay. All compounds tested in the cell based assay showed antagonism against the human $5HT_6$ receptor (<15% agonism) except for the compounds of examples 111 and 112 which were weak partial agonists ($E_{max}$=27% and 19% respectively).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:
1. A compound of formula (I):

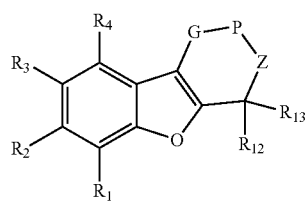

wherein:
G is —$(CR_5R_6)_n$—, where n=1,2
Z is —$(CR_{10}R_{11})_m$—, where m=1,2
P is N—$R_7$ or $CR_{21}$—$OR_{22}$
$R_1$ and $R_4$ are independently H, halogen, $CF_3$, $CHF_2$, $CH_2F$, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_1$ or $R_4$ optionally substituted from 1 to 3 times with substituents selected from the group consisting of halogen, OH, $OR_{17}$, —$C(O)R_{17}$, —$C(O)OR_{17}$, —$C(O)NR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_2$ and $R_3$ are independently H, $R_{14}S(O)_2$—, or $R_{14}S(O)$—;

$R_5$, $R_6$, $R_{10}$, and $R_{11}$ are independently H, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen, each $R_5$, $R_6$, $R_{10}$, or $R_{11}$ optionally substituted from 1 to 3 times with substituents selected from the group consisting of halogen, OH, $OR_{17}$, —$C(O)R_{17}$, —$C(O)OR_{17}$, —$C(O)OR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen; or $R_6$ and $R_{10}$ can combine to form a —$(CH_2)_n$—, wherein n represents an integer from 2 to 3;

$R_7$ is independently H, OH, $OR_{15}$, —$C(O)R_{15}$, —$C(O)OR_{15}$, —$C(O)NR_{15}R_{16}$, —$S(O)R_{15}$, —$S(O)_2R_{15}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen, each $R_7$ optionally substituted from 1 to 3 times with substituents selected from the group consisting of halogen, OH, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_{12}$ and $R_{13}$ are independently H, halogen, $CF_3$, $CHF_2$, $CH_2F$, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_{12}$ or $R_{13}$ optionally substituted from 1 to 3 times with substituents selected from the group consisting of halogen, OH, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen; or $R_{14}$ is independently a substituted or unsubstituted mono or polycyclic aryl or substituted or unsubstituted mono or polycyclic heteroaryl containing from 1 to 5 heteroatoms selected from the group consisting of oxygen, nitrogen, and sulfur, each $R_{14}$ optionally substituted from 1 to 4 times for each cyclic ring with substituents selected from the group consisting of H, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, halogen, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen, each one of the $R_{14}$ substituents further optionally substituted from 1 to 3 times with substituents selected from the group consisting of halogen, H, OH, $OR_{17}$, —$C(O)R_{17}$, —$C(O)OR_{17}$, —$C(O)NR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_{15}$, $R_{16}$, $R_{17}$, and $R_{18}$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl or a monocyclic heteroaryl containing from 1-5 heteroatoms selected from the group consisting of nitrogen, oxygen, and sulfur, each $R_{15}$, $R_{16}$, $R_{17}$, or $R_{18}$ optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and a monocyclic aryl; or $R_{15}$ and $R_{16}$ or $R_{17}$ and $R_{18}$ can combine to form a 3- to 7-membered heterocyclyl or a mono heteroaryl each containing from 1 to 5 heteroatoms selected from the group consisting of nitrogen, sulfur, and oxygen, wherein the heterocyclyl or heteroaryl are optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl, and monocyclic heteroaryl;

$R_{21}$ and $R_{22}$ are independently H or $C_1$-$C_6$ alkyl;

with the provisos that (a) when n=2, m=1 (b) at least one of $R_2$ and $R_3$, but not both, is H;

or an oxide thereof, a pharmaceutically acceptable salt thereof, or a solvate thereof.

2. The compound according to claim 1 which has the formula (Ia):

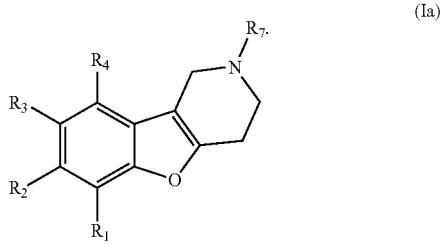

(Ia)

3. The compound according to claim 2, wherein
$R_1$ and $R_4$ are H or $C_1$-$C_6$ alkyl;
$R_2$ is $R_{14}S(O)_2$—;
$R_3$ is H;
$R_7$ is H or $C_1$-$C_6$ alkyl; and
$R_{14}$ is substituted or unsubstituted phenyl, substituted or unsubstituted heteroaryl, substituted or unsubstituted polycyclic aryl, or substituted or unsubstituted polycyclic heteroaryl.

4. The compound according to claim 3, wherein
$R_7$ is H, methyl, or ethyl.

5. The compound according to claim 2, wherein
$R_1$ and $R_4$ are H or $C_1$-$C_6$ alkyl;
$R_2$ is H;
$R_3$ is $R_{14}S(O)_2$—;
$R_7$ is H or $C_1$-$C_6$ alkyl; and
$R_{14}$ is substituted or unsubstituted phenyl, substituted or unsubstituted heteroaryl, substituted or unsubstituted polycyclic aryl, or substituted or unsubstituted polycyclic heteroaryl.

6. The compound according to claim 5, wherein $R_7$ is methyl.

7. The compound according to claim 5, wherein $R_7$ is H.

8. The compound according to claim 2, wherein
$R_1$ is Br, Cl, F, or I;
$R_4$ is H;
$R_7$ is H or $C_1$-$C_6$ alkyl; and
$R_{14}$ is substituted or unsubstituted phenyl, substituted or unsubstituted heteroaryl, substituted or unsubstituted polycyclic aryl, or substituted or unsubstituted polycyclic heteroaryl.

9. The compound according to claim 2, wherein
$R_1$ is OMe, OEt, $OCF_3$, or OBn;
$R_4$ is H or $C_1$-$C_6$ alkyl;
$R_7$ is H or $C_1$-$C_6$ alkyl; and
$R_{14}$ is substituted or unsubstituted phenyl, substituted or unsubstituted heteroaryl, substituted or unsubstituted polycyclic aryl, or substituted or unsubstituted polycyclic heteroaryl.

10. The compound according to claim 2, wherein
$R_1$ is H, $C_1$-$C_6$ alkyl, Cl, O—$C_1$-$C_6$ alkyl;
$R_2$ is $R_{14}S(O)$—;
$R_3$ is H
$R_4$ is H;
$R_7$ is H or $C_1$-$C_6$ alkyl; and
$R_{14}$ is substituted or unsubstituted phenyl, substituted or unsubstituted heteroaryl, substituted or unsubstituted polycyclic aryl, or substituted or unsubstituted polycyclic heteroaryl.

11. The compound according to claim 2, wherein
$R_1$ is H, $C_1$-$C_6$ alkyl, Cl, O—$C_1$-$C_6$ alkyl;
$R_2$ is H;
$R_3$ is $R_{14}S(O)$—;
$R_4$ is H;
$R_7$ is H or $C_1$-$C_6$ alkyl; and
$R_{14}$ is substituted or unsubstituted phenyl, substituted or unsubstituted heteroaryl, substituted or unsubstituted polycyclic aryl, or substituted or unsubstituted polycyclic heteroaryl.

12. The compound according to claim 1 which has the formula (Ib):

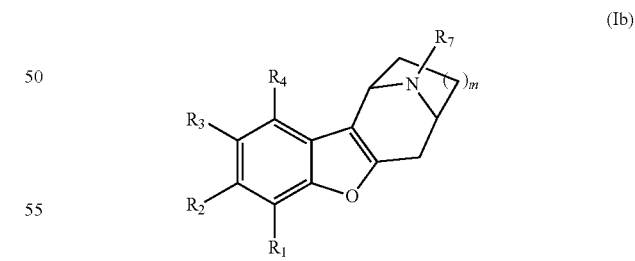

(Ib)

wherein:
m is 1 or 2;
$R_1$ is H or $C_1$-$C_6$ alkyl;
$R_4$ is H or $C_1$-$C_6$ alkyl;
$R_7$ is H or $C_1$-$C_6$ alkyl; and
$R_{14}$ is substituted or unsubstituted phenyl, substituted or unsubstituted heteroaryl, substituted or unsubstituted polycyclic aryl, or substituted or unsubstituted polycyclic heteroaryl.

13. The compound according to claim 12, wherein m is 1.

14. The compound according to claim 13, wherein $R_2$ is H and $R_3$ is $R_{14}S(O)_2$—.

15. The compound according to claim 14, wherein $R_2$ is $R_{14}S(O)_2$— and $R_3$ is H.

16. The compound of claim 12, wherein m is 2.

17. The compound of claim 16, wherein $R_2$ is H and $R_3$ is $R_{14}S(O)_2$—.

18. The compound according to claim 16, wherein $R_2$ is $R_{14}S(O)_2$— and $R_3$ is H.

19. The compound according to claim 1 which has the formula (Ic):

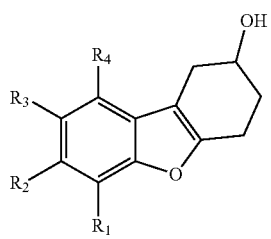

(Ic)

$R_1$ is H, $C_1$-$C_6$ alkyl, Cl, O—$C_1$-$C_6$ alkyl;
$R_2$ is $R_{14}S(O)_2$—;
$R_3$ is H
$R_4$ is H;
$R_{14}$ is substituted or unsubstituted phenyl, substituted or unsubstituted heteroaryl, substituted or unsubstituted polycyclic aryl, or substituted or unsubstituted polycyclic heteroaryl.

20. The compound according to claim 19 wherein:
$R_1$ is H, $C_1$-$C_6$ alkyl, Cl, O—$C_1$-$C_6$ alkyl;
$R_2$ is H;
$R_3$ is $R_{14}S(O)_2$—;
$R_4$ is H;
$R_{14}$ is substituted or unsubstituted phenyl, substituted or unsubstituted heteroaryl, substituted or unsubstituted polycyclic aryl, or substituted or unsubstituted polycyclic heteroaryl.

21. The compound according to claim 1, wherein $R_{14}$ is a substituted or unsubstituted monocyclic aryl.

22. The compound according to claim 21, wherein the monocyclic aryl is a substituted or unsubstituted phenyl.

23. The compound according to claim 21, wherein $R_{14}$ is a substituted or unsubstituted polycyclic aryl.

24. The compound according to claim 23, wherein the substituted or unsubstituted polycyclic aryl is selected from the group consisting of naphthyl, azulenyl, fluorenyl, phenanthrenyl, anthracenyl, pyrenyl, triphenylenyl, chrysenyl, and naphthacenyl.

25. The compound according to claim 1, wherein $R_{14}$ is a substituted or unsubstituted monocyclic heteroaryl.

26. The compound according to claim 25, wherein the substituted or unsubstituted monocyclic heteroaryl is selected from the group consisting of pyrrolyl, pyrazolyl, imidazolyl, triazolyl, furyl, thiophenyl, oxazolyl, isoxazolyl, thiazolyl, isothiazolyl, oxadiazolyl, thiadiazolyl, pyridyl, pyrazinyl, pyrimidinyl, pyridazinyl, and triazinyl.

27. The compound according to claim 1 wherein $R_{14}$ is a substituted or unsubstituted polycyclic heteroaryl.

28. The compound according to claim 27, wherein the substituted or unsubstituted polycyclic heteroaryl is selected from the group consisting of thienopyrrolyl, furopyrrolyl, indolyl, azaindolyl, isoindolyl, indolinyl indolizinyl, indazolyl, benzimidazolyl, imidazopyridinyl, benzotriazolyl, benzoxazolyl, benzoxadiazolyl, benzothiazolyl, pyrazolopyridinyl, triazolopyridinyl, thienopyridinyl, benzothiadiazolyl, benzofuyl, benzothiophenyl, quinolinyl, isoquinolinyl, tetrahydroquinolinyl, tetrahydroisoquinolinyl, cinnolinyl, quinazolinyl, quinolizilinyl, phthalazinyl, benzotriazinyl, chromenyl, and naphthyridinyl.

29. The compound according to claim 28, wherein the compound is present in the form of a pharmaceutical acceptable salt.

30. The compound according to claim 1, wherein the compound is present in the form of an oxide.

31. The compound according to claim 1, wherein the compound is a (+)-stereoisomer.

32. The compound according to claim 1, wherein the compound is a (−)-stereoisomer.

33. A pharmaceutical composition comprising:
a compound according to claim 1 and a pharmaceutically acceptable carrier.

34. A process for preparation of a product compound of formula (I):

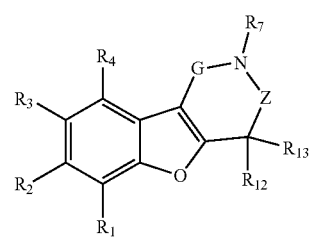

(I)

wherein:
G is —$(CR_5R_6)_n$—, where n=1, 2
Z is —$(CR_{10}R_{11})_m$—, where m=1, 2
$R_1$ and $R_4$ are independently H, halogen, $CF_3$, $CHF_2$, $CH_2F$, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_1$ or $R_4$ optionally substituted from 1 to 3 times with substituents selected from the group consisting of halogen, OH, $OR_{17}$, —$C(O)R_{17}$, —$C(O)OR_{17}$, —$C(O)NR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_2$ and $R_3$ are independently H, $R_{14}S(O)_2$—, $R_{14}S(O)$—, $R_{14}S$—, $R_{14}$—$(CR_{19}R_{20})$—;

$R_5$, $R_6$, $R_{10}$, and $R_{11}$ are independently H, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen, each $R_5$, $R_6$, $R_{10}$, or $R_{11}$ optionally substituted from 1 to 3 times with substituents selected from the group consisting of halogen, OH, $OR_{17}$, —$C(O)R_{17}$, —$C(O)OR_{17}$, —$C(O)NR_{17}R_{18}$, —$NHR_{17}$, —$NR_{17}R_{18}$, —SR$_{17}$, —S(O)R$_{17}$, —S(O)$_2$R$_{17}$, NH$_2$, CN, NO$_2$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, mono or polycyclic aryl, and mono or polycyclic heteroaryl containing from 1 to 5 heteroatoms selected from the group consisting of nitrogen, sulfur, and oxygen; or R$_6$ and R$_{10}$ can combine to form a —(CH$_2$)$_n$—, wherein n represents an integer from 2 to 3;

R$_7$ is independently H, OH, OR$_{15}$, —C(O)R$_{15}$, —C(O)OR$_{15}$, —C(O)NR$_{15}$R$_{16}$, —S(O)R$_{15}$, —S(O)$_2$R$_{15}$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, aryl C$_1$-C$_6$ alkyl, mono or polycyclic aryl, or mono or polycyclic heteroaryl containing from 1 to 5 heteroatoms selected from the group consisting of nitrogen, sulfur, and oxygen, each R$_7$ optionally substituted from 1 to 3 times with substituents selected from the group consisting of halogen, OH, NH$_2$, CN, NO$_2$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, mono or polycyclic aryl, and mono or polycyclic heteroaryl containing from 1 to 5 heteroatoms selected from the group consisting of nitrogen, sulfur, and oxygen;

R$_{12}$ and R$_{13}$ are independently H, halogen, CF$_3$, CHF$_2$, CH$_2$F, OH, OR$_{15}$, —C(O)R$_{15}$, —C(O)OR$_{15}$, —C(O)NR$_{15}$R$_{16}$, —NHR$_{15}$, —NR$_{15}$R$_{16}$, —SR$_{15}$, —S(O)R$_{15}$, —S(O)$_2$R$_{15}$, NH$_2$, CN, NO$_2$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, mono or polycyclic aryl, or mono or polycyclic heteroaryl containing from 1 to 5 heteroatoms selected from the group consisting of nitrogen, sulfur, and oxygen, each R$_{12}$ or R$_{13}$ optionally substituted from 1 to 3 times with substituents selected from the group consisting of halogen, OH, NH$_2$, CN, NO$_2$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, mono or polycyclic aryl, and mono or polycyclic heteroaryl containing from 1 to 5 heteroatoms selected from the group consisting of nitrogen, sulfur, and oxygen; or R$_{14}$ is independently a substituted or unsubstituted mono or polycyclic aryl or substituted or unsubstituted mono or polycyclic heteroaryl containing from 1 to 5 heteroatoms selected from the group consisting of oxygen, nitrogen, and sulfur, each R$_{14}$ optionally substituted from 1 to 4 times for each cyclic ring with substituents selected from the group consisting of H, OH, OR$_{15}$, —C(O)R$_{15}$, —C(O)OR$_{15}$, —C(O)NR$_{15}$R$_{16}$, —NHR$_{15}$, —NR$_{15}$R$_{16}$, —SR$_{15}$, —S(O)R$_{15}$, —S(O)$_2$R$_{15}$, NH$_2$, CN, NO$_2$, halogen, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, mono or polycyclic aryl, and mono or polycyclic heteroaryl containing from 1 to 5 heteroatoms selected from the group consisting of nitrogen, sulfur, and oxygen, each one of the R$_{14}$ substituents further optionally substituted from 1 to 3 times with substituents selected from the group consisting of halogen, H, OH, OR$_{17}$, —C(O)R$_{17}$, —C(O)OR$_{17}$, —C(O)NR$_{17}$R$_{18}$, —NHR$_{17}$, —NR$_{17}$R$_{18}$, —SR$_{17}$, —S(O)R$_{17}$, —S(O)$_2$R$_{17}$, NH$_2$, CN, NO$_2$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, mono or polycyclic aryl, and mono or polycyclic heteroaryl containing from 1 to 5 heteroatoms selected from the group consisting of nitrogen, sulfur, and oxygen;

R$_{15}$, R$_{16}$, R$_{17}$, and R$_{18}$ are independently H, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, a monocyclic aryl or a monocyclic heteroaryl containing from 1-5 heteroatoms selected from the group consisting of nitrogen, oxygen, and sulfur, each R$_{15}$, R$_{16}$, R$_{17}$, or R$_{18}$ optionally substituted from 1 to 3 times with substituents selected from the group consisting of halogen, OH, CN, NO$_2$, NH$_2$, H, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, and a monocyclic aryl; or R$_{15}$ and R$_{16}$ or R$_{17}$ and R$_{18}$ can combine to form a 3- to 7-membered heterocyclyl or a mono heteroaryl each containing from 1 to 5 heteroatoms selected from the group consisting of nitrogen, sulfur, and oxygen, wherein the heterocyclyl or heteroaryl are optionally substituted from 1 to 3 times with substituents selected from the group consisting of halogen, OH, CN, NO$_2$, NH$_2$, H, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, a monocyclic aryl, and monocyclic heteroaryl;

R$_{19}$ and R$_{20}$ are independently H or C$_1$-C$_6$ alkyl, wherein R$_{19}$ and R$_{20}$ can combine to form a —(CH$_2$)$_n$— where n represents an integer from 4-7;

with the proviso that at least one of R$_2$ and R$_3$, but not both, is H;

or an oxide thereof, a pharmaceutically acceptable salt thereof, or a solvate thereof, said process comprising:

providing a first intermediate compound having the structure:

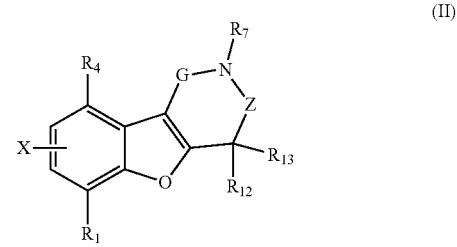

(II)

wherein X is Br, Cl, or I
and
converting the first intermediate compound to the compound of formula (I).

35. The process according to claim 34, wherein said converting comprises:
reacting the first intermediate compound with a heteroarylsulfonyl salt, arylsulfonyl salt, thiophenol, aldehyde or ketone under conditions effective to produce the compound of formula (I).

36. The process according to claim 34, wherein said converting comprises:
sulfonating the first intermediate compound in the presence of an organolithium and sulfur dioxide under conditions effective to produce a lithium sulfinate intermediate compound having the structure:

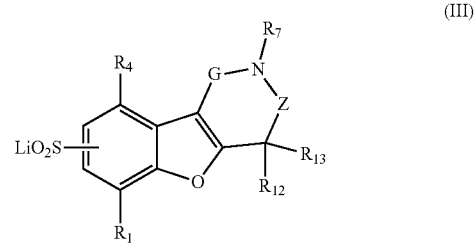

(III)

and
subjecting the lithium sulfinate intermediate compound to arylation or heteroarylation under conditions effective to produce the compound of formula (I).

37. The process according to claim 36, wherein the organolithium is selected from the group consisting of n-butyllithium, t-butyllithium, sec-butyllithium, phenyl lithium, and lithium diisopropyl amide.

38. The process according to claim 34, wherein said converting comprises:

sulfonating the first intermediate compound in the presence of an organolithium and sulfur dioxide under conditions effective to produce a lithium sulfinate intermediate compound having the structure:

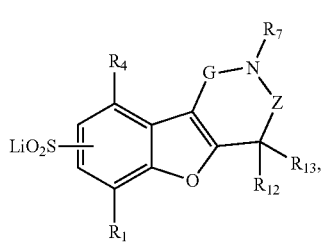

(III)

halogenating the lithium sulfinate intermediate compound under conditions effective to produce a halosulfonyl intermediate compound having the structure:

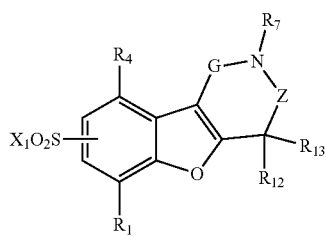

(V)

wherein $X_1$ is Cl, Br, or I; and arylating the halosulfonyl intermediate compound under conditions effective to produce the compound of formula (I).

39. A process for the preparation of a compound of formula (VI) having the structure:

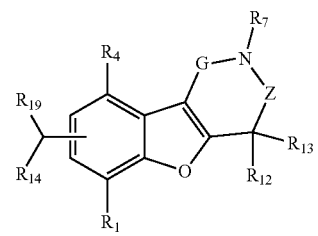

(VI)

wherein:

G is $-(CR_5R_6)_n-$, where n=1, 2

Z is $-(CR_{10}R_{11})_m-$, where m=1, 2

$R_1$ and $R_4$ are independently H, halogen, $CF_3$, $CHF_2$, $CH_2F$, OH, $OR_{15}$, $-C(O)R_{15}$, $-C(O)OR_{15}$, $-C(O)NR_{15}R_{16}$, $-NHR_{15}$, $-NR_{15}R_{16}$, $-SR_{15}$, $-S(O)R_{15}$, $-S(O)_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_1$ or $R_4$ optionally substituted from 1 to 3 times with substituents selected from the group consisting of halogen, OH, $OR_{17}$, $-C(O)R_{17}$, $-C(O)OR_{17}$, $-C(O)NR_{17}R_{18}$, $-NHR_{17}$, $-NR_{17}R_{18}$, $-SR_{17}$, $-S(O)R_{17}$, $-S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_5$, $R_6$, $R_{10}$, and $R_{11}$ are independently H, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen, each $R_5$, $R_6$, $R_{10}$, or $R_{11}$ optionally substituted from 1 to 3 times with substituents selected from the group consisting of halogen, OH, $OR_{17}$, $-C(O)R_{17}$, $-C(O)OR_{17}$, $-C(O)NR_{17}R_{18}$, $-NHR_{17}$, $-NR_{17}R_{18}$, $-SR_{17}$, $-S(O)R_{17}$, $-S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen; or $R_6$ and $R_{10}$ can combine to form a $-(CH_2)_n-$, wherein n represents an integer from 2 to 3;

$R_7$ is independently H, OH, $OR_{15}$, $-C(O)R_{15}$, $-C(O)OR_{15}$, $-C(O)NR_{15}R_{16}$, $-S(O)R_{15}$, $-S(O)_2R_{15}$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen, each $R_7$ optionally substituted from 1 to 3 times with substituents selected from the group consisting of halogen, OH, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_{12}$ and $R_{13}$ are independently H, halogen, $CF_3$, $CHF_2$, $CH_2F$, OH, $OR_{15}$, $-C(O)R_{15}$, $-C(O)OR_{15}$, $-C(O)NR_{15}R_{16}$, $-NHR_{15}$, $-NR_{15}R_{16}$, $-SR_{15}$, $-S(O)R_{15}$, $-S(O)_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_{12}$ or $R_{13}$ optionally substituted from 1 to 3 times with substituents selected from the group consisting of halogen, OH, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen; or $R_{14}$ is independently a substituted or unsubstituted mono or polycyclic aryl or substituted or unsubstituted mono or polycyclic heteroaryl containing from 1 to 5 heteroatoms selected from the group consisting of oxygen, nitrogen, and sulfur, each $R_{14}$ optionally substituted from 1 to 4 times for each cyclic ring with substituents selected from the group consisting of H, OH, OR$_{15}$, —C(O)R$_{15}$, —C(O)OR$_{15}$, —C(O)NR$_{15}$R$_{16}$, —NHR$_{15}$, —NR$_{15}$R$_{16}$, —SR$_{15}$, —S(O)R$_{15}$, —S(O)$_2$R$_{15}$, NH$_2$, CN, NO$_2$, halogen, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, mono or polycyclic aryl, and mono or polycyclic heteroaryl containing from 1 to 5 heteroatoms selected from the group consisting of nitrogen, sulfur, and oxygen, each one of the R$_{14}$ substituents further optionally substituted from 1 to 3 times with substituents selected from the group consisting of halogen, H, OH, OR$_{17}$, —C(O)R$_{17}$, —C(O)OR$_{17}$, —C(O)NR$_{17}$R$_{18}$, —NHR$_{17}$, —NR$_{17}$R$_{18}$, —SR$_{17}$, —S(O)R$_{17}$, —S(O)$_2$R$_{17}$, NH$_2$, CN, NO$_2$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, mono or polycyclic aryl, and mono or polycyclic heteroaryl containing from 1 to 5 heteroatoms selected from the group consisting of nitrogen, sulfur, and oxygen;

R$_{15}$, R$_{16}$, R$_{17}$, and R$_{18}$ are independently H, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, a monocyclic aryl or a monocyclic heteroaryl containing from 1-5 heteroatoms selected from the group consisting of nitrogen, oxygen, and sulfur, each R$_{15}$, R$_{16}$, R$_{17}$, or R$_{18}$ optionally substituted from 1 to 3 times with substituents selected from the group consisting of halogen, OH, CN, NO$_2$, NH$_2$, H, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, and a monocyclic aryl; or R$_{15}$ and R$_{16}$ or R$_{17}$ and R$_{18}$ can combine to form a 3- to 7-membered heterocyclyl or a mono heteroaryl each containing from 1 to 5 heteroatoms selected from the group consisting of nitrogen, sulfur, and oxygen, wherein the heterocyclyl or heteroaryl are optionally substituted from 1 to 3 times with substituents selected from the group consisting of halogen, OH, CN, NO$_2$, NH$_2$, H, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, a monocyclic aryl, and monocyclic heteroaryl;

R$_{19}$ is independently H or C$_1$-C$_6$ alkyl;

with the proviso that at least one of R$_2$ and R$_3$, but not both, is H;

or an oxide thereof, a pharmaceutically acceptable salt thereof, or a solvate thereof, said process comprising:
providing a first intermediate compound having the structure:

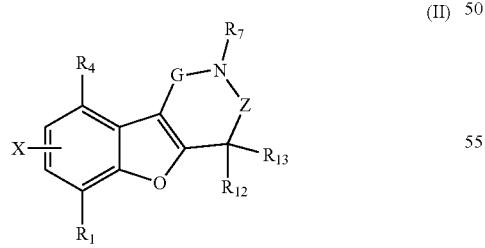

(II)

wherein X is Br, Cl, or I
reacting the first intermediate compound (II) with a lithiating agent;
quenching the lithiated first intermediate compound with an aldehyde or ketone under conditions effective to produce the second intermediate compound (VII) of the following formula:

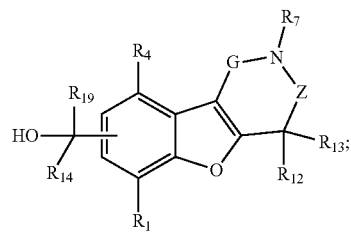

(VII)

and
reacting the second intermediate compound (VII) under conditions effective to de-oxygenate a hydroxyl group attached to the carbon adjacent to R$_{14}$ and produce the compound of formula (VI).

40. A process for the preparation of a compound of formula (VIII):

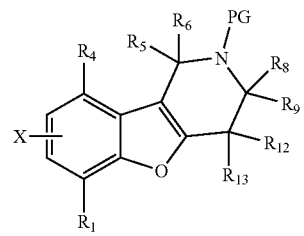

(VIII)

wherein
X is Br, Cl, or I;
R$_1$ and R$_4$ are independently H, halogen, CF$_3$, CHF$_2$, CH$_2$F, OH, OR$_{15}$, —C(O)R$_{15}$, —C(O)OR$_{15}$, —C(O)NR$_{15}$R$_{16}$, —NHR$_{15}$, —NR$_{15}$R$_{16}$, —SR$_{15}$, —S(O)R$_{15}$, —S(O)$_2$R$_{15}$, NH$_2$, CN, NO$_2$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, mono or polycyclic aryl, or mono or polycyclic heteroaryl containing from 1 to 5 heteroatoms selected from the group consisting of nitrogen, sulfur, and oxygen, each R$_1$ or R$_4$ optionally substituted from 1 to 3 times with substituents selected from the group consisting of halogen, OH, OR$_{17}$, —C(O)R$_{17}$, —C(O)OR$_{17}$, —C(O)NR$_{17}$R$_{18}$, —NHR$_{17}$, —NR$_{17}$R$_{18}$, —SR$_{17}$, —S(O)R$_{17}$, —S(O)$_2$R$_{17}$, NH$_2$, CN, NO$_2$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, mono or polycyclic aryl, and mono or polycyclic heteroaryl containing from 1 to 5 heteroatoms selected from the group consisting of nitrogen, sulfur, and oxygen;

R$_5$, R$_6$, R$_8$, and R$_9$ are independently H, C$_1$-C$_6$ alkyl, C$_2$-C$_6$ alkenyl, C$_2$-C$_6$ alkynyl, C$_1$-C$_6$ alkoxy, C$_3$-C$_6$ cycloalkyl, C$_4$-C$_7$ cycloalkylalkyl, aryl C$_1$-C$_6$ alkyl, mono or polycyclic aryl, or mono or polycyclic heteroaryl containing from 1 to 5 heteroatoms selected from the group consisting of nitrogen, sulfur, and oxygen, each R$_5$, R$_6$, R$_8$, or R$_9$ optionally substituted from 1 to 3 times with substituents selected from the group consisting of halogen, OH, OR$_{17}$, —C(O)R$_{17}$, —C(O)OR$_{17}$, —C(O)NR$_{17}$R$_{18}$, —NHR$_{17}$, —NR$_{17}$R$_{18}$, —SR$_{17}$, —S(O)R$_{17}$, —S(O)$_2$R$_{17}$, NH$_2$, CN, NO$_2$, C$_1$-C$_6$ alkyl, C$_2$-C$_6$ alkenyl, C$_2$-C$_6$ alkynyl, C$_3$-C$_6$ cycloalkyl, C$_4$-C$_7$ cycloalkylalkyl, mono or polycyclic aryl, and mono or polycyclic heteroaryl containing from 1 to 5 heteroatoms selected from the group consisting of nitrogen, sulfur, and oxygen; or $R_6$ and $R_8$ can combine to form a —$(CH_2)_n$—, wherein n represents an integer from 2 to 3;

$R_{12}$ and $R_{13}$ are independently H, halogen, $CF_3$, $CHF_2$, $CH_2F$, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_{12}$ or $R_{13}$ optionally substituted from 1 to 3 times with substituents selected from the group consisting of halogen, OH, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_{15}$, $R_{16}$, $R_{17}$, and $R_{18}$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl or a monocyclic heteroaryl containing from 1-5 heteroatoms selected from the group consisting of nitrogen, oxygen, and sulfur, each $R_{15}$, $R_{16}$, $R_{17}$, or $R_{18}$ optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and a monocyclic aryl; or $R_{15}$ and $R_{16}$ or $R_{17}$ and $R_{18}$ can combine to form a 3- to 7-membered heterocyclyl or a mono heteroaryl each containing from 1 to 5 heteroatoms selected from the group consisting of nitrogen, sulfur, and oxygen, wherein the heterocyclyl or heteroaryl are optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl, and monocyclic heteroaryl, or an oxide thereof, a pharmaceutically acceptable salt thereof, or a solvate thereof, said process comprises:

providing a phenoxylamine derivative compound having the formula:

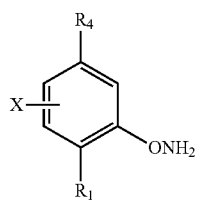

(IX)

and reacting the phenoxylamine derivative compound with a piperidone derivative compound having the structure:

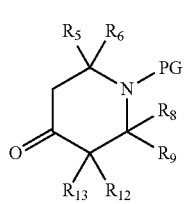

(X)

wherein PG is H or a protective group under conditions effective to form the compound of formula (VIII).

41. A process for preparation of a compound of formula (XI):

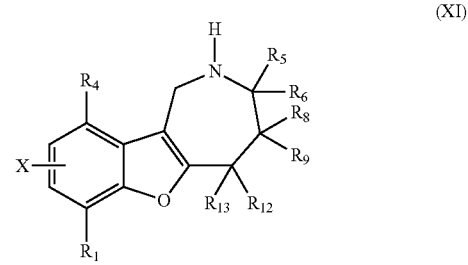

(XI)

wherein

X is Br, Cl, or I;

$R_1$ and $R_4$ are independently H, halogen, $CF_3$, $CHF_2$, $CH_2F$, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_1$ or $R_4$ optionally substituted from 1 to 3 times with substituents selected from the group consisting of halogen, OH, $OR_{17}$, —$C(O)R_{17}$, —$C(O)OR_{17}$, —$C(O)NR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_5$, $R_6$, $R_8$, and $R_9$ are independently H, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen, each $R_5$, $R_6$, $R_8$, or $R_9$ optionally substituted from 1 to 3 times with substituents selected from the group consisting of halogen, OH, $OR_{17}$, —$C(O)R_{17}$, —$C(O)OR_{17}$, —$C(O)NR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_{12}$ and $R_{13}$ are independently H, halogen, $CF_3$, $CHF_2$, $CH_2F$, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_{12}$ or $R_{13}$ optionally substituted from 1 to 3 times with substituents selected from the group consisting of halogen, OH, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_{15}$, $R_{16}$, $R_{17}$, and $R_{18}$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl or a monocyclic heteroaryl containing from 1-5 heteroatoms selected from the group consisting of nitrogen, oxygen, and sulfur, each $R_{15}$, $R_{16}$, $R_{17}$, or $R_{18}$ optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and a monocyclic aryl; or $R_{15}$ and $R_{16}$ or $R_{17}$ and $R_{18}$ can combine to form a 3- to 7-membered heterocyclyl or a mono heteroaryl each containing from 1 to 5 heteroatoms selected from the group consisting of nitrogen, sulfur, and oxygen, wherein the heterocyclyl or heteroaryl are optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl, and monocyclic heteroaryl, or an oxide thereof, a pharmaceutically acceptable salt thereof, or a solvate thereof, said process comprises:

providing a starting compound having the structure:

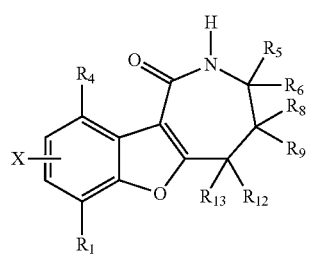

(XII)

and converting said starting compound under conditions effective to form the compound of formula (XI).

42. The process according to claim 41, wherein said providing a starting compound comprises:

providing a precursor compound having the structure:

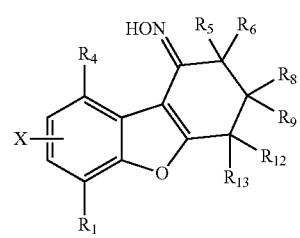

(XIII)

and converting the precursor compound under conditions effective to form the starting compound.

43. The process according to claim 42, wherein said providing a precursor compound comprises:

providing a reactant compound having the structure:

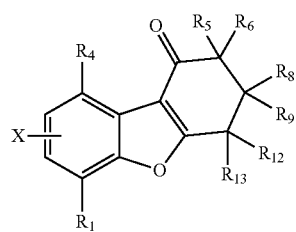

(XIV)

and converting the reactant compound under conditions effective to form the precursor compound.

44. The process according to claim 43, wherein said providing a reactant compound comprises:

reacting a phenoxylamine derivative having the formula (IX) with a diketone compound having the structure:

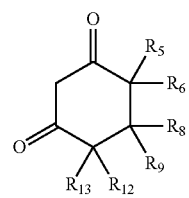

(XV)

under conditions effective to form said reactant compound.

45. The process according to claim 44, wherein the phenoxylamine is prepared by reacting a phenol derivative having the formula:

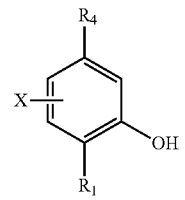

(XVI)

with an aminating reagent under conditions effective to form said phenoxylamine.

46. The process according to claim 45, wherein the aminating reagent is hydroxylamine-O-sulfonic acid or O-mesitylsulfonyl-hydroxylamine.

47. A process for preparation of a compound formula (XVII):

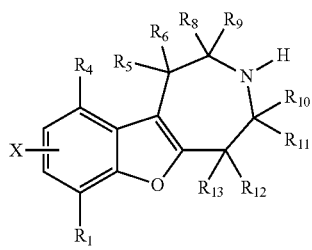

(XVII)

wherein
X is Br, Cl, or I;
$R_1$ and $R_4$ are independently H, halogen, $CF_3$, $CHF_2$, $CH_2F$, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_1$ or $R_4$ optionally substituted from 1 to 3 times with substituents selected from the group consisting of halogen, OH, $OR_{17}$, —$C(O)R_{17}$, —$C(O)OR_{17}$, —$C(O)NR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;
$R_5$, $R_6$, $R_8$, and $R_9$ are independently H, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen, each $R_5$, $R_6$, $R_8$, and $R_9$ are optionally substituted from 1 to 3 times with substituents selected from the group consisting of halogen, OH, $OR_{17}$, —$C(O)R_{17}$, —$C(O)OR_{47}$, —$C(O)NR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;
$R_{10}$ and $R_{11}$ are independently H, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen, each $R_{10}$ or $R_{11}$ optionally substituted from 1 to 3 times with substituents selected from the group consisting of halogen, OH, $OR_{17}$, —$C(O)R_{17}$, —$C(O)OR_{17}$, —$C(O)NR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;
$R_{12}$ and $R_{13}$ are independently H, halogen, $CF_3$, $CHF_2$, $CH_2F$, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_{12}$ or $R_{13}$ optionally substituted from 1 to 3 times with substituents selected from the group consisting of halogen, OH, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_{15}$, $R_{16}$, $R_{17}$, and $R_{18}$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl or a monocyclic heteroaryl containing from 1-5 heteroatoms selected from the group consisting of nitrogen, oxygen, and sulfur, each $R_{15}$, $R_{16}$, $R_{17}$, or $R_{18}$ optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and a monocyclic aryl; or $R_{15}$ and $R_{16}$ or $R_{17}$ and $R_{18}$ can combine to form a 3- to 7-membered heterocyclyl or a mono heteroaryl each containing from 1 to 5 heteroatoms selected from the group consisting of nitrogen, sulfur, and oxygen, wherein the heterocyclyl or heteroaryl are optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl, and monocyclic heteroaryl, or an oxide thereof, a pharmaceutically acceptable salt thereof, or a solvate thereof, said process comprises:

providing a starting compound having the structure:

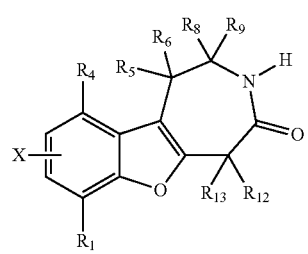

(XVIII)

and converting said starting compound under conditions effective to form the compound of formula (XVII).

48. The process according to claim 47, wherein said providing a starting compound comprises:

providing a precursor compound having the structure:

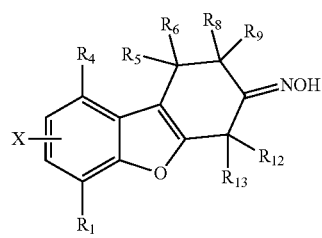

(XIX)

and converting the precursor compound under conditions effective to form the starting compound.

49. The process according to claim 48, wherein said providing a precursor compound comprises:

providing a reactant compound having the structure:

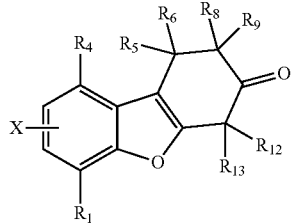

(XX)

and converting the reactant compound under conditions effective to form the precursor compound.

50. A process for preparation of a compound formula (XXI):

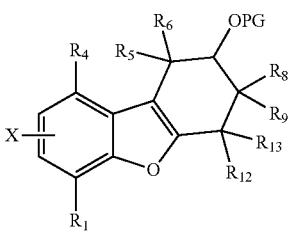

(XXI)

wherein

PG is a protecting group that can be removed under acidic or basic conditions

X is Br, Cl, or I;

$R_1$ and $R_4$ are independently H, halogen, $CF_3$, $CHF_2$, $CH_2F$, OH, $OR_{15}$, —$C(O)R_{15}$, —$C(O)OR_{45}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_1$ or $R_4$ optionally substituted from 1 to 3 times with substituents selected from the group consisting of halogen, OH, $OR_{17}$, —$C(O)R_{17}$, —$C(O)OR_{17}$, —$C(O)NR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_5$, $R_6$, $R_8$, and $R_9$ are independently H, $C_1$-$C_6$ alkyl, $C_2$-$C_6$ alkenyl, $C_2$-$C_6$ alkynyl, $C_1$-$C_6$ alkoxy, $C_3$-$C_6$ cycloalkyl, $C_4$-$C_7$ cycloalkylalkyl, aryl $C_1$-$C_6$ alkyl, mono or polycyclic aryl, or mono or polycyclic heteroaryl containing from 1 to 5 heteroatoms selected from the group consisting of nitrogen, sulfur, and oxygen, each $R_5$, $R_6$, $R_8$, and $R_9$ are optionally substituted from 1 to 3 times with substituents selected from the group consisting of halogen, OH, $OR_{17}$, —$C(O)R_{17}$, —$C(O)OR_{17}$, —$C(O)NR_{17}R_{18}$, —$NHR_{17}$, —$NR_{17}R_{18}$, —$SR_{17}$, —$S(O)R_{17}$, —$S(O)_2R_{17}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_{12}$ and $R_{13}$ are independently H, halogen, $CF_3$, $CHF_2$, $CH_2F$, OH, $OR_{15}$, —$C(O)R_{15}$, —$C(O)OR_{15}$, —$C(O)NR_{15}R_{16}$, —$NHR_{15}$, —$NR_{15}R_{16}$, —$SR_{15}$, —$S(O)R_{15}$, —$S(O)_2R_{15}$, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, or mono or polycyclic heteroaryl containing from 1 to 5 heteroatoms selected from the group consisting of nitrogen, sulfur, and oxygen, each $R_{12}$ or $R_{13}$ optionally substituted from 1 to 3 times with substituents selected from the group consisting of halogen, OH, $NH_2$, CN, $NO_2$, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, mono or polycyclic aryl, and mono or polycyclic heteroaryl containing from 1 to 5 heteroatoms selected from the group consisting of nitrogen, sulfur, and oxygen;

$R_{15}$, $R_{16}$, $R_{17}$, and $R_{18}$ are independently H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl or a monocyclic heteroaryl containing from 1-5 heteroatoms selected from the group consisting of nitrogen, oxygen, and sulfur, each $R_{15}$, $R_{16}$, $R_{17}$, or $R_{18}$ optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, and a monocyclic aryl; or $R_{15}$ and $R_{16}$ or $R_{17}$ and $R_{18}$ can combine to form a 3- to 7-membered heterocyclyl or a mono heteroaryl each containing from 1 to 5 heteroatoms selected from the group consisting of nitrogen, sulfur, and oxygen, wherein the heterocyclyl or heteroaryl are optionally substituted from 1 to 3 times with substituents selected from the group consisting of halogen, OH, CN, $NO_2$, $NH_2$, H, $C_1$-$C_6$ alkyl, $C_2$-$C_6$ alkenyl, $C_2$-$C_6$ alkynyl, $C_3$-$C_6$ cycloalkyl, $C_4$-$C_7$ cycloalkylalkyl, a monocyclic aryl, and monocyclic heteroaryl, or an oxide thereof, a pharmaceutically acceptable salt thereof, or a solvate thereof, said process comprises:

providing a starting compound having the structure:

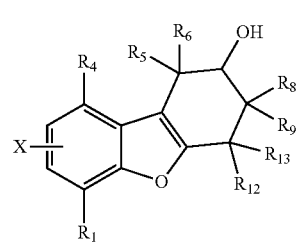

(XXII)

and converting said starting compound under conditions effective to form the compound of formula (XXI).

51. The process according to claim 50, wherein said providing a starting compound comprises:

providing a precursor compound having the structure:

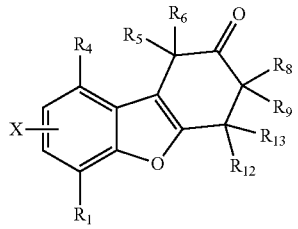

(XXIII)

and converting the precursor compound under conditions effective to form the starting compound.

52. The process according to claim 51, wherein said providing a precursor compound comprises:

reacting a phenoxylamine derivative having the formula (IX)

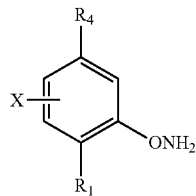

(IX)

with a diketone derivative compound having the structure:

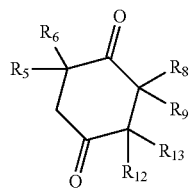

(XXIV)

under conditions effective to form said precursor compound.

* * * * *